(12) United States Patent
Schubert et al.

(10) Patent No.: US 8,080,400 B2
(45) Date of Patent: Dec. 20, 2011

(54) CRYSTAL STRUCTURE OF MONOACYLGLYCEROL LIPASE (MGLL)

(75) Inventors: Carsten Schubert, Phoenixville, PA (US); Bruce L. Grasberger, Trappe, PA (US); Celine Schalk-Hihi, Phoenixville, PA (US); Diane M. Maguire, Downingtown, PA (US); Frank A. Lewandowski, Washington Crossing, PA (US); Cynthia M. Milligan, Rutledge, PA (US); Richard S. Alexander, Newark, DE (US)

(73) Assignee: Janssen Pharmaceutica N.V., Beerse (BE)

( * ) Notice: Subject to any disclaimer, the term of this patent is extended or adjusted under 35 U.S.C. 154(b) by 0 days.

(21) Appl. No.: 12/429,279

(22) Filed: Apr. 24, 2009

(65) Prior Publication Data

US 2009/0269785 A1 Oct. 29, 2009

(51) Int. Cl.
*C12N 9/18* (2006.01)

(52) U.S. Cl. .................. 435/197; 435/196; 435/198

(58) Field of Classification Search .................. None
See application file for complete search history.

(56) References Cited

U.S. PATENT DOCUMENTS

| | | | |
|---|---|---|---|
| 4,906,122 A | 3/1990 | Barrett | |
| 5,030,103 A | 7/1991 | Buist | |
| 5,200,910 A | 4/1993 | Subbiah | |
| 5,365,456 A | 11/1994 | Subbiah | |
| 5,583,973 A | 12/1996 | DeLisi | |
| 5,612,894 A | 3/1997 | Wertz | |
| 5,733,720 A | 3/1998 | Olivo | |
| 5,763,263 A | 6/1998 | Dehlinger | |
| 5,942,428 A | 8/1999 | Mohammadi | |
| 5,994,503 A | 11/1999 | Xu | |
| 5,998,593 A | 12/1999 | Huff | |
| 6,037,117 A | 3/2000 | Qiu | |
| 6,071,700 A | 6/2000 | He | |
| 6,075,014 A | 6/2000 | Weston | |
| 6,075,123 A | 6/2000 | Lahti | |
| 6,080,576 A | 6/2000 | Zambrowicz | |
| 6,093,573 A | 7/2000 | Beamer | |
| 6,172,262 B1 | 1/2001 | McQuade | |

OTHER PUBLICATIONS

Wall et al. A novel poxyvirus gene and its human homolog are similar to an *E. coli* lysophospholipase. Virus Research (1997) 52, 157-167.*

Karlsson, M. et al. "Exon-Intron Organization and Chromosomal Localization of the Mouse Monoglyceride Lipase Gene". GENE, Elsevier, Amsterdam, NL, vol. 272, No. 1-2, Jul. 11, 2001, pp. 11-18, XP004274834.

(Continued)

*Primary Examiner* — Nashaat Nashed
(74) *Attorney, Agent, or Firm* — Andrea Jo Kamage

(57) ABSTRACT

A number of soluble engineered forms of MGLL that are suitable for high-throughput screening and protein crystallization, as well as a crystallized form of monoacylglycerol lipase protein (MGLL) and descriptions of the X-ray diffraction patterns are disclosed. The engineered constructs of MGLL permit the expression and purification of protein suitable for crystallography or high-throughput screening and identification of ligands, which can function as active agents to MGLL. The X-ray diffraction patterns allow the three dimensional structure of MGLL to be determined at atomic resolution so that ligand binding sites on MGLL can be identified and the interactions of ligands with MGLL amino acid residues can be modeled. Models prepared using such maps permit the design of ligands which can function as active agents which include, but are not limited to, those that function as inhibitors of MGLL.

2 Claims, 11 Drawing Sheets

OTHER PUBLICATIONS

Yoneda, Kazunari et al. "Crystallization and Preliminary X-ray Crystallographic Studies of monoacylglycerol Lipase of the Moderately Thermophilic *Bacillus* sp. H257". Acta Crystallographica Section D Biological Crystallography, vol. 58, No. 7, Jul. 2002, pp. 1232-1233, XP002538245.

Saario, Susanna M. et al. "fatty Acid Amide Hydrolase Inhibitors from Virtual Screening of the Endocannabinoid System", Journal of Medicinal Chemistry, American Chemical Society, Washington, US, vol. 49, No. 15, Jan. 1, 2006, XP002494326.

Viso, Alma et al. "The Medicinal Chemistry of Agents Targeting Monoacylglycerol Lipase", Current Topics in Medicinal Chemistry, vol. 8, No. 3, Feb. 2008, pp. 231-246, XP002538246.

Adams, P. D., K. Gopal, et al. (2004). "Recent developments in the PHENIX software for automated crystallographic structure determination." J Synchrotron Radiat 11(Pt 1): 53-5.

Adams, P. D., R. W. Grosse-Kunstleve, et al. (2002). "PHENIX: building new software for automated crystallographic structure determination." Acta Crystallogr D Biol Crystallogr 58(Pt 11): 1948-54.

Altschul, S. F. (1993). "A protein alignment scoring system sensitive at all evolutionary distances." J. Mol. Evol. 36: 290-300.

Altschul, S. F., M. S. Boguski, et al. (1994). "Issues in searching molecular sequence databases." Nature Genetics 6: 119-129.

Altschul, S. F., W. Gish, et al. (1990). "Basic local alignment search tool." J Mol Biol 215(3): 403-10.

Bacon, D. J. and J. Moult (1992). "Docking by Least-squares Fitting of Molecular Surface Patterns." J.Mol.Biol. 225: 849-858.

Bartlett, P. A., G. T. Shea, et al. (1989). "Caveat: A Program to Facilitate the Structure-Derived Design of Biologically Active Molecules." In Molecular Recognition in Chemical and Biological Problems, Special Pub., Royal Chem. Soc. 78: 82-196.

Bohm, H.-J. (1992). "The Computer Program LUDI: A New Method for the De Novo Design of Enzyme Inhibitors." J. Computer-Aided Molecular Design 6: 61-78.

Boutselakis, H., D. Dimitropoulos, et al. (2003). "E-MSD: the European Bioinformatics Institute Macromolecular Structure Database." Nucleic Acids Res 31(1): 458-62.

Bradford, M. M. (1976). "A rapid and sensitive method for the quantitation of microgram quantities of protein utilizing the principle of protein-dye binding." Anal Biochem 72: 248-54.

Brady, L., A. M. Brzozowski, et al. (1990). "A serine protease triad forms the catalytic centre of a triacylglycerol lipase." Nature 343(6260): 767-70.

Brzozowski, A. M., U. Derewenda, et al. (1991). "A model for interfacial activation in lipases from the structure of a fungal lipase-inhibitor complex." Nature 351(6326): 491-4.

Carriere, F., K. Thirstrup, et al. (1997). "Pancreatic lipase structure-function relationships by domain exchange." Biochemistry 36(1): 239-48.

Chahinian, H., L. Nini, et al. (2002). "Distinction between esterases and lipases: a kinetic study with vinyl esters and TAG." Lipids 37(7): 653-62.

Cohen, N., J. Blaney, et al. (1990). "Molecular Modeling Software and Methods for Medicinal Chemistry." J. Med. Chem. 33: 883-894.

Dinh, T. P., T. F. Freund, et al. (2002). "A role for monoglyceride lipase in 2-arachidonoylglycerol inactivation." Chem Phys Lipids 121(1-2): 149-58.

Dinh, T. P., S. Kathuria, et al. (2004). "RNA interference suggests a primary role for monoacylglycerol lipase in the degradation of the endocannabinoid 2-arachidonoylglycerol." Mol Pharmacol 66(5): 1260-4.

Dugi, K. A., H. L. Dichek, et al. (1995). "Human hepatic and lipoprotein lipase: the loop covering the catalytic site mediates lipase substrate specificity." J Biol Chem 270(43): 25396-25401.

Dugi, K. S., H. L. Dichek, et al. (1992). "Human lipoprotein lipase: the loop covering the catalytic site is essential for interaction with lipid substrates." J Biol Chem 267(35): 25086-25091.

Emsley, P. and K. Cowtan (2004). "Coot: model-building tools for molecular graphics." Acta Crystallogr D Biol Crystallogr 60(Pt 12 Pt 1): 2126-2132.

Farquhar-Smith, W. P., M. Egertova, et al. (2000). "Cannabinoid Cb(1) receptor expression in rat spinal cord." Mol Cell Neurosci 15(6): 510-21.

Faustinella, F., L. C. Smith, et al. (1992). "Functional topology of a surface loop shielding the catalytic center in lipoprotein lipase." Biochemistry 31(32): 7219-7223.

Galiegue, S., S. Mary, et al. (1995). "Expression of central and peripheral cannabinoid receptors in human immune tissues and leukocyte subpopulations." Eur J Biochem 232(1): 54-61.

Gonsiorek, W., C. Lunn, et al. (2000). "Endocannabinoid 2-arachidonyl glycerol is a full agonist through human type 2 cannabinoid receptor: antagonism by anandamide." Mol Pharmacol 57(5): 1045-1050.

Goodford, P. J. (1985). "A Computational Procedure for Determining Energetically Favorable Binding Sites on Biologically Important Macromolecules." J. Med. Chem. 28: 849-857.

Goodsell, D. S. and A. J. Olsen (1990). "Automated Docking of Substrates to Proteins by SimulatedAnnealing." Proteins: Structure. Function, and Genetics 8: 195-202.

Guindon, J., J. Desroches, et al. (2007). "The antinociceptive effects of intraplantar injections of 2-arachidonoyl glycerol are mediated by cannabinoid CB2 receptors." Br J Pharmacol 150(6): 693-701.

Hanus, L., A. Breuer, et al. (1999). "HU-308: a specific agonist for CB(2), a peripheral cannabinoid receptor." Proc Natl Acad Sci U S A 96(25): 14228-14233.

Heikinheimo, P., A. Goldman, et al. (1999). "Of barn owls and bankers: a lush variety of alpha/beta hydrolases." Structure 7(6): R141-6.

Henikoff, J. G. (1992). "Amino acid substitution matrices from protein blocks." Proc. Natl. Acad. Sci. Usa(89): 10915-10919.

Higgins, D. G., J. D. Thompson, et al. (1996). "Using Clustal for multiple sequence alignments." Methods Enzymol 266: 383-402.

Hohmann, A. G. (2002). "Spinal and peripheral mechanisms of cannabinoid antinociception: behavioral, neurophysiological and neuroanatomical perspectives." Chem Phys Lipids 121(1-2): 173-190.

Hohmann, A. G., J. N. Farthing, et al. (2004). "Selective activation of cannabinoid CB2 receptors suppresses hyperalgesia evoked by intradermal capsaicin." J Pharmacol Exp Ther 308(2): 446-453.

Hohmann, A. G. and M. Herkenham (1999). "Cannabinoid receptors undergo axonal flow in sensory nerves." Neuroscience 92(4): 1171-1175.

Hohmann, A. G., R. L. Suplita, et al. (2005). "An endocannabinoid mechanism for stress-induced analgesia." Nature 435(7045): 1108-1112.

Holmquist, M. (2000). "Alpha/Beta-hydrolase fold enzymes: structures, functions and mechanisms." Curr Protein Pept Sci 1(2): 209-235.

Ibrahim, M. M., M. L. Rude, et al. (2006). "CB2 cannabinoid receptor mediation of antinociception." Pain 122(1-2): 36-42.

Kaneko, T., N. Tanaka, et al. (2005). "Crystal structures of RsbQ, a stress-response regulator in Bacillus subtilis." Protein Sci 14(2): 558-565.

Karlin, S. and S. F. Altschul (1990). "Methods for assessing the statistical significance of molecular sequence features by using general scoring schemes." Proc. Natl. Acad. Sci. USA 87: 2264-2268.

Karlsson, M., J. A. Contreras, et al. (1997). "cDNA cloning, tissue distribution, and identification of the relationship to esterases, lysophospholipases, and haloperoxidases." J Biol Chem 272(43): 27218-27223.

Karlsson, M., H. Tornqvist, et al. (2000). "Expression, purification, and characterization of histidine-tagged mouse monoglyceride lipase from baculovirus-infected insect cells." Protein Expr Purif 18(3): 286-292.

Kuntz, I. D., J. M. Blaney, et al. (1982). "A geometric approach to macromolecule-ligand interactions." J Mol Biol 161(2): 269-288.

Levitt, M. (1992). "Accurate modeling of protein conformation by automatic segment matching." J Mol Biol 226(2): 507-533.

Lipinski, C., F. Lombardo, et al. (1997). "Experimental and computational approaches to estimate solubility andpermeability in drug discovery and development settings " Advanced Drug Delivery Reviews 23(1-3): 3-25.

Longenecker, K. L., S. M. Garrard, et al. (2001). "Protein crystallization by rational mutagenesis of surface residues: Lys to Ala mutations promote crystallization of RhoGDI." Acta Crystallogr D Biol Crystallogr 57(Pt 5): 679-688.

Makara, J. K., M. Mor, et al. (2005). "Selective inhibition of 2-AG hydrolysis enhances endocannabinoid signaling in hippocampus." Nat Neurosci 8(9): 1139-1141.

Malan, T. P., Jr., M. M. Ibrahim, et al. (2001). "CB2 cannabinoid receptor-mediated peripheral antinociception." Pain 93(3): 239-245.

Malan, T. P., Jr., M. M. Ibrahim, et al. (2002). "Inhibition of pain responses by activation of CB(2) cannabinoid receptors." Chem Phys Lipids 121(1-2): 191- 200.

Maresz, K., E. J. Carrier, et al. (2005). "Modulation of the cannabinoid CB2 receptor in microglial cells in response to inflammatory stimuli." J Neurochem 95(2): 437-45.

Martin, Y. C. (1992). "3D Database Searching in Drug Design." J. Med. Chem. 35: 2145-2154.

Mateja, A., Y. Devedjiev, et al. (2002). "The impact of Glu-->Ala and Glu-->Asp mutations on the crystallization properties of RhoGDI: the structure of RhoGDI at 1.3 A resolution." Acta Crystallogr D Biol Crystallogr 58 (Pt 12): 1983-1991.

Matsuda, L. A., S. J. Lolait, et al. (1990). "Structure of a cannabinoid receptor and functional expression of the cloned cDNA." Nature 346(6284): 561-564.

Matteucci and J. Caruthers (1981). "Synthesis of Deoxyoligonucleotides on a Polymer Support", J. Am. Chem. Soc. 103(3): 185-3191.

Mccoy, A. J., R. W. Grosse-Kunstleve, et al. (2007). "Phaser crystallographic software." Journal of Applied Crystallography 40(4): 658-674.

Meng, E. C., B. K. Shoichet, et al. (1992). "Automated docking with grid-based energy evaluation." J. Comp. Chem. 13: 505-524.

Miranker, A. and M. Karplus (1991). "Functionality Maps of Binding Sites: A Multiple Copy Simultaneous Search Method." Proteins: Structure, Function and Genetics 11: 29-34.

Munro, S., K. L. Thomas, et al. (1993). "Molecular characterization of a peripheral receptor for cannabinoids." Nature 365(6441): 61-65.

Navia, M. A. and M. A. Murcko (1992). "The Use of Structural Information in Drug Design." Current Opinions in Structural Biology 2: 202-210.

Nini, L., L. Sarda, et al. (2001). "Lipase-catalysed hydrolysis of short-chain substrates in solution and in emulsion: a kinetic study." Biochim Biophys Acta 1534 (1) : 34-44.

Nishibata, Y. and A. Itai (1991). "Automatic creation of drug candidate structures based on receptor structure. Starting point for artificial lead generation." Tetrahedron 47: 8985-8990.

Norton, P. A. and J. M. Coffin (1985). "Bacterial beta-galactosidase as a marker of Rous sarcoma virus gene expression and replication." Mol Cell Biol 5(2): 281-290.

Ollis, D. L., E. Cheah, et al. (1992). "The alpha/beta hydrolase fold." Protein Eng 5(3): 197-211.

Otwinowski, Z. and W. Minor (1997). Processing of X-ray Diffraction Data Collected in Oscillation Mode. Methods in Enzymology. C. W. Carter and R. M. Sweet. New York, Academic Press. 276: 307-326.

Pantoliano, M. W., E. C. Petrella, et al. (2001). "High-density miniaturized thermal shift assays as a general strategy for drug discovery." J Biomol Screen 6(6): 429-440.

Quartilho, A., H. P. Mata, et al. (2003). "Inhibition of inflammatory hyperalgesia by activation of peripheral CB2 cannabinoid receptors." Anesthesiology 99(4): 955-960.

Rice, A. S., W. P. Farquhar-Smith, et al. (2002). "Endocannabinoids and pain: spinal and peripheral analgesia in inflammation and neuropathy." Prostaglandins Leukot Essent Fatty Acids 66(2-3): 243-256.

Richardson, J. D. (2000). "Cannabinoids modulate pain by multiple mechanisms of actions." The Journal of Pain 1(1): 2-14.

Richardson, J. D., S. Kilo, et al. (1998). "Cannabinoids reduce hyperalgesia and inflammation via interaction with peripheral CB1 receptors." Pain 75(1): 111-119.

Rotstein, S. H. and M. A. Murcko (1993). "GroupBuild: a fragment-based method for de novo drug design." J Med Chem 36(12): 1700-1710.

Roussel, A., S. Canaan, et al. (1999). "Crystal structure of human gastric lipase and model of lysosomal acid lipase, two lipolytic enzymes of medical interest." J Biol Chem 274(24): 16995-7002.

Roussel, A., N. Miled, et al. (2002). "Crystal structure of the open form of dog gastric lipase in complex with a phosphonate inhibitor." J Biol Chem 277(3): 2266-2274.

Saario, S. M., O. M. Salo, et al. (2005). "Characterization of the sulfhydryl-sensitive site in the enzyme responsible for hydrolysis of 2-arachidonoylglycerol in rat cerebellar membranes." Chem Biol 12(6): 649-656.

Saario, S. M., J. R. Savinainen, et al. (2004). "Monoglyceride lipase-like enzymatic activity is responsible for hydrolysis of 2-arachidonoylglycerol in rat cerebellar membranes." Biochem Pharmacol 67(7): 1381-1387.

Schrag, J. D., Y. G. Li, et al. (1991). "Ser-His-Glu triad forms the catalytic site of the lipase from *Geotrichum candidum*." Nature 351(6329): 761-764.

Somma-Delpero, C., A. Valette, et al. (1995). "Purification and properties of a monoacylglycerol lipase in human erythrocytes." Biochem J 312 (Pt 2): 519-525.

Sugiura, T., S. Kondo, et al. (2000). "Evidence that 2-arachidonoylglycerol but not N-palmitoylethanolamine or anandamide is the physiological ligand for the cannabinoid CB2 receptor. Comparison of the agonistic activities of various cannabinoid receptor ligands in HL-60 cells." J Biol Chem 275(1): 605-612.

Sussman, J. L., D. Lin, et al. (1998). "Protein Data Bank (PDB): database of three-dimensional structural information of biological macromolecules." Acta Crystallogr D Biol Crystallogr 54(Pt 6 Pt 1): 1078-1084.

Tatusova, T. A. and T. L. Madden (1999). "Blast 2 Sequences, a new tool for comparing protein and nucleotide sequences." FEMS Microbiol Lett 174(2): 247-250.

Terwilliger, T. C., R. W. Grosse-Kunstleve, et al. (2008). "Iterative model building, structure refinement and density modification with the Phenix AutoBuild wizard." Acta Crystallogr D Biol Crystallogr 64(Pt 1): 61-69.

Thompson, J. D., D. G. Higgins, et al. (1994). "ClustalW: improving the sensitivity of progressive multiple sequence alignment through sequence weighting, position-specific gap penalties and weight matrix choice." Nucleic Acids Res 22(22): 4673-4680.

Tornqvist, H. and P. Belfrage (1976). "Purification and some properties of a monoacylglycerol-hydrolyzing enzyme of rat adipose tissue." J Biol Chem 251(3): 813-819.

Travis, J. (1993). "Proteins and Organic Solvents Make an Eye-Opening Mix." Science 262: 1374.

Van Den Berg, B., M. Tessari, et al. (1995). "NMR structures of phospholipase A2 reveal conformational changes during interfacial activation." Nat Struct Biol 2(5): 402-406.

Van Den Berg, B., M. Tessari, et al. (1995). "Solution structure of porcine pancreatic phospholipase A2 complexed with micelles and a competitive inhibitor." J Biomol Nmr 5(2): 110-121.

Van Tilbeurgh, H., L. Sarda, et al. (1992). "Structure of the pancreatic lipase-procolipase complex." Nature 359(6391): 159-162.

Vandevoorde, S. and D. M. Lambert (2005). "Focus on the three key enzymes hydrolysing endocannabinoids as new drug targets." Curr Pharm Des 11(20): 2647-2668.

Walczak, J. S., V. Pichette, et al. (2005). "Behavioral, pharmacological and molecular characterization of the saphenous nerve partial ligation: a new model of neuropathic pain." Neuroscience 132(4): 1093-1102.

Wang, X., C. S. Wang, et al. (1997). "The crystal structure of bovine bile salt activated lipase: insights into the bile salt activation mechanism." Structure 5(9): 1209-1218.

Winkler, F. K., A. D'arcy, et al. (1990). "Structure of human pancreatic lipase." Nature 343(6260): 771-774.

* cited by examiner

Figure 1:

A. SEQ ID NO: 1

```
  1 mpeessprrt pqsipyqdlp hlvnadgqyl fcrywkptgt pkalifvshg agehsgryee
 61 larmlmglldl lvfahdhvgh gqsegermvv sdfhvfvrdv lqhvdsmqkd ypglpvfllg
121 hsmggaiail taaerpghfa gmvlisplvl anpesattfk vlaakvlnlv lpnlslgpid
181 ssvlsrnkte vdiynsdpli craglkvcfg iqllnavsrv eralpkltvp flllqgsadr
241 lcdskgayll melaksqdkt lkiyegayhv lhkelpevtn svfheinmwv sqrtatagta
301 spp
```

B. SEQ ID NO: 2

```
  1 METGPEDPSS mpeessprrt pqsipyqdlp hlvnadgqyl fcrywkptgt pkalifvshg
 61 agehsgryee larmlmglldl lvfahdhvgh gqsegermvv sdfhvfvrdv lqhvdsmqkd
121 ypglpvfllg hsmggaiail taaerpghfa gmvlisplvl anpesattfk vlaakvlnlv
181 lpnlslgpid ssvlsrnkte vdiynsdpli craglkvcfg iqllnavsrv eralpkltvp
241 flllqgsadr lcdskgayll melaksqdkt lkiyegayhv lhkelpevtn svfheinmwv
301 sqrtatagta spp
```

C.

Identities = 303/303 (100%), Positives = 303/303 (100%), Gaps = 0/303 (0%)

```
Iso 2    1   MPEESSPRRTPQSIPYQDLPHLVNADGQYLFCRYWKPTGTPKALIFVSHGAGEHSGRYEE    60
             MPEESSPRRTPQSIPYQDLPHLVNADGQYLFCRYWKPTGTPKALIFVSHGAGEHSGRYEE
Iso 1   11   MPEESSPRRTPQSIPYQDLPHLVNADGQYLFCRYWKPTGTPKALIFVSHGAGEHSGRYEE    70

Iso 2   61   LARMLMGLLDLLVFAHDHVGHGQSEGERMVVSDFHVFVRDVLQHVDSMQKDYPGLPVFLLG   120
             LARMLMGLLDLLVFAHDHVGHGQSEGERMVVSDFHVFVRDVLQHVDSMQKDYPGLPVFLLG
Iso 1   71   LARMLMGLLDLLVFAHDHVGHGQSEGERMVVSDFHVFVRDVLQHVDSMQKDYPGLPVFLLG   130

Iso 2  121   HSMGGAIAILTAAERPGHFAGMVLISPLVLANPESATTFKVLAAKVLNLVLPNLSLGPID   180
             HSMGGAIAILTAAERPGHFAGMVLISPLVLANPESATTFKVLAAKVLNLVLPNLSLGPID
Iso 1  131   HSMGGAIAILTAAERPGHFAGMVLISPLVLANPESATTFKVLAAKVLNLVLPNLSLGPID   190

Iso 2  181   SSVLSRNKTEVDIYNSDPLICRAGLKVCFGIQLLNAVSRVERALPKLTVPFLLLQGSADR   240
             SSVLSRNKTEVDIYNSDPLICRAGLKVCFGIQLLNAVSRVERALPKLTVPFLLLQGSADR
Iso 1  191   SSVLSRNKTEVDIYNSDPLICRAGLKVCFGIQLLNAVSRVERALPKLTVPFLLLQGSADR   250

Iso 2  241   LCDSKGAYLLMELAKSQDKTLKIYEGAYHVLHKELPEVTNSVFHEINMWVSQRTATAGTA   300
             LCDSKGAYLLMELAKSQDKTLKIYEGAYHVLHKELPEVTNSVFHEINMWVSQRTATAGTA
Iso 1  251   LCDSKGAYLLMELAKSQDKTLKIYEGAYHVLHKELPEVTNSVFHEINMWVSQRTATAGTA   310

Iso 2  301   SPP   303
             SPP
Iso 1  311   SPP   313
```

```
hMGLL iso2  MPEESSPRRTPQSIPYQDLPHLVNADGQYLFCRYWKPTGTPKALIFVSHGAGEHSGRYEE  (60)
RsbQ        --------------AGHMTSILSRN------HVKVKGSGKASLMFAPGFGCDQSVWNA  (26)
                          ********       :::   :::::      **** hMGLL iso2  LARMLMGLDLLVFAHDHVGHGQSEGERMVVSDFHVFVRDVLQHVDSMQKDYPGLPVFLLG  (120)
RsbQ        VAPAFE-EDHRVILEDYVGSGHSDLRAYDLNRYQTLDG-YAQDVLDVCEALDLKETVFVG  (84)
            ******     ::::    ******  ********   ******            :::::

hMGLL iso2  HSMCGAIAILTAAERPGHFAGMVLISP---LVLANPESATTFKVLAAKVLNLVLPNLSL  (176)
RsbQ        HSVGALIGMLASIRRPELFSHLVMVGPSPCYLNDPPEYGGFEEEQLLGLLEMMEKNYI  (143)
            :************    :::::::::   ::    ::  ****************** hMGLL iso2  GPIDSSVLSRNK---TEVDIYNSDPLICRAGLKVCFGIQLLNAVSRVERALPKLTVPFLL  (233)
RsbQ        GWATVFAATVLNQPDRPEIKEELESRFCSTDPVIARQFAKAAFFSDHREDLSKVTVPSLI  (203)
            ************   ************   *************  *******    :::

hMGLL iso2  LQGSADRL-CDSKGAYFLMELAKSQDKTLKIYEGAYEVLHKELPEVTNSVFHEINMWVSQ  (292)
RsbQ        LQCADDILAPATVGKYMHQHLPYS---SLKQMEARGHCPHMSHPDETIQLIGDYLKAHV-  (269)
            ::::       **********   :::::::::    ****************** hMGLL iso2  RTATAGTASPP  (303)
RsbQ        -----------
```

B.                                   C.

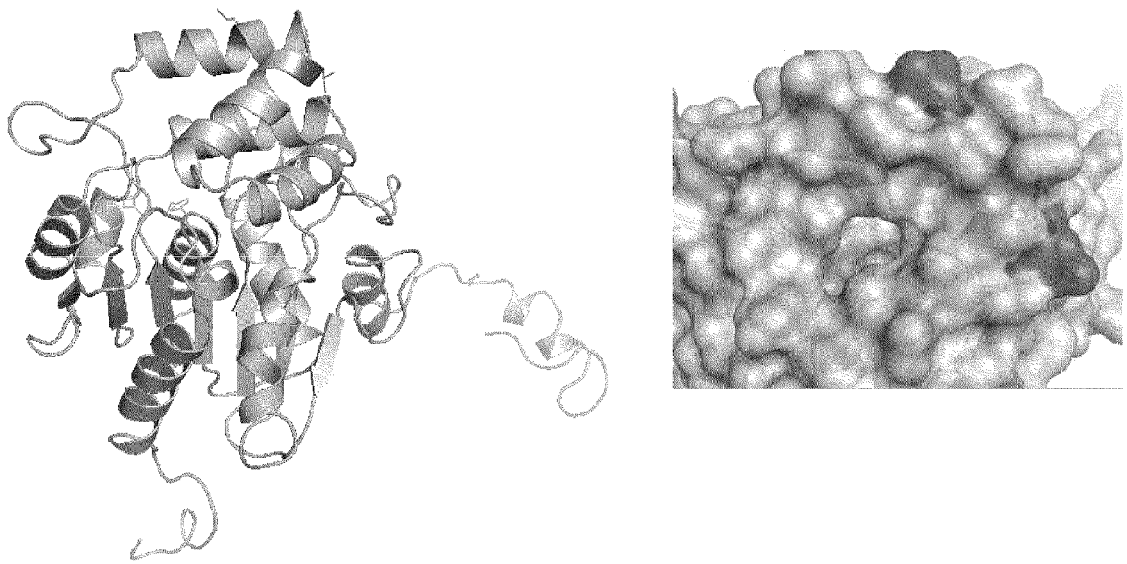

Figure 3:

A.
SEQ ID NO: 3, wt-MGLL (hMGLL 1-303)
      TEV Cleavage Site

MVDhhhhhhEnlyfqgMPEESSPRRTPQSIPYQDLPHLVNADGQYLFCRYWKPTGTPKALIFVSHGAGEHSG
RYEELARMLMGLDLLVFAHDHVGHGQSEGERMVVSDFHVFVRDVLQHVDSMQKDYPGLPVFLLGHSMGGAIA
ILTAAERPGHFAGMVLISPLVLANPESATTFKVLAAKVLNLVLPNLSLGPIDSSVLSRNKTEVDIYNSDPLI
CRAGLKVCFGIQLLNAVSRVERALPKLTVPFLLLQGSADRLCDSKGAYLLMELAKSQDKTLKIYEGAYHVLH
KELPEVTNSVFHEINMWVSQRTATAGTASPP B.
SEQ ID NO: 4, mut-MGLL (hMGLL 1-303 L169S, L176S)
      TEV Cleavage Site

MVDhhhhhhEnlyfqgMPEESSPRRTPQSIPYQDLPHLVNADGQYLFCRYWKPTGTPKALIFVSHGAGEHSG
RYEELARMLMGLDLLVFAHDHVGHGQSEGERMVVSDFHVFVRDVLQHVDSMQKDYPGLPVFLLGHSMGGAIA
ILTAAERPGHFAGMVLISPLVLANPESATTFKVLAAKVLNsVLPNLSsGPIDSSVLSRNKTEVDIYNSDPLI
CRAGLKVCFGIQLLNAVSRVERALPKLTVPFLLLQGSADRLCDSKGAYLLMELAKSQDKTLKIYEGAYHVLH
KELPEVTNSVFHEINMWVSQRTATAGTASPP C.
SEQ ID NO: 5, TEV Cleaved mut-MGLL (hMGLL 1-303 L169S, L176S)

gMPEESSPRRTPQSIPYQDLPHLVNADGQYLFCRYWKPTGTPKALIFVSHGAGEHSGRYEELARMLMGLDLL
VFAHDHVGHGQSEGERMVVSDFHVFVRDVLQHVDSMQKDYPGLPVFLLGHSMGGAIAILTAAERPGHFAGMV
LISPLVLANPESATTFKVLAAKVLNsVLPNLSsGPIDSSVLSRNKTEVDIYNSDPLICRAGLKVCFGIQLLN
AVSRVERALPKLTVPFLLLQGSADRLCDSKGAYLLMELAKSQDKTLKIYEGAYHVLHKELPEVTNSVFHEIN
MWVSQRTATAGTASPP

D.
SEQ ID NO: 6, mut-MGLL (hMGLL 1-303 L169S, L176S, K36A)
      TEV Cleavage Site

MVDhhhhhhEnlyfqgMPEESSPRRTPQSIPYQDLPHLVNADGQYLFCRYWaPTGTPKALIFVSHGAGEHSG
RYEELARMLMGLDLLVFAHDHVGHGQSEGERMVVSDFHVFVRDVLQHVDSMQKDYPGLPVFLLGHSMGGAIA
ILTAAERPGHFAGMVLISPLVLANPESATTFKVLAAKVLNsVLPNLSsGPIDSSVLSRNKTEVDIYNSDPLI
CRAGLKVCFGIQLLNAVSRVERALPKLTVPFLLLQGSADRLCDSKGAYLLMELAKSQDKTLKIYEGAYHVLH
KELPEVTNSVFHEINMWVSQRTATAGTASPP E.
SEQ ID NO: 7, TEV Cleaved mut-MGLL (hMGLL 1-303 L169S, L176S, K36A)

gMPEESSPRRTPQSIPYQDLPHLVNADGQYLFCRYWaPTGTPKALIFVSHGAGEHSGRYEELARMLMGLDLL
VFAHDHVGHGQSEGERMVVSDFHVFVRDVLQHVDSMQKDYPGLPVFLLGHSMGGAIAILTAAERPGHFAGMV
LISPLVLANPESATTFKVLAAKVLNsVLPNLSsGPIDSSVLSRNKTEVDIYNSDPLICRAGLKVCFGIQLLN
AVSRVERALPKLTVPFLLLQGSADRLCDSKGAYLLMELAKSQDKTLKIYEGAYHVLHKELPEVTNSVFHEIN
MWVSQRTATAGTASPP

Figure 7:
A. Compound 1:
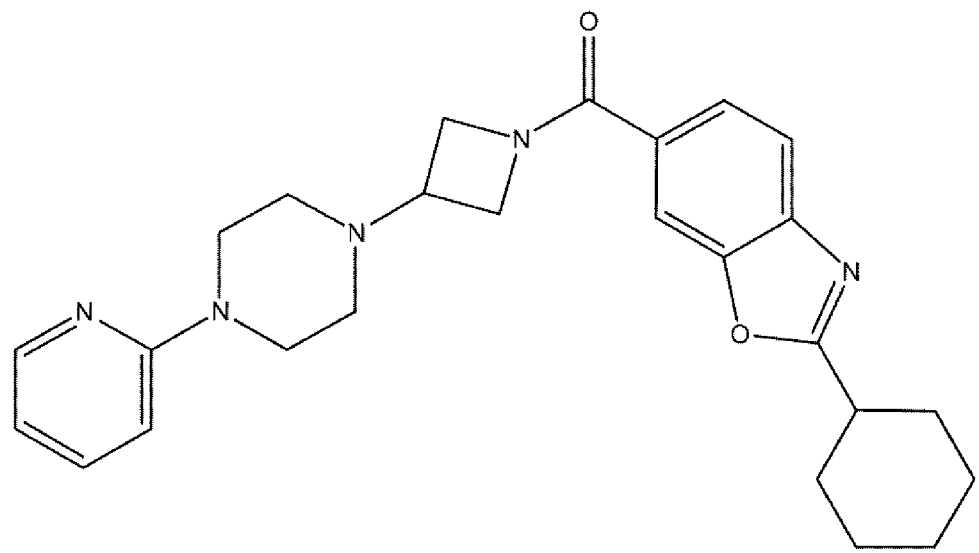
B. Compound 2:
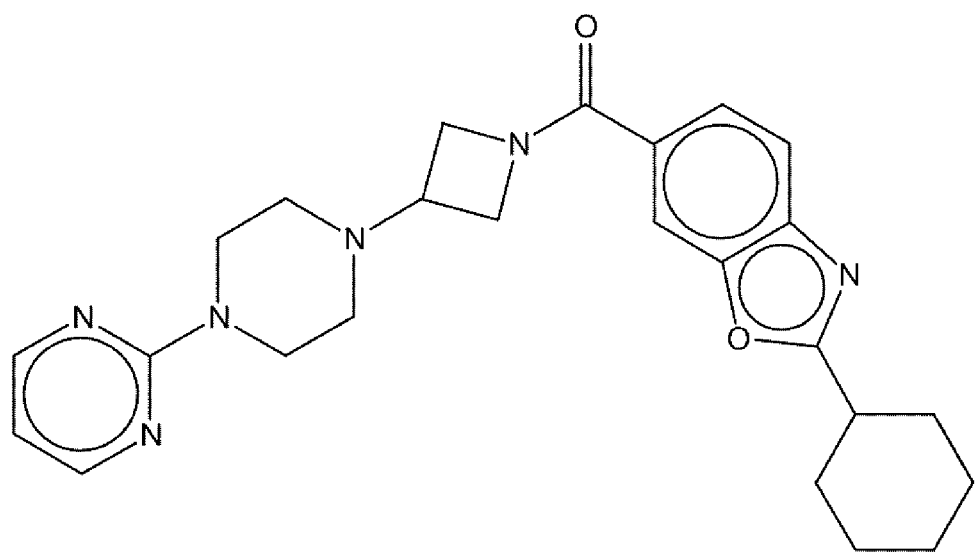

CRYSTAL STRUCTURE OF MONOACYLGLYCEROL LIPASE (MGLL)

TECHNICAL FIELD

The present invention generally pertains to the fields of molecular biology, protein purification, high-throughput screening, protein crystallization, X-ray diffraction analysis, three-dimensional structural determination, molecular modelling, and structure based rational drug design. The present invention provides a number of soluble engineered forms of MGLL that are suitable for high-throughput screening and protein crystallization, as well as a crystallized form of monoacylglycerol lipase protein (MGLL) and descriptions of the X-ray diffraction patterns.

SEQUENCE LISTING

The instant application contains a Sequence Listing which has been submitted in ASCII format via EFS-Web and is hereby incorporated by reference in its entirety. Said ASCII copy, created on Oct. 11, 2010, is named PRD297US.txt and is 25,305 bytes in size.

The forms of MGLL provided by the present invention permit the expression and purification of protein suitable for high-throughput screening and crystallography. Thus forms of MGLL of the present invention have applications to the screening of MGLL to identify active agents which include, but are not limited to, those that find use as inhibitors of MGLL.

The X-ray diffraction patterns of the crystal of the present invention are of sufficient resolution so that the three-dimensional structure of MGLL can be determined at atomic resolution, ligand-binding sites on MGLL can be identified, and the interactions of ligands with amino acid residues of MGLL can be modeled. The high resolution maps provided by the present invention and the models prepared using such maps permit the design of ligands which can function as active agents. Thus, the three-dimensional structure of MGLL of the present invention has applications to the design of active agents, which include, but are not limited to, those that find use as inhibitors of MGLL.

BACKGROUND OF THE INVENTION

Various publications, which may include patents, published applications, technical articles and scholarly articles, are cited throughout the specification in parentheses, and full citations of each may be found at the end of the specification. Each of these cited publications is incorporated by reference herein, in its entirety.

$\Delta^9$-Tetrahydrocannabinol (THC) is the main psychoactive substance found in the *cannabis* plant. THC activates two distinct G protein-coupled receptors, cannabinoid 1 receptor (CB1) and cannabinoid 2 receptor (CB2) (Matsuda et al. 1990; Munro et al. 1993). CB1 is primarily expressed in the central nervous system (CNS) (Hohmann and Herkenham 1999; Farquhar-Smith et al. 2000; Rice et al. 2002; Walczak et al. 2005). CB2 expression, however, seems to be restricted to only peripheral tissues (Munro et al. 1993; Galiegue et al. 1995).

CNS mediated analgesic effects of cannabinoids have been well documented, but there is also accumulating evidence suggesting that cannabinoids can produce antinociception through peripheral mechanisms involving CB1 or CB2 (Hohmann 2002) (Malan et al. 2002). Richardson et al. demonstrated that cannabinoid antihyperalgesic effects were predominantly mediated by CB1 (Richardson et al. 1998; Richardson 2000). Hanus et al. showed that intraperitoneal injection of a CB2 selective agonist could suppress the late-phase response in the formalin test (Hanus et al. 1999). It was also shown that a CB2 selective agonist could attenuate thermal nociception and hyperalgesia (Malan et al. 2001; Malan et al. 2002; Quartilho et al. 2003) or suppress hyperalgesia evoked by intradermal administration of capsaicin (Hohmann et al. 2004). Ibrahim et al. showed that activation of CB2 with a selective CB2 agonist inhibited experimental neuropathic pain (Ibrahim et al. 2006). Taken together, the accumulating evidence clearly suggests great potential therapeutic value in targeting CB2 as a peripheral target for the treatment of pain. It should be noted that a significant advantage of this approach is that it would preclude unwanted CNS side effects caused by targeting CB1.

An arachidonic acid derivative, 2-arachidonyl glycerol (2-AG), is one of the two major and most well studied endogenous ligands for CB1 and CB2 (Gonsiorek et al. 2000). It has been shown that 2-AG acts as a potent and full-efficacy agonist of CB2 (Gonsiorek et al. 2000; Sugiura et al. 2000; Maresz et al. 2005) and that 2-AG is primarily hydrolysed by monoacylglycerol lipase (MGLL) (Dinh et al. 2002; Dinh et al. 2004; Saario et al. 2004). A non-competitive MGLL inhibitor that blocked 2-AG hydrolysis was found to enhance 2-AG levels and antinociception in stress models (Hohmann et al. 2005; Makara et al. 2005). It was also demonstrated that local administration of either 2-AG or a selective MGLL inhibitor induced a dose-dependent antinociceptive effect in an inflammatory pain model. Furthermore, local administration of the selective MGLL inhibitor in combination with 2-AG produced an additive antinociceptive effect (Guindon et al. 2007). Thus selective inhibition of MGLL may provide a novel therapeutic approach for the treatment of pain. Hitting this target, however, is inconceivable without good knowledge of the enzyme (Vandevoorde and Lambert 2005).

Lipases are lipolytic enzymes that have been differentiated from carboxylesterases by the fact that lipases have improved kinetics of hydrolysis for emulsions formed in oversaturated solutions. Carboxylesterases have been shown to have maximal activity using solutions of short-chain esters, with half-maximal activity at substrate concentrations far below the solubility limit. Exceeding the solubility limit was shown to have no effect on carboxylesterase activity. Lipases, on the other hand, were shown to have maximal activity using emulsified substrates, with half-maximal activity at substrate concentrations near the solubility limit (Chahinian et al. 2002). Early work with porcine pancreatic lipase showed that activity was low using a solution of ester substrates and abruptly increased as soon as an emulsion was formed. It was speculated that the porcine pancreatic lipase was activated by a conformational change of the enzyme as it bound to its water-insoluble substrate. The work with porcine pancreatic lipase was reviewed by Nini et al. (Nini et al. 2001).

In general, lipases share a similar $\alpha/\beta$ hydrolase fold with a catalytic Ser-His-Asp triad buried beneath a flexible cap-domain which is also referred to as a "lid" or "flap" (Brady et al. 1990; Winkler et al. 1990; Schrag et al. 1991). Although there is little conservation in the primary sequence of the cap-domain, it is generally formed of loops and one or more amphipathic helices. The cap-domains of human and dog gastric lipase are composed of intricate mixtures of 8 helices, turns, and random coils (Roussel et al. 1999; Roussel et al. 2002). In the crystal structure of human pancreatic lipase the lid adopts a helix-turn helix motif composed of two short amphipathic helices (van Tilbeurgh et al. 1992).

It has long been proposed that higher lipase activity for substrates presented as multimolecular aggregates (interfacial activation) is due to a conformational change in the cap-domain. It has also been proposed that changes from a closed to an open conformation of the lid is triggered by interaction with the substrate or lipid membrane (Brzozowski et al. 1991; van den Berg et al. 1995; van den Berg et al. 1995; Nini et al. 2001). Several other reports have also indicated that the loop covering the active site mediates lipase substrate specificity (Dugi et al. 1992; Dugi et al. 1995). It was demonstrated that movement of the helical lid results in a change in the hydrophobic-hydrophilic balance of the exterior surface of the lipase with the hydrophobic side of the lid becoming completely exposed in the active enzyme (Faustinella et al. 1992). Some lipases, such as guinea pig pancreatic lipase and bile salt-activated lipase, do not have a lid domain. Their active sites are freely accessible to solvent. As expected, based on the lack of the a cap-domain, these lipases are not activated by a lipid/water interface (Wang et al. 1997) (Carriere et al. 1997).

Although much has been learned about the structure of lipases through determination of three-dimensional structures of several microbial lipases and mammalian lipases, the three-dimensional structure of MGLL is unknown and its mechanism of action is not well understood. Furthermore, MGLL shows very little sequence similarity with other mammalian lipases and is unique among lipases in having monoglycerides as its only substrates. MGLL seems to be only distantly related to microbial proteins that include esterases, lysophospholipases, and haloperoxidases (Karlsson et al. 1997). A virtual molecular model of MGLL was built based on the crystal structure of chloroperoxidase (Saario et al. 2005; Saario et al. 2006). The model shows an alpha beta hydrolase fold with a lid domain comprised of four helices. The model, however, is only a virtual model and gives little insight into the actual mechanism of action of MGLL.

A crystal structure of MGLL would greatly facilitate the effort to discover MGLL selective inhibitors. A potential problem for crystallization experiments with MGLL is that detergents have been required to purify and stabilize MGLL in solution for both recombinant MGLL and MGLL from endogenous sources. (Tornqvist and Belfrage 1976; Somma-Delpero et al. 1995; Karlsson et al. 2000). Without detergent the purified MGLL protein was prone to aggregation. Crystallizing a detergent-solubilized protein into a structure of sufficient regularity to enable high-resolution X-ray crystallography can be problematic because well-ordered protein crystals can be difficult to obtain (U.S. Pat. No. 6,172,262B1).

The present invention provides a number of soluble engineered forms of monoacylglycerol lipase protein (MGLL) that do not require detergent for purification. The forms of MGLL provided by the present invention permit the expression and purification of protein suitable for identifying active agents in high-throughput screening and for crystallography. The present invention also provides a crystallized form of MGLL and descriptions of the X-ray diffraction patterns. Selective point mutations of hydrophobic residues in the cap-domain of MGLL generated soluble protein that did not require detergent for purification and stability. The protein displayed monomeric behaviour by gel filtration and was suitable for crystallization and high-throughput screening. In addition, selective mutation of surface lysine residues produced protein that generated crystals of improved quality. The crystal structure of MGLL was determined at atomic resolution. The forms of MGLL provide protein that can be used to identify inhibitors in high-throughput screens and the crystal structure of MGLL provides an important tool for structure-based drug design of MGLL inhibitors.

SUMMARY OF THE INVENTION

According to a first aspect of the present invention, there is provided a composition comprising a form of MGLL, or a fragment, or target structural motif or derivative thereof, wherein one or more hydrophobic residues of the cap-domain is mutated to improve solubility.

The present invention also provides a composition comprising a form of MGLL, or a fragment, or target structural motif or derivative thereof, wherein one or more hydrophobic Leucine residues of the cap-domain is mutated to improve solubility.

The present invention further provides a composition comprising a form of MGLL comprising one or more mutated hydrophobic Leucine residues of the cap-domain, wherein said one or more mutated hydrophobic Leucine residues of the cap-domain is selected from the group consisting of Leucine 162, Leucine 167, Leucine 169, Leucine 171, Leucine 174, Leucine 176, and Leucine 184, numbering based on the reference sequence for human MGLL Isoform 2 (SEQ ID NO: 1).

The present invention provides a composition comprising a form of MGLL, comprising one or more mutated hydrophobic residues of the cap-domain, wherein said one or more hydrophobic residues of the cap-domain is mutated to Serine, Glutamine, or Arginine.

In another aspect of the invention, the present invention includes a form of MGLL comprising one or more mutated hydrophobic Leucine residues of the cap-domain further comprising a Lysine mutated to an Alanine.

The present invention also includes a form of MGLL comprising one or more mutated hydrophobic Leucine residues of the cap-domain further comprising a Lysine mutated to an Alanine, wherein said Lysine residue is selected from the group consisting of Lysine 36, Lysine 160, Lysine 165, Lysine 188, Lysine 206, Lysine 226, Lysine 259 and Lysine 269, numbering based on the reference sequence for human MGLL Isoform 2.

The present invention further includes a method of identifying an agent that binds to the forms of MGLL of the present invention, comprising the steps of contacting the form of MGLL with the agent; measuring the binding of the agent to the form of MGLL; and, determining that the agent binds to the form of MGLL; thereby identifying an agent that binds to the form of MGLL.

In a preferred embodiment, the present invention includes a method of identifying an agent that binds to the forms of MGLL, wherein the form of MGLL has an amino acid sequence selected from the group consisting of SEQ ID NO: 4, SEQ ID NO: 5, SEQ ID NO: 6, and SEQ ID NO: 7.

In another preferred embodiment, the present invention includes a method of identifying an agent that binds to the forms of MGLL, wherein the binding is measured by the thermal stability of the form of MGLL.

The present invention further includes a method of identifying an agent that inhibits the activity of the forms of MGLL of the present invention comprising the steps of contacting the form of MGLL with the agent; measuring the biological activity of the form of MGLL in the presence of the agent; measuring the biological activity of the form of MGLL without the agent; and, comparing the biological activity of the form of MGLL measured in the presence of the agent and without the agent; thereby identifying the agent that decreases the biological activity the biological activity of the form of MGLL, when the activity measured in the presence of the agent is less than the activity measured without the agent.

In a preferred embodiment, the present invention includes a method of identifying an agent that inhibits the activity of the forms of MGLL, wherein the form of MGLL has an amino acid sequence selected from the group consisting of SEQ ID NO: 4, SEQ ID NO: 5, SEQ ID NO: 6, and SEQ ID NO: 7.

In another preferred embodiment, the present invention includes a method of identifying an agent that inhibits the activity of the forms of MGLL of the present invention, wherein the biological activity is measured with an enzyme assay.

The present invention further includes methods of producing and using three-dimensional structure information derived from the crystal structure of monoacylglycerol lipase protein (MGLL).

The present invention also includes specific crystallization conditions to obtain crystals of the inhibitor-MGLL complex. The crystals are subsequently used to obtain a 3-dimensional structure of the complex using X-ray crystallography. The obtained data is used for rational drug discovery with the aim to design compounds that are inhibitors of MGLL.

The present invention includes a crystal comprising monoacylglycerol lipase (MGLL), or a fragment, or target structural motif or derivative thereof, and a ligand, wherein the ligand is a small molecule inhibitor. In another embodiment, the crystal has a spacegroup of $C222_1$.

In another aspect of the invention, the present invention includes a crystal comprising a form of MGLL which comprises a peptide having at least 95% sequence identity to SEQ ID NO: 7.

In another aspect of the invention, the invention includes a computer system comprising: (a) a database containing information on the three dimensional structure of a crystal comprising MGLL, or a fragment or a target structural motif or derivative thereof, and a ligand, wherein the ligand is a small molecule inhibitor, stored on a computer readable storage medium; and, (b) a user interface to view the information.

The present invention also includes a method of evaluating the potential of an agent to associate with MGLL comprising: (a) exposing MGLL to the agent; and (b) detecting the association of said agent to MGLL amino acid residues SER48-HIS54, ARG57, TYR58, HIS77, HIS80, MET88, PHE93, PHE96, GLY120-ILE127, ILE145-VAL161, ALA163, SER176-ASN195, ASP197, ILE200, CYS201, ALA203, LEU205-VAL207, PHE209-SER218, ASP239-ASP243, TYR268-LEU275, THR279 thereby evaluating the potential of the agent.

The invention further includes a method of evaluating the potential of an agent to associate with the peptide having the sequence of SEQ ID NO: 7, comprising: (a) exposing SEQ ID NO: 7 to the agent; and (b) detecting the level of association of the agent to SEQ ID NO: 7, thereby evaluating the potential of the agent.

Further included in the present invention is a method of identifying a potential agonist or antagonist against monoacylglycerol lipase comprising: (a) employing the three dimensional structure of MGLL cocrystallized with a small molecule inhibitor to design or select said potential agonist or antagonist.

The invention comprises a method of locating the attachment site of an inhibitor to monoacylglycerol lipase, comprising: (a) obtaining X-ray diffraction data for a crystal of MGLL; (b) obtaining X-ray diffraction data for a complex of MGLL and an inhibitor; (c) subtracting the X-ray diffraction data obtained in step (a) from the X-ray diffraction data obtained in step (b) to obtain the difference in the X-ray diffraction data; (d) obtaining phases that correspond to X-ray diffraction data obtained in step (a); (e) utilizing the phases obtained in step (d) and the difference in the X-ray diffraction data obtained in step (c) to compute a difference Fourier image of the inhibitor; and, (f) locating the attachment site of the inhibitor to MGLL based on the computations obtained in step (e).

The present invention further comprises a method of obtaining a modified inhibitor comprising: (a) obtaining a crystal comprising MGLL and an inhibitor; (b) obtaining the atomic coordinates of the crystal; (c) using the atomic coordinates and one or more molecular modelling techniques to determine how to modify the interaction of the inhibitor with MGLL; and, (d) modifying the inhibitor based on the determinations obtained in step (c) to produce a modified inhibitor.

In another aspect of the invention, the invention includes an isolated protein fragment comprising a binding pocket or active site defined by structure coordinates of MGLL amino acid residues SER48-HIS54, ARG57, TYR58, HIS77, HIS80, MET88, PHE93, PHE96, GLY120-ILE127, ILE145-VAL161, ALA163, SER176-ASN195, ASP197, ILE200, CYS201, ALA203, LEU205-VAL207, PHE209-SER218, ASP239-ASP243, TYR268-LEU275, THR279.

In another aspect of the invention, the invention includes an isolated nucleic acid molecule encoding the fragment which comprises a binding pocket or active site defined by structure coordinates of MGLL amino acid residues SER48-HIS54, ARG57, TYR58, HIS77, HIS80, MET88, PHE93, PHE96, GLY120-ILE127, ILE145-VAL161, ALA163, SER176-ASN195, ASP197, ILE200, CYS201, ALA203, LEU205-VAL207, PHE209-SER218, ASP239-ASP243, TYR268-LEU275, THR279. In another aspect of the invention, the invention includes a method of screening for an agent that associates with MGLL, comprising: (a) exposing a protein molecule fragment to the agent; and (b) detecting the level of association of the agent to the fragment. In another aspect of the invention, the invention includes a kit comprising a protein molecule fragment.

The invention additionally comprises a method for the production of a crystal complex comprising a MGLL polypeptide-ligand comprising: (a) contacting the MGLL polypeptide with said ligand in a suitable solution comprising PEG MME 5K, Na Citrate pH5.5 and n-Octyl-Beta-D-Glucopyranoside; and b) crystallizing said resulting complex of MGLL polypeptide-ligand from said solution.

The invention further includes a method for the production of a crystal comprising MGLL and a ligand wherein the ligand is a small molecule inhibitor comprising crystallizing a peptide comprising SEQ ID NO: 7 with a potential inhibitor.

The invention includes a method for identifying a potential inhibitor of monoacylglycerol lipase comprising: a) using a three dimensional structure of MGLL as defined by atomic coordinates according to Table 5; b) replacing one or more MGLL amino acids selected from SER48-HIS54, ARG57, TYR58, HIS77, HIS80, MET88, PHE93, PHE96, GLY120-ILE127, ILE145-VAL161, ALA163, SER176-ASN195, ASP197, ILE200, CYS201, ALA203, LEU205-VAL207, PHE209-SER218, ASP239-ASP243, TYR268-LEU275, THR279 in said three-dimensional structure with a different amino acid to produce a modified MGLL; c) using said three-dimensional structure to design or select said potential inhibitor; d) synthesizing said potential inhibitor; and, e) contacting said potential inhibitor with said modified MGLL in the presence of a substrate to test the ability of said potential inhibitor to inhibit MGLL or said modified MGLL. Also included in the invention is an inhibitor identified by the method.

BRIEF DESCRIPTION OF THE DRAWINGS

A preferred embodiment of the present invention will now be described, by way of an example only, with reference to the accompanying drawings wherein:

FIG. 1: A. Shown is SEQ ID NO: 1, the amino acid sequence of human monoglyceride lipase isoform 2 (Karlsson et al. 2001), accession NP_001003794, version NP_001003794.1, GI:51242953. B. Shown is SEQ ID NO: 2, the amino acid sequence of human monoglyceride lipase isoform 1 (Wall et al. 1997), Accession NP_009214, Version NP_009214.1, GI:6005786. C. Shown is the sequence alignment for SEQ ID NO: 1 and residues 11-314 of SEQ ID NO: 2, which are human monoglyceride lipase isoform 2 and isoform 1, respectively. Sequence alignment was done with the online BLAST 2 SEQUENCES software (Tatusova and Madden 1999).

FIG. 2: A. Shown is the sequence alignment of human MGLL isoform 2 (SEQ ID NO: 1) and crystallized RsbQ (SEQ ID NO: 11) (RsbQ, PDB 1WOM). Sequence alignment was done with the ClustalW software. Homologous residues are shown in black. Identical residues are shown in green. Position of helices and β sheets are indicated by red stars and green columns, respectively. The active site residues are highlighted in red. Leu 169 and Leu 176 are indicated by blue arrows. B. Shown is ribbon diagram representation of a homology model of human MGLL isoform 2 based on RsbQ (Pdb 1bro). Leu 169 and Leu 176 are shown in magenta. The active site residues are shown in green. C. Shown is surface representation of a homology model of human MGLL isoform 2 based on RsbQ (Pdb 1bro). Leu 169 and Leu 176 are shown in magenta. The active site residues are shown in green.

FIG. 3: A. Shown is SEQ ID NO: 3, the amino acid sequence of the construct used to express wt-MGLL (hMGLL 1-303) (SEQ ID NO: 3). The N-terminal His tag is shown in non-capitalized text and the TEV cleavage site is shown in bold non-capitalized text with an arrow over the site of cleavage. B. Shown is SEQ ID NO: 4, the amino acid sequence of the construct used to express a form of mut-MGLL (hMGLL 1-303 L169S, L176S). The N-terminal His tag is shown in non-capitalized text, the TEV cleavage site is shown in bold non-capitalized text with an arrow over the site of cleavage, and the mutations are shown in bold non-capitalized text. C. Shown is SEQ ID NO: 5, the amino acid sequence of mut-MGLL (hMGLL 1-303 L169S, L176S) after TEV cleavage of the N-terminal His tag. The one amino acid from the TEV cleavage site that remains after TEV cleavage is shown in bold non-capitalized text and the mutations are shown in bold non-capitalized text. D. Shown is SEQ ID NO: 6, the amino acid sequence of the construct used to express a form of mut-MGLL (hMGLL 1-303 L169S, L176S, K36A). The N-terminal His tag is shown in non-capitalized text, the TEV cleavage site is shown in bold non-capitalized text with an arrow over the site of cleavage, and the mutations are shown in bold non-capitalized text. E. Shown is SEQ ID NO: 7, the amino acid sequence of mut-MGLL (hMGLL 1-303 L169S, L176S, K36A) after TEV cleavage of the N-terminal His tag. The one amino acid from the TEV cleavage site that remains after TEV cleavage is shown in bold non-capitalized text and the mutations are shown in bold non-capitalized text.

FIG. 7: A. Shown is the structure of Compound 1. B. Shown is the structure of Compound 2.

Figure 4:
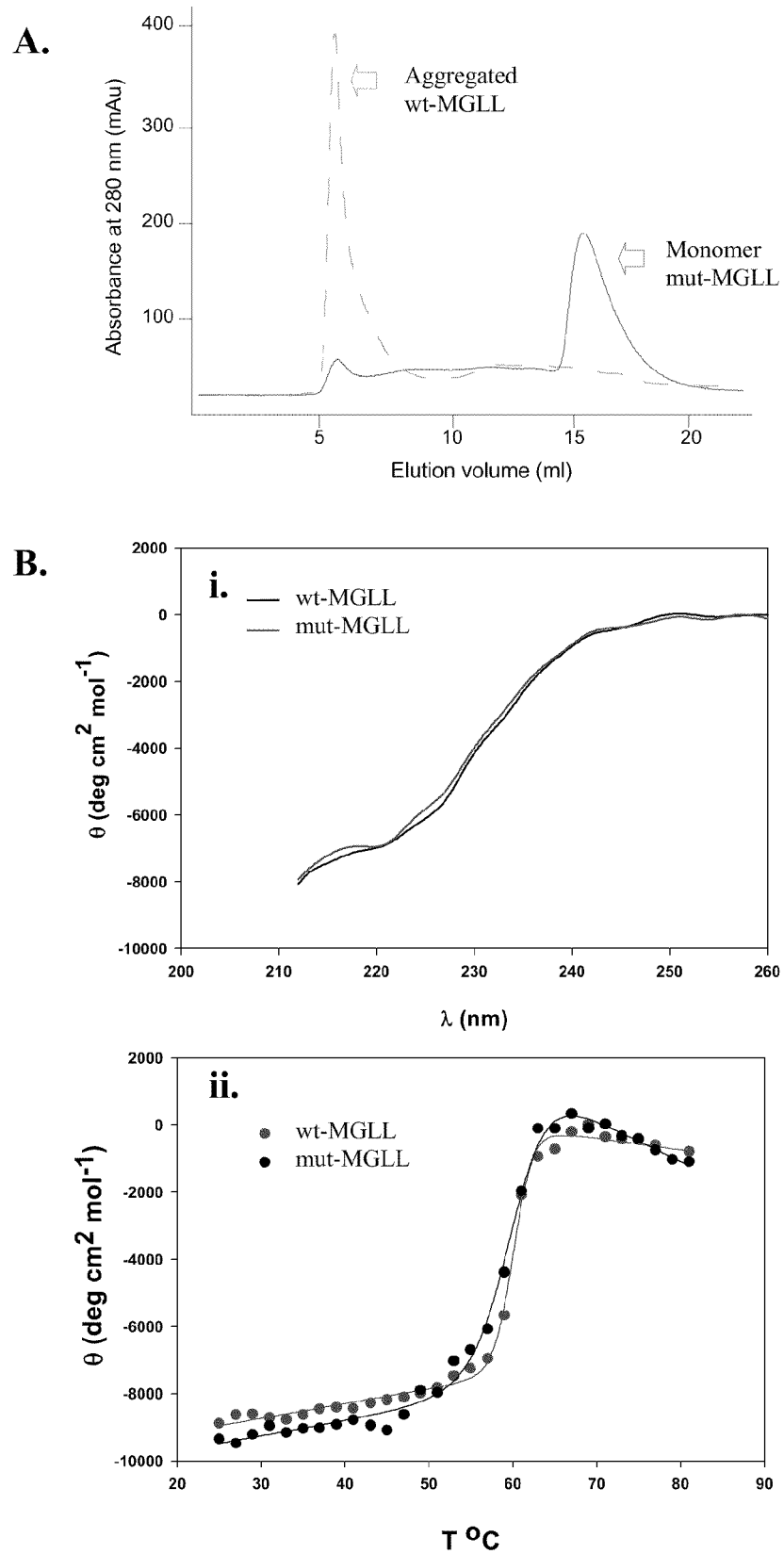
FIG. 4: A. Shown are size exclusion elution profiles for wt-MGLL (hMGLL 1-303) (SEQ ID NO: 3) (magenta dotted lines) and TEV cleaved mut-MGLL (hMGLL 1-303 L169S, L176S) (SEQ ID NO: 5) (blue solid line) purified in the absence of detergent showing 100% aggregation for wt-MGLL (hMGLL 1-303) (SEQ ID NO: 3) and 90% monomer for TEV cleaved mut-MGLL (hMGLL 1-303 L169S, L176S) (SEQ ID NO: 5). B. Shown is circular dichroism structural analysis of wt-MGLL (hMGLL 1-303) (SEQ ID NO: 3) and TEV cleaved mut-MGLL (hMGLL 1-303 L169S, L176S) (SEQ ID NO: 5). Far UV scans from 200 to 260 nm are shown in (i) and temperature melts from 25 to 80° C. monitored at 210 nm are shown in (ii).

Table 1: Shown is a table of the forms of MGLL of the present invention and the purification yield in mg/liter.

Table 2: Shown is a table of the kinetic constants of the various MGLL constructs using 4MC-B or C-A as substrates. Values for the 4MC-B substrate are the average of 2 or 4 separate assays. The $k_{cat}/K_M$ values for the C-A substrate are the average values for the hydrolysis of five different substrate concentrations at $[S] \ll K_M$.

Table 3: Shown are the data collection and refinement statistics for the complex of TEV cleaved mut-MGLL (hMGLL 1-303 L169S, L176S, K36A) (SEQ ID NO: 7) and Compound 2.

Table 4: Shown is are the superposition statistics for selected α/β hydrolases without the cap-domain superimposed onto MGLL without the cap-domain Table 5: Shown are the coordinates for the complex of TEV cleaved mut-MGLL (hMGLL 1-303 L169S, L176S, K36A) (SEQ ID NO: 10) and Compound 2.

DEFINITIONS

As is generally the case in biotechnology and chemistry, the description of the present invention has required the use of a number of terms of art. Although it is not practical to do so exhaustively, definitions for some of these terms are provided here for ease of reference. Unless defined otherwise, all technical and scientific terms used herein have the same meaning as commonly understood by one of ordinary skill in the art to which this invention belongs. Definitions for other terms may also appear elsewhere herein. However, the definitions provided here and elsewhere herein should always be considered in determining the intended scope and meaning of the defined terms. Although any methods and materials similar or equivalent to those described herein can be used in the practice of the present invention, the preferred methods and materials are described.

The term "comprising" means "including principally, but not necessarily solely". Furthermore, variations of the word "comprising", such as "comprise" and "comprises", have correspondingly varied meanings.

As used herein, the terms "containing", "having" and "including" are used in their open, non-limiting sense.

As used herein, "sequence" means the linear order in which monomers occur in a polymer, for example, the order of amino acids in a polypeptide or the order of nucleotides in a polynucleotide.

The terms "polypeptide," "protein," and "peptide" are used herein interchangeably to refer to amino acid chains in which the amino acid residues are linked by peptide bonds or modified peptide bonds. The amino acid chains can be of any length of greater than two amino acids. Unless otherwise specified, the terms "polypeptide," "protein," and "peptide" also encompass various modified forms thereof. Such modified forms may be naturally occurring modified forms or chemically modified forms. Examples of modified forms include, but are not limited to, glycosylated forms, phosphorylated forms, myristoylated forms, palmitoylated forms, ribosylated forms, acetylated forms, ubiquitinated forms, etc. Modifications also include intra-molecular crosslinking and covalent attachment to various moieties such as lipids, flavin, biotin, polyethylene glycol or derivatives thereof, etc. In addition, modifications may also include cyclization, branching and cross-linking. Further, amino acids other than the conventional twenty amino acids encoded by the codons of genes may also be included in a polypeptide.

As used herein, a protein or nucleic acid molecule is said to be "isolated" when the protein or nucleic acid molecule is substantially separated from contaminants from the source of the protein or nucleic acid.

As used herein, the term "native protein" refers to a protein comprising an amino acid sequence identical to that of a protein isolated from its natural source or organism.

As used herein, the term "amino acids" refers to the L-isomers of the naturally occurring amino acids. The naturally occurring amino acids are glycine, alanine, valine, leucine, isoleucine, serine, methionine, threonine, phenylalanine, tyrosine, tryptophan, cysteine, proline, histidine, aspartic acid, asparagine, glutamic acid, glutamine, γ-carboxylglutamic acid, arginine, ornithine, and lysine. Unless specifically indicated, all amino acids are referred to in this application are in the L-form.

As used herein, the term "nonnatural amino acids" refers to amino acids that are not naturally found in proteins. For example, selenomethionine.

As used herein, the term "positively charged amino acid" includes any amino acids having a positively charged side chain under normal physiological conditions. Examples of positively charged naturally occurring amino acids are arginine, lysine, and histidine.

As used herein, the term "negatively charged amino acid" includes any amino acids having a negatively charged side chains under normal physiological conditions. Examples of negatively charged naturally occurring amino acids are aspartic acid and glutamic acid.

As used herein, the term "hydrophobic amino acid" includes any amino acids having an uncharged, nonpolar side chain that is relatively insoluble in water. Examples of naturally occurring hydrophobic amino acids are alanine, leucine, isoleucine, valine, proline, phenylalanine, tryptophan, and methionine.

As used herein, the term "hydrophilic amino acid" refers to any amino acids having an uncharged, polar side chain that is relatively soluble in water. Examples of naturally occurring hydrophilic amino acids are serine, threonine, tyrosine, asparagine, glutamine and cysteine.

As used herein, "nucleic acid" is defined as RNA or DNA that encodes a protein or peptide as defined herein, or is complementary to nucleic acid sequence encoding such peptides, or hybridizes to such nucleic acid and remains stably bound to it under appropriate stringency conditions. Nucleic acid sequences can be composed of natural nucleotides of the following bases: thymidine, adenine, cytosine, guanine, and uracil; abbreviated T, A, C, G, and U, respectively, and/or synthetic analogs of the natural nucleotides.

The term "oligonucleotide" or "oligo" refers to a single-stranded DNA or RNA sequence of a relatively short length, for example, less than 100 residues long. For many methods, oligonucleotides of about 16-25 nucleotides in length are useful, although longer oligonucleotides of greater than about 25 nucleotides may sometimes be utilized. Some oligonucleotides can be used as "primers" for the synthesis of complimentary nucleic acid strands. For example, DNA primers can hybridize to a complimentary nucleic acid sequence to prime the synthesis of a complimentary DNA strand in reactions using DNA polymerases. Oligonucleotides are also useful for hybridization in several methods of nucleic acid detection, for example, in Northern blotting or in situ hybridization.

"Recombinant" refers to a nucleic acid, a protein encoded by a nucleic acid, a cell, or a viral particle, that has been modified using molecular biology techniques to something other than its natural state. For example, recombinant cells can contain nucleotide sequence that is not found within the native (non-recombinant) form of the cell or can express native genes that are otherwise abnormally, under-expressed, or not expressed at all. Recombinant cells can also contain genes found in the native form of the cell wherein the genes are modified and re-introduced into the cell by artificial means. The term also encompasses cells that contain an endogenous nucleic acid that has been modified without removing the nucleic acid from the cell; such modifications include those obtained, for example, by gene replacement, and site-specific mutation.

The term "high stringency" as used herein refers to the conditions under which two nucleic acids may be hybridized, and may include, for example, the concentration of salts and/or detergents in a solution, the temperature of a solution that is used during the hybridization of the two nucleic acids and time period of the hybridization. Accordingly, the term "high stringency" as used herein refers to conditions in a solution that are conducive to hybridization of two nucleic acids only where such nucleic acids share a high degree of complementarity. The degree of complementarity may include, but not be limited to, a range of from about 90% to 100%. Thus, "high stringency" conditions may involve, but are not limited to, the use of a varying temperature and a buffer comprising various concentrations of detergents, salts, and divalent cations.

As used herein, "vector" refers to a nucleic acid molecule into which a heterologous nucleic acid can be or is inserted. Some vectors can be introduced into a host cell allowing for replication of the vector or for expression of a protein that is encoded by the vector or construct. Vectors typically have selectable markers, for example, genes that encode proteins allowing for drug resistance, origins of replication sequences, and multiple cloning sites that allow for insertion of a heterologous sequence. Vectors are typically plasmid-based and are designated by a lower case "p" followed by a combination of letters and/or numbers. Starting plasmids disclosed herein are either commercially available, publicly available on an unrestricted basis, or can be constructed from available plasmids by application of procedures known in the art. Many plasmids and other cloning and expression vectors that can be used in accordance with the present invention are well-known and readily available to those of skill in the art. Moreover, those of skill readily may construct any number of other plasmids suitable for use in the invention. The properties, construction and use of such plasmids, as well as other vectors, in the present invention will be readily apparent to those of skill from the present disclosure.

As used herein, the term "activity" refers to an activity exerted by MGLL as determined in vivo or in vitro, according to standard techniques. Examples of such activity include, but are not limited to, direct activity such as the ability to bind to a ligand or an analog thereof, enzymatic activity, or functional changes of cell physiology that result from changes in activity.

The term "high-throughput assay" or "high-throughput screening" refers to assay designs that allow easy screening of multiple samples simultaneously and/or in rapid succession, and may include the capacity for robotic manipulation. Another desired feature of high-throughput assays is an assay design that is optimized to reduce reagent usage, or minimize the number of manipulations in order to achieve the analysis desired. Examples of high-throughput assay formats include, but are not limited to, formats that utilize 96-well, 384-well, and 1536-well plates, or "lab on a chip" microchannel chips used for liquid handling experiments. It is well known by those in the art that as miniaturization of plastic molds and liquid handling devices are advanced, or as improved assay devices are designed, greater numbers of samples can be processed using the forms of the present invention. Any high-throughput screening may be utilized to test new compounds, which are identified or designed for their ability to interact with MGLL. For general information on high-throughput screening see, for example, (Devlin (editor) 1998); and (U.S. Pat. No. 5,763,263).

By the term "selecting" or "select" compounds it is intended to encompass both (a) choosing compounds from a group previously unknown to be modulators of a protein complex or interacting protein members thereof, and (b) testing compounds that are known to be capable of binding, or modulating the functions and activities of, a protein complex or interacting protein members thereof. The compounds encompass numerous chemical classes, including but not limited to, small organic or inorganic compounds, natural or synthetic molecules, such as antibodies, proteins or fragments thereof, antisense nucleotides, interfering RNA (iRNA) and ribozymes, and derivatives, mimetics and analogs thereof. Preferably, they are small organic compounds, i.e., those having a molecular weight of no greater than 10,000 daltons, more preferably less than 5,000 daltons.

As used herein, the term "atomic coordinates" or "structure coordinates" refers to mathematical coordinates that describe the positions of atoms in crystals of MGLL in Protein Data Bank (PDB) format, including X, Y, Z and B, for each atom. The diffraction data obtained from the crystals are used to calculate an electron density map of the repeating unit of the crystal. The electron density maps may be used to establish the positions (i.e. coordinates X, Y and Z) of the individual atoms within the crystal. Those of skill in the art understand that a set of structure coordinates determined by X-ray crystallography is not without standard error. For the purpose of this invention, any set of structure coordinates for MGLL from any source having a root mean square deviation of non-hydrogen atoms of less than about 1.5 Å when superimposed on the non-hydrogen atom positions of the corresponding atomic coordinates of Table 5 are considered substantially identical or homologous. In a more preferred embodiment, any set of structure coordinates for MGLL from any source having a root mean square deviation of non-hydrogen atoms of less than about 0.75 Å. when superimposed on the non-hydrogen atom positions of the corresponding atomic coordinates of Table 5 are considered substantially identical or homologous.

The term "atom type" refers to the chemical element whose coordinates are measured. The abbreviations in column 3 of Table 5 identifies the element.

The terms "X," "Y" and "Z" refer to the crystallographically-defined atomic position of the element measured with respect to the chosen crystallographic origin. The term "B" refers to a thermal factor that measures the mean variation of an atom's position with respect to its average position.

As used herein, the term "crystal" refers to any three-dimensional ordered array of molecules that diffracts X-rays.

As used herein, the term "carrier" in a composition refers to a diluent, adjuvant, excipient, or vehicle with which the product is mixed.

As used herein, the term "composition" refers to the combining of distinct elements or ingredients to form a whole. A composition comprises more than one element or ingredient. For the purposes of this invention, a composition will often, but not always comprise a carrier.

As used herein, "MGLL" is used to mean a protein obtained as a result of expression of monoacylglycerol lipase. Within the meaning of this term, it will be understood that human MGLL encompasses all proteins encoded by monoacylglycerol lipase, mutants thereof, conservative amino acid substitutions, alternative splice proteins thereof, and phosphorylated proteins thereof. Additionally, as used herein, it will be understood that the term "MGLL" includes monoacylglycerol lipase and homologues from other animals. As an example, MGLL includes the protein comprising SEQ ID NO: 7 and variants thereof comprising at least about 70% amino acid sequence identity to SEQ ID NO: 7, or preferably 80%, 85%, 90% and 95% sequence identity to SEQ ID NO: 7, or more preferably, at least about 95% or more sequence identity to SEQ ID NO: 7.

As used herein, the term "SAR," an abbreviation for Structure-Activity Relationships, collectively refers to the structure-activity/structure property relationships pertaining to the relationship(s) between a compound's activity/properties and its chemical structure.

As used herein, the term "molecular structure" refers to the three dimensional arrangement of molecules of a particular compound or complex of molecules (e.g., the three dimensional structure of MGLL and ligands that interact with MGLL.

As used herein, the term "molecular modeling" refers to the use of computational methods, preferably computer assisted methods, to draw realistic models of what molecules look like and to make predictions about structure activity relationships of ligands. The methods used in molecular modeling range from molecular graphics to computational chemistry.

As used herein, the term "molecular model" refers to the three dimensional arrangement of the atoms of a molecule connected by covalent bonds or the three dimensional arrangement of the atoms of a complex comprising more than one molecule, e.g., a protein-ligand complex.

As used herein, the term "molecular graphics" refers to three dimensional (3D) representations of the molecules; for instance, a 3D representation produced using computer assisted computational methods.

As used herein, "computer readable medium" refers to any medium, which can be read and accessed directly by a computer. Such media include, but are not limited to: magnetic storage media, such as floppy discs, hard disc storage media, and magnetic tape; optical storage media such as optical discs or CD-ROM; electrical storage media such as RAM and ROM; and hybrids of these categories such as magnetic/optical storage media.

As used herein, "recorded" refers to a process for storing information on computer readable media. A skilled artisan can readily adopt any of the presently known methods for recording information on computer readable media to generate manufactures comprising an amino acid sequence and/or atomic coordinate/X-ray diffraction data information of the present invention.

As used herein, "a computer-based system" refers to the hardware means, software means, and data storage means used to analyze the sequence and/or X-ray diffraction data of the present invention. The minimum hardware means of the computer-based systems of the present invention comprises a central processing unit (CPU), input means, output means, and data storage means. A skilled artisan can readily appreciate which of the currently available computer-based systems are suitable for use in the present invention. A visualization device, such as a monitor, is optionally provided to visualize structure data.

As stated above, the computer-based systems of the present invention comprise a data storage means having stored therein sequence and/or atomic coordinate/X-ray diffraction data of the present invention and the necessary hardware means and software means for supporting and implementing an analysis means. As used herein, "data storage means" refers to memory which can store sequence or atomic coordinate/X-ray diffraction data of the present invention, or a memory access means which can access manufactures having recorded thereon the sequence or X-ray data of the present invention.

As used herein, "search means" or "analysis means" refers to one or more programs which are implemented on the computer-based system to compare a target sequence or target structural motif with the sequence or X-ray data stored within the data storage means. Search means are used to identify fragments or regions of a protein which match a particular target sequence or target motif. A variety of known algorithms are disclosed publicly and a variety of commercially available software for conducting search means are and can be used in the computer-based systems of the present invention. A skilled artisan can readily recognize that any one of the available algorithms or implementing software packages for conducting computer analyses can be adapted for use in the present computer-based systems.

As used herein, "a target structural motif," or "target motif," refers to any rationally selected sequence or combination of sequences in which the sequence(s) are chosen based on a three-dimensional configuration or electron density map which is formed upon the folding of the target motif. There are a variety of target motifs known in the art. Protein target motifs include, but are not limited to, enzymatic active sites, inhibitor binding sites, structural subdomains, epitopes, functional domains and signal sequences. Similar motifs are known for RNA. A variety of structural formats for the input and output means can be used to input and output the information in the computer-based systems of the present invention.

As used herein, the term "computational chemistry" refers to calculations of the physical and chemical properties of the molecules.

As used herein, the term "molecular replacement" refers to a method that involves generating a preliminary model of a crystal of MGLL whose coordinates are unknown, by orienting and positioning the said atomic coordinates described in the present invention so as best to account for the observed diffraction pattern of the unknown crystal. Phases can then be calculated from this model and combined with the observed amplitudes to give an approximate Fourier synthesis of the structure whose coordinates are unknown. (Rossmann 1972)

As used herein, the term "homolog" refers to the MGLL protein molecule or the nucleic acid molecule which encodes the protein, or a functional domain from said protein from a first source having at least about 70% or 75% sequence identity, or at least about 80% sequence identity, or more preferably at least about 85% sequence identity, or even more preferably at least about 90% sequence identity, and most preferably at least about 95%, 97% or 99% amino acid or nucleotide sequence identity, with the protein, encoding nucleic acid molecule or any functional domain thereof, from a second source. The second source may be a version of the molecule from the first source that has been genetically altered by any available means to change the primary amino acid or nucleotide sequence or may be from the same or a different species than that of the first source.

As used herein, the term "active site" refers to regions on MGLL or a structural motif of MGLL that are directly involved in the function or activity of human MGLL.

As used herein, the terms "binding site" or "binding pocket" refer to a region of human MGLL or a molecular complex comprising MGLL that, as a result of the primary amino acid sequence of human MGLL and/or its three-dimensional shape, favourably associates with another chemical entity or compound including ligands, cofactors, or inhibitors. For the purpose of this invention, any active site, binding site or binding pocket defined by a set of structure coordinates for MGLL or for a homolog of MGLL from any source having a root mean square deviation of non-hydrogen atoms of less than about 1.5 Å. when superimposed on the non-hydrogen atom positions of the corresponding atomic coordinates of Table 5 are considered substantially identical or homologous. In a more preferred embodiment, any set of structure coordinates for MGLL or a homolog of MGLL from any source having a root mean square deviation of non-hydrogen atoms of less than about 0.75 Å. when superimposed on the non-hydrogen atom positions of the corresponding atomic coordinates of Table 5 are considered substantially identical or homologous.

The term "root mean square deviation" means the square root of the arithmetic mean of the squares of the deviations from the mean.

As used herein, the term "hydrogen bond" refers to two hydrophilic atoms (either O or N), which share a hydrogen that is covalently bonded to only one atom, while interacting with the other.

As used herein, the term "hydrophobic interaction" refers to interactions made by two hydrophobic residues or atoms (such as C).

As used herein, the term "conjugated system" refers to more than two double bonds adjacent to each other, in which electrons are completely delocalized with the entire system. This also includes aromatic residues.

As used herein, the term "aromatic residue" refers to amino acids with side chains having a delocalized conjugated system. Examples of aromatic residues are phenylalanine, tryptophan, and tyrosine.

As used herein, the phrase "inhibiting the binding" refers to preventing or reducing the direct or indirect association of one or more molecules, peptides, proteins, enzymes, or receptors, or preventing or reducing the normal activity of one or more molecules, peptides, proteins, enzymes or receptors, e.g., preventing or reducing the direct or indirect association with human MGLL.

As used herein, the term "competitive inhibitor" refers to inhibitors that bind to human MGLL, thus directly competing with a substrate or ligand. Competitive inhibition may, in some instances, be reversed completely by increasing the substrate or ligand concentration.

As used herein, the term "uncompetitive inhibitor" refers to one that inhibits the functional activity of human MGLL by binding to a different site than does its substrate(s). As used herein, the term "non-competitive inhibitor" refers to one that can bind to either the free or bound form of MGLL. Those of skill in the art may identify inhibitors as competitive, uncompetitive, or non-competitive by computer fitting enzyme kinetic data using standard methods. See, for example, (Segel 1975)

As used herein, the term "R or S-isomer" refers to two possible stereoisomers of a chiral carbon according to the Cahn-Ingold-Prelog system adopted by International Union of Pure and Applied Chemistry (IUPAC). Each group attached to the chiral carbon is first assigned to a preference or priority a, b, c, or d on the basis of the atomic number of the atom that is directly attached to the chiral carbon. The group with the highest atomic number is given the highest preference a, the group with next highest atomic number is given the next highest preference b, and so on. The group with the lowest preference (d) is then directed away from the viewer. If the trace of a path from a to b to c is counter clockwise, the isomer is designated (S); in the opposite direction, clockwise, the isomer is designated (R).

As used herein, the term "stereoisomers" is a general term for all isomers of individual molecules that differ only in the orientation of their atoms in space. It includes enantiomers and isomers of compounds with more than one chiral center that are not mirror images of one another (diastereomers).

As used herein, the term "chiral center" refers to a carbon atom to which four different groups are attached.

As used herein, the term "enantiomer" or "enantiomeric" refers to a molecule that is nonsuperimposable on its mirror image and hence optically active wherein the enantiomer rotates the plane of polarized light in one direction and its mirror image rotates the plane of polarized light in the opposite direction.

As used herein, the term "racemic" refers to a mixture of equal parts of enantiomers and which is optically active.

As used herein, the term "resolution" refers to the separation or concentration or depletion of one of the two enantiomeric forms of a molecule. In the context of this application. The term "resolution" also refers to the amount of detail, which can be resolved by the diffraction experiment. Or in other terms, since the inherent disorder of a protein crystal diffraction pattern fades away at some diffraction angle theta$_{max}$, the corresponding distance d$_{min}$ of the reciprocal lattices is determined by Bragg's law. In practice in protein crystallography it is usual to quote the nominal resolution of a protein electron density in terms of d$_{min}$, the minimum lattice distance to which data is included in the calculation of the map.

As used herein, the term "ligand" refers to any molecule, or chemical entity, which binds with or to MGLL, a subunit of MGLL, a domain of MGLL, a target structural motif of MGLL, or a fragment of MGLL. Thus, ligands include, but are not limited to, small molecule inhibitors, for example.

As used herein, the term "small molecule inhibitor" refers to compounds useful in the present invention having measurable MGLL inhibiting activity. In addition to small organic molecules, peptides, antibodies, cyclic peptides and peptidomimetics are contemplated as being useful in the disclosed methods. Preferred inhibitors are small molecules, preferably less than 10,000 daltons, and more preferably less than 5,000 daltons.

As used herein the terms "bind," "binding," "bond," or "bonded" when used in reference to the association of atoms, molecules, or chemical groups, refer to any physical contact or association of two or more atoms, molecules, or chemical groups.

As used herein, the terms "covalent bond" or "valence bond" refer to a chemical bond between two atoms in a molecule created by the sharing of electrons, usually in pairs, by the bonded atoms.

As used herein, "noncovalent bond" refers to an interaction between atoms and/or molecules that does not involve the formation of a covalent bond between them.

DETAILED DESCRIPTION OF ILLUSTRATIVE EMBODIMENTS

It is to be understood at the outset, that the figures and examples provided herein are to exemplify, and not to limit the invention and its various embodiments.

The present invention includes a crystal comprising monoacylglycerol lipase (MGLL), or a fragment, or target structural motif or derivative thereof, and a ligand, wherein the ligand is a small molecule inhibitor. In one embodiment, the fragment or derivative thereof is a peptide comprising SEQ ID NO: 7.

In another embodiment, the crystal has a spacegroup of C222$_1$. In a different embodiment, the crystal effectively diffracts X-rays for determination of atomic coordinates to a resolution of at least about 3.2 Å. In a preferred embodiment, the ligand is in crystalline form. In a highly preferred embodiment, the ligand is the structure depicted in FIG. 7A or FIG. 7B, and, derivatives thereof.

The present invention also includes a crystal comprising MGLL, which comprises a peptide having at least 95% sequence identity to SEQ ID NO. 6. In a preferred embodiment, the crystal comprising SEQ ID NO: 7 comprises an atomic structure characterized by the coordinates of Table 5. In another preferred embodiment, the crystal comprises a unit cell selected from the group consisting of: a cell having dimensions of a=93.95, b=128.45, c=60.6.

In another aspect of the invention, the invention includes a computer system comprising: (a) a database containing information on the three dimensional structure of a crystal comprising MGLL, or a fragment or a target structural motif or derivative thereof, and a ligand, wherein the ligand is a small molecule inhibitor, stored on a computer readable storage medium; and, (b) a user interface to view the information. In one embodiment, the information comprises diffraction data obtained from a crystal comprising SEQ ID NO: 7.

In another embodiment, the information comprises an electron density map of a crystal form comprising SEQ ID NO: 7. In a different embodiment, the information comprises the structure coordinates of Table 5 or homologous structure coordinates comprising a root mean square deviation of non-hydrogen atoms of less than about 1.5 Å when superimposed on the non-hydrogen atom positions of the corresponding atomic coordinates of Table 5. In a preferred embodiment, the information comprises structure coordinates comprising a root mean square deviation of non-hydrogen atoms of less than about 0.75 Å when superimposed on the non-hydrogen atom positions of the corresponding atomic coordinates of Table 5. In a highly preferred embodiment, the information comprises the structure coordinates for amino acids SER48-HIS54, ARG57, TYR58, HIS77, HIS80, MET88, PHE93, PHE96, GLY120-ILE127, ILE145-VAL161, ALA163, SER176-ASN195, ASP197, ILE200, CYS201, ALA203, LEU205-VAL207, PHE209-SER218, ASP239-ASP243, TYR268-LEU275, THR279 according to Table 5 or similar structure coordinates for said amino acids comprising a root mean square deviation of non-hydrogen atoms of less than about 1.5 Å to 0.75 Å when superimposed on the non-hydrogen atom positions of the corresponding atomic coordinates of Table 5.

The present invention also includes a method of evaluating the potential of an agent to associate with MGLL comprising: (a) exposing MGLL to the agent; and (b) detecting the association of said agent to MGLL amino acid residues SER48-HIS54, ARG57, TYR58, HIS77, HIS80, MET88, PHE93, PHE96, GLY120-ILE127, ILE145-VAL161, ALA163, SER176-ASN195, ASP197, ILE200, CYS201, ALA203, LEU205-VAL207, PHE209-SER218, ASP239-ASP243, TYR268-LEU275, THR279 thereby evaluating the potential. In one embodiment of the invention, the agent is a virtual compound. In another embodiment of the invention, step (a) comprises comparing the atomic structure of the compound to the three dimensional structure of MGLL. In a different embodiment, the comparing of step (a) comprises employing a computational means to perform a fitting operation between the compound and at least one binding site of MGLL. In a preferred embodiment, the binding site is defined by structure coordinates for amino acids SER48-HIS54, ARG57, TYR58, HIS77, HIS80, MET88, PHE93, PHE96, GLY120-ILE127, ILE145-VAL161, ALA163, SER176-ASN195, ASP197, ILE200, CYS201, ALA203, LEU205-VAL207, PHE209-SER218, ASP239-ASP243, TYR268-LEU275, THR279 according to Table 5 or similar structure coordinates for said amino acids comprising a root mean square deviation of non-hydrogen atoms of less than about 1.5 Å when superimposed on the non-hydrogen atom positions of the corresponding atomic coordinates of Table 5. In a highly preferred embodiment, step (a) comprise exposing the agent to crystalline SEQ ID NO: 7 and the detecting of step (b) comprises determining the three dimensional structure of the agent-SEQ ID NO: 7 complex.

The present invention includes a method of identifying a potential agonist or antagonist against MGLL comprising: (a) employing the three dimensional structure of MGLL cocrystallized with a small molecule inhibitor to design or select said potential agonist or antagonist. In one embodiment, the three dimensional structure corresponds to the atomic structure characterized by the coordinates of Table 5 or similar structure coordinates comprising a root mean square deviation of non-hydrogen atoms of less than about 1.5 Å when superimposed on the non-hydrogen atom positions of the corresponding atomic coordinates of Table 5. In a different embodiment, the method further comprises the steps of: (b) synthesizing the potential agonist or antagonist; and (c) contacting the potential agonist or antagonist with MGLL.

The instant invention comprises a method of locating the attachment site of an inhibitor to MGLL, comprising: (a) obtaining X-ray diffraction data for a crystal of MGLL; (b) obtaining X-ray diffraction data for a complex of MGLL and an inhibitor; (c) subtracting the X-ray diffraction data obtained in step (a) from the X-ray diffraction data obtained in step (b) to obtain the difference in the X-ray diffraction data; (d) obtaining phases that correspond to X-ray diffraction data obtained in step (a); (e) utilizing the phases obtained in step (d) and the difference in the X-ray diffraction data obtained in step (c) to compute a difference Fourier image of the inhibitor; and, (f) locating the attachment site of the inhibitor to MGLL based on the computations obtained in step (e).

The present invention further comprises a method of obtaining a modified inhibitor comprising: (a) obtaining a crystal comprising MGLL and an inhibitor; (b) obtaining the atomic coordinates of the crystal; (c) using the atomic coordinates and one or more molecular modeling techniques to determine how to modify the interaction of the inhibitor with MGLL; and, (d) modifying the inhibitor based on the determinations obtained in step (c) to produce a modified inhibitor. In one embodiment, the crystal comprises a peptide having a sequence comprising SEQ ID NO: 7. In a different embodiment, the one or more molecular modeling techniques are selected from the group consisting of graphic molecular modeling and computational chemistry. In a preferred embodiment, step (a) comprises detecting the interaction of the inhibitor to MGLL amino acid residues SER48-HIS54, ARG57, TYR58, HIS77, HIS80, MET88, PHE93, PHE96, GLY120-ILE127, ILE145-VAL161, ALA163, SER176-ASN195, ASP197, ILE200, CYS201, ALA203, LEU205-VAL207, PHE209-SER218, ASP239-ASP243, TYR268-LEU275, THR279. In another embodiment of the invention, the invention includes an MGLL inhibitor identified by this method.

In another aspect of the invention, the invention includes an isolated protein fragment comprising a binding pocket or active site defined by structure coordinates of MGLL amino acid residues SER48-HIS54, ARG57, TYR58, HIS77, HIS80, MET88, PHE93, PHE96, GLY120-ILE127, ILE145-VAL161, ALA163, SER176-ASN195, ASP197, ILE200, CYS201, ALA203, LEU205-VAL207, PHE209-SER218, ASP239-ASP243, TYR268-LEU275, THR279. In one embodiment, the isolated fragment is linked to a solid support.

In another aspect of the invention, the invention includes an isolated nucleic acid molecule encoding the fragment, which comprises a binding pocket or active site defined by structure coordinates of MGLL. In one embodiment, a vector comprises the nucleic acid molecule. In another embodiment, a host cell comprises the vector. In yet another aspect of the invention, the invention includes a method of producing a protein fragment, comprising culturing the host cell under conditions in which the fragment is expressed. In another aspect of the invention, the invention includes a method of screening for an agent that associates with MGLL, comprising: (a) exposing a protein molecule fragment to the agent; and (b) detecting the level of association of the agent to the fragment. In another aspect of the invention, the invention includes a kit comprising a protein molecule fragment.

In another aspect of the invention, the invention includes a method for the production of a crystal complex comprising an MGLL polypeptide-ligand comprising: (a) contacting the MGLL polypeptide with said ligand in a suitable solution comprising PEG MME 5K, Na Citrate pH 5.5, and n-Octyl-Beta-D-Glucopyranoside; and, b) crystallizing said resulting complex of MGLL polypeptide-ligand from said solution. In one embodiment, the MGLL polypeptide is a polypeptide SEQ ID NO: 7. In another embodiment, PEG MME has an average molecular weight range from 2000 to 10000, wherein said PEG MME is present in solution at a range from about 1% w/v to about 5% w/v and said n-Octyl-Beta-D-Glucopyranoside is present in solution at a range of from about 0.2% to 2%. In a preferred embodiment, PEG MME has an average molecular weight of about 5000 and is present in solution at about 2.4% w/v and said n-Octyl-Beta-D-Glucopyranoside is present in solution at about 0.6%.

The invention further includes a method for the production of a crystal comprising MGLL and a ligand wherein the ligand is a small molecule inhibitor comprising crystallizing a peptide comprising SEQ ID NO: 7 with a potential inhibitor.

The invention includes a method for identifying a potential inhibitor of MGLL comprising: a) using a three dimensional structure of MGLL as defined by atomic coordinates according to Table 5; b) replacing one or more MGLL amino acids selected from SER48-HIS54, ARG57, TYR58, HIS77, HIS80, MET88, PHE93, PHE96, GLY120-ILE127, ILE145-VAL161, ALA163, SER176-ASN195, ASP197, ILE200, CYS201, ALA203, LEU205-VAL207, PHE209-SER218, ASP239-ASP243, TYR268-LEU275, THR279 in said three-dimensional structure with a different amino acid to produce a modified MGLL; c) using said three-dimensional structure to design or select said potential inhibitor; d) synthesizing said potential inhibitor; and, e) contacting said potential inhibitor with said modified MGLL in the presence of a substrate to test the ability of said potential inhibitor to inhibit MGLL or said modified MGLL. In another embodiment, the potential inhibitor is selected from a database. In a preferred embodiment, the potential inhibitor is designed de novo. In another preferred embodiment, the potential inhibitor is designed from a known inhibitor. In a highly preferred embodiment, the step of employing said three-dimensional structure to design or select said potential inhibitor comprises the steps of: a) identifying chemical entities or fragments capable of associating with modified MGLL; and b) assembling the identified chemical entities or fragments into a single molecule to provide the structure of said potential inhibitor. In one embodiment, the potential inhibitor is a competitive inhibitor of SEQ ID NO: 7. In a different embodiment, the potential inhibitor is a non-competitive or uncompetitive inhibitor of SEQ ID NO: 7. In yet another embodiment, an inhibitor is identified by the method.

Engineered Forms and Fragments

Engineered forms of MGLL or fragments thereof, for instance engineered forms or fragments comprising active sites defined by two or more amino acids selected from the group consisting of: SER48-HIS54, ARG57, TYR58, HIS77, HIS80, MET88, PHE93, PHE96, GLY120-ILE127, ILE145-VAL161, ALA163, SER176-ASN195, ASP197, ILE200, CYS201, ALA203, LEU205-VAL207, PHE209-SER218, ASP239-ASP243, TYR268-LEU275, THR279 may be prepared by any available means including synthetic or recombinant means. Such fragments may then be used in the assays as described herein, for example, but not limited to, high-throughput assays to detect interactions between prospective agents and the active site within the fragment.

For recombinant expression or production of the forms or fragments of the invention, nucleic acid molecules encoding the form or fragment may be prepared. Nucleic acid molecules encoding engineered forms or fragments of the invention may differ in sequence because of the degeneracy in the genetic code or may differ in sequence as they encode proteins or protein fragments that differ in amino acid sequence. Homology or sequence identity between two or more such nucleic acid molecules is determined by BLAST (Basic Local Alignment Search Tool) analysis using the algorithm employed by the programs blastp, blastn, blastx, tblastn and tblastx (Karlin and Altschul 1990) and (Altschul 1993), fully incorporated by reference, which are tailored for sequence similarity searching.

The approach used by the BLAST program is to first consider similar segments between a query sequence and a database sequence, then to evaluate the statistical significance of all matches that are identified and finally to summarize only those matches which satisfy a preselected threshold of significance. For a discussion of basic issues in similarity searching of sequence databases, see (Altschul et al. 1994) which is fully incorporated by reference. The search parameters for histogram, descriptions, alignments, expect (i.e., the statistical significance threshold for reporting matches against database sequences), cutoff, matrix and filter are at the default settings. For a discussion of default scoring matrix used by blastp, blastx, tblastn, and tblastx, see (Henikoff 1992).

The encoding nucleic acid molecules of the present invention or fragments thereof (i.e., synthetic oligonucleotides) and those that are used as probes or specific primers for polymerase chain reaction (PCR) or to synthesize gene sequences encoding proteins of the invention can easily be synthesized by chemical techniques, for example, the phosphotriester method of (Matteucci and Caruthers 1981) or using automated synthesis methods. In addition, larger DNA segments can readily be prepared by well-known methods, such as synthesis of a group of oligonucleotides that define various modular segments of the gene, followed by ligation of oligonucleotides to build the complete modified gene.

The encoding nucleic acid molecules of the present invention may further be modified so as to contain a detectable label for diagnostic and probe purposes. A variety of such labels are known in the art and can readily be employed with the encoding molecules herein described. Suitable labels include, but are not limited to, biotin, radiolabeled nucleotides and the like. A skilled artisan can employ any of the art-known labels to obtain a labeled encoding nucleic acid molecule.

The present invention further provides recombinant DNA molecules (rDNA) that contain a coding sequence for a protein or protein fragment as described herein. As used herein, an rDNA molecule is a DNA molecule that has been subjected to molecular manipulation. Methods for generating rDNA molecules are well known in the art, for example, see (Sambrook et al. 1989). In the preferred rDNA molecules, a coding DNA sequence is operably linked to expression control sequences and/or vector sequences.

The choice of vector and expression control sequences to which one of the protein encoding sequences of the present invention is operably linked depends directly, as is well known in the art, on the functional properties desired (e.g., protein expression, and the host cell to be transformed). A vector of the present invention may be capable of directing the replication or insertion into the host chromosome, and preferably also expression, of the structural gene included in the rDNA molecule.

Expression control elements that are used for regulating the expression of an operably linked protein encoding sequence are known in the art and include, but are not limited to, inducible promoters, constitutive promoters, secretion signals, and other regulatory elements. Preferably, the inducible promoter is readily controlled, such as being responsive to a nutrient in the host cell's medium.

The present invention further provides host cells transformed with a nucleic acid molecule that encodes a protein or protein fragment of the present invention. The host cell can be either prokaryotic or eukaryotic. Eukaryotic cells useful for expression of a protein of the invention are not limited, so long as the cell line is compatible with cell culture methods and compatible with the propagation of the expression vector and expression of the gene product. Preferred eukaryotic host cells include, but are not limited to, insect, yeast, and mammalian cells. Preferred eukaryotic host cells include *Spodoptera frugiperda* (Sf9 or Sf21) insect cells.

Transformed host cells of the invention may be cultured under conditions that allow the production of the recombinant protein. Optionally the recombinant protein is isolated from the medium or from the cells; recovery and purification of the protein may not be necessary in some instances where some impurities may be tolerated.

Kits may also be prepared with any of the above described nucleic acid molecules, proteins, protein fragments, vector and/or host cells optionally packaged with the reagents needed for a specific assay, such as those described above. In such kits, the protein, protein fragments, or other reagents may be attached to a solid support, such as glass or plastic beads.

High-Throughput Assays

Compound identification methods can be performed using conventional laboratory assay formats or in high-throughput assays, including, but not limited to, those described below.

Immunoassays are a group of techniques used for the measurement of specific biochemical substances, commonly at low concentrations in complex mixtures such as biological fluids. The assays depend upon suitably prepared and selected antibodies with specificity and high affinity for their complementary antigens. A substance to be measured must, of necessity, be antigenic, either an immunogenic macromolecule or a haptenic small molecule. To each sample a known limited amount of specific antibody is added and the fraction of the antigen combining with it, often expressed as the bound:free ratio, is estimated by quantifying the signal from the antibody. Quantification can be achieved with a number of readily identifiable labels and used for various types of assays, including, but not limited to, radioisotopes for radioimmunoassays (RIA), fluorescent molecules for fluoroimmunoassays (FIA), stable free radicals for spin immunoassays, chemiluminescent molecules for chemiluminescent immunoassays (CLIA), colloidal gold particles for immunogold assays, and enzymes for enzyme-linked immunosorbent assays (ELISA).

A common immunoassay format is the ELISA, which avoids the hazards of radiochemicals and the expense of fluorescence detection systems. Instead, an ELISA is a form of quantitative immunoassay based on the use of antibodies (or antigens) that may be linked to an insoluble carrier surface, which is then used to "capture" the relevant antigen (or antibody) the test solution. The antigen-antibody complex is then detected by measuring the activity of an appropriate enzyme that can be covalently attached to the capture antigen (or antibody) or to a subsequent "detection" antibody (or antigen). For more information on ELISA techniques, see, for example, (Crowther 1995); (Kemeny (editor) and Challacombe (editor) 1988), (Kemeny 1991), and (Ishikawa 1999).

Colorimetric assays for enzymes are methods of quantitative chemical analysis in which the concentration or amount of a compound is determined by comparing the color produced by the reaction of a reagent with both standard and test amounts of the compound, often using a calorimeter. A calorimeter is a device for measuring color intensity or differences in color intensity, either visually or photoelectrically. Standard calorimetric assays of beta-galactosidase enzymatic activity are well known to those skilled in the art, see for example, (Norton and Coffin 1985). A calorimetric assay can be performed on whole cell lysates using O-nitrophenyl-beta-D-galacto-pyranoside (ONPG, Sigma) as the substrate in a standard calorimetric beta-galactosidase assay (Sambrook et al. 1989). Automated calorimetric assays are also available for the detection of beta-galactosidase activity, as described in U.S. Pat. No. 5,733,720.

Enzymatic substrates that become fluorescent after being acted upon by an enzyme generally are well known. Such fluorescent substrates typically have two components that are bound to one another through, for example, a covalent chemical bond. One component is a fluorescent molecule that is capable of fluorescing by first accepting light energy and then emitting light energy. The other component is an entity that prevents the fluorescent molecule from accepting or emitting light energy when the two components are covalently bound to one another. In the presence of an appropriate enzyme, the enzyme cleaves the covalent bond between the two components and separates one component from the other to permit the fluorescent molecule to accept and emit light energy. In other words, the enzyme frees the fluorescent molecule and allows it to fluoresce. Ideally, fluorescent substrates should be soluble and stable in aqueous buffers, should have a high affinity for the enzymes that act upon them, and should yield a strong signal upon enzymatic action (U.S. Pat. No. 5,998,593A).

Detecting fluorescence emitted from the fluorescent component of a fluorescent enzyme substrate is typically achieved in two steps. In particular, the fluorescent molecule is first excited with light energy and subsequently the fluorescence emitted from the fluorescent component is then detected. Generally, fluorescent molecules can be excited with light energy from, for example, a laser or another suitable light source. Fluorescence is detected with a device designed to detect light energy of a wavelength that is emitted by the fluorescent molecule. Such excitation and emission detection systems generally are designed to operate at particular wavelength ranges (U.S. Pat. No. 5,998,593A).

Thermofluor® assays detect small changes in the intrinsic melting temperature of proteins based on binding of ligands. Compounds that interact preferentially with the native form of the protein will increase the $T_m$, the temperature at which half of the protein is unfolded (Pantoliano et al. 2001). The technique monitors changes in the fluorescent intensity of dyes such as 1-anilinonaphthalene-8-sulfonic acid (1,8-ANS). The fluorescent dyes are quenched in aqueous environments but increase in fluorescence on binding to the hydrophobic core of denatured proteins.

Modeling the Three-Dimensional Structure of MGLL

The atomic coordinate data provided in Table 5, or the coordinate data derived from homologous proteins may be used to build a three-dimensional model of MGLL. Any available computational methods may be used to build the three dimensional model. As a starting point, the X-ray diffraction pattern obtained from the assemblage of the molecules or atoms in a crystalline version of MGLL or an MGLL homolog can be used to build an electron density map using tools well known to those skilled in the art of crystallography and X-ray diffraction techniques. Additional phase information extracted either from the diffraction data and available in the published literature and/or from supplementing experiments may then be used to complete the reconstruction.

For basic concepts and procedures of collecting, analyzing, and utilizing X-ray diffraction data for the construction of electron densities see, for example, (Campbell 1984), (Cantor and Schimmel 1980), (Brunger 1993), (Woolfson 1997), (Drenth 1999), (Tsirelson and Ozerov 1996), and (U.S. Pat. No. 5,942,428A); (U.S. Pat. No. 6,037,117A); (U.S. Pat. No. 5,200,910A); and (U.S. Pat. No. 5,365,456A), each of which is herein specifically incorporated by reference in their entirety.

For basic information on molecular modeling, see, for example, (Schlecht 1998); (Gans et al. 1996); (Cohen (editor) 1996); and (Smith 1996). U.S. patents which provide detailed information on molecular modeling include (U.S. Pat. No. 4,906,122A; U.S. Pat. No. 5,030,103A; U.S. Pat. No. 5,583, 973A; U.S. Pat. No. 5,612,894A; U.S. Pat. No. 5,994,503A; U.S. Pat. No. 6,071,700A; U.S. Pat. No. 6,075,014A; U.S. Pat. No. 6,075,123A; U.S. Pat. No. 6,080,576A; U.S. Pat. No. 6,093,573A), each of which are incorporated by reference herein in their entirety.

Methods of Using the Atomic Coordinates to Identify and Design Ligands of Interest The atomic coordinates of the invention, such as those described in Table 5, or coordinates substantially identical to or homologous to those of Table 5 may be used with any available methods to prepare three dimensional models of MGLL as well as to identify and design MGLL ligands, inhibitors or antagonists or agonist molecules. Such a method provides the amino acid sequence and/or X-ray diffraction data in a form which allows a skilled artisan to analyze and molecular model the three-dimensional structure of MGLL or related molecules, including a subdomain thereof.

For instance, three-dimensional modeling may be performed using the experimentally determined coordinates derived from X-ray diffraction patterns, such as those in Table 5, for example, wherein such modeling includes, but is not limited to, drawing pictures of the actual structures, building physical models of the actual structures, and determining the structures of related subunits and MGLL/ligand and MGLL subunit/ligand complexes using the coordinates. Such molecular modeling can utilize known X-ray diffraction molecular modeling algorithms or molecular modeling software to generate atomic coordinates corresponding to the three-dimensional structure of MGLL.

As described above, molecular modeling involves the use of computational methods, preferably computer assisted methods, to build realistic models of molecules that are identifiably related in sequence to the known crystal structure. It also involves modeling new small molecule inhibitors bound to MGLL starting with the structures of MGLL and or MGLL complexed with known ligands or inhibitors. The methods utilized in ligand modeling range from molecular graphics (i.e., 3D representations) to computational chemistry (i.e., calculations of the physical and chemical properties) to make predictions about the binding of ligands or activities of ligands; to design new ligands; and to predict novel molecules, including ligands such as drugs, for chemical synthesis, collectively referred to as rational drug design.

One approach to rational drug design is to search for known molecular structures that might bind to an active site. Using molecular modeling, rational drug design programs can look at a range of different molecular structures of drugs that may fit into the active site of an enzyme, and by moving them in a three-dimensional environment it can be decided which structures actually fit the site well.

An alternative but related rational drug design approach starts with the known structure of a complex with a small molecule ligand and models modifications of that small molecule in an effort to make additional favourable interactions with MGLL.

The present invention includes the use of molecular and computer modeling techniques to design and select and design ligands, such as small molecule agonists or antagonists or other therapeutic agents that interact with MGLL. For example, the invention as herein described includes the design of ligands that act as competitive inhibitors of at least one MGLL function by binding to all, or a portion of, the active sites or other regions of MGLL.

This invention also includes the design of compounds that act as uncompetitive inhibitors of at least one function of MGLL. These inhibitors may bind to all, or a portion of, the active sites or other regions of MGLL already bound to its substrate and may be more potent and less non-specific than competitive inhibitors that compete for MGLL active sites. Similarly, non-competitive inhibitors that bind to and inhibit at least one function of MGLL whether or not it is bound to another chemical entity may be designed using the atomic coordinates of MGLL or complexes comprising MGLL of this invention.

The atomic coordinates of the present invention also provide the needed information to probe a crystal of MGLL with molecules composed of a variety of different chemical features to determine optimal sites for interaction between candidate inhibitors and/or activators and MGLL. For example, high resolution X-ray diffraction data collected from crystals saturated with solvent allows the determination of where each type of solvent molecule sticks. Small molecules that bind to those sites can then be designed and synthesized and tested for their inhibitory activity (Travis 1993).

The present invention also includes methods for computationally screening small molecule databases and libraries for chemical entities, agents, ligands, or compounds that can bind in whole, or in part, to MGLL. In this screening, the quality of fit of such entities or compounds to the binding site or sites may be judged either by shape complementarity or by estimated interaction energy (Meng et al. 1992).

The design of compounds that bind to, promote or inhibit the functional activity of MGLL according to this invention generally involves consideration of two factors. First, the compound must be capable of physically and structurally associating with MGLL. Non-covalent molecular interactions important in the association of MGLL with the compound include hydrogen bonding, van der Waals and hydrophobic interactions. Second, the compound must be able to assume a conformation that allows it to associate with MGLL. Although certain portions of the compound may not directly participate in the association with MGLL, those portions may still influence the overall conformation of the molecule. This, in turn, may have a significant impact on binding affinities, therapeutic efficacy, drug-like qualities and potency. Such conformational requirements include the overall three-dimensional structure and orientation of the chemical entity or compound in relation to all or a portion of the active site or other region of MGLL, or the spacing between functional groups of a compound comprising several chemical entities that directly interact with MGLL.

The potential, predicted, inhibitory agonist, antagonist or binding effect of a ligand or other compound on MGLL may be analyzed prior to its actual synthesis and testing by the use of computer modeling techniques. If the theoretical structure of the given compound suggests insufficient interaction and association between it and MGLL, synthesis and testing of the compound may be obviated. However, if computer modeling indicates a strong interaction, the molecule may then be synthesized and tested for its ability to interact with MGLL. In this manner, synthesis of inoperative compounds may be avoided. In some cases, inactive compounds are synthesized predicted on modeling and then tested to develop a SAR (structure-activity relationship) for compounds interacting with a specific region of MGLL.

One skilled in the art may use one of several methods to screen chemical entities fragments, compounds, or agents for their ability to associate with MGLL and more particularly with the individual binding pockets or active sites of MGLL. This process may begin by visual inspection of, for example, the active site on the computer screen based on the atomic coordinates of MGLL or MGLL complexed with a ligand. Selected chemical entities, compounds, or agents may then be positioned in a variety of orientations, or docked within an individual binding pocket of MGLL. Docking may be accomplished using software such as QUANTA, available from Accelrys, Inc., San Diego, Calif.; and SYBYL, available for Tripos, St. Louis, Mo.; followed by energy minimization and molecular dynamics with standard molecular mechanics forcefields, such as CHARMm; available from Accelrys, Inc., San Diego, Calif.; and AMBER, University of California, San Francisco.

Specialized computer programs may also assist in the process of selecting chemical entities. These include but are not limited to: GRID (Goodford 1985), available from Oxford University, Oxford, UK); MCSS (Miranker and Karplus 1991), available from Molecular Simulations, Burlington, Mass.; AUTODOCK (Goodsell and Olsen 1990), available from Scripps Research Institute, La Jolla, Calif.; and DOCK (Kuntz et al. 1982), available from University of California, San Francisco, Calif.

The use of software such as GRID, a program that determines probable interaction sites between probes with various functional group characteristics and the macromolecular surface, is used to analyze the surface sites to determine structures of similar inhibiting proteins or compounds. The GRID calculations, with suitable inhibiting groups on molecules (e.g., protonated primary amines) as the probe, are used to identify potential hotspots around accessible positions at suitable energy contour levels. The program DOCK may be used to analyze an active site or ligand-binding site and suggest ligands with complementary steric properties.

Once suitable chemical entities, compounds, or agents have been selected, they can be assembled into a single ligand or compound or inhibitor or activator. Assembly may proceed by visual inspection of the relationship of the fragments to each other on the three-dimensional image. This may be followed by manual model building using software such as QUANTA or SYBYL.

Useful programs to aid in connecting the individual chemical entities, compounds, or agents include but are not limited to: CAVEAT (Bartlett et al. 1989); 3D Database systems such as MACCS-3D (Martin 1992), available from MDL Information Systems, San Leandro, Calif.; and HOOK, available from Molecular Simulations, Burlington, Mass.

Several methodologies for searching three-dimensional databases to test pharmacophore hypotheses and select compounds for screening are available. These include the program CAVEAT (Bacon and Moult 1992). For instance, CAVEAT uses databases of cyclic compounds which can act as "spacers" to connect any number of chemical fragments already positioned in the active site. This allows one skilled in the art to quickly generate hundreds of possible ways to connect the fragments already known or suspected to be necessary for tight binding.

Instead of proceeding to build an inhibitor activator, agonist or antagonist of MGLL in a step-wise fashion one chemical entity at a time as described above, such compounds may be designed as a whole or "de novo" using either an empty active site or optionally including some portion(s) of a known molecule(s). These methods include: LUDI (Bohm 1992), available from Biosym Technologies, San Diego, Calif.; LEGEND (Nishibata and Itai 1991), available from Molecular Simulations, Burlington, Mass.; and LeapFrog, available from Tripos Associates, St. Louis, Mo., USA.

For instance, the program LUDI can determine a list of interaction sites into which to place both hydrogen bonding and hydrophobic fragments. LUDI then uses a library of linkers to connect up to four different interaction sites into fragments. Then smaller "bridging" groups such as —CH2— and —COO— are used to connect these fragments. For example, for the enzyme DHFR, the placements of key functional groups in the well-known inhibitor methotrexate were reproduced by LUDI. See also, (Rotstein and Murcko 1993).

Other molecular modeling techniques may also be employed in accordance with this invention. See, e.g., (Cohen et al. 1990). See also, (Navia and Murcko 1992).

Once a compound has been designed or selected by the above methods, the affinity with which that compound may bind or associate with MGLL may be tested and optimized by computational evaluation and/or by testing biological activity after synthesizing the compound. Inhibitors or compounds may interact with the MGLL in more than one conformation that is similar in overall binding energy. In those cases, the deformation energy of binding is taken to be the difference between the energy of the free compound and the average energy of the conformations observed when the compound binds to MGLL.

A compound designed or selected as binding or associating with MGLL may be further computationally optimized so that in its bound state it would preferably lack repulsive electrostatic interaction with MGLL. Such non-complementary (e.g., electrostatic) interactions include repulsive charge-charge, dipole-dipole and charge-dipole interactions. Specifically, the sum of all electrostatic interactions between the inhibitor and MGLL when the inhibitor is bound, preferably make a neutral or favourable contribution to the enthalpy of binding. Weak binding compounds will also be designed by these methods so as to determine SAR.

Specific computer software is available in the art to evaluate compound deformation energy and electrostatic interaction. Examples of programs designed for such uses include: Gaussian 92, revision C (Frisch et al. 1992); AMBER, University of California, San Francisco; QUANTA and CHARMm, available from Accelrys, Inc., San Diego, Calif.; and Insight II/Discover, from Biosysm Technologies Inc., San Diego, Calif., USA. Other hardware systems and software packages will be known to those skilled in the art.

Once a compound that associates with MGLL has been optimally selected or designed, as described above, substitutions may then be made in some of its atoms or side groups in order to improve or modify its binding properties. Generally, initial substitutions are conservative, i.e., the replacement group will have approximately the same size, shape, hydrophobicity and charge as the original group. It should, of course, be understood that components known in the art to alter conformation may be avoided. Such substituted chemical compounds may then be analyzed for efficiency of fit to MGLL by the same computer methods described in detail, above.

Use of Homology Structure Modeling to Design Ligands with Modulated Binding or Activity to MGLL.

The present invention includes the use of the atomic coordinates and structures of MGLL and/or MGLL complexed with an inhibitor to design modifications to starting compounds and derivatives thereof that will bind more tightly or interact more specifically to the target enzyme.

The structure of a complex between the MGLL and the starting compound can be used to guide the modification of that compound to produce new compounds that have other desirable properties for applicable industrial and other uses (e.g., as pharmaceuticals), such as chemical stability, solubility or membrane permeability. (Lipinski et al. 1997).

Binding compounds, agonists, antagonists and such that are known in the art. Such compounds can be diffused into or soaked with the stabilized crystals of MGLL to form a complex for collecting X-ray diffraction data. Alternatively, the compounds, known and unknown in the art, can be cocrystallized with MGLL by mixing the compound with MGLL before precipitation.

To produce custom high affinity and very specific compounds, the structure of MGLL can be compared to the structure of a selected non-targeted molecule and a hybrid constructed by changing the structure of residues at the binding site for a ligand for the residues at the same positions of the non-target molecule. The process whereby this modeling is achieved is referred to as homology structure modeling. This is done computationally by removing the side chains from the molecule or target of known structure and replacing them with the side chains of the unknown structure put in sterically plausible positions. In this way it can be understood how the shapes of the active site cavities of the targeted and non-targeted molecules differ. This process, therefore, provides information concerning how a bound ligand can be chemically altered in order to produce compounds that will bind tightly and specifically to the desired target but will simultaneously be sterically prevented from binding to the non-targeted molecule. Likewise, knowledge of portions of the bound ligands that are facing to the solvent would allow introduction of other functional groups for additional pharmaceutical purposes. The use of homology structure modeling to design molecules (ligands) that bind more tightly to the target enzyme than to the non-target enzyme has wide spread applicability.

Databases and Computer Systems

An amino acid sequence or nucleotide sequence of MGLL and/or X-ray diffraction data, useful for computer molecular modeling of MGLL or a portion thereof, can be provided in a variety of mediums to facilitate use thereof. In one application of this embodiment, databases comprising data pertaining to MGLL, or at least one subdomain thereof, amino acid and nucleic acid sequence and/or X-ray diffraction data of the present invention is recorded on computer readable medium. A skilled artisan can readily appreciate how any of the presently known computer readable media can be used to create a manufacture comprising computer readable medium having recorded thereon an amino acid sequence and/or X-ray diffraction data of the present invention.

A variety of data storage structures are available to a skilled artisan for creating a computer readable medium having recorded thereon an amino acid sequence and/or atomic coordinate/X-ray diffraction data of the present invention. The choice of the data storage structure will generally be based on the means chosen to access the stored information. In addition, a variety of data processor programs and formats can be used to store the sequence and X-ray data information of the present invention on computer readable media. The sequence information can be represented in a word processing text file, formatted in commercially-available software such as WordPerfect and MICROSOFT Word, or represented in the form of an ASCII file, stored in a database application, such as DB2, Sybase, Oracle, or the like. A skilled artisan can readily adapt any number of dataprocessor structuring formats (e.g., text file or database) in order to obtain computer readable media having recorded thereon the information of the present invention.

By providing computer readable media having sequence and/or atomic coordinates based on X-ray diffraction data, a skilled artisan can routinely access the sequence and atomic coordinate or X-ray diffraction data to model a related molecule, a subdomain, mimetic, or a ligand thereof. Computer algorithms are publicly and commercially available which allow a skilled artisan to access this data provided in a computer readable medium and analyze it for molecular modeling and/or RDD (rational drug design). See, e.g., (Mary Ann Liebert (Publishers) 1995).

The present invention further provides systems, particularly computer-based systems, which contain the sequence and/or diffraction data described herein. Such systems are designed to do structure determination and RDD for MGLL or at least one subdomain thereof. Non-limiting examples are microcomputer workstations available from Silicon Graphics Incorporated and Sun Microsystems running UNIX based, Windows NT or IBM OS/2 operating systems.

A variety of comparing means can also be used to compare a target sequence or target motif with the data storage means to identify structural motifs or electron density maps derived in part from the atomic coordinate/X-ray diffraction data. A skilled artisan can readily recognize that any one of the publicly available computer modeling programs can be used as the search means for the computer-based systems of the present invention.

Integrated Procedures Which Utilize the Present Invention

Molecular modeling is provided by the present invention for rational drug design (RDD) of mimetics and ligands of MGLL. As described above, the drug design paradigm uses computer-modeling programs to determine potential mimetics and ligands which are expected to interact with sites on the protein. The potential mimetics or ligands are then screened for activity and/or binding and/or interaction. For MGLL-related mimetics or ligands, screening methods can be selected from assays for at least one biological activity of MGLL, e.g., such as hydrolysis by MGLL.

Thus, the tools and methodologies provided by the present invention may be used in procedures for identifying and designing ligands which bind in desirable ways with the target. Such procedures utilize an iterative process whereby ligands are synthesized, tested and characterized. New ligands can be designed based on the information gained in the testing and characterization of the initial ligands and then such newly identified ligands can themselves be tested and characterized. This series of processes may be repeated as many times as necessary to obtain ligands with the desirable binding properties.

The following steps (1-7) serve as an example of the overall procedure:

1. A biological activity of a target is selected (e.g., hydrolysis by MGLL).
2. A ligand is identified that appears to be in some way associated with the chosen biological activity (e.g., the ligand may be an inhibitor of a known activity). The activity of the ligand may be tested by in vivo and/or in vitro methods. A ligand of the present invention can be, but is not limited to, at least one selected from a lipid, a nucleic acid, a compound, a protein, an element, an antibody, a saccharide, an isotope, a carbohydrate, an imaging agent, a lipoprotein, a glycoprotein, an enzyme, a detectable probe, and antibody or fragment thereof, or any combination thereof, which can be detectably labeled as for labeling antibodies. Such labels include, but are not limited to, enzymatic labels, radioisotope or radioactive compounds or elements, fluorescent compounds or metals, chemiluminescent compounds and bioluminescent compounds. Alternatively, any other known diagnostic or therapeutic agent can be used in a method of the invention. Suitable compounds are then tested for activities in relationship to the target. Complexes between MGLL and ligands are made either by co-crystallization or more commonly by diffusing the small molecule ligand into the crystal. X-ray diffraction data from the complex crystal are measured and a difference electron density map is calculated. This process provides the precise location of the bound ligand on the target molecule. The difference Fourier is calculated using measure diffraction amplitudes and the phases of these reflections calculated from the coordinates.
3. Using the methods of the present invention, X-ray crystallography is utilized to create electron density maps and/or molecular models of the interaction of the ligand with the target molecule. The entry of the coordinates of the target into the computer programs discussed above results in the calculation of most probable structure of the macromolecule. These structures are combined and refined by additional calculations using such programs to determine the probable or actual three-dimensional structure of the target including potential or actual active or binding sites of ligands. Such molecular modeling (and related) programs useful for rational drug design of ligands or mimetics are also provided by the present invention.
4. The electron density maps and/or molecular models obtained in Step 3 are compared to the electron density maps and/or molecular models of a non-ligand containing target and the observed/calculated differences are used to specifically locate the binding of the ligand on the target or subunit.
5. Modeling tools, such as computational chemistry and computer modeling, are used to adjust or modify the structure of the ligand so that it can make additional or different interactions with the target. The ligand design uses computer-modeling programs which calculate how different molecules interact with the various sites of the target, subunit, or a fragment thereof. Thus, this procedure determines potential ligands or ligand mimetics.
6. The newly designed ligand from Step 5 can be tested for its biological activity using appropriate in vivo or in vitro tests, including the high-throughput screening methods discussed above. The potential ligands or mimetics are then screened for activity relating to MGLL, or at least a fragment thereof. Such screening methods are selected from assays for at least one biological activity of the native target. The resulting ligands or mimetics, provided by methods of the present invention, are useful for treating, screening or preventing diseases in animals, such as mammals (including humans).
7. Of course, each of the above steps can be modified as desired by those of skill in the art so as to refine the procedure for the particular goal in mind. Also, additional X-ray diffraction data may be collected on MGLL, MGLL/ligand complexes, MGLL structural target motifs and MGLL subunit/ligand complexes at any step or phase of the procedure. Such additional diffraction data can be used to reconstruct electron density maps and molecular models, which may further assist in the design and selection of ligands with the desirable binding attributes.

It is to be understood that the present invention is considered to include stereoisomers as well as optical isomers, e.g., mixtures of enantiomers as well as individual enantiomers and diastereomers, which arise as a consequence of structural asymmetry in selected compounds, ligands or mimetics of the present series.

Some of the compounds or agents disclosed or discovered by the methods herein may contain one or more asymmetric centers and thus give rise to enantiomers, diastereomers, and other stereoisomeric forms. The present invention is also meant to encompass all such possible forms as well as their racemic and resolved forms and mixtures thereof. When the compounds described or discovered herein contain olefinic double bonds or other centers of geometric asymmetry, and unless otherwise specified, it is intended to include both E and Z geometric isomers. All tautomers are intended to be encompassed by the present invention as well.

EXAMPLES

Without further description, it is believed that one of ordinary skill in the art can, using the preceding description and the following illustrative examples, make and utilize the present invention and practice the claimed methods. The following working examples therefore, specifically point out preferred embodiments of the present invention, and are not to be construed as limiting in any way the remainder of the disclosure.

BLAST Search and Sequence Alignment

The reference sequences for MGLL Isoform 2 (Karlsson et al. 2001) and Isoform 1 (Wall et al. 1997) are shown in FIG. 1: A and FIG. 1: B, respectively. Note that the sequences of MGLL Isoform 2 and MGLL Isoform 1 are 100% identical, except that MGLL Isoform 1 has an additional 10 amino acids at the N-terminus. The alignment for MGLL Isoform 2 and MGLL Isoform 1 is shown in FIG. 1: C. The numbering of amino acids for MGLL Isoform 2 (SEQ ID NO: 1) was used throughout the following description to refer to amino acids in the engineered constructs of the present invention.

A BLAST search (Altschul et al. 1990) against the sequence data set deposited in the Protein Data Bank (Sussman et al. 1998) was conducted to identify a protein of known crystal structure with reasonable sequence homology to MGLL. The closest relative to MGLL found in the Protein Data Bank was RsbQ, a stress-response regulator in *Bacillus*

*subtilis* (Kaneko et al. 2005). RsbQ shares 25% sequence identity with human MGLL. RsbQ also had the highest sequence identity and smallest insertions and deletions relative to MGLL of any structure available in the PDB at the time of this work. The protein RsbQ, PDB ID 1wom (Kaneko et al. 2005), was used as a template. The sequences of RsbQ and MGLL isoform 2 were aligned using the ClustalW software (Thompson et al. 1994; Higgins et al. 1996). RsbQ is a α/β hydrolase with a catalytic triad composed of Ser96, His247 and Asp219. The Asp-His-Ser catalytic triad of MGLL matched the corresponding residues in RsbQ. This alignment was duplicated within the GeneMine software (Lee and Irizarry 2001) and adjusted to eliminate insertions or deletions within elements of secondary structure without disturbing the alignment of the catalytic residues. The final alignment of human MGLL isoform 2 and RsbQ is shown in FIG. 2A. Although the sequence identity between MGLL and RsbQ is low for generating a homology model for MGLL, it was estimated that a low accuracy model would be sufficient to identify hydrophobic residues in the outside of the molecule that could trigger aggregation.

Homology Model

A homology model of MGLL was created using RsbQ as a template and the "quick refine" option in GeneMine software (FIG. 2A) (Levitt 1992) (Lee and Irizarry 2001). The model shows a α/β hydrolase domain and a cap-domain composed of 4 helices. Helix 151-185 of the cap-domain shows amphiphilic properties, characteristic of proteins involved in lipid binding. The helix contains a slight bend due to the presence of a proline residue at position 172. 14 out of the 32 residues constituting the helix are hydrophobic (FIG. 2A). 7 of the hydrophobic residues are Leucines (Leu 152, 157, 159, 171, 174, 176, 184). In the model, the side chains of Leu 159 and 176 point towards the solvent, possibly constituting a recognition site for the interaction of MGLL with the membrane. It should be noted that because of the low accuracy of the model, other Leucine residues, whose side chains appear to point toward the core of the molecule in the homology model, may also contribute to the hydrophobic properties of MGLL and trigger the need for detergent.

Construct Design

A library of constructs was designed in an effort to generate MGLL protein that would be less prone to aggregation, not require detergent for purification, and be more suitable for high-throughput screening and crystallization. A total of 52 mut-MGLL constructs were generated by mixing and matching the cap-domain mutations, surface mutations, and truncations (Table 1). Seven different hydrophobic Leucine residues (designated as Leu or L) of the cap-domain were selected for mutations (Leu 162, 167, 169, 171, 174, 176, and 184). The Leucine residues were replaced by Serine (designated as Ser or S), Glutamine (designated as Gln, or Q), or Arginine (designated as Arg or R). In addition, eight Lysine residues (designated as Lys or K) were identified at the surface of the MGLL homology model (Lys 36, 160, 165, 188, 206, 226, 259 and 269) and were mutated to Alanine (designated as Ala or A) to increase crystal contacts, promote crystallization, and improve crystal quality. The surface mutations were introduced into the mut-MGLL (hMGLL 1-303 L169S, 176S) double cap-domain mutant construct either independently or in combination with other surface mutations. N-terminal and C-terminal truncation constructs were also designed (Table 1). The N-terminus was truncated at amino acid 9, 19, 26, and 33. The C-terminus was truncated at 297 and 292. The N-terminal and C-terminal truncations were introduced independently or combined with other truncations and were introduced into the mut-MGLL (hMGLL 1-303 L169S, 176S) double cap-domain mutant construct (Table 1). All constructs, including the wt-MGLL (hMGLL 1-303) (SEQ ID NO: 3) construct, were engineered with an N-terminal histidine tag (His tag) followed by a TEV protease cleavage site so that the tag could be cleaved after purification. TEV is highly site-specific protease that is found in the Tobacco Etch Virus (Invitrogen).

Cloning

The cDNA for MGLL was cloned from human brain DNA and used as a template to generate a PCR fragment of full-length wt-MGLL corresponding to amino acids 1-303 of the reference sequence for human MGLL Isoform 2 (SEQ ID NO: 1) The sequences for the 3' and 5' PCR primers are shown below.

```
5' primer:
gagaatttggtattttcaaggtatgccagaggaaagttcccc
(SEQ ID NO: 8)

3' primer:
tggatgtgtatgtttctatcagggtggggacgaagttcc
(SEQ ID NO: 9)
```

The PCR product was purified (GENECLEAN SPIN kits, Qbiogene, Inc), treated with T4 polymerase (New England Biolabs), ligated into the modified pENTR.11cLIC vector, and transformed into TOP10 one shot competent cells (Invitrogen). After sequence confirmation, the mutations were added by Quickchange mutagenesis, (Stratagene). The sequence confirmed plasmids were purified for transfection into insect cells using the BaculoDirect Baculovirus Expression System (Invitrogen). All of the resulting proteins contained an N-terminal His tag followed by a TEV cleavage site and the amino acids of the different MGLL constructs. Viral stock was propagated for two more amplifications at a low multiplicity of infection (MOI) to render a P2 virus stock.

Recombinant Production of wt-MGLL and mut-MGLL

Large-scale expression was carried out in 2-liter shake flasks or WAVE bioreactors (WAVE Products Group, GE Healthcare). The P2 virus was expanded to generate a high titer P3 stock by infecting Sf9 cells in suspension at MOI of 0.3 and harvesting the virus after 72 hours. Cell paste for wt-MGLL (hMGLL 1-303) (SEQ ID NO: 3) and mut-MGLL were obtained by infecting Sf9 cells at a density of $1.5 \times 10^6$ cells/ml with a MOI of 1. Infected cultures were maintained at 27° C. under constant shaking at 140 rpm. Cells were harvested 65-72 hours post-infection by centrifugation at 1000×g for 10 minutes at 4° C. Cell viability were determined by Guava ViaCount or Trypan Blue and routinely were between 60 and 80% at time of harvest. Cell pellets were washed once in phosphate-buffered saline with broad range protease inhibitors and stored at −80° C.

Purification of Wild-Type MGLL (wt-MGLL)

A pilot purification of wt-MGLL (hMGLL 1-303) (SEQ ID NO: 3), performed in the complete absence of detergent, generated no protein (data not shown). A second purification of wt-MGLL (hMGLL 1-303) (SEQ ID NO: 3) was done with detergent in the lysis buffer only. Frozen cell pellets for wt-MGLL (hMGLL 1-303) (SEQ ID NO: 3) were thawed, resuspended, and lysed in Bugbuster® lysis buffer for 1 hour at 4° C. Bugbuster® lysis buffer is a proprietary lysis buffer from Invitrogen that contains detergent. The lysate was clarified by centrifugation at 40,000×g for 1 hr. No detergent was added at this point or during the rest of the purification. From this point forward, the purification protocol and buffers were the same as described below for mut-MGLL. An average of 2.2 mg of wt-MGLL (hMGLL 1-303) (SEQ ID NO: 3) per liter of cell culture was obtained. Further analysis by size exclusion chromatography showed complete aggregation of the purified wt-MGLL (hMGLL 1-303) (SEQ ID NO: 3), which confirmed the need for detergent for wt-MGLL purification as previously described in the literature.

Purification of mut-MGLL

Mutant MGLL (mut-MGLL) constructs were purified in the absence of detergent. Frozen cell pellets were thawed and resuspended in buffer A (50 mM Hepes buffer pH 7.5, 400 mM NaCl, 5% glycerol, 0.05% BME, 1× Complete EDTA-free protease inhibitor cocktail tablets (Roche)), dounce homogenized and mechanically lysed with a microfluidizer processor (Microfluidics). The extract was clarified by centrifugation at 40,000×g for 1 hr. The cleared lysate was loaded on a 1 ml His-Trap FF Crude column (GE-Healthcare) at 4° C. using the AktaXpress system. For larger preparations, a 5 ml His-Trap FF Crude column was used. The column was washed with 10-15 column volumes (CV) of buffer A containing 30 mM imidazole and mut-MGLL was eluted with 5 CV of 50 mM Hepes buffer pH 7.5, 400 mM NaCl, 5% glycerol, 0.05% BME, 400 mM imidazole. In most preparations, 30 mM imidazole was included in Buffer A from the beginning of the preparation to reduce non-specific binding on the His-Trap column. In addition, a slightly lower imidazole concentration of 350 mM was used in the final elution during later preparations to further improve purity. Glycerol concentration was also reduced to 4% to avoid back pressure problems on the AktaXpress, after it was determined that mut-MGLL constructs were stable in 2% glycerol. The elution peak was directly loaded on a Superdex 200 HR 16/60 preequilibrated with 50 mM Hepes pH7.5 buffer containing 200 mM NaCl, 2% glycerol, 2 mM DTT, 2 mM EDTA.DTT. Fractions were analysed by SDS-PAGE. Fractions containing mut-MGLL were pooled. Purification yields were determined by Bradford assay using the protein assay kit from BioRad according to manufacturer's instruction with BSA as a standard (Bradford 1976).

The majority of constructs containing N-terminal and/or C-terminal truncations did not have high enough expression to allow for purification of soluble protein (Table 1).

Constructs that were evaluated containing just the cap-domain mutations generated between 0.7 and 4.5 mg/L, except the mut-MGLL construct containing the L174Q mutation, which showed no expression (Table 1). Analysis by size exclusion chromatography showed that the purified mut-MGLL proteins were 90% monomeric and only 10% aggregated compared to 100% aggregation for wt-MGLL (hMGLL 1-303) (SEQ ID NO: 3) (FIG. 1A), which indicated that the mutations significantly improved protein solubility and eliminated the need for detergent during purification.

Constructs that were evaluated with a combination of cap-domain and surface mutations showed expression levels between 0.5 and 3.6 mg/L and were also ~90% monomeric on SDS Page as well (data not shown).

TEV Cleavage

To remove the N-terminal His tag, 0.2 units of TEV Protease for each ug of mut-MGLL were added to the mut-MGLL pool. The reaction was done overnight at 4° C. Cleavage of the histidine tag was monitored by SDS-PAGE.

Complex Formation

For crystallization trials, compounds were added in a 1:2 molar ratio (mut-MGLL:compound). TEV cleaved mut-MGLL was first diluted to 0.3 mg/ml with buffer containing 50 mM Hepes pH 7.5, 200 mM NaCl, 2% Glycerol, 2 mM DTT, and 2 mM EDTA. Compounds were added to the diluted protein and the mixture was incubated overnight at 4° C. After the overnight incubation, the mixture was concentrated to a final protein concentration of 6.0 mg/ml using a Ultrafree membrane (10 KDa cut-off). At this stage the purity was >98% as determined by SDS-PAGE and the protein was ready for crystallization trials.

Circular Dichroism (CD)

One construct, TEV cleaved mut-MGLL (hMGLL 1-303 L169S, L176S) (SEQ ID NO: 5), was selected for further characterization by CD to ensure that the mutations introduced did not adversely affect protein conformation and activity. Circular dichroism experiments were performed on a Circular Dichroism Spectrometer Model 202 from Aviv Instruments Inc. The CD scans of wt-MGLL (hMGLL 1-303) (SEQ ID NO: 3) and TEV cleaved mut-MGLL (hMGLL 1-303 L169S, L176S) (SEQ ID NO: 5) (5 μM protein in 10 mM cacodylic acid pH 7 and 140 mM NaCl) were measured from 200 to 260 nm. Temperature melts were monitored at 210 nm. The CD spectra were converted to molar ellipticity and are shown in FIG. 1B.

The CD scans for the wt-MGLL (hMGLL 1-303) (SEQ ID NO: 3) purified in the presence of detergent and TEV cleaved mut-MGLL (hMGLL 1-303 L169S, L176S) (SEQ ID NO: 5) were similar indicating that the two enzymes had a similar conformation (FIG. 1B). The scans were characteristic of proteins with high alpha-helical content as expected for a lipase.

Kinetic Analysis

To ensure that the mutations engineered did not adversely affect protein activity, a number of the newly generated MGLL mutants were analyzed using by enzyme assay and then compared to wt-MGLL (hMGLL 1-303) (SEQ ID NO: 3). A small fluorescent substrate, 4-methyl coumarin butyrate (4MC-B) was used to compare the activity of the engineered mutants to the activity of wt-MGLL (hMGLL 1-303) (SEQ ID NO: 3). The catalytic efficiency ($k_{cat}/K_M$) for the hydrolysis of the 4MC-B was similar for wt-MGLL (hMGLL 1-303) (SEQ ID NO: 3) and all MGLL mutants tested (Table 2). A larger more aliphatic fluorescent substrate, Coumarin Arachidonate (C-A), structurally more closely related to the MGLL natural substrate, 2-AG, was used to compare the activity of wt-MGLL (hMGLL 1-303) (SEQ ID NO: 3) to TEV cleaved mut-MGLL (hMGLL 1-303 L169S, L176S) (SEQ ID NO: 5). The catalytic efficiency for the hydrolysis of the C-A substrate was equivalent between wt-MGLL (hMGLL 1-303) (SEQ ID NO: 3) and TEV cleaved mut-MGLL (hMGLL 1-303 L169S, L176S) (SEQ ID NO: 5), which confirmed that the mutations did not affect MGLL activity (Table 2).

The Michaelis-Menten parameters for the hydrolysis of 4-methylcoumarin butyrate (4MC-B) and coumarin arachidonate (C-A) substrate were determined using 4-5 nM of MGLL in 20 mM Pipes pH 7 and 150 mM NaCl at 37° C. The change in fluorescence due to substrate hydrolysis was monitored using excitation/emission wavelengths of 335/440 in a Safire II instrument from Tecan. The hyperbolic rates versus substrate concentration curves for the hydrolysis of 4MC-B were fit to the Michaelis-Menten equation using Excel.

$$v = \frac{V_{max} * [S]}{K_M + [S]}$$

The solubility limit of coumarin arachidonate (C-A) substrate did not allow for the determination of $K_M$ and $k_{cat}$. The apparent $k_{cat}/K_M$ ratio for the hydrolysis of C-A was determined at $[S] \ll K_M$. The apparent $K_M$ for C-A was estimated to be >30 μM. The $k_{cat}/K_M$ values reported are the average from independent values determined from five substrate concentrations ranging from 700 to 40 nM.

Thermal Stability

The Thermofluor® assay is a powerful tool to screen for small molecule inhibitors interacting with a protein's active site or allosteric site. The assay detects small changes in the intrinsic melting temperature of proteins based on binding of ligands. Compounds that interact preferentially with the native form of the protein will increase the $T_m$, the temperature at which half of the protein is unfolded (Pantoliano et al. 2001). The technique monitors changes in the fluorescent intensity of dyes such as 1-anilinonaphthalene-8-sulfonic acid (1,8-ANS). The fluorescent dyes are quenched in aqueous environments but increase in fluorescence on binding to the hydrophobic core of denatured proteins.

Thermofluor® assays were conducted to characterize wt-MGLL (hMGLL 1-303) (SEQ ID NO: 3) and mut-MGLL (hMGLL 1-303 L169S, L176S) and evaluate if the MGLL mutants could be used for high-throughput screening using Thermofluor®. Three microliters of protein at a concentration of 0.05 mg/ml in 50 mM Pipes pH 7, 200 mM NaCl, 100 µM 1,8-ANS, and 0.001% Tween was added to pre-dispensed compound plates. Wells were overlaid with silicone oil (1 µL, Fluka, type DC 200) to prevent evaporation. Final compound concentrations varied from 150 to 0.15 µM. Assay plates were heated at a rate of 1° C./min for all experiments over a temperature range sufficient to measure protein unfolding. Fluorescence was measured by continuous illumination with UV light (Hamamatsu LC6) supplied via fiber optic and filtered through a custom band-pass filter (380-400 nm; >60D cutoff). Fluorescence emission was detected by measuring light intensity using a CCD camera (Sensys, Roper Scientific) filtered to detect emission at 500±25 nm, resulting in simultaneous and independent readings of all 384 wells. One or more images were collected at each temperature, and the sum of the pixel intensity in a given area of the assay plate was recorded vs temperature, and fit to standard equations to yield the $T_m$.

Figure 5:
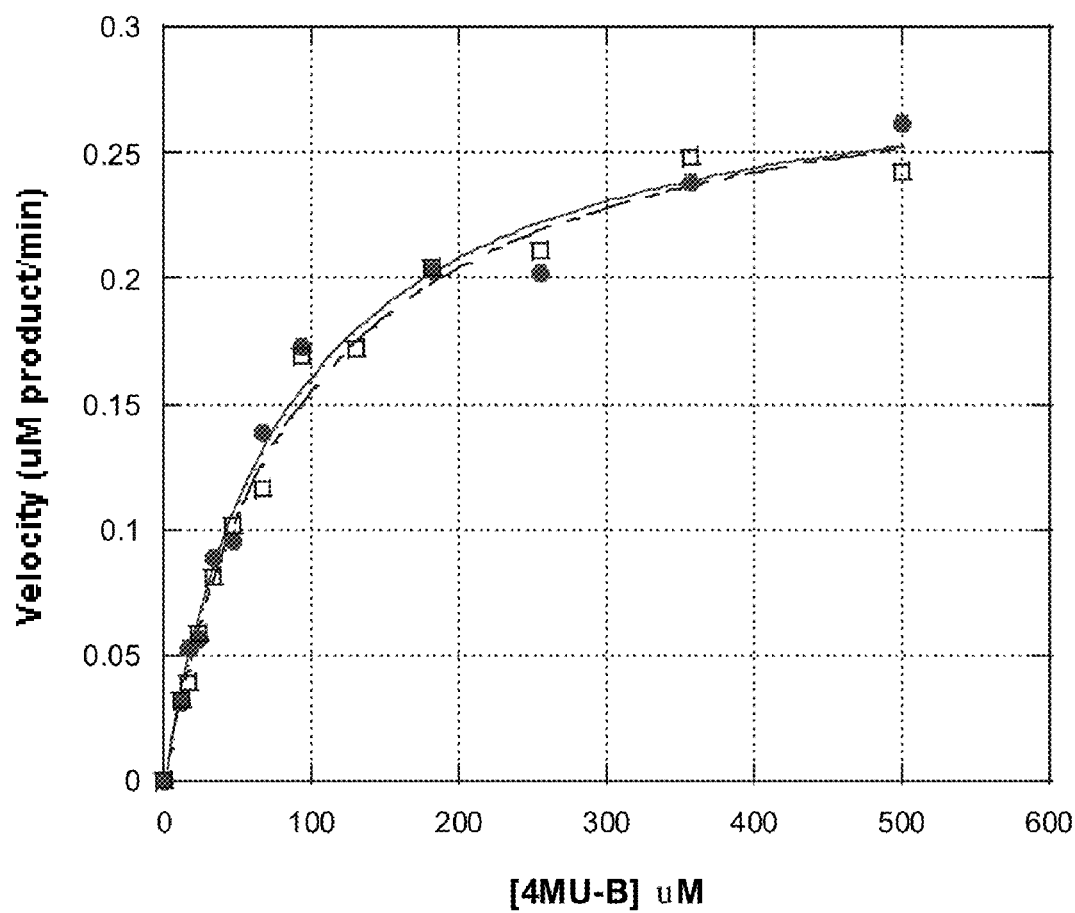
FIG. 5: Shown are duplicate Michaelis-Menten curves for the hydrolysis of TEV cleaved mut-MGLL (hMGLL 1-303 L169S, L176S) (SEQ ID NO: 5).
Figure 6:
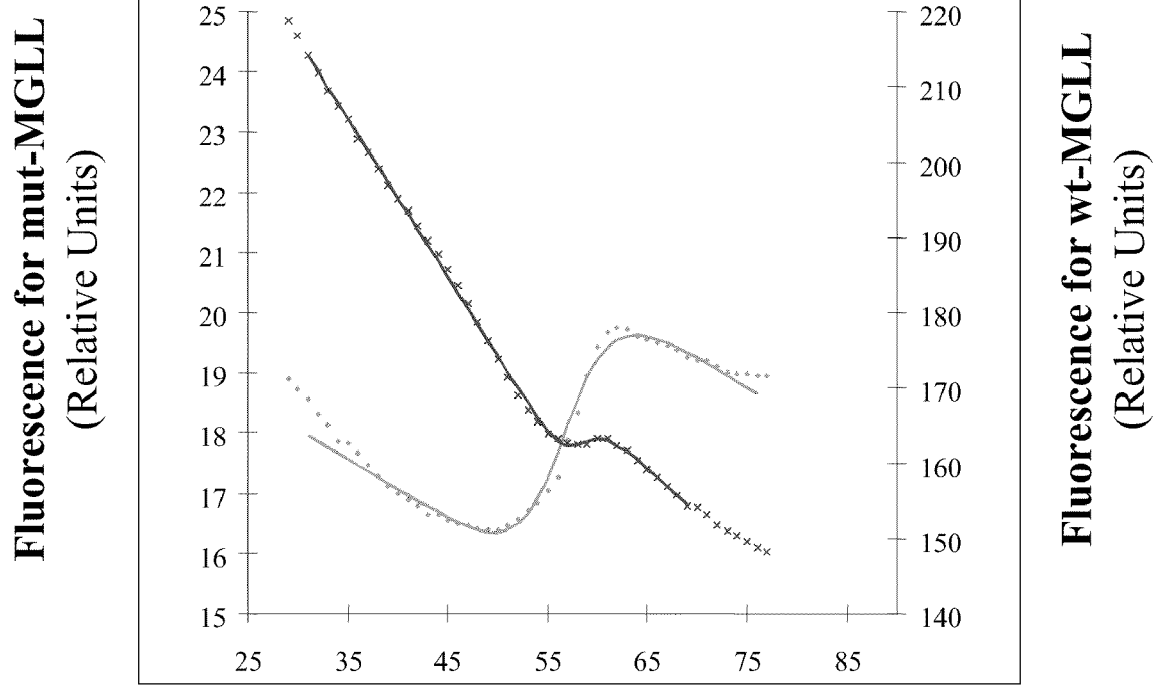
FIG. 6: Shown are thermal shift data of the melting transitions for wt-MGLL (hMGLL 1-303) (SEQ ID NO: 3) (green line) and TEV cleaved mut-MGLL (hMGLL 1-303 L169S, L176S) (SEQ ID NO: 5) (red line). The midpoint of the melting transition was 58° C. for wt-MGLL (hMGLL 1-303) (SEQ ID NO: 3) and 56.7° C. for TEV cleaved mut-MGLL (hMGLL 1-303 L169S, L176S) (SEQ ID NO: 5).
Figure 8:
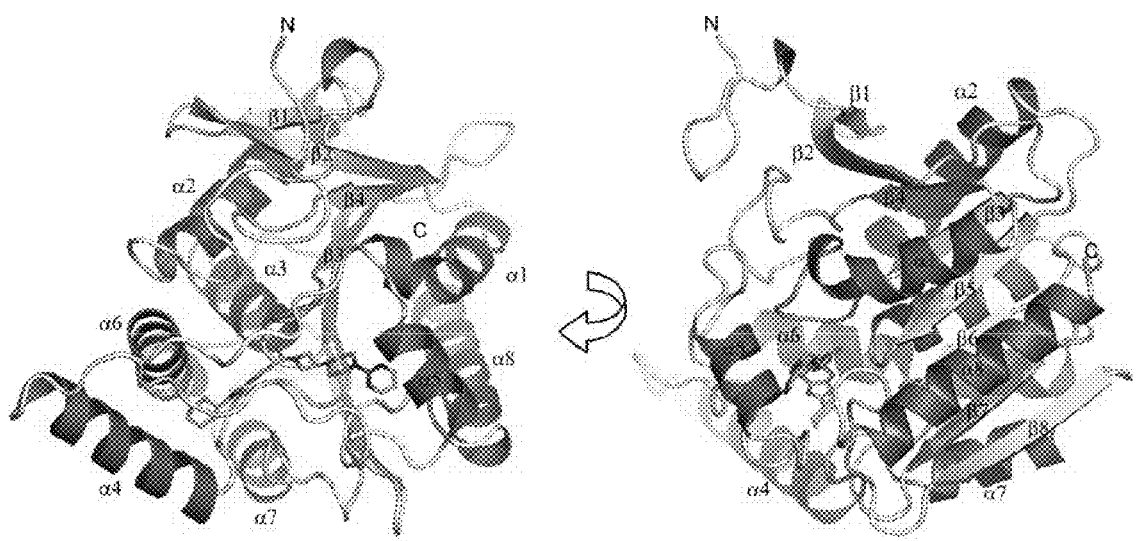
FIG. 8: Shown is a ribbon diagram of the structure of the complex of TEV cleaved mut-MGLL (hMGLL 1-303 L169S, L176S, K36A) (SEQ ID NO: 7) and Compound 2. Color-coding is according to secondary structure (α-helices: magenta, β-sheets: yellow). The ligand (Compound 2) is drawn in ball-and-stick representation (green). The protein adopts a typical α/β hydrolase fold comprised of 8 β-sheets, with β2 being antiparallel to the other sheets. The inhibitor is located in the active site, which is capped by loops connecting α4 to α6.
Figure 9:
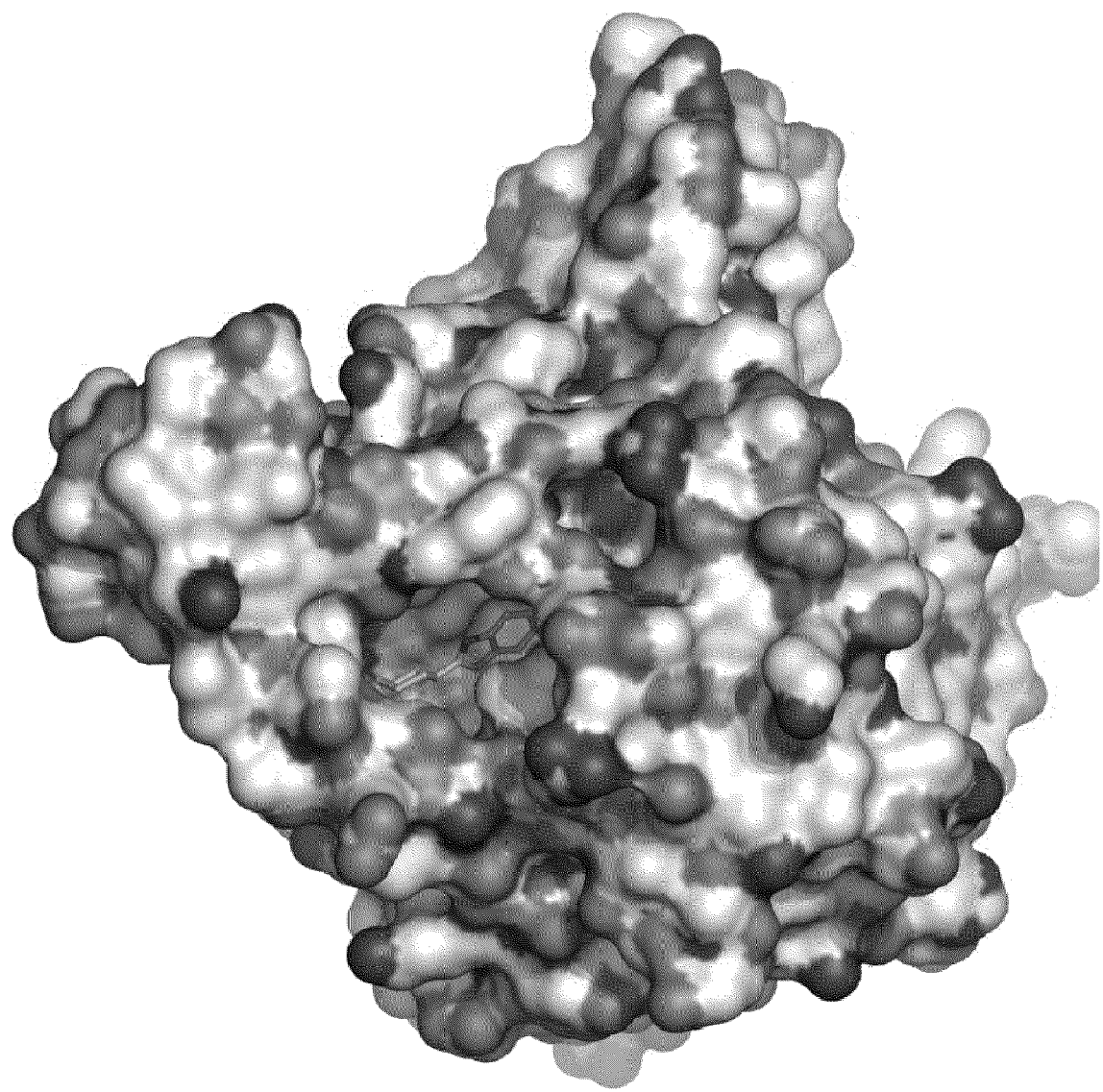
FIG. 9: Shown is a surface representation of the structure for the complex of TEV cleaved mut-MGLL (hMGLL 1-303 L169S, L176S, K36A) (SEQ ID NO: 7) and Compound 2.

The study using Thermofluor® showed that wt-MGLL (hMGLL 1-303) (SEQ ID NO: 3) had a very poor transition, characteristic for aggregated or unfolded proteins (FIG. 5). TEV cleaved mut-MGLL (hMGLL 1-303 L169S, L176S) (SEQ ID NO: 5), however, gave a strong transition with a $T_m$ value of 56.7° C., indicating that the engineered mutation produced a more soluble MGLL protein that was suitable for high-throughput screening.

Crystallization

All mutants were purified according to the procedure described above and submitted for crystallization trials. Purity greater than 95% as determine by SDS Page was achieved for all constructs. Combinations of high-throughput and manual crystallization screens were used. Several constructs generated crystals but only crystallization conditions containing detergent yielded crystals (data not shown). Apo proteins generated crystals diffracting between 8.0 Å and 9.0 Å only, despite extensive optimization trials. Co-crystallization with methyl arachidonyl fluorophosphonate (MAFP) did not significantly improve diffraction.

Co-crystallization of TEV cleaved mut-MGLL (hMGLL 1-303 L169S, L176S, K36A) (SEQ ID NO: 7) with Compound 1 generated crystals that diffracted to 2.3 Å, but with diffused scattering in one orientation. Further optimization experiments did not improve data quality with that complex. High quality diffraction was achieved by co-crystallization of TEV cleaved mut-MGLL (hMGLL 1-303 L169S, L176S, K36A) (SEQ ID NO: 7) with Compound 2, a compound that was 10 fold more potent than Compound 1. Crystallization of the TEV cleaved mut-MGLL (hMGLL 1-303 L169S, L176S, K36A) (SEQ ID NO: 7) and Compound 2 complex was achieved at 22° C. with a hanging droplet containing 6 mg/ml protein solution combined with a modified well solution containing 8% polyethylene glycol monomethyl ether 5000 molecular weight (PEG MME 5K), 100 mM Na Citrate pH 5.5 and 2% n-Octyl-Beta-D-Glucopyranoside (OBG), which was suspended over a well solution containing 6% PEG MME 5K, 100 mM Na Citrate pH 5.5 and 2% OBG. Crystals, however, were not generated spontaneously. A seed solution generated from poor quality crystals obtained previously was used to seed crystallization droplets. The optimal volume ratios for obtaining good quality crystals were 1 ul protein solution, 0.5 ul well solution, and 0.2 ul diluted seed stock solution. Any increase in protein concentration resulted in heavy showers and stacked plate crystals despite adjustments in crystallization reagent concentration. Protein supplied at concentrations higher than 6 mg/ml and diluted to 6 mg/ml before crystallization trials also resulted in heavy crystal showers. Final resolution was 1.3 Å for the TEV cleaved mut-MGLL (hMGLL 1-303 L169S, L176S, K36A) (SEQ ID NO: 7) and Compound 2 complex.

Structure Determination

Crystals were harvested, transferred to 16% PEG MME 5K, 100 mM Na-MES pH 6.0, 25% glycerol and flash frozen in liquid nitrogen. Datasets were collected on a Rigaku M007HF generator at 100K or at the ID19 beamline at IMCA-CAD at the Advanced Photon Source, Chicago. A summary of the data-collection statistics is in Table 3. The data was processed in the HKL2000 suite (Otwinowski and Minor 1997) and the structure was solved by molecular replacement using a modified structure of "Non-haem bromoperoxidase BPO-A1" (PDB ID 1A8Q) as search model in *PHASER* (McCoy et al. 2007). The initial rebuilding was performed using the default protocol in the AutoBuild Wizard in *PHENIX* (Adams et al. 2002; Adams et al. 2004; Terwilliger et al. 2008), refinement and automated water picking was carried out in *PHENIX.refine* (Adams et al. 2002; Adams et al. 2004; Terwilliger et al. 2008); *Coot* (Emsley and Cowtan 2004) was employed for model building, ligand placement and manual assignment of water molecules. Ligand restraints were generated in *PHENIX.elbow* (Adams et al. 2002; Adams et al. 2004) and the final model validated using tools implemented in Coot; Figures were generated in *PyMol* (DeLano 2002). Coordinates for the structure of the complex of TEV cleaved mut-MGLL (hMGLL 1-303 L169S, L176S, K36A) (SEQ ID NO: 7) with Compound 2 are included as Table 5.

Overall Structure of MGLL

MGLL is part of the sub-family of lipid hydrolases, which in turn is part of a larger family of α/β-hydrolases with diverse catalytic functions. Members of this super-family include: ester hydrolases, lipid hydrolases, thioester hydrolases, peptide hydrolases, haloperoxidases, dehalogenases epoxide hydrolases and C—C bond breaking enzymes (Holmquist 2000). All of these enzymes share a common folding motif called the α/β-hydrolase fold (Ollis et al. 1992; Heikinheimo et al. 1999). This fold is characterized by eight β-sheets flanked on both sides by α-helices. β-sheet 2 is antiparallel to the other sheets and the first and last helix (α1 or αA and α6 or αF) are located on one side of the sheets, whereas the remainder of the helices are present on the opposite side. The α/β-hydrolase fold tolerates a vide variety of inserts without losing the core folding motif. These inserts serve to modify and regulate the catalytic activity of the respective proteins. They can occur in several locations, but are mostly located in a loop region between strand β6 and helix α6.

Herein is described the structure of the inhibitor bound form of human MGLL Isoform 2 (TEV cleaved mut-MGLL (hMGLL 1-303 L169S, L176S, K36A) (SEQ ID NO: 7) with Compound 2), which has been determined by molecular replacement to a resolution of 1.3 Å. The structure of MGLL conforms very closely to the canonical α/β-hydrolase fold. The structure is characterized by eight β-sheets, which form a partial β-barrel adorned on both sides with eight α-helices. MGLL contains two additional helices (α4 (αD'$_1$) and α5 D'$_2$)), which are part of the cap-domain and are inserted in the protein sequence between sheet β6 and helix α6 (αD). Helices α1 (αA) and (α8 (αF) are located on the concave side of the barrel and helices α2 (αB), α3 (αC), α6(D) and α7(E) are on the convex side. Both cap-domain helices are oriented in front of the molecule perpendicular to the plane of the β-barrel.

Interestingly the overall structure of this mammalian MGLL is closer to bacterial lipases than any mammalian lipase when the structure is compared to the latest release of the Protein Databank using the protein structure-matching tool (SSM) at the European Institute of Bioinformatics (EBI) (Boutselakis et al. 2003). The 3D-alignment produces several close hits against bacterial Bromoperoxidases, Chloroperoxidases and Arylesterases. The same hits were also produced by a PHI-blast search of the Protein Databank against the protein sequence alone. Since no similar 3D-hits were found against any diacylglycerol lipases or triacylglycerol lipases, it can be inferred that the structural requirements for cleavage of triacylglycerol and diacylglycerol esters are substantially different from those required for the cleavage of mono-glycerol esters. It appears as if these classes of proteins, even though they perform similar functions, represent a different branch on the evolutionary tree of lipases.

Figure 10:
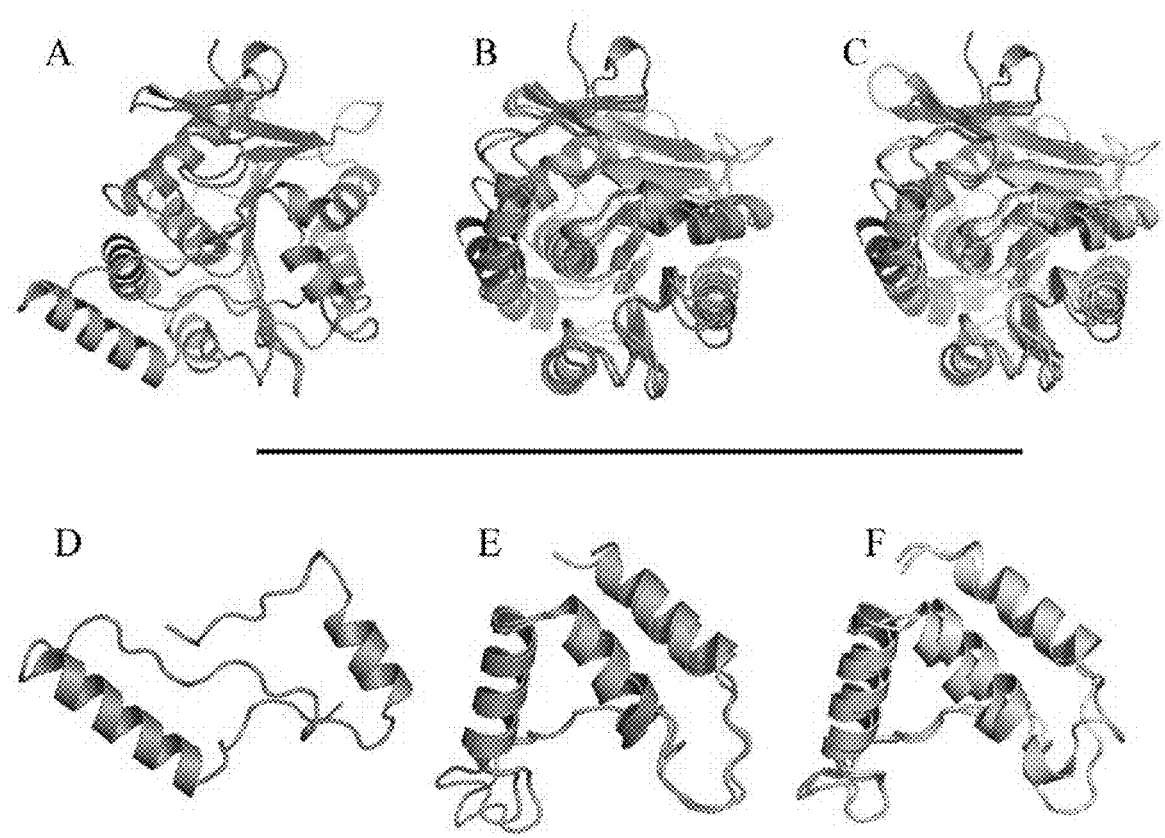
FIG. 10: A. Shown is a ribbon diagram of MGLL with the cap-domain (residues 145-206) colored cyan to illustrate the location of the cap-domain. B. Shown is an overlay of the ribbon diagram of MGLL (orange) onto Bromoperoxidase A1 (salmon) and Chloroperoxidase L (green); C. Shown is an overlay of the ribbon diagram of MGLL (orange) onto P. putida Esterase (grey) and Gamma Lactamase (yellow). The cap-domain was omitted for clarity to show the good alignment between the core α/β-hydrolase in all structures. D. Shown is a ribbon diagram of the MGLL cap-domain. Superposition of different cap-domains highlighting the different arrangement between MGLL and other hydrolases. E. Shown is an overlay of the ribbon diagrams of the cap-domains of Bromoperoxidase A1 (salmon) and Chloroperoxidase L (green); F. Shown is an overlay of the ribbon diagrams of the cap-domains of P. putida Esterase (grey) and Gamma Lactamase (yellow).
Figure 11:
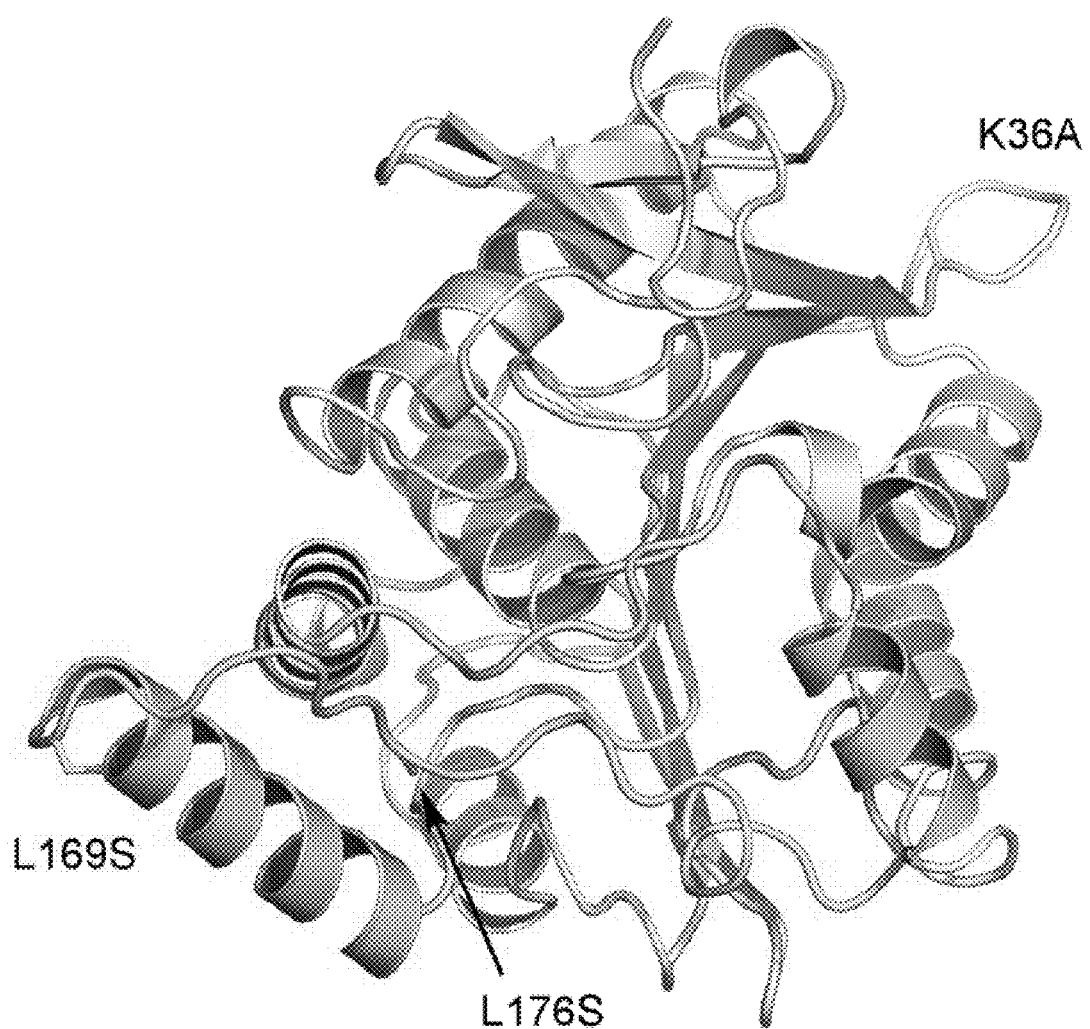
FIG. 11: Shown is a ribbon diagram of MGLL showing the location of mutations L169S and L176S in the cap-domain that prevented protein aggregation and K36A on the loop between β2 and β4 that would make interactions with a symmetry mate if present in the wild-type protein.

Superposition of several hits from the 3D-alignment (Chloroperoxidase L, PDBID:1A88; Bromoperoxidase A1, PDBID:1A8Q; P. putida Esterase, PDBID:1ZOI; Gamma Lactamase, PDBID: 1HKH) shows that the (α/β-hydroxylase core without the cap-domain superimposes very well (Table 4 and FIG. 10). The largest differences are seen in the first 20 residues of the N-terminus of MGLL, for which there is no complement in the other proteins. Further differences are evident in helix α6 (D). In MGLL α6 continuously spans approximately 20 residues, whereas in the other structures it is partially unraveled and split into two pieces connected by a short loop.

MGLL Binding Pocket

Compound 2 is bound in an extended and closed binding pocket, which is located between helices α4, α6, α7 and α5. Even though the solvent accessible surface area of the compound (712 Å$^2$) is fairly large, it is almost completely enclosed by the protein. The protein accomplishes this by employing a so-called "cap-domain", "lid", or "flap", which regulates access to the binding site based on the membrane bound state of the protein. The cap-domain is compromised of residues from helices α4 to α5 (also referred to as αD'$_1$ and αD'$_2$ throughout the literature). The catalytic triad of MGLL consists of residues Ser122, Asp239, His269 and is located in the center of the binding pocket. The catalytic nucleophile Ser122 resides on a tight turn between strand β5 and helix α3, which is also commonly referred to as the "nucleophilic elbow". The structurally conserved network of hydrogen-bond donors, which comprises the nucleophilic elbow and the loop connecting α1 and β3 (Gly50, Ala51, Met 123 and Gly124) is called the oxyanion hole and serves to stabilize the anionic transition state of the catalytic reaction. The amide carbonyl of Compound 2 points into the oxyanion hole and forms a critical hydrogen bond with the backbone amide nitrogen of Met123 adjacent to the catalytic Serine. The azetidine-piperazine-pyrazine part of the ligand projects into a narrow amphiphilic pocket and fills the available space almost completely. This portion of the ligand does not participate in hydrogen bond interactions with the protein, but one of the pyrazine nitrogens forms an H-bond to a water-network involving two buried water molecules and the side-chains of residues Glu53, Arg57 and His272. A face-to-face π-stacking interaction with of the pyrazine ring with Tyr194 provides further interaction energy.

The binding pocket on the benzoxazole-cyclohexane site of the ligand is less occluded than its counter part on the opposite site. The benzoxazole portion of the ligand is located in a hydrophobic environment constituted mainly from side chains of aliphatic residues. The cyclohexane portion projects into a more spacious void, and along with the benzoxazole, is the only part of the inhibitor, which is accessible by solvent in the protein bound state. These parts of the ligand form mostly van der Waals interactions with the protein. The cyclohexane part of the molecule is less well ordered than the remainder of the ligand. This can be explained by the fact that this region of the cap-domain (α4 and part of the loop connecting to α5) with which the inhibitor interacts, is displays significantly higher temperature factors as compared to the rest of the protein. The elevated temperature factors signify the inherent flexibility of this region, which probably facilitates its displacement from the surface of the protein during ligand binding and release.

Enabling Mutations

In order to obtain the MGLL structure several enabling mutations were required. Two mutations in the lid sub-domain (L169S and L176S) helped to increase solubility of the protein enough to prevent aggregation and to eliminate the need for detergents in protein purification. L169S is located at the C-terminal end of helix α4 (αD'$_1$) and L176S on a loop connecting (α4 to α5. Interestingly, the cap-domain in the engineered protein still contains quite a few surface exposed aliphatic residues, but the mutations are apparently sufficient to reverse the inherent lipophilic character of the protein enough to prevent aggregation in solution.

The K36A surface mutation was inspired by a series of reports indicating that the replacement of flexible residues with high conformational entropy present on the surface of proteins helps to promote crystallization under certain circumstances (Longenecker et al. 2001; Mateja et al. 2002). The K36A mutation is present on a loop connecting sheets β$_2$ and β3. This loop interacts with the cap-domain of a neighboring symmetry related molecule between Val170 and Pro172. Analysis of this packing interaction reveals that the Lysine would have fit snugly into this packing interface, so the immediate reason necessitating its absence for crystallization is not obvious.

The mutation appears nevertheless to be beneficial, since this particular part of the cap-domain exhibits relatively high temperature factors and is less well ordered than other parts of the molecule. It is conceivable that this high dynamic mobility would cause the lid to clash into Lys36 in certain parts of the conformational pool. The K36A mutation would eliminate this potential for clashes and may thus contribute to the successful crystallization of the molecule.

Tables

TABLE 1

| Engineered forms of MGLL | Purification yield mg/L |
|---|---|
| Cap Mutations | |
| mut-MGLL (1-303) L169S, L176S | 4.5 |
| mut-MGLL (1-303) L167Q | 2.3 |
| mut-MGLL (1-303) L171Q | 0.7 |
| mut-MGLL (1-303) L174Q | 0 |
| mut-MGLL (1-303) L167Q, L171Q | 5 |
| mut-MGLL (1-303) L167Q, L174Q | 7 |
| mut-MGLL (1-303) L171Q, L174Q | 1.5 |
| mut-MGLL (1-303) L167Q, L171Q, L174Q | 0 |
| mut-MGLL (1-303) L169Q, L176Q | *N.D. |
| mut-MGLL (1-303) L169S | *N.D. |
| mut-MGLL (1-303) L176S | *N.D. |
| mut-MGLL (1-303) L162S | *N.D. |
| mut-MGLL (1-303) L162Q | *N.D. |
| mut-MGLL (1-303) L162R | *N.D. |
| mut-MGLL (1-303) L184S | *N.D. |
| mut-MGLL (1-303) L184Q | *N.D. |
| mut-MGLL (1-303) L184R | *N.D. |
| mut-MGLL (1-303) L169S | *N.D. |
| mut-MGLL (1-303) L169Q | *N.D. |
| mut-MGLL (1-303) L169R | *N.D. |
| mut-MGLL (1-303) L176S | *N.D. |
| mut-MGLL (1-303) L176Q | *N.D. |
| mut-MGLL (1-303) L176R | *N.D. |
| mut-MGLL (1-303) L167S | *N.D. |
| mut-MGLL (1-303) L167R | *N.D. |
| mut-MGLL (1-303) L171S | *N.D. |
| mut-MGLL (1-303) L171R | *N.D. |
| mut-MGLL (1-303) L174S | *N.D. |
| mut-MGLL (1-303) L174R | *N.D. |
| Cap Mutations + Surface Mutations | |
| mut-MGLL (1-303) L169S, L176S, K36A | 3.6 |
| mut-MGLL (1-303) L169S, L176S, K160A | 0.7 |
| mut-MGLL (1-303) L169S, L176S, K165A | 0.5 |
| mut-MGLL (1-303) L169S, L176S, K226A | 2.3 |
| mut-MGLL (1-303) L169S, L176S, K36A, K226A | 1.5 |
| mut-MGLL (1-303) L169S, L176S, K36A, K188A | *N.D. |
| mut-MGLL (1-303) L169S, L176S, K36A, K206A | *N.D. |
| mut-MGLL (1-303) L169S, L176S, K36A, K269A | *N.D. |
| mut-MGLL (1-303) L169S, L176S, K188A | *N.D. |
| mut-MGLL (1-303) L169S, L176S, K206A | *N.D. |
| mut-MGLL (1-303) L169S, L176S, K259A | *N.D. |
| Cap Mutations + Truncations | |
| mut-MGLL (9-303) L169S, L176S | 2 |
| mut-MGLL (9-297) L169S, L176S | 1 |
| mut-MGLL (1-292) L169S, L176S | 0.5 |
| mut-MGLL (19-303) L169S, L176S | 0 |
| mut-MGLL (19-297) L169S, L176S | 0 |
| mut-MGLL (19-292) L169S, L176S | 0 |
| mut-MGLL (26-303) L169S, L176S | 0 |
| mut-MGLL (26-297) L169S, L176S | 0 |
| mut-MGLL (26-292) L169S, L176S | 0 |
| mut-MGLL (33-303) L169S, L176S | 0 |
| mut-MGLL (33-297) L169S, L176S | 0 |
| mut-MGLL (33-292) L169S, L176S | 0 |

*N.D. is Not Determined

TABLE 2

4MC-B

| Construct | $K_M$ (uM) | $K_{cat}$ (uM$^{-1}$min$^{-1}$) | $K_{cat}/K_M$ (uM$^{-1}$min$^{-1}$) |
|---|---|---|---|
| wt-MGLL.1-303 | 162 | 68 | 0.42 |
| CAP MUTANTS | | | |
| mut-MGLL. 1-303, L169S, L176S | 136 | 48 | 0.35 |
| mut-MGLL 9-303, L169S, L176S | 88 | 27 | 0.31 |
| mut-MGLL 9-297, L169S, L176S | 126 | 26 | 0.21 |
| mut-MGLL 1-303, L171Q | 105 | 51 | 0.48 |
| mut-MGLL 1-303, L167Q, L171Q | 84 | 59 | 0.71 |
| mut-MGLL. 1-303, L167Q, L174Q | 84 | 70 | 0.83 |
| mut-MGLL 1-303, L171Q, L174Q | 89 | 47 | 0.52 |
| CAP + SURFACE MUTANTS | | | |
| mut-MGLL 1-303, L169S, L176S, K36A | 124 | 51 | 0.41 |
| mut-MGLL. 1-303, L169S, L176S, K160A | 90 | 30 | 0.33 |
| mut-MGLL. 1-303, L169S, L176S, K165A | 137 | 27 | 0.2 |
| mut-MGLL 1-303, L169S, L176S, K226A | 110 | 38 | 0.35 |
| mut-MGLL 1-303, L169S, L176S, K36A, K226A | 123 | 30 | 0.25 |

C-A

| Construct | $K_{cat}/K_M$ (uM$^{-1}$min$^{-1}$) |
|---|---|
| wt-MGLL 1-303 | 0.09 |
| mut-MGLL 1-303, L169S, L176S | 0.1 |

TABLE 3

|  | mut-MGLL complex with Compound 2 |
|---|---|
| Data collection | |
| Wavelength (Å) | 1.0 |
| Resolution (Å) | 1.3 |
| Space group | C222$_1$ |
| Unit cell parameters (Å) | a = 93.95, b = 128.45, c = 60.6 |
| No. of reflections | 336035 |
| No. of unique reflections | 79954 |
| Redundancy | 4.2 (1.8) |
| Completeness (%) | 89.2 (53.3) |
| R$_{merge}$ | 6.2 (31.9) |
| I/σ(I) | 19.0 (1.75) |
| Refinement | |
| No. of reflections | 75577 |
| No. of reflections in R$_{free}$ set | 1896 |
| Total No. of non H atoms | 2720 |
| No. of protein atoms | 2320 |
| No. of ligand atoms | 33 |
| No. of solvent molecules | 377 |
| R-factor (%) | 17.8 |
| R$_{free}$ (%) | 20.6 |
| R.M.S. Deviation from ideal geometry | |
| Bonds (Å) | 0.006 |
| Angles (°) | 1.050 |
| B-factors (Å$^2$) | |
| Protein | 14.8 |
| Ligand | 10.2 |
| Ramachandran Plot | |
| Preferred Regions (%) | 96.6 |
| Allowed regions (%) | 3.0 |
| Disallowed regions (%) | 0.4 |

TABLE 4

|  | Chloro-peroxidase L | Bromoperoxidase A1 | *P. fluorescens* Arylesterase | Gamma Lactamase |
|---|---|---|---|---|
| Distance [Å] | 1.23 | 1.27 | 1.29 | 1.44 |
| No. of matching residues | 168 | 165 | 175 | 173 |

TABLE 5

(Table 5 discloses SEQ ID NO: 10):

```
CRYST1    93.947  128.145   60.602   90.00  90.00  90.00 C 2 2 21
SCALE1      0.010644 -0.000000 -0.000000      0.00000
SCALE2      0.000000  0.007804  0.000000      0.00000
SCALE3      0.000000  0.000000  0.016501      0.00000
ATOM      1  N    PRO  A   7     -24.135  50.110  -0.751  1.00  38.62   N
ATOM      2  CA   PRO  A   7     -24.819  48.812  -0.835  1.00  48.66   C
ATOM      3  C    PRO  A   7     -23.834  47.683  -1.121  1.00  27.13   C
ATOM      4  CB   PRO  A   7     -25.762  48.987  -2.031  1.00  56.71   C
ATOM      5  CG   PRO  A   7     -25.901  50.460  -2.210  1.00  69.43   C
ATOM      6  CD   PRO  A   7     -24.588  51.041  -1.797  1.00  66.62   C
ATOM      7  O    PRO  A   7     -23.163  47.709  -2.152  1.00  27.37   O
ATOM      8  N    ARG  A   8     -23.737  46.710  -0.219  1.00  19.22   N
ATOM      9  CA   ARG  A   8     -22.858  45.567  -0.448  1.00  17.80   C
ATOM     10  C    ARG  A   8     -23.445  44.739  -1.589  1.00  10.71   C
ATOM     11  CB   ARG  A   8     -22.696  44.715   0.818  1.00  16.23   C
ATOM     12  CG   ARG  A   8     -22.085  45.452   2.003  1.00  25.04   C
ATOM     13  CD   ARG  A   8     -20.586  45.608   1.857  1.00  23.77   C
ATOM     14  NE   ARG  A   8     -19.862  44.389   2.217  1.00  19.99   N
ATOM     15  CZ   ARG  A   8     -19.479  44.080   3.453  1.00  18.56   C
ATOM     16  NH1  ARG  A   8     -19.744  44.894   4.472  1.00  16.20   N
ATOM     17  NH2  ARG  A   8     -18.816  42.959   3.671  1.00  13.17   N
ATOM     18  O    ARG  A   8     -24.639  44.451  -1.605  1.00  11.63   O
ATOM     19  N    ARG  A   9     -22.589  44.386  -2.546  1.00  17.31   N
ATOM     20  CA   ARG  A   9     -23.017  43.667  -3.747  1.00  15.23   C
ATOM     21  C    ARG  A   9     -22.202  42.401  -3.960  1.00  12.13   C
ATOM     22  O    ARG  A   9     -21.048  42.328  -3.554  1.00  15.48   O
ATOM     23  CB   ARG  A   9     -22.851  44.558  -4.984  1.00  20.10   C
ATOM     24  CG   ARG  A   9     -23.745  45.788  -5.019  1.00  21.95   C
ATOM     25  CD   ARG  A   9     -23.339  46.711  -6.167  1.00  29.40   C
ATOM     26  NE   ARG  A   9     -24.116  47.949  -6.182  1.00  31.93   N
ATOM     27  CZ   ARG  A   9     -25.269  48.098  -6.824  1.00  41.04   C
ATOM     28  NH1  ARG  A   9     -25.782  47.087  -7.507  1.00  25.69   N
ATOM     29  NH2  ARG  A   9     -25.911  49.259  -6.786  1.00  35.67   N
ATOM     30  N    THR  A  10     -22.815  41.422  -4.621  1.00  13.54   N
ATOM     31  CA   THR  A  10     -22.103  40.220  -5.047  1.00  14.38   C
ATOM     32  C    THR  A  10     -21.025  40.604  -6.058  1.00  21.65   C
ATOM     33  O    THR  A  10     -21.064  41.705  -6.620  1.00  18.22   O
ATOM     34  CB   THR  A  10     -23.056  39.216  -5.709  1.00  14.17   C
ATOM     35  OG1  THR  A  10     -23.504  39.739  -6.972  1.00  14.78   O
ATOM     36  CG2  THR  A  10     -24.260  38.949  -4.824  1.00  13.27   C
ATOM     37  N    PRO  A  11     -20.050  39.708  -6.288  1.00  18.16   N
ATOM     38  CA   PRO  A  11     -19.002  39.977  -7.280  1.00  20.97   C
ATOM     39  C    PRO  A  11     -19.595  40.202  -8.663  1.00  18.43   C
```

TABLE 5-continued (Table 5 discloses SEQ ID NO: 10):

| ATOM | 40 | O | PRO | A | 11 | −18.911 | 40.714 | −9.553 | 1.00 | 28.22 | O |
|---|---|---|---|---|---|---|---|---|---|---|---|
| ATOM | 41 | CB | PRO | A | 11 | −18.166 | 38.692 | −7.261 | 1.00 | 23.08 | C |
| ATOM | 42 | CG | PRO | A | 11 | −18.376 | 38.133 | −5.880 | 1.00 | 20.36 | C |
| ATOM | 43 | CD | PRO | A | 11 | −19.814 | 38.445 | −5.561 | 1.00 | 18.78 | C |
| ATOM | 44 | N | GLN | A | 12 | −20.857 | 39.834 | −8.837 | 1.00 | 16.57 | N |
| ATOM | 45 | CA | GLN | A | 12 | −21.559 | 40.039 | −10.095 | 1.00 | 20.23 | C |
| ATOM | 46 | C | GLN | A | 12 | −22.422 | 41.311 | −10.049 | 1.00 | 22.29 | C |
| ATOM | 47 | O | GLN | A | 12 | −23.222 | 41.573 | −10.953 | 1.00 | 24.66 | O |
| ATOM | 48 | CB | GLN | A | 12 | −22.396 | 38.797 | −10.439 | 1.00 | 25.03 | C |
| ATOM | 49 | CG | GLN | A | 12 | −21.571 | 37.496 | −10.571 | 1.00 | 15.70 | C |
| ATOM | 50 | CD | GLN | A | 12 | −21.138 | 36.897 | −9.229 | 1.00 | 17.63 | C |
| ATOM | 51 | OE1 | GLN | A | 12 | −20.084 | 36.261 | −9.130 | 1.00 | 21.07 | O |
| ATOM | 52 | NE2 | GLN | A | 12 | −21.951 | 37.096 | −8.198 | 1.00 | 14.53 | N |
| ATOM | 53 | N | SER | A | 13 | −22.250 | 42.082 | −8.974 | 1.00 | 21.48 | N |
| ATOM | 54 | CA | SER | A | 13 | −22.858 | 43.409 | −8.801 | 1.00 | 20.72 | C |
| ATOM | 55 | C | SER | A | 13 | −24.332 | 43.457 | −8.369 | 1.00 | 23.48 | C |
| ATOM | 56 | O | SER | A | 13 | −24.984 | 44.492 | −8.496 | 1.00 | 31.32 | O |
| ATOM | 57 | CB | SER | A | 13 | −22.605 | 44.294 | −10.028 | 1.00 | 28.85 | C |
| ATOM | 58 | OG | SER | A | 13 | −21.220 | 44.583 | −10.147 | 1.00 | 30.46 | O |
| ATOM | 59 | N | ILE | A | 14 | −24.847 | 42.350 | −7.835 | 1.00 | 14.51 | N |
| ATOM | 60 | CA | AILE | A | 14 | −26.217 | 42.289 | −7.340 | 0.50 | 15.83 | C |
| ATOM | 61 | C | ILE | A | 14 | −26.235 | 42.614 | −5.846 | 1.00 | 16.95 | C |
| ATOM | 62 | O | ILE | A | 14 | −25.442 | 42.063 | −5.084 | 1.00 | 15.91 | O |
| ATOM | 63 | CB | AILE | A | 14 | −26.824 | 40.881 | −7.537 | 0.50 | 15.33 | C |
| ATOM | 64 | CG1 | AILE | A | 14 | −26.665 | 40.422 | −8.991 | 0.50 | 17.26 | C |
| ATOM | 65 | CG2 | AILE | A | 14 | −28.283 | 40.859 | −7.120 | 0.50 | 16.38 | C |
| ATOM | 66 | CD1 | AILE | A | 14 | −27.420 | 41.277 | −9.991 | 0.50 | 17.84 | C |
| ATOM | 67 | CA | BILE | A | 14 | −26.216 | 42.309 | −7.341 | 0.50 | 15.20 | C |
| ATOM | 68 | CB | BILE | A | 14 | −26.875 | 40.935 | −7.587 | 0.50 | 16.62 | C |
| ATOM | 69 | CG1 | BILE | A | 14 | −26.944 | 40.644 | −9.088 | 0.50 | 33.69 | C |
| ATOM | 70 | CG2 | BILE | A | 14 | −28.261 | 40.883 | −6.973 | 0.50 | 19.08 | C |
| ATOM | 71 | CD1 | BILE | A | 14 | −27.766 | 39.427 | −9.436 | 0.50 | 19.98 | C |
| ATOM | 72 | N | PRO | A | 15 | −27.141 | 43.507 | −5.417 | 1.00 | 16.97 | N |
| ATOM | 73 | CA | PRO | A | 15 | −27.184 | 43.839 | −3.985 | 1.00 | 14.74 | C |
| ATOM | 74 | C | PRO | A | 15 | −27.555 | 42.632 | −3.125 | 1.00 | 12.12 | C |
| ATOM | 75 | O | PRO | A | 15 | −28.517 | 41.925 | −3.421 | 1.00 | 14.38 | O |
| ATOM | 76 | CB | PRO | A | 15 | −28.292 | 44.898 | −3.903 | 1.00 | 18.44 | C |
| ATOM | 77 | CG | PRO | A | 15 | −28.364 | 45.482 | −5.283 | 1.00 | 18.54 | C |
| ATOM | 78 | CD | PRO | A | 15 | −28.069 | 44.335 | −6.209 | 1.00 | 17.88 | C |
| ATOM | 79 | N | TYR | A | 16 | −26.805 | 42.419 | −2.048 | 1.00 | 10.96 | N |
| ATOM | 80 | CA | TYR | A | 16 | −27.138 | 41.352 | −1.097 | 1.00 | 10.67 | C |
| ATOM | 81 | C | TYR | A | 16 | −28.503 | 41.516 | −0.436 | 1.00 | 12.83 | C |
| ATOM | 82 | O | TYR | A | 16 | −29.123 | 40.536 | −0.034 | 1.00 | 13.23 | O |
| ATOM | 83 | CB | TYR | A | 16 | −26.052 | 41.183 | −0.025 | 1.00 | 9.62 | C |
| ATOM | 84 | CG | TYR | A | 16 | −24.826 | 40.476 | −0.542 | 1.00 | 8.84 | C |
| ATOM | 85 | CD1 | TYR | A | 16 | −24.876 | 39.117 | −0.866 | 1.00 | 8.85 | C |
| ATOM | 86 | CD2 | TYR | A | 16 | −23.633 | 41.153 | −0.724 | 1.00 | 8.95 | C |
| ATOM | 87 | CE1 | TYR | A | 16 | −23.765 | 38.465 | −1.346 | 1.00 | 8.41 | C |
| ATOM | 88 | CE2 | TYR | A | 16 | −22.515 | 40.516 | −1.210 | 1.00 | 10.20 | C |
| ATOM | 89 | CZ | TYR | A | 16 | −22.587 | 39.168 | −1.531 | 1.00 | 8.74 | C |
| ATOM | 90 | OH | TYR | A | 16 | −21.451 | 38.558 | −2.013 | 1.00 | 10.69 | O |
| ATOM | 91 | N | GLN | A | 17 | −28.983 | 42.753 | −0.314 | 1.00 | 14.18 | N |
| ATOM | 92 | CA | GLN | A | 17 | −30.280 | 42.981 | 0.326 | 1.00 | 17.55 | C |
| ATOM | 93 | C | GLN | A | 17 | −31.422 | 42.262 | −0.388 | 1.00 | 15.26 | C |
| ATOM | 94 | O | GLN | A | 17 | −32.478 | 42.023 | 0.195 | 1.00 | 23.55 | O |
| ATOM | 95 | CB | GLN | A | 17 | −30.581 | 44.479 | 0.434 | 1.00 | 24.16 | C |
| ATOM | 96 | CG | GLN | A | 17 | −30.565 | 45.205 | −0.895 | 1.00 | 28.39 | C |
| ATOM | 97 | CD | GLN | A | 17 | −30.822 | 46.694 | −0.755 | 1.00 | 82.31 | C |
| ATOM | 98 | OE1 | GLN | A | 17 | −31.628 | 47.121 | 0.072 | 1.00 | 39.90 | O |
| ATOM | 99 | NE2 | GLN | A | 17 | −30.142 | 47.492 | −1.572 | 1.00 | 47.43 | N |
| ATOM | 100 | N | ASP | A | 18 | −31.190 | 41.907 | −1.648 | 1.00 | 17.60 | N |
| ATOM | 101 | CA | ASP | A | 18 | −32.195 | 41.258 | −2.480 | 1.00 | 23.44 | C |
| ATOM | 102 | C | ASP | A | 18 | −32.059 | 39.734 | −2.474 | 1.00 | 19.90 | C |
| ATOM | 103 | O | ASP | A | 18 | −32.862 | 39.029 | −3.085 | 1.00 | 23.24 | O |
| ATOM | 104 | CB | ASP | A | 18 | −32.068 | 41.765 | −3.922 | 1.00 | 23.94 | C |
| ATOM | 105 | CG | ASP | A | 18 | −32.228 | 43.271 | −4.029 | 1.00 | 69.17 | C |
| ATOM | 106 | OD1 | ASP | A | 18 | −32.980 | 43.855 | −3.221 | 1.00 | 35.65 | O |
| ATOM | 107 | OD2 | ASP | A | 18 | −31.604 | 43.873 | −4.928 | 1.00 | 45.97 | O |
| ATOM | 108 | N | LEU | A | 19 | −31.041 | 39.233 | −1.785 | 1.00 | 14.53 | N |
| ATOM | 109 | CA | LEU | A | 19 | −30.671 | 37.821 | −1.885 | 1.00 | 16.13 | C |
| ATOM | 110 | C | LEU | A | 19 | −30.589 | 37.165 | −0.516 | 1.00 | 14.97 | C |
| ATOM | 111 | O | LEU | A | 19 | −30.294 | 37.835 | 0.469 | 1.00 | 13.14 | O |
| ATOM | 112 | CB | LEU | A | 19 | −29.303 | 37.700 | −2.550 | 1.00 | 14.55 | C |
| ATOM | 113 | CG | LEU | A | 19 | −29.136 | 38.357 | −3.924 | 1.00 | 17.35 | C |
| ATOM | 114 | CD1 | LEU | A | 19 | −27.694 | 38.277 | −4.394 | 1.00 | 16.13 | C |
| ATOM | 115 | CD2 | LEU | A | 19 | −30.080 | 37.710 | −4.927 | 1.00 | 21.15 | C |
| ATOM | 116 | N | PRO | A | 20 | −30.821 | 35.844 | −0.446 | 1.00 | 12.60 | N |
| ATOM | 117 | CA | PRO | A | 20 | −30.533 | 35.158 | 0.818 | 1.00 | 9.83 | C |

TABLE 5-continued (Table 5 discloses SEQ ID NO: 10):

| ATOM | 118 | C   | PRO | A | 20 | −29.035 | 35.204 | 1.093  | 1.00 | 10.92 | C |
|------|-----|-----|-----|---|----|---------|--------|--------|------|-------|---|
| ATOM | 119 | O   | PRO | A | 20 | −28.221 | 34.932 | 0.209  | 1.00 | 10.00 | O |
| ATOM | 120 | CB  | PRO | A | 20 | −30.996 | 33.714 | 0.551  | 1.00 | 12.85 | C |
| ATOM | 121 | CG  | PRO | A | 20 | −31.910 | 33.798 | −0.652 | 1.00 | 12.45 | C |
| ATOM | 122 | CD  | PRO | A | 20 | −31.355 | 34.929 | −1.471 | 1.00 | 13.91 | C |
| ATOM | 123 | N   | HIS | A | 21 | −28.659 | 35.564 | 2.315  | 1.00 | 9.52  | N |
| ATOM | 124 | CA  | HIS | A | 21 | −27.255 | 35.688 | 2.652  | 1.00 | 8.77  | C |
| ATOM | 125 | C   | HIS | A | 21 | −27.013 | 35.531 | 4.145  | 1.00 | 8.21  | C |
| ATOM | 126 | O   | HIS | A | 21 | −27.963 | 35.527 | 4.940  | 1.00 | 11.76 | O |
| ATOM | 127 | CB  | HIS | A | 21 | −26.707 | 37.044 | 2.193  | 1.00 | 12.50 | C |
| ATOM | 128 | CG  | HIS | A | 21 | −27.346 | 38.212 | 2.880  | 1.00 | 12.08 | C |
| ATOM | 129 | ND1 | HIS | A | 21 | −28.470 | 38.836 | 2.386  | 1.00 | 17.03 | N |
| ATOM | 130 | CD2 | HIS | A | 21 | −27.033 | 38.852 | 4.032  | 1.00 | 18.83 | C |
| ATOM | 131 | CE1 | HIS | A | 21 | −28.819 | 39.819 | 3.200  | 1.00 | 26.65 | C |
| ATOM | 132 | NE2 | HIS | A | 21 | −27.966 | 39.847 | 4.206  | 1.00 | 21.10 | N |
| ATOM | 133 | N   | LEU | A | 22 | −25.747 | 35.406 | 4.502  | 1.00 | 8.64  | N |
| ATOM | 134 | CA  | LEU | A | 22 | −25.311 | 35.446 | 5.895  | 1.00 | 6.76  | C |
| ATOM | 135 | C   | LEU | A | 22 | −23.982 | 36.170 | 5.920  | 1.00 | 9.47  | C |
| ATOM | 136 | O   | LEU | A | 22 | −23.294 | 36.247 | 4.898  | 1.00 | 14.08 | O |
| ATOM | 137 | CB  | LEU | A | 22 | −25.178 | 34.038 | 6.483  | 1.00 | 13.24 | C |
| ATOM | 138 | CG  | LEU | A | 22 | −24.073 | 33.100 | 6.000  | 1.00 | 15.59 | C |
| ATOM | 139 | CD1 | LEU | A | 22 | −22.694 | 33.547 | 6.456  | 1.00 | 17.18 | C |
| ATOM | 140 | CD2 | LEU | A | 22 | −24.349 | 31.688 | 6.516  | 1.00 | 20.78 | C |
| ATOM | 141 | N   | VAL | A | 23 | −23.620 | 36.746 | 7.058  | 1.00 | 6.83  | N |
| ATOM | 142 | CA  | VAL | A | 23 | −22.341 | 37.409 | 7.176  | 1.00 | 6.32  | C |
| ATOM | 143 | C   | VAL | A | 23 | −21.464 | 36.555 | 8.079  | 1.00 | 6.79  | C |
| ATOM | 144 | O   | VAL | A | 23 | −21.885 | 36.200 | 9.196  | 1.00 | 7.54  | O |
| ATOM | 145 | CB  | VAL | A | 23 | −22.500 | 38.837 | 7.772  | 1.00 | 7.74  | C |
| ATOM | 146 | CG1 | VAL | A | 23 | −21.163 | 39.562 | 7.798  | 1.00 | 10.24 | C |
| ATOM | 147 | CG2 | VAL | A | 23 | −23.538 | 39.638 | 6.977  | 1.00 | 9.52  | C |
| ATOM | 148 | N   | ASN | A | 24 | −20.288 | 36.172 | 7.603  | 1.00 | 6.28  | N |
| ATOM | 149 | CA  | ASN | A | 24 | −19.422 | 35.309 | 8.392  | 1.00 | 7.25  | C |
| ATOM | 150 | C   | ASN | A | 24 | −18.643 | 36.082 | 9.467  | 1.00 | 8.55  | C |
| ATOM | 151 | O   | ASN | A | 24 | −18.799 | 37.308 | 9.611  | 1.00 | 10.11 | O |
| ATOM | 152 | CB  | ASN | A | 24 | −18.509 | 34.447 | 7.496  | 1.00 | 6.73  | C |
| ATOM | 153 | CG  | ASN | A | 24 | −17.357 | 35.219 | 6.885  | 1.00 | 8.40  | C |
| ATOM | 154 | OD1 | ASN | A | 24 | −17.116 | 36.389 | 7.213  | 1.00 | 8.49  | O |
| ATOM | 155 | ND2 | ASN | A | 24 | −16.601 | 34.553 | 6.007  | 1.00 | 8.52  | N |
| ATOM | 156 | N   | ALA | A | 25 | −17.824 | 35.369 | 10.233 | 1.00 | 8.14  | N |
| ATOM | 157 | CA  | ALA | A | 25 | −17.137 | 35.971 | 11.376 | 1.00 | 8.35  | C |
| ATOM | 158 | C   | ALA | A | 25 | −16.101 | 37.007 | 10.966 | 1.00 | 11.92 | C |
| ATOM | 159 | O   | ALA | A | 25 | −15.619 | 37.777 | 11.803 | 1.00 | 15.43 | O |
| ATOM | 160 | CB  | ALA | A | 25 | −16.497 | 34.897 | 12.238 | 1.00 | 12.36 | C |
| ATOM | 161 | N   | ASP | A | 26 | −15.737 | 37.019 | 9.687  | 1.00 | 10.81 | N |
| ATOM | 162 | CA  | ASP | A | 26 | −14.794 | 37.998 | 9.162  | 1.00 | 11.24 | C |
| ATOM | 163 | C   | ASP | A | 26 | −15.527 | 39.170 | 8.504  | 1.00 | 9.54  | C |
| ATOM | 164 | O   | ASP | A | 26 | −14.896 | 40.025 | 7.867  | 1.00 | 15.54 | O |
| ATOM | 165 | CB  | ASP | A | 26 | −13.840 | 37.328 | 8.166  | 1.00 | 11.66 | C |
| ATOM | 166 | CG  | ASP | A | 26 | −12.891 | 36.357 | 8.840  | 1.00 | 22.26 | C |
| ATOM | 167 | OD1 | ASP | A | 26 | −12.372 | 36.694 | 9.930  | 1.00 | 24.50 | O |
| ATOM | 168 | OD2 | ASP | A | 26 | −12.657 | 35.258 | 8.288  | 1.00 | 19.65 | O |
| ATOM | 169 | N   | GLY | A | 27 | −16.847 | 39.201 | 8.644  | 1.00 | 8.36  | N |
| ATOM | 170 | CA  | GLY | A | 27 | −17.647 | 40.275 | 8.091  | 1.00 | 10.32 | C |
| ATOM | 171 | C   | GLY | A | 27 | −17.901 | 40.175 | 6.598  | 1.00 | 12.61 | C |
| ATOM | 172 | O   | GLY | A | 27 | −18.324 | 41.148 | 5.976  | 1.00 | 12.32 | O |
| ATOM | 173 | N   | GLN | A | 28 | −17.661 | 38.998 | 6.021  | 1.00 | 9.34  | N |
| ATOM | 174 | CA  | GLN | A | 28 | −17.881 | 38.776 | 4.588  | 1.00 | 8.07  | C |
| ATOM | 175 | C   | GLN | A | 28 | −19.263 | 38.219 | 4.330  | 1.00 | 6.30  | C |
| ATOM | 176 | O   | GLN | A | 28 | −19.725 | 37.332 | 5.051  | 1.00 | 8.36  | O |
| ATOM | 177 | CB  | GLN | A | 28 | −16.833 | 37.810 | 4.037  | 1.00 | 9.11  | C |
| ATOM | 178 | CG  | GLN | A | 28 | −15.413 | 38.318 | 4.197  | 1.00 | 10.98 | C |
| ATOM | 179 | CD  | GLN | A | 28 | −14.370 | 37.258 | 3.910  | 1.00 | 11.09 | C |
| ATOM | 180 | OE1 | GLN | A | 28 | −13.533 | 37.414 | 3.005  | 1.00 | 15.32 | O |
| ATOM | 181 | NE2 | GLN | A | 28 | −14.409 | 36.177 | 4.668  | 1.00 | 8.14  | N |
| ATOM | 182 | N   | TYR | A | 29 | −19.950 | 38.742 | 3.326  | 1.00 | 6.77  | N |
| ATOM | 183 | CA  | TYR | A | 29 | −21.250 | 38.230 | 2.942  | 1.00 | 6.19  | C |
| ATOM | 184 | C   | TYR | A | 29 | −21.135 | 36.937 | 2.139  | 1.00 | 6.61  | C |
| ATOM | 185 | O   | TYR | A | 29 | −20.410 | 36.886 | 1.130  | 1.00 | 8.93  | O |
| ATOM | 186 | CB  | TYR | A | 29 | −22.002 | 39.271 | 2.106  | 1.00 | 9.22  | C |
| ATOM | 187 | CG  | TYR | A | 29 | −22.628 | 40.389 | 2.924  | 1.00 | 8.73  | C |
| ATOM | 188 | CD1 | TYR | A | 29 | −21.838 | 41.288 | 3.634  | 1.00 | 10.30 | C |
| ATOM | 189 | CD2 | TYR | A | 29 | −23.999 | 40.536 | 2.983  | 1.00 | 10.59 | C |
| ATOM | 190 | CE1 | TYR | A | 29 | −22.413 | 42.307 | 4.381  | 1.00 | 11.19 | C |
| ATOM | 191 | CE2 | TYR | A | 29 | −24.582 | 41.561 | 3.725  | 1.00 | 10.78 | C |
| ATOM | 192 | CZ  | TYR | A | 29 | −23.773 | 42.435 | 4.413  | 1.00 | 8.82  | C |
| ATOM | 193 | OH  | TYR | A | 29 | −24.344 | 43.451 | 5.158  | 1.00 | 12.21 | O |
| ATOM | 194 | N   | LEU | A | 30 | −21.853 | 35.911 | 2.585  | 1.00 | 6.17  | N |
| ATOM | 195 | CA  | LEU | A | 30 | −21.936 | 34.654 | 1.848  | 1.00 | 5.98  | C |

TABLE 5-continued (Table 5 discloses SEQ ID NO: 10):

| ATOM | 196 | C   | LEU | A | 30 | −23.334 | 34.514 | 1.280  | 1.00 | 7.23  | C |
|------|-----|-----|-----|---|----|---------|--------|--------|------|-------|---|
| ATOM | 197 | O   | LEU | A | 30 | −24.333 | 34.704 | 1.975  | 1.00 | 9.08  | O |
| ATOM | 198 | CB  | LEU | A | 30 | −21.629 | 33.462 | 2.760  | 1.00 | 8.48  | C |
| ATOM | 199 | CG  | LEU | A | 30 | −20.300 | 33.501 | 3.519  | 1.00 | 8.51  | C |
| ATOM | 200 | CD1 | LEU | A | 30 | −20.093 | 32.171 | 4.263  | 1.00 | 11.37 | C |
| ATOM | 201 | CD2 | LEU | A | 30 | −19.126 | 33.807 | 2.603  | 1.00 | 10.67 | C |
| ATOM | 202 | N   | PHE | A | 31 | −23.418 | 34.168 | −0.003 | 1.00 | 6.05  | N |
| ATOM | 203 | CA  | PHE | A | 31 | −24.692 | 33.900 | −0.642 | 1.00 | 6.03  | C |
| ATOM | 204 | C   | PHE | A | 31 | −25.241 | 32.543 | −0.202 | 1.00 | 6.46  | C |
| ATOM | 205 | O   | PHE | A | 31 | −24.484 | 31.573 | −0.167 | 1.00 | 6.52  | O |
| ATOM | 206 | CB  | PHE | A | 31 | −24.508 | 33.934 | −2.167 | 1.00 | 6.59  | C |
| ATOM | 207 | CG  | PHE | A | 31 | −25.711 | 33.500 | −2.921 | 1.00 | 7.69  | C |
| ATOM | 208 | CD1 | PHE | A | 31 | −26.739 | 34.395 | −3.200 | 1.00 | 10.06 | C |
| ATOM | 209 | CD2 | PHE | A | 31 | −25.835 | 32.185 | −3.363 | 1.00 | 8.63  | C |
| ATOM | 210 | CE1 | PHE | A | 31 | −27.869 | 33.984 | −3.895 | 1.00 | 12.38 | C |
| ATOM | 211 | CE2 | PHE | A | 31 | −26.955 | 31.778 | −4.049 | 1.00 | 10.13 | C |
| ATOM | 212 | CZ  | PHE | A | 31 | −27.974 | 32.674 | −4.321 | 1.00 | 11.21 | C |
| ATOM | 213 | N   | CYS | A | 32 | −26.527 | 32.483 | 0.110  | 1.00 | 5.60  | N |
| ATOM | 214 | CA  | CYS | A | 32 | −27.173 | 31.252 | 0.594  | 1.00 | 5.42  | C |
| ATOM | 215 | C   | CYS | A | 32 | −28.256 | 30.757 | −0.343 | 1.00 | 7.15  | C |
| ATOM | 216 | O   | CYS | A | 32 | −28.868 | 31.533 | −1.082 | 1.00 | 7.80  | O |
| ATOM | 217 | CB  | CYS | A | 32 | −27.782 | 31.476 | 1.982  | 1.00 | 7.97  | C |
| ATOM | 218 | SG  | CYS | A | 32 | −26.589 | 31.940 | 3.264  | 1.00 | 9.76  | S |
| ATOM | 219 | N   | ARG | A | 33 | −28.524 | 29.455 | −0.263 | 1.00 | 6.41  | N |
| ATOM | 220 | CA  | ARG | A | 33 | −29.521 | 28.801 | −1.095 | 1.00 | 6.58  | C |
| ATOM | 221 | C   | ARG | A | 33 | −30.301 | 27.808 | −0.238 | 1.00 | 6.95  | C |
| ATOM | 222 | O   | ARG | A | 33 | −29.699 | 27.074 | 0.576  | 1.00 | 9.26  | O |
| ATOM | 223 | CB  | ARG | A | 33 | −28.790 | 28.056 | −2.217 | 1.00 | 12.39 | C |
| ATOM | 224 | CG  | ARG | A | 33 | −29.458 | 28.057 | −3.570 | 1.00 | 21.52 | C |
| ATOM | 225 | CD  | ARG | A | 33 | −28.543 | 27.396 | −4.608 | 1.00 | 13.00 | C |
| ATOM | 226 | NE  | ARG | A | 33 | −27.652 | 28.315 | −5.317 | 1.00 | 9.53  | N |
| ATOM | 227 | CZ  | ARG | A | 33 | −28.037 | 29.049 | −6.361 | 1.00 | 8.94  | C |
| ATOM | 228 | NH1 | ARG | A | 33 | −29.287 | 28.978 | −6.788 | 1.00 | 13.78 | N |
| ATOM | 229 | NH2 | ARG | A | 33 | −27.172 | 29.848 | −6.972 | 1.00 | 10.48 | N |
| ATOM | 230 | N   | TYR | A | 34 | −31.619 | 27.773 | −0.405 | 1.00 | 8.28  | N |
| ATOM | 231 | CA  | TYR | A | 34 | −32.485 | 26.905 | 0.388  | 1.00 | 9.23  | C |
| ATOM | 232 | C   | TYR | A | 34 | −33.474 | 26.170 | −0.498 | 1.00 | 12.77 | C |
| ATOM | 233 | O   | TYR | A | 34 | −33.998 | 26.735 | −1.466 | 1.00 | 12.90 | O |
| ATOM | 234 | CB  | TYR | A | 34 | −33.270 | 27.722 | 1.427  | 1.00 | 9.73  | C |
| ATOM | 235 | CG  | TYR | A | 34 | −32.366 | 28.475 | 2.366  | 1.00 | 10.63 | C |
| ATOM | 236 | CD1 | TYR | A | 34 | −31.785 | 27.835 | 3.453  | 1.00 | 11.93 | C |
| ATOM | 237 | CD2 | TYR | A | 34 | −32.066 | 29.820 | 2.157  | 1.00 | 10.99 | C |
| ATOM | 238 | CE1 | TYR | A | 34 | −30.933 | 28.511 | 4.301  | 1.00 | 12.94 | C |
| ATOM | 239 | CE2 | TYR | A | 34 | −31.212 | 30.505 | 3.005  | 1.00 | 9.78  | C |
| ATOM | 240 | CZ  | TYR | A | 34 | −30.651 | 29.838 | 4.072  | 1.00 | 10.20 | C |
| ATOM | 241 | OH  | TYR | A | 34 | −29.795 | 30.492 | 4.921  | 1.00 | 11.98 | O |
| ATOM | 242 | N   | TRP | A | 35 | −33.742 | 24.916 | −0.154 | 1.00 | 10.36 | N |
| ATOM | 243 | CA  | TRP | A | 35 | −34.792 | 24.152 | −0.817 | 1.00 | 10.15 | C |
| ATOM | 244 | C   | TRP | A | 35 | −35.623 | 23.508 | 0.286  | 1.00 | 11.14 | C |
| ATOM | 245 | O   | TRP | A | 35 | −35.197 | 22.524 | 0.909  | 1.00 | 11.77 | O |
| ATOM | 246 | CB  | TRP | A | 35 | −34.206 | 23.065 | −1.721 | 1.00 | 10.42 | C |
| ATOM | 247 | CG  | TRP | A | 35 | −33.285 | 23.499 | −2.831 | 1.00 | 12.61 | C |
| ATOM | 248 | CD1 | TRP | A | 35 | −33.609 | 23.625 | −4.160 | 1.00 | 13.17 | C |
| ATOM | 249 | CD2 | TRP | A | 35 | −31.879 | 23.777 | −2.736 | 1.00 | 9.72  | C |
| ATOM | 250 | NE1 | TRP | A | 35 | −32.500 | 23.988 | −4.884 | 1.00 | 13.29 | N |
| ATOM | 251 | CE2 | TRP | A | 35 | −31.421 | 24.082 | −4.041 | 1.00 | 11.08 | C |
| ATOM | 252 | CE3 | TRP | A | 35 | −30.959 | 23.791 | −1.677 | 1.00 | 9.17  | C |
| ATOM | 253 | CZ2 | TRP | A | 35 | −30.091 | 24.403 | −4.310 | 1.00 | 11.75 | C |
| ATOM | 254 | CZ3 | TRP | A | 35 | −29.643 | 24.108 | −1.943 | 1.00 | 9.91  | C |
| ATOM | 255 | CH2 | TRP | A | 35 | −29.218 | 24.414 | −3.254 | 1.00 | 12.71 | C |
| ATOM | 256 | N   | ALA | A | 36 | −36.793 | 24.077 | 0.554  | 1.00 | 13.64 | N |
| ATOM | 257 | CA  | ALA | A | 36 | −37.613 | 23.643 | 1.682  | 1.00 | 14.33 | C |
| ATOM | 258 | C   | ALA | A | 36 | −38.871 | 22.927 | 1.209  | 1.00 | 17.02 | C |
| ATOM | 259 | CB  | ALA | A | 36 | −37.990 | 24.850 | 2.559  | 1.00 | 16.53 | C |
| ATOM | 260 | O   | ALA | A | 36 | −39.523 | 23.383 | 0.274  | 1.00 | 19.88 | O |
| ATOM | 261 | N   | PRO | A | 37 | −39.221 | 21.807 | 1.859  | 1.00 | 14.84 | N |
| ATOM | 262 | CA  | PRO | A | 37 | −40.460 | 21.101 | 1.510  | 1.00 | 20.24 | C |
| ATOM | 263 | C   | PRO | A | 37 | −41.685 | 21.874 | 2.015  | 1.00 | 18.75 | C |
| ATOM | 264 | O   | PRO | A | 37 | −41.540 | 22.811 | 2.801  | 1.00 | 20.85 | O |
| ATOM | 265 | CB  | PRO | A | 37 | −40.315 | 19.769 | 2.257  | 1.00 | 19.92 | C |
| ATOM | 266 | CG  | PRO | A | 37 | −39.457 | 20.111 | 3.431  | 1.00 | 20.70 | C |
| ATOM | 267 | CD  | PRO | A | 37 | −38.444 | 21.075 | 2.875  | 1.00 | 14.82 | C |
| ATOM | 268 | N   | THR | A | 38 | −42.872 | 21.479 | 1.572  | 1.00 | 25.39 | N |
| ATOM | 269 | CA  | THR | A | 38 | −44.096 | 22.193 | 1.923  | 1.00 | 30.82 | C |
| ATOM | 270 | C   | THR | A | 38 | −44.415 | 22.120 | 3.413  | 1.00 | 36.92 | C |
| ATOM | 271 | O   | THR | A | 38 | −44.878 | 23.097 | 4.002  | 1.00 | 62.88 | O |
| ATOM | 272 | CB  | THR | A | 38 | −45.298 | 21.661 | 1.127  | 1.00 | 40.57 | C |
| ATOM | 273 | OG1 | THR | A | 38 | −45.516 | 20.283 | 1.455  | 1.00 | 75.45 | O |

TABLE 5-continued (Table 5 discloses SEQ ID NO: 10):

| ATOM | 274 | CG2 | THR | A | 38 | −45.039 | 21.786 | −0.365 | 1.00 | 33.30 | C |
|---|---|---|---|---|---|---|---|---|---|---|---|
| ATOM | 275 | N   | GLY | A | 39 | −44.169 | 20.963 | 4.019  | 1.00 | 26.40 | N |
| ATOM | 276 | CA  | GLY | A | 39 | −44.489 | 20.769 | 5.423  | 1.00 | 34.27 | C |
| ATOM | 277 | C   | GLY | A | 39 | −43.270 | 20.683 | 6.320  | 1.00 | 44.58 | C |
| ATOM | 278 | O   | GLY | A | 39 | −42.160 | 21.033 | 5.914  | 1.00 | 35.00 | O |
| ATOM | 279 | N   | THR | A | 40 | −43.481 | 20.224 | 7.550  | 1.00 | 28.10 | N |
| ATOM | 280 | CA  | THR | A | 40 | −42.392 | 20.033 | 8.500  | 1.00 | 24.60 | C |
| ATOM | 281 | C   | THR | A | 40 | −41.346 | 19.088 | 7.915  | 1.00 | 26.04 | C |
| ATOM | 282 | O   | THR | A | 40 | −41.672 | 17.976 | 7.501  | 1.00 | 22.08 | O |
| ATOM | 283 | CB  | THR | A | 40 | −42.902 | 19.444 | 9.829  | 1.00 | 30.60 | C |
| ATOM | 284 | OG1 | THR | A | 40 | −43.947 | 20.276 | 10.349 | 1.00 | 44.32 | O |
| ATOM | 285 | CG2 | THR | A | 40 | −41.772 | 19.352 | 10.852 | 1.00 | 25.32 | C |
| ATOM | 286 | N   | PRO | A | 41 | −40.083 | 19.532 | 7.871  | 1.00 | 20.06 | N |
| ATOM | 287 | CA  | PRO | A | 41 | −39.027 | 18.659 | 7.350  | 1.00 | 14.83 | C |
| ATOM | 288 | C   | PRO | A | 41 | −38.722 | 17.536 | 8.332  | 1.00 | 15.43 | C |
| ATOM | 289 | O   | PRO | A | 41 | −38.907 | 17.706 | 9.542  | 1.00 | 18.25 | O |
| ATOM | 290 | CB  | PRO | A | 41 | −37.807 | 19.590 | 7.246  | 1.00 | 15.58 | C |
| ATOM | 291 | CG  | PRO | A | 41 | −38.331 | 20.986 | 7.462  | 1.00 | 21.18 | C |
| ATOM | 292 | CD  | PRO | A | 41 | −39.568 | 20.847 | 8.283  | 1.00 | 20.08 | C |
| ATOM | 293 | N   | LYS | A | 42 | −38.244 | 16.407 | 7.817  | 1.00 | 12.49 | N |
| ATOM | 294 | CA  | LYS | A | 42 | −37.840 | 15.276 | 8.648  | 1.00 | 15.17 | C |
| ATOM | 295 | C   | LYS | A | 42 | −36.405 | 15.425 | 9.127  | 1.00 | 13.51 | C |
| ATOM | 296 | O   | LYS | A | 42 | −36.002 | 14.831 | 10.133 | 1.00 | 15.33 | O |
| ATOM | 297 | CB  | LYS | A | 42 | −37.978 | 13.968 | 7.866  | 1.00 | 20.90 | C |
| ATOM | 298 | CG  | LYS | A | 42 | −39.415 | 13.620 | 7.520  | 1.00 | 33.71 | C |
| ATOM | 299 | CD  | LYS | A | 42 | −39.587 | 12.137 | 7.262  | 1.00 | 65.22 | C |
| ATOM | 300 | CE  | LYS | A | 42 | −38.819 | 11.702 | 6.034  | 1.00 | 53.35 | C |
| ATOM | 301 | NZ  | LYS | A | 42 | −39.110 | 10.284 | 5.687  | 1.00 | 78.02 | N |
| ATOM | 302 | N   | ALA | A | 43 | −35.630 | 16.213 | 8.387  | 1.00 | 11.61 | N |
| ATOM | 303 | CA  | ALA | A | 43 | −34.228 | 16.414 | 8.693  | 1.00 | 9.88  | C |
| ATOM | 304 | C   | ALA | A | 43 | −33.707 | 17.595 | 7.880  | 1.00 | 7.84  | C |
| ATOM | 305 | O   | ALA | A | 43 | −34.377 | 18.073 | 6.961  | 1.00 | 9.50  | O |
| ATOM | 306 | CB  | ALA | A | 43 | −33.421 | 15.156 | 8.373  | 1.00 | 13.77 | C |
| ATOM | 307 | N   | LEU | A | 44 | −32.517 | 18.047 | 8.250  | 1.00 | 8.06  | N |
| ATOM | 308 | CA  | LEU | A | 44 | −31.815 | 19.114 | 7.551  | 1.00 | 7.73  | C |
| ATOM | 309 | C   | LEU | A | 44 | −30.613 | 18.507 | 6.858  | 1.00 | 7.26  | C |
| ATOM | 310 | O   | LEU | A | 44 | −30.001 | 17.577 | 7.379  | 1.00 | 8.67  | O |
| ATOM | 311 | CB  | LEU | A | 44 | −31.312 | 20.154 | 8.560  | 1.00 | 10.75 | C |
| ATOM | 312 | CG  | LEU | A | 44 | −32.320 | 20.734 | 9.558  | 1.00 | 14.46 | C |
| ATOM | 313 | CD1 | LEU | A | 44 | −31.600 | 21.580 | 10.594 | 1.00 | 18.22 | C |
| ATOM | 314 | CD2 | LEU | A | 44 | −33.367 | 21.546 | 8.837  | 1.00 | 14.89 | C |
| ATOM | 315 | N   | ILE | A | 45 | −30.232 | 19.069 | 5.718  | 1.00 | 7.30  | N |
| ATOM | 316 | CA  | ILE | A | 45 | −28.991 | 18.659 | 5.084  | 1.00 | 7.17  | C |
| ATOM | 317 | C   | ILE | A | 45 | −28.270 | 19.843 | 4.445  | 1.00 | 6.26  | C |
| ATOM | 318 | O   | ILE | A | 45 | −28.850 | 20.592 | 3.644  | 1.00 | 7.44  | O |
| ATOM | 319 | CB  | ILE | A | 45 | −29.206 | 17.489 | 4.079  | 1.00 | 7.19  | C |
| ATOM | 320 | CG1 | ILE | A | 45 | −27.868 | 16.995 | 3.511  | 1.00 | 7.97  | C |
| ATOM | 321 | CG2 | ILE | A | 45 | −30.224 | 17.865 | 3.008  | 1.00 | 9.73  | C |
| ATOM | 322 | CD1 | ILE | A | 45 | −27.975 | 15.599 | 2.857  | 1.00 | 11.27 | C |
| ATOM | 323 | N   | PHE | A | 46 | −27.021 | 20.011 | 4.837  | 1.00 | 5.88  | N |
| ATOM | 324 | CA  | PHE | A | 46 | −26.169 | 21.039 | 4.251  | 1.00 | 5.70  | C |
| ATOM | 325 | C   | PHE | A | 46 | −25.371 | 20.481 | 3.084  | 1.00 | 5.52  | C |
| ATOM | 326 | O   | PHE | A | 46 | −24.738 | 19.426 | 3.211  | 1.00 | 7.72  | O |
| ATOM | 327 | CB  | PHE | A | 46 | −25.216 | 21.629 | 5.298  | 1.00 | 5.92  | C |
| ATOM | 328 | CG  | PHE | A | 46 | −24.325 | 22.708 | 4.757  | 1.00 | 6.50  | C |
| ATOM | 329 | CD1 | PHE | A | 46 | −23.082 | 22.413 | 4.216  | 1.00 | 7.76  | C |
| ATOM | 330 | CD2 | PHE | A | 46 | −24.758 | 24.027 | 4.769  | 1.00 | 7.33  | C |
| ATOM | 331 | CE1 | PHE | A | 46 | −22.267 | 23.423 | 3.693  | 1.00 | 7.27  | C |
| ATOM | 332 | CE2 | PHE | A | 46 | −23.954 | 25.038 | 4.250  | 1.00 | 8.02  | C |
| ATOM | 333 | CZ  | PHE | A | 46 | −22.715 | 24.742 | 3.711  | 1.00 | 8.11  | C |
| ATOM | 334 | N   | VAL | A | 47 | −25.375 | 21.211 | 1.970  | 1.00 | 5.46  | N |
| ATOM | 335 | CA  | VAL | A | 47 | −24.617 | 20.813 | 0.783  | 1.00 | 6.17  | C |
| ATOM | 336 | C   | VAL | A | 47 | −23.379 | 21.693 | 0.648  | 1.00 | 7.61  | C |
| ATOM | 337 | O   | VAL | A | 47 | −23.491 | 22.930 | 0.600  | 1.00 | 8.01  | O |
| ATOM | 338 | CB  | VAL | A | 47 | −25.480 | 20.904 | −0.495 | 1.00 | 9.99  | C |
| ATOM | 339 | CG1 | VAL | A | 47 | −24.642 | 20.584 | −1.753 | 1.00 | 10.76 | C |
| ATOM | 340 | CG2 | VAL | A | 47 | −26.673 | 19.965 | −0.389 | 1.00 | 9.71  | C |
| ATOM | 341 | N   | SER | A | 48 | −22.210 | 21.053 | 0.604  | 1.00 | 5.98  | N |
| ATOM | 342 | CA  | SER | A | 48 | −20.915 | 21.711 | 0.581  | 1.00 | 6.93  | C |
| ATOM | 343 | C   | SER | A | 48 | −20.251 | 21.506 | −0.791 | 1.00 | 7.30  | C |
| ATOM | 344 | O   | SER | A | 48 | −19.782 | 20.401 | −1.130 | 1.00 | 6.87  | O |
| ATOM | 345 | CB  | SER | A | 48 | −20.035 | 21.111 | 1.688  | 1.00 | 8.37  | C |
| ATOM | 346 | OG  | SER | A | 48 | −18.758 | 21.704 | 1.745  | 1.00 | 8.59  | O |
| ATOM | 347 | N   | HIS | A | 49 | −20.194 | 22.579 | −1.580 | 1.00 | 5.91  | N |
| ATOM | 348 | CA  | HIS | A | 49 | −19.621 | 22.526 | −2.923 | 1.00 | 5.97  | C |
| ATOM | 349 | C   | HIS | A | 49 | −18.089 | 22.530 | −2.893 | 1.00 | 5.83  | C |
| ATOM | 350 | O   | HIS | A | 49 | −17.461 | 22.768 | −1.861 | 1.00 | 5.76  | O |
| ATOM | 351 | CB  | HIS | A | 49 | −20.161 | 23.674 | −3.800 | 1.00 | 6.87  | C |

TABLE 5-continued (Table 5 discloses SEQ ID NO: 10):

| ATOM | 352 | CG | HIS | A | 49 | −19.608 | 25.028 | −3.457 | 1.00 | 4.44 | C |
|---|---|---|---|---|---|---|---|---|---|---|---|
| ATOM | 353 | ND1 | HIS | A | 49 | −18.365 | 25.450 | −3.876 | 1.00 | 5.38 | N |
| ATOM | 354 | CD2 | HIS | A | 49 | −20.152 | 26.072 | −2.781 | 1.00 | 6.37 | C |
| ATOM | 355 | CE1 | HIS | A | 49 | −18.151 | 26.685 | −3.445 | 1.00 | 7.05 | C |
| ATOM | 356 | NE2 | HIS | A | 49 | −19.224 | 27.087 | −2.786 | 1.00 | 5.73 | N |
| ATOM | 357 | N | GLY | A | 50 | −17.475 | 22.238 | −4.039 | 1.00 | 6.83 | N |
| ATOM | 358 | CA | GLY | A | 50 | −16.033 | 22.155 | −4.121 | 1.00 | 6.75 | C |
| ATOM | 359 | C | GLY | A | 50 | −15.362 | 23.413 | −4.651 | 1.00 | 6.47 | C |
| ATOM | 360 | O | GLY | A | 50 | −16.022 | 24.420 | −4.955 | 1.00 | 6.59 | O |
| ATOM | 361 | N | ALA | A | 51 | −14.050 | 23.344 | −4.781 | 1.00 | 5.98 | N |
| ATOM | 362 | CA | ALA | A | 51 | −13.268 | 24.487 | −5.244 | 1.00 | 5.62 | C |
| ATOM | 363 | C | ALA | A | 51 | −13.654 | 24.862 | −6.662 | 1.00 | 8.12 | C |
| ATOM | 364 | O | ALA | A | 51 | −13.866 | 23.984 | −7.511 | 1.00 | 7.71 | O |
| ATOM | 365 | CB | ALA | A | 51 | −11.805 | 24.181 | −5.188 | 1.00 | 8.37 | C |
| ATOM | 366 | N | GLY | A | 52 | −13.719 | 26.164 | −6.927 | 1.00 | 6.60 | N |
| ATOM | 367 | CA | GLY | A | 52 | −13.966 | 26.656 | −8.270 | 1.00 | 9.14 | C |
| ATOM | 368 | C | GLY | A | 52 | −15.413 | 26.649 | −8.709 | 1.00 | 7.08 | C |
| ATOM | 369 | O | GLY | A | 52 | −15.730 | 27.192 | −9.773 | 1.00 | 8.55 | O |
| ATOM | 370 | N | GLU | A | 53 | −16.302 | 26.044 | −7.927 | 1.00 | 5.30 | N |
| ATOM | 371 | CA | GLU | A | 53 | −17.719 | 26.013 | −8.276 | 1.00 | 6.20 | C |
| ATOM | 372 | C | GLU | A | 53 | −18.570 | 26.767 | −7.242 | 1.00 | 5.56 | C |
| ATOM | 373 | O | GLU | A | 53 | −18.087 | 27.730 | −6.635 | 1.00 | 6.90 | O |
| ATOM | 374 | CB | GLU | A | 53 | −18.233 | 24.582 | −8.536 | 1.00 | 8.29 | C |
| ATOM | 375 | CG | GLU | A | 53 | −17.953 | 23.602 | −7.388 | 1.00 | 6.83 | C |
| ATOM | 376 | CD | GLU | A | 53 | −18.750 | 22.300 | −7.486 | 1.00 | 10.34 | C |
| ATOM | 377 | OE1 | GLU | A | 53 | −19.440 | 22.076 | −8.496 | 1.00 | 10.71 | O |
| ATOM | 378 | OE2 | GLU | A | 53 | −18.712 | 21.494 | −6.522 | 1.00 | 9.53 | O |
| ATOM | 379 | N | HIS | A | 54 | −19.811 | 26.356 | −7.054 | 1.00 | 5.72 | N |
| ATOM | 380 | CA | HIS | A | 54 | −20.727 | 27.085 | −6.173 | 1.00 | 6.19 | C |
| ATOM | 381 | C | HIS | A | 54 | −21.987 | 26.260 | −5.929 | 1.00 | 5.74 | C |
| ATOM | 382 | O | HIS | A | 54 | −22.179 | 25.207 | −6.563 | 1.00 | 7.20 | O |
| ATOM | 383 | CB | HIS | A | 54 | −21.089 | 28.443 | −6.801 | 1.00 | 7.71 | C |
| ATOM | 384 | CG | HIS | A | 54 | −21.857 | 28.312 | −8.079 | 1.00 | 6.04 | C |
| ATOM | 385 | ND1 | HIS | A | 54 | −23.223 | 28.457 | −8.149 | 1.00 | 7.69 | N |
| ATOM | 386 | CD2 | HIS | A | 54 | −21.445 | 27.990 | −9.332 | 1.00 | 6.29 | C |
| ATOM | 387 | CE1 | HIS | A | 54 | −23.622 | 28.253 | −9.395 | 1.00 | 8.02 | C |
| ATOM | 388 | NE2 | HIS | A | 54 | −22.561 | 27.967 | −10.129 | 1.00 | 7.68 | N |
| ATOM | 389 | N | SER | A | 55 | −22.869 | 26.749 | −5.064 | 1.00 | 6.06 | N |
| ATOM | 390 | CA | SER | A | 55 | −24.028 | 25.992 | −4.616 | 1.00 | 5.79 | C |
| ATOM | 391 | C | SER | A | 55 | −25.064 | 25.729 | −5.710 | 1.00 | 6.93 | C |
| ATOM | 392 | O | SER | A | 55 | −25.864 | 24.794 | −5.609 | 1.00 | 8.85 | O |
| ATOM | 393 | CB | SER | A | 55 | −24.697 | 26.711 | −3.434 | 1.00 | 7.37 | C |
| ATOM | 394 | OG | SER | A | 55 | −25.185 | 27.981 | −3.824 | 1.00 | 9.12 | O |
| ATOM | 395 | N | GLY | A | 56 | −25.093 | 26.577 | −6.736 | 1.00 | 7.19 | N |
| ATOM | 396 | CA | GLY | A | 56 | −26.086 | 26.425 | −7.789 | 1.00 | 9.39 | C |
| ATOM | 397 | C | GLY | A | 56 | −25.890 | 25.189 | −8.663 | 1.00 | 8.15 | C |
| ATOM | 398 | O | GLY | A | 56 | −26.812 | 24.773 | −9.367 | 1.00 | 11.61 | O |
| ATOM | 399 | N | ARG | A | 57 | −24.706 | 24.599 | −8.591 | 1.00 | 7.21 | N |
| ATOM | 400 | CA | ARG | A | 57 | −24.409 | 23.405 | −9.371 | 1.00 | 8.23 | C |
| ATOM | 401 | C | ARG | A | 57 | −25.023 | 22.147 | −8.738 | 1.00 | 12.55 | C |
| ATOM | 402 | O | ARG | A | 57 | −24.861 | 21.049 | −9.268 | 1.00 | 15.41 | O |
| ATOM | 403 | CB | ARG | A | 57 | −22.900 | 23.280 | −9.594 | 1.00 | 11.50 | C |
| ATOM | 404 | CG | ARG | A | 57 | −22.300 | 24.548 | −10.261 | 1.00 | 11.08 | C |
| ATOM | 405 | CD | ARG | A | 57 | −21.326 | 24.258 | −11.403 | 1.00 | 14.23 | C |
| ATOM | 406 | NE | ARG | A | 57 | −21.863 | 23.251 | −12.312 | 1.00 | 16.18 | N |
| ATOM | 407 | CZ | ARG | A | 57 | −22.803 | 23.478 | −13.219 | 1.00 | 20.13 | C |
| ATOM | 408 | NH1 | ARG | A | 57 | −23.305 | 24.698 | −13.381 | 1.00 | 23.25 | N |
| ATOM | 409 | NH2 | ARG | A | 57 | −23.241 | 22.477 | −13.971 | 1.00 | 20.33 | N |
| ATOM | 410 | N | TYR | A | 58 | −25.759 | 22.318 | −7.639 | 1.00 | 8.94 | N |
| ATOM | 411 | CA | TYR | A | 58 | −26.351 | 21.196 | −6.889 | 1.00 | 8.78 | C |
| ATOM | 412 | C | TYR | A | 58 | −27.876 | 21.187 | −6.952 | 1.00 | 10.23 | C |
| ATOM | 413 | O | TYR | A | 58 | −28.545 | 20.471 | −6.201 | 1.00 | 10.07 | O |
| ATOM | 414 | CB | TYR | A | 58 | −25.808 | 21.182 | −5.437 | 1.00 | 10.33 | C |
| ATOM | 415 | CG | TYR | A | 58 | −24.356 | 20.813 | −5.471 | 1.00 | 7.86 | C |
| ATOM | 416 | CD1 | TYR | A | 58 | −23.367 | 21.764 | −5.755 | 1.00 | 8.45 | C |
| ATOM | 417 | CD2 | TYR | A | 58 | −23.968 | 19.487 | −5.324 | 1.00 | 9.90 | C |
| ATOM | 418 | CE1 | TYR | A | 58 | −22.039 | 21.403 | −5.859 | 1.00 | 8.11 | C |
| ATOM | 419 | CE2 | TYR | A | 58 | −22.649 | 19.117 | −5.413 | 1.00 | 8.69 | C |
| ATOM | 420 | CZ | TYR | A | 58 | −21.682 | 20.061 | −5.696 | 1.00 | 9.51 | C |
| ATOM | 421 | OH | TYR | A | 58 | −20.374 | 19.682 | −5.811 | 1.00 | 12.95 | O |
| ATOM | 422 | N | GLU | A | 59 | −28.429 | 21.975 | −7.869 | 1.00 | 9.80 | N |
| ATOM | 423 | CA | GLU | A | 59 | −29.868 | 22.136 | −7.978 | 1.00 | 11.59 | C |
| ATOM | 424 | C | GLU | A | 59 | −30.645 | 20.816 | −8.039 | 1.00 | 10.87 | C |
| ATOM | 425 | O | GLU | A | 59 | −31.608 | 20.616 | −7.297 | 1.00 | 10.96 | O |
| ATOM | 426 | CB | GLU | A | 59 | −30.203 | 22.987 | −9.208 | 1.00 | 13.77 | C |
| ATOM | 427 | CG | GLU | A | 59 | −31.654 | 23.394 | −9.288 | 1.00 | 14.77 | C |
| ATOM | 428 | CD | GLU | A | 59 | −32.069 | 24.310 | −8.144 | 1.00 | 16.52 | C |
| ATOM | 429 | OE1 | GLU | A | 59 | −31.216 | 25.088 | −7.671 | 1.00 | 20.67 | O |

TABLE 5-continued (Table 5 discloses SEQ ID NO: 10):

| ATOM | 430 | OE2 | GLU | A | 59 | −33.245 | 24.251 | −7.728 | 1.00 | 25.13 | O |
|---|---|---|---|---|---|---|---|---|---|---|---|
| ATOM | 431 | N | GLU | A | 60 | −30.235 | 19.916 | −8.930 | 1.00 | 10.53 | N |
| ATOM | 432 | CA | GLU | A | 60 | −30.993 | 18.683 | −9.117 | 1.00 | 10.68 | C |
| ATOM | 433 | C | GLU | A | 60 | −30.896 | 17.758 | −7.908 | 1.00 | 9.92 | C |
| ATOM | 434 | O | GLU | A | 60 | −31.894 | 17.181 | −7.476 | 1.00 | 10.77 | O |
| ATOM | 435 | CB | GLU | A | 60 | −30.553 | 17.959 | −10.391 | 1.00 | 14.50 | C |
| ATOM | 436 | CG | GLU | A | 60 | −30.925 | 18.708 | −11.667 | 1.00 | 24.44 | C |
| ATOM | 437 | CD | GLU | A | 60 | −32.401 | 19.063 | −11.722 | 1.00 | 89.95 | C |
| ATOM | 438 | OE1 | GLU | A | 60 | −33.241 | 18.168 | −11.485 | 1.00 | 55.36 | O |
| ATOM | 439 | OE2 | GLU | A | 60 | −32.723 | 20.237 | −12.003 | 1.00 | 106.69 | O |
| ATOM | 440 | N | LEU | A | 61 | −29.694 | 17.608 | −7.372 | 1.00 | 8.91 | N |
| ATOM | 441 | CA | ALEU | A | 61 | −29.506 | 16.811 | −6.161 | 0.50 | 9.95 | C |
| ATOM | 442 | C | LEU | A | 61 | −30.339 | 17.376 | −5.013 | 1.00 | 10.94 | C |
| ATOM | 443 | O | LEU | A | 61 | −31.003 | 16.637 | −4.278 | 1.00 | 9.90 | O |
| ATOM | 444 | CB | ALEU | A | 61 | −28.031 | 16.777 | −5.757 | 0.50 | 11.94 | C |
| ATOM | 445 | CG | ALEU | A | 61 | −27.140 | 15.693 | −6.367 | 0.50 | 9.56 | C |
| ATOM | 446 | CD1 | ALEU | A | 61 | −25.700 | 15.937 | −5.975 | 0.50 | 8.30 | C |
| ATOM | 447 | CD2 | ALEU | A | 61 | −27.591 | 14.303 | −5.926 | 0.50 | 9.49 | C |
| ATOM | 448 | CA | BLEU | A | 61 | −29.513 | 16.807 | −6.168 | 0.50 | 9.77 | C |
| ATOM | 449 | CB | BLEU | A | 61 | −28.039 | 16.757 | −5.782 | 0.50 | 12.63 | C |
| ATOM | 450 | CG | BLEU | A | 61 | −27.659 | 15.622 | −4.834 | 0.50 | 14.96 | C |
| ATOM | 451 | CD1 | BLEU | A | 61 | −28.276 | 14.307 | −5.303 | 0.50 | 15.85 | C |
| ATOM | 452 | CD2 | BLEU | A | 61 | −26.151 | 15.511 | −4.742 | 0.50 | 14.56 | C |
| ATOM | 453 | N | ALA | A | 62 | −30.303 | 18.694 | −4.849 | 1.00 | 8.48 | N |
| ATOM | 454 | CA | ALA | A | 62 | −31.054 | 19.331 | −3.778 | 1.00 | 10.11 | C |
| ATOM | 455 | C | ALA | A | 62 | −32.555 | 19.111 | −3.938 | 1.00 | 13.13 | C |
| ATOM | 456 | O | ALA | A | 62 | −33.267 | 18.881 | −2.955 | 1.00 | 10.27 | O |
| ATOM | 457 | CB | ALA | A | 62 | −30.732 | 20.826 | −3.722 | 1.00 | 10.95 | C |
| ATOM | 458 | N | ARG | A | 63 | −33.052 | 19.194 | −5.169 | 1.00 | 9.46 | N |
| ATOM | 459 | CA | ARG | A | 63 | −34.475 | 18.973 | −5.402 | 1.00 | 13.75 | C |
| ATOM | 460 | C | ARG | A | 63 | −34.891 | 17.549 | −5.042 | 1.00 | 11.63 | C |
| ATOM | 461 | O | ARG | A | 63 | −35.964 | 17.327 | −4.481 | 1.00 | 12.65 | O |
| ATOM | 462 | CB | ARG | A | 63 | −34.846 | 19.301 | −6.849 | 1.00 | 11.63 | C |
| ATOM | 463 | CG | ARG | A | 63 | −34.838 | 20.793 | −7.131 | 1.00 | 15.77 | C |
| ATOM | 464 | CD | ARG | A | 63 | −35.202 | 21.085 | −8.579 | 1.00 | 27.72 | C |
| ATOM | 465 | NE | ARG | A | 63 | −35.167 | 22.516 | −8.871 | 1.00 | 33.09 | N |
| ATOM | 466 | CZ | ARG | A | 63 | −35.623 | 23.058 | −9.995 | 1.00 | 84.41 | C |
| ATOM | 467 | NH1 | ARG | A | 63 | −36.156 | 22.291 | −10.937 | 1.00 | 43.78 | N |
| ATOM | 468 | NH2 | ARG | A | 63 | −35.549 | 24.370 | −10.175 | 1.00 | 46.62 | N |
| ATOM | 469 | N | MET | A | 64 | −34.035 | 16.584 | −5.362 | 1.00 | 10.52 | N |
| ATOM | 470 | CA | AMET | A | 64 | −34.299 | 15.192 | −5.002 | 0.75 | 11.44 | C |
| ATOM | 471 | C | MET | A | 64 | −34.394 | 15.041 | −3.485 | 1.00 | 11.99 | C |
| ATOM | 472 | O | MET | A | 64 | −35.315 | 14.410 | −2.965 | 1.00 | 12.08 | O |
| ATOM | 473 | CB | AMET | A | 64 | −33.212 | 14.277 | −5.575 | 0.75 | 11.53 | C |
| ATOM | 474 | CG | AMET | A | 64 | −33.399 | 12.800 | −5.229 | 0.75 | 11.45 | C |
| ATOM | 475 | SD | AMET | A | 64 | −32.651 | 12.319 | −3.663 | 0.75 | 14.16 | S |
| ATOM | 476 | CE | AMET | A | 64 | −30.923 | 12.298 | −4.124 | 0.75 | 13.84 | C |
| ATOM | 477 | CA | BMET | A | 64 | −34.318 | 15.202 | −5.003 | 0.25 | 12.08 | C |
| ATOM | 478 | CB | BMET | A | 64 | −33.259 | 14.270 | −5.583 | 0.25 | 12.80 | C |
| ATOM | 479 | CG | BMET | A | 64 | −33.680 | 12.815 | −5.583 | 0.25 | 26.52 | C |
| ATOM | 480 | SD | BMET | A | 64 | −32.270 | 11.723 | −5.382 | 0.25 | 12.18 | S |
| ATOM | 481 | CE | BMET | A | 64 | −31.712 | 12.205 | −3.742 | 0.25 | 0.00 | C |
| ATOM | 482 | N | LEU | A | 65 | −33.437 | 15.628 | −2.777 | 1.00 | 9.40 | N |
| ATOM | 483 | CA | LEU | A | 65 | −33.394 | 15.534 | −1.319 | 1.00 | 10.14 | C |
| ATOM | 484 | C | LEU | A | 65 | −34.594 | 16.228 | −0.671 | 1.00 | 10.86 | C |
| ATOM | 485 | O | LEU | A | 65 | −35.174 | 15.723 | 0.296 | 1.00 | 10.56 | O |
| ATOM | 486 | CB | LEU | A | 65 | −32.082 | 16.117 | −0.793 | 1.00 | 8.51 | C |
| ATOM | 487 | CG | LEU | A | 65 | −30.836 | 15.282 | −1.120 | 1.00 | 10.20 | C |
| ATOM | 488 | CD1 | LEU | A | 65 | −29.562 | 16.095 | −0.943 | 1.00 | 11.61 | C |
| ATOM | 489 | CD2 | LEU | A | 65 | −30.803 | 14.004 | −0.274 | 1.00 | 12.05 | C |
| ATOM | 490 | N | MET | A | 66 | −34.973 | 17.383 | −1.209 | 1.00 | 11.05 | N |
| ATOM | 491 | CA | AMET | A | 66 | −36.136 | 18.088 | −0.703 | 0.50 | 11.92 | C |
| ATOM | 492 | C | MET | A | 66 | −37.395 | 17.241 | −0.931 | 1.00 | 14.01 | C |
| ATOM | 493 | O | MET | A | 66 | −38.328 | 17.265 | −0.120 | 1.00 | 14.48 | O |
| ATOM | 494 | CB | AMET | A | 66 | −36.239 | 19.471 | −1.354 | 0.50 | 7.66 | C |
| ATOM | 495 | CG | AMET | A | 66 | −37.413 | 20.298 | −0.867 | 0.50 | 16.42 | C |
| ATOM | 496 | SD | AMET | A | 66 | −38.927 | 19.913 | −1.763 | 0.50 | 19.91 | S |
| ATOM | 497 | CE | AMET | A | 66 | −38.623 | 20.747 | −3.320 | 0.50 | 29.87 | C |
| ATOM | 498 | CA | BMET | A | 66 | −36.151 | 18.103 | −0.735 | 0.50 | 10.75 | C |
| ATOM | 499 | CB | BMET | A | 66 | −36.301 | 19.432 | −1.483 | 0.50 | 20.22 | C |
| ATOM | 500 | CG | BMET | A | 66 | −37.520 | 20.250 | −1.071 | 0.50 | 16.81 | C |
| ATOM | 501 | SD | BMET | A | 66 | −37.739 | 21.751 | −2.054 | 0.50 | 18.63 | S |
| ATOM | 502 | CE | BMET | A | 66 | −38.028 | 21.070 | −3.685 | 0.50 | 28.73 | C |
| ATOM | 503 | N | GLY | A | 67 | −37.404 | 16.473 | −2.021 | 1.00 | 12.11 | N |
| ATOM | 504 | CA | GLY | A | 67 | −38.501 | 15.567 | −2.320 | 1.00 | 18.68 | C |
| ATOM | 505 | C | GLY | A | 67 | −38.616 | 14.423 | −1.324 | 1.00 | 13.55 | C |
| ATOM | 506 | O | GLY | A | 67 | −39.651 | 13.763 | −1.249 | 1.00 | 17.32 | O |
| ATOM | 507 | N | LEU | A | 68 | −37.550 | 14.180 | −0.570 | 1.00 | 14.11 | N |

TABLE 5-continued (Table 5 discloses SEQ ID NO: 10):

| ATOM | 508 | CA  | LEU | A | 68 | −37.555 | 13.207 | 0.520  | 1.00 | 15.51 | C |
|------|-----|-----|-----|---|----|---------|--------|--------|------|-------|---|
| ATOM | 509 | C   | LEU | A | 68 | −37.984 | 13.857 | 1.838  | 1.00 | 15.63 | C |
| ATOM | 510 | O   | LEU | A | 68 | −37.854 | 13.257 | 2.911  | 1.00 | 17.55 | O |
| ATOM | 511 | CB  | LEU | A | 68 | −36.164 | 12.605 | 0.693  | 1.00 | 14.48 | C |
| ATOM | 512 | CG  | LEU | A | 68 | −35.579 | 11.827 | −0.482 | 1.00 | 16.34 | C |
| ATOM | 513 | CD1 | LEU | A | 68 | −34.187 | 11.326 | −0.122 | 1.00 | 19.31 | C |
| ATOM | 514 | CD2 | LEU | A | 68 | −36.495 | 10.672 | −0.866 | 1.00 | 25.16 | C |
| ATOM | 515 | N   | ASP | A | 69 | −38.477 | 15.090 | 1.742  | 1.00 | 15.49 | N |
| ATOM | 516 | CA  | ASP | A | 69 | −38.936 | 15.859 | 2.903  | 1.00 | 13.48 | C |
| ATOM | 517 | C   | ASP | A | 69 | −37.799 | 16.365 | 3.800  | 1.00 | 14.51 | C |
| ATOM | 518 | O   | ASP | A | 69 | −37.982 | 16.554 | 5.007  | 1.00 | 15.76 | O |
| ATOM | 519 | CB  | ASP | A | 69 | −39.958 | 15.059 | 3.724  | 1.00 | 18.23 | C |
| ATOM | 520 | CG  | ASP | A | 69 | −40.801 | 15.939 | 4.622  | 1.00 | 52.91 | C |
| ATOM | 521 | OD1 | ASP | A | 69 | −41.032 | 17.110 | 4.255  | 1.00 | 35.35 | O |
| ATOM | 522 | OD2 | ASP | A | 69 | −41.236 | 15.461 | 5.690  | 1.00 | 43.13 | O |
| ATOM | 523 | N   | LEU | A | 70 | −36.622 | 16.574 | 3.219  | 1.00 | 11.72 | N |
| ATOM | 524 | CA  | LEU | A | 70 | −35.529 | 17.218 | 3.940  | 1.00 | 12.54 | C |
| ATOM | 525 | C   | LEU | A | 70 | −35.487 | 18.700 | 3.571  | 1.00 | 11.28 | C |
| ATOM | 526 | O   | LEU | A | 70 | −35.809 | 19.083 | 2.444  | 1.00 | 12.36 | O |
| ATOM | 527 | CB  | LEU | A | 70 | −34.174 | 16.572 | 3.621  | 1.00 | 12.49 | C |
| ATOM | 528 | CG  | LEU | A | 70 | −33.854 | 15.265 | 4.351  | 1.00 | 19.34 | C |
| ATOM | 529 | CD1 | LEU | A | 70 | −34.549 | 14.111 | 3.654  | 1.00 | 21.20 | C |
| ATOM | 530 | CD2 | LEU | A | 70 | −32.350 | 15.016 | 4.415  | 1.00 | 16.83 | C |
| ATOM | 531 | N   | LEU | A | 71 | −35.100 | 19.533 | 4.530  | 1.00 | 9.16  | N |
| ATOM | 532 | CA  | LEU | A | 71 | −34.777 | 20.916 | 4.226  | 1.00 | 9.27  | C |
| ATOM | 533 | C   | LEU | A | 71 | −33.307 | 20.979 | 3.834  | 1.00 | 8.70  | C |
| ATOM | 534 | O   | LEU | A | 71 | −32.415 | 20.689 | 4.639  | 1.00 | 8.84  | O |
| ATOM | 535 | CB  | LEU | A | 71 | −35.051 | 21.799 | 5.440  | 1.00 | 10.92 | C |
| ATOM | 536 | CG  | LEU | A | 71 | −35.014 | 23.311 | 5.176  | 1.00 | 14.41 | C |
| ATOM | 537 | CD1 | LEU | A | 71 | −35.732 | 24.045 | 6.305  | 1.00 | 17.57 | C |
| ATOM | 538 | CD2 | LEU | A | 71 | −33.592 | 23.831 | 5.014  | 1.00 | 17.60 | C |
| ATOM | 539 | N   | VAL | A | 72 | −33.060 | 21.347 | 2.586  | 1.00 | 7.86  | N |
| ATOM | 540 | CA  | VAL | A | 72 | −31.708 | 21.395 | 2.055  | 1.00 | 8.85  | C |
| ATOM | 541 | C   | VAL | A | 72 | −31.214 | 22.828 | 2.109  | 1.00 | 8.92  | C |
| ATOM | 542 | O   | VAL | A | 72 | −31.950 | 23.753 | 1.749  | 1.00 | 7.86  | O |
| ATOM | 543 | CB  | VAL | A | 72 | −31.668 | 20.911 | 0.591  | 1.00 | 7.35  | C |
| ATOM | 544 | CG1 | VAL | A | 72 | −30.227 | 20.797 | 0.097  | 1.00 | 9.49  | C |
| ATOM | 545 | CG2 | VAL | A | 72 | −32.412 | 19.583 | 0.451  | 1.00 | 9.13  | C |
| ATOM | 546 | N   | PHE | A | 73 | −29.986 | 23.021 | 2.561  | 1.00 | 6.35  | N |
| ATOM | 547 | CA  | PHE | A | 73 | −29.439 | 24.374 | 2.612  | 1.00 | 6.13  | C |
| ATOM | 548 | C   | PHE | A | 73 | −27.967 | 24.386 | 2.237  | 1.00 | 7.10  | C |
| ATOM | 549 | O   | PHE | A | 73 | −27.275 | 23.372 | 2.342  | 1.00 | 6.36  | O |
| ATOM | 550 | CB  | PHE | A | 73 | −29.728 | 25.081 | 3.959  | 1.00 | 6.94  | C |
| ATOM | 551 | CG  | PHE | A | 73 | −29.071 | 24.458 | 5.160  | 1.00 | 7.16  | C |
| ATOM | 552 | CD1 | PHE | A | 73 | −29.459 | 23.209 | 5.624  | 1.00 | 8.74  | C |
| ATOM | 553 | CD2 | PHE | A | 73 | −28.101 | 25.156 | 5.873  | 1.00 | 9.73  | C |
| ATOM | 554 | CE1 | PHE | A | 73 | −28.858 | 22.649 | 6.746  | 1.00 | 11.57 | C |
| ATOM | 555 | CE2 | PHE | A | 73 | −27.503 | 24.609 | 7.010  | 1.00 | 11.39 | C |
| ATOM | 556 | CZ  | PHE | A | 73 | −27.889 | 23.356 | 7.450  | 1.00 | 11.64 | C |
| ATOM | 557 | N   | ALA | A | 74 | −27.487 | 25.535 | 1.771  | 1.00 | 5.58  | N |
| ATOM | 558 | CA  | ALA | A | 74 | −26.122 | 25.665 | 1.312  | 1.00 | 6.13  | C |
| ATOM | 559 | C   | ALA | A | 74 | −25.710 | 27.124 | 1.322  | 1.00 | 5.53  | C |
| ATOM | 560 | O   | ALA | A | 74 | −26.562 | 28.008 | 1.381  | 1.00 | 5.91  | O |
| ATOM | 561 | CB  | ALA | A | 74 | −25.996 | 25.112 | −0.117 | 1.00 | 7.97  | C |
| ATOM | 562 | N   | HIS | A | 75 | −24.418 | 27.365 | 1.229  | 1.00 | 5.08  | N |
| ATOM | 563 | CA  | HIS | A | 75 | −23.942 | 28.683 | 0.855  | 1.00 | 4.98  | C |
| ATOM | 564 | C   | HIS | A | 75 | −22.762 | 28.529 | −0.070 | 1.00 | 6.30  | C |
| ATOM | 565 | O   | HIS | A | 75 | −22.151 | 27.455 | −0.160 | 1.00 | 6.97  | O |
| ATOM | 566 | CB  | HIS | A | 75 | −23.603 | 29.556 | 2.073  | 1.00 | 5.32  | C |
| ATOM | 567 | CG  | HIS | A | 75 | −22.565 | 28.985 | 2.985  | 1.00 | 6.21  | C |
| ATOM | 568 | ND1 | HIS | A | 75 | −22.865 | 28.561 | 4.263  | 1.00 | 7.36  | N |
| ATOM | 569 | CD2 | HIS | A | 75 | −21.228 | 28.821 | 2.835  | 1.00 | 6.89  | C |
| ATOM | 570 | CE1 | HIS | A | 75 | −21.758 | 28.146 | 4.854  | 1.00 | 6.18  | C |
| ATOM | 571 | NE2 | HIS | A | 75 | −20.747 | 28.289 | 4.012  | 1.00 | 6.86  | N |
| ATOM | 572 | N   | ASP | A | 76 | −22.428 | 29.608 | −0.771 | 1.00 | 5.01  | N |
| ATOM | 573 | CA  | ASP | A | 76 | −21.200 | 29.646 | −1.548 | 1.00 | 5.14  | C |
| ATOM | 574 | C   | ASP | A | 76 | −20.058 | 29.931 | −0.589 | 1.00 | 5.33  | C |
| ATOM | 575 | O   | ASP | A | 76 | −20.124 | 30.898 | 0.189  | 1.00 | 5.80  | O |
| ATOM | 576 | CB  | ASP | A | 76 | −21.280 | 30.708 | −2.658 | 1.00 | 6.05  | C |
| ATOM | 577 | CG  | ASP | A | 76 | −22.301 | 30.360 | −3.726 | 1.00 | 7.92  | C |
| ATOM | 578 | OD1 | ASP | A | 76 | −22.795 | 29.212 | −3.750 | 1.00 | 7.77  | O |
| ATOM | 579 | OD2 | ASP | A | 76 | −22.637 | 31.243 | −4.548 | 1.00 | 7.72  | O |
| ATOM | 580 | N   | HIS | A | 77 | −19.043 | 29.077 | −0.577 | 1.00 | 5.59  | N |
| ATOM | 581 | CA  | HIS | A | 77 | −17.908 | 29.282 | 0.298  | 1.00 | 5.52  | C |
| ATOM | 582 | C   | HIS | A | 77 | −17.261 | 30.624 | −0.020 | 1.00 | 5.25  | C |
| ATOM | 583 | O   | HIS | A | 77 | −17.368 | 31.144 | −1.141 | 1.00 | 6.90  | O |
| ATOM | 584 | CB  | HIS | A | 77 | −16.872 | 28.166 | 0.122  | 1.00 | 7.14  | C |
| ATOM | 585 | CG  | HIS | A | 77 | −17.404 | 26.795 | 0.413  | 1.00 | 6.26  | C |

TABLE 5-continued (Table 5 discloses SEQ ID NO: 10):

| ATOM | 586 | ND1 | HIS | A | 77 | −17.922 | 26.440 | 1.641 | 1.00 | 8.66 | N |
|---|---|---|---|---|---|---|---|---|---|---|---|
| ATOM | 587 | CD2 | HIS | A | 77 | −17.465 | 25.679 | −0.357 | 1.00 | 7.29 | C |
| ATOM | 588 | CE1 | HIS | A | 77 | −18.313 | 25.176 | 1.605 | 1.00 | 9.31 | C |
| ATOM | 589 | NE2 | HIS | A | 77 | −18.035 | 24.689 | 0.407 | 1.00 | 9.66 | N |
| ATOM | 590 | N | VAL | A | 78 | −16.572 | 31.196 | 0.956 | 1.00 | 6.80 | N |
| ATOM | 591 | CA | AVAL | A | 78 | −15.924 | 32.466 | 0.703 | 0.50 | 6.73 | C |
| ATOM | 592 | C | VAL | A | 78 | −15.026 | 32.332 | −0.531 | 1.00 | 7.87 | C |
| ATOM | 593 | CB | AVAL | A | 78 | −15.163 | 32.972 | 1.947 | 0.50 | 15.02 | C |
| ATOM | 594 | CG1 | AVAL | A | 78 | −13.972 | 32.076 | 2.248 | 0.50 | 3.02 | C |
| ATOM | 595 | CG2 | AVAL | A | 78 | −14.756 | 34.438 | 1.771 | 0.50 | 5.54 | C |
| ATOM | 596 | O | VAL | A | 78 | −14.417 | 31.286 | −0.791 | 1.00 | 7.09 | O |
| ATOM | 597 | CA | BVAL | A | 78 | −15.839 | 32.437 | 0.752 | 0.50 | 10.12 | C |
| ATOM | 598 | CB | BVAL | A | 78 | −14.889 | 32.695 | 1.942 | 0.50 | 4.36 | C |
| ATOM | 599 | CG1 | BVAL | A | 78 | −13.801 | 33.684 | 1.564 | 0.50 | 10.71 | C |
| ATOM | 600 | CG2 | BVAL | A | 78 | −15.667 | 33.180 | 3.151 | 0.50 | 15.80 | C |
| ATOM | 601 | N | GLY | A | 79 | −15.002 | 33.392 | −1.338 | 1.00 | 7.60 | N |
| ATOM | 602 | CA | GLY | A | 79 | −14.198 | 33.399 | −2.552 | 1.00 | 8.95 | C |
| ATOM | 603 | C | GLY | A | 79 | −14.813 | 32.627 | −3.704 | 1.00 | 5.87 | C |
| ATOM | 604 | O | GLY | A | 79 | −14.131 | 32.419 | −4.721 | 1.00 | 8.58 | O |
| ATOM | 605 | N | HIS | A | 80 | −16.072 | 32.226 | −3.569 | 1.00 | 4.89 | N |
| ATOM | 606 | CA | HIS | A | 80 | −16.745 | 31.427 | −4.592 | 1.00 | 4.97 | C |
| ATOM | 607 | C | HIS | A | 80 | −18.108 | 31.959 | −4.922 | 1.00 | 6.40 | C |
| ATOM | 608 | O | HIS | A | 80 | −18.766 | 32.612 | −4.100 | 1.00 | 6.52 | O |
| ATOM | 609 | CB | HIS | A | 80 | −16.888 | 29.958 | −4.138 | 1.00 | 5.51 | C |
| ATOM | 610 | CG | HIS | A | 80 | −15.581 | 29.255 | −3.999 | 1.00 | 7.26 | C |
| ATOM | 611 | ND1 | HIS | A | 80 | −15.113 | 28.348 | −4.931 | 1.00 | 9.83 | N |
| ATOM | 612 | CD2 | HIS | A | 80 | −14.609 | 29.374 | −3.067 | 1.00 | 4.47 | C |
| ATOM | 613 | CE1 | HIS | A | 80 | −13.918 | 27.921 | −4.561 | 1.00 | 4.41 | C |
| ATOM | 614 | NE2 | HIS | A | 80 | −13.591 | 28.527 | −3.431 | 1.00 | 11.14 | N |
| ATOM | 615 | N | GLY | A | 81 | −18.558 | 31.659 | −6.134 | 1.00 | 7.03 | N |
| ATOM | 616 | CA | GLY | A | 81 | −19.903 | 31.969 | −6.550 | 1.00 | 7.68 | C |
| ATOM | 617 | C | GLY | A | 81 | −20.301 | 33.409 | −6.297 | 1.00 | 7.61 | C |
| ATOM | 618 | O | GLY | A | 81 | −19.609 | 34.336 | −6.722 | 1.00 | 8.19 | O |
| ATOM | 619 | N | GLN | A | 82 | −21.410 | 33.585 | −5.595 | 1.00 | 7.12 | N |
| ATOM | 620 | CA | GLN | A | 82 | −21.947 | 34.916 | −5.350 | 1.00 | 7.50 | C |
| ATOM | 621 | C | GLN | A | 82 | −21.557 | 35.462 | −3.983 | 1.00 | 8.34 | C |
| ATOM | 622 | O | GLN | A | 82 | −22.111 | 36.478 | −3.553 | 1.00 | 9.53 | O |
| ATOM | 623 | CB | GLN | A | 82 | −23.459 | 34.917 | −5.510 | 1.00 | 7.66 | C |
| ATOM | 624 | CG | GLN | A | 82 | −23.918 | 34.420 | −6.890 | 1.00 | 7.96 | C |
| ATOM | 625 | CD | GLN | A | 82 | −25.416 | 34.400 | −7.029 | 1.00 | 11.20 | C |
| ATOM | 626 | OE1 | GLN | A | 82 | −26.058 | 35.446 | −7.145 | 1.00 | 12.46 | O |
| ATOM | 627 | NE2 | GLN | A | 82 | −25.998 | 33.207 | −7.017 | 1.00 | 9.37 | N |
| ATOM | 628 | N | SER | A | 83 | −20.630 | 34.787 | −3.306 | 1.00 | 6.24 | N |
| ATOM | 629 | CA | SER | A | 83 | −20.130 | 35.262 | −2.022 | 1.00 | 5.93 | C |
| ATOM | 630 | C | SER | A | 83 | −18.974 | 36.210 | −2.224 | 1.00 | 7.64 | C |
| ATOM | 631 | O | SER | A | 83 | −18.346 | 36.241 | −3.292 | 1.00 | 9.96 | O |
| ATOM | 632 | CB | SER | A | 83 | −19.670 | 34.088 | −1.157 | 1.00 | 6.90 | C |
| ATOM | 633 | OG | SER | A | 83 | −20.781 | 33.296 | −0.820 | 1.00 | 5.65 | O |
| ATOM | 634 | N | GLU | A | 84 | −18.684 | 36.989 | −1.185 | 1.00 | 8.21 | N |
| ATOM | 635 | CA | GLU | A | 84 | −17.549 | 37.900 | −1.200 | 1.00 | 8.55 | C |
| ATOM | 636 | C | GLU | A | 84 | −16.218 | 37.169 | −1.054 | 1.00 | 10.87 | C |
| ATOM | 637 | O | GLU | A | 84 | −16.181 | 35.963 | −0.796 | 1.00 | 10.07 | O |
| ATOM | 638 | CB | GLU | A | 84 | −17.701 | 38.956 | −0.097 | 1.00 | 8.81 | C |
| ATOM | 639 | CG | GLU | A | 84 | −18.819 | 39.932 | −0.371 | 1.00 | 10.32 | C |
| ATOM | 640 | CD | GLU | A | 84 | −18.897 | 41.045 | 0.662 | 1.00 | 14.70 | C |
| ATOM | 641 | OE1 | GLU | A | 84 | −18.584 | 40.792 | 1.844 | 1.00 | 12.02 | O |
| ATOM | 642 | OE2 | GLU | A | 84 | −19.285 | 42.171 | 0.285 | 1.00 | 17.48 | O |
| ATOM | 643 | N | GLY | A | 85 | −15.123 | 37.909 | −1.214 | 1.00 | 10.41 | N |
| ATOM | 644 | CA | GLY | A | 85 | −13.785 | 37.373 | −1.061 | 1.00 | 11.16 | C |
| ATOM | 645 | C | GLY | A | 85 | −13.025 | 37.311 | −2.371 | 1.00 | 12.67 | C |
| ATOM | 646 | O | GLY | A | 85 | −13.611 | 37.083 | −3.428 | 1.00 | 12.70 | O |
| ATOM | 647 | N | GLU | A | 86 | −11.717 | 37.516 | −2.307 | 1.00 | 12.86 | N |
| ATOM | 648 | CA | GLU | A | 86 | −10.900 | 37.312 | −3.497 | 1.00 | 15.49 | C |
| ATOM | 649 | C | GLU | A | 86 | −11.139 | 35.894 | −4.012 | 1.00 | 14.29 | C |
| ATOM | 650 | O | GLU | A | 86 | −11.252 | 34.955 | −3.220 | 1.00 | 11.66 | O |
| ATOM | 651 | CB | GLU | A | 86 | −9.429 | 37.536 | −3.177 | 1.00 | 16.36 | C |
| ATOM | 652 | CG | GLU | A | 86 | −9.114 | 38.976 | −2.782 | 1.00 | 31.32 | C |
| ATOM | 653 | CD | GLU | A | 86 | −7.662 | 39.174 | −2.392 | 1.00 | 101.84 | C |
| ATOM | 654 | OE1 | GLU | A | 86 | −6.862 | 38.229 | −2.567 | 1.00 | 54.48 | O |
| ATOM | 655 | OE2 | GLU | A | 86 | −7.321 | 40.277 | −1.912 | 1.00 | 74.42 | O |
| ATOM | 656 | N | ARG | A | 87 | −11.240 | 35.739 | −5.329 | 1.00 | 12.44 | N |
| ATOM | 657 | CA | ARG | A | 87 | −11.629 | 34.455 | −5.910 | 1.00 | 11.77 | C |
| ATOM | 658 | C | ARG | A | 87 | −10.641 | 33.329 | −5.596 | 1.00 | 10.94 | C |
| ATOM | 659 | O | ARG | A | 87 | −9.435 | 33.443 | −5.846 | 1.00 | 11.69 | O |
| ATOM | 660 | CB | ARG | A | 87 | −11.803 | 34.562 | −7.432 | 1.00 | 12.45 | C |
| ATOM | 661 | CG | ARG | A | 87 | −12.817 | 35.592 | −7.926 | 1.00 | 17.92 | C |
| ATOM | 662 | CD | ARG | A | 87 | −14.243 | 35.195 | −7.585 | 1.00 | 18.43 | C |
| ATOM | 663 | NE | ARG | A | 87 | −14.578 | 35.661 | −6.249 | 1.00 | 11.89 | N |

TABLE 5-continued (Table 5 discloses SEQ ID NO: 10):

| ATOM | 664 | CZ | ARG | A | 87 | −15.736 | 35.459 | −5.638 | 1.00 | 12.44 | C |
|---|---|---|---|---|---|---|---|---|---|---|---|
| ATOM | 665 | NH1 | ARG | A | 87 | −16.707 | 34.782 | −6.235 | 1.00 | 13.57 | N |
| ATOM | 666 | NH2 | ARG | A | 87 | −15.916 | 35.950 | −4.414 | 1.00 | 13.60 | N |
| ATOM | 667 | N | MET | A | 88 | −11.172 | 32.232 | −5.059 | 1.00 | 9.91 | N |
| ATOM | 668 | CA | MET | A | 88 | −10.380 | 31.028 | −4.820 | 1.00 | 11.60 | C |
| ATOM | 669 | C | MET | A | 88 | −9.109 | 31.274 | −4.009 | 1.00 | 12.66 | C |
| ATOM | 670 | O | MET | A | 88 | −8.019 | 30.791 | −4.335 | 1.00 | 13.08 | O |
| ATOM | 671 | CB | MET | A | 88 | −10.068 | 30.294 | −6.129 | 1.00 | 13.27 | C |
| ATOM | 672 | CG | MET | A | 88 | −11.227 | 29.455 | −6.646 | 1.00 | 23.14 | C |
| ATOM | 673 | SD | MET | A | 88 | −10.720 | 28.240 | −7.892 | 1.00 | 20.98 | S |
| ATOM | 674 | CE | MET | A | 88 | −9.588 | 27.226 | −6.961 | 1.00 | 30.54 | C |
| ATOM | 675 | N | VAL | A | 89 | −9.285 | 32.044 | −2.942 | 1.00 | 9.61 | N |
| ATOM | 676 | CA | AVAL | A | 89 | −8.252 | 32.187 | −1.938 | 0.50 | 8.87 | C |
| ATOM | 677 | C | VAL | A | 89 | −8.935 | 32.155 | −0.579 | 1.00 | 8.58 | C |
| ATOM | 678 | O | VAL | A | 89 | −10.128 | 32.442 | −0.452 | 1.00 | 10.43 | O |
| ATOM | 679 | CB | AVAL | A | 89 | −7.439 | 33.484 | −2.102 | 0.50 | 20.29 | C |
| ATOM | 680 | CG1 | AVAL | A | 89 | −6.728 | 33.502 | −3.451 | 0.50 | 21.26 | C |
| ATOM | 681 | CG2 | AVAL | A | 89 | −8.335 | 34.689 | −1.951 | 0.50 | 11.60 | C |
| ATOM | 682 | CA | BVAL | A | 89 | −8.264 | 32.316 | −1.942 | 0.50 | 15.07 | C |
| ATOM | 683 | CB | BVAL | A | 89 | −7.752 | 33.771 | −2.069 | 0.50 | 13.11 | C |
| ATOM | 684 | CG1 | BVAL | A | 89 | −7.120 | 34.254 | −0.767 | 0.50 | 15.31 | C |
| ATOM | 685 | CG2 | BVAL | A | 89 | −6.786 | 33.900 | −3.241 | 0.50 | 28.13 | C |
| ATOM | 686 | N | VAL | A | 90 | −8.184 | 31.737 | 0.427 | 1.00 | 9.08 | N |
| ATOM | 687 | CA | VAL | A | 90 | −8.738 | 31.651 | 1.774 | 1.00 | 11.86 | C |
| ATOM | 688 | C | VAL | A | 90 | −7.583 | 31.817 | 2.759 | 1.00 | 11.67 | C |
| ATOM | 689 | O | VAL | A | 90 | −6.506 | 31.267 | 2.556 | 1.00 | 10.65 | O |
| ATOM | 690 | CB | VAL | A | 90 | −9.530 | 30.322 | 1.992 | 1.00 | 9.75 | C |
| ATOM | 691 | CG1 | VAL | A | 90 | −8.584 | 29.132 | 2.112 | 1.00 | 10.71 | C |
| ATOM | 692 | CG2 | VAL | A | 90 | −10.449 | 30.428 | 3.209 | 1.00 | 12.69 | C |
| ATOM | 693 | N | SER | A | 91 | −7.793 | 32.610 | 3.807 | 1.00 | 11.86 | N |
| ATOM | 694 | CA | SER | A | 91 | −6.708 | 32.895 | 4.745 | 1.00 | 11.26 | C |
| ATOM | 695 | C | SER | A | 91 | −6.179 | 31.607 | 5.380 | 1.00 | 10.82 | C |
| ATOM | 696 | O | SER | A | 91 | −4.972 | 31.401 | 5.489 | 1.00 | 13.74 | O |
| ATOM | 697 | CB | SER | A | 91 | −7.170 | 33.884 | 5.817 | 1.00 | 14.65 | C |
| ATOM | 698 | OG | SER | A | 91 | −8.265 | 33.367 | 6.549 | 1.00 | 16.21 | O |
| ATOM | 699 | N | ASP | A | 92 | −7.105 | 30.743 | 5.789 | 1.00 | 10.07 | N |
| ATOM | 700 | CA | ASP | A | 92 | −6.784 | 29.407 | 6.285 | 1.00 | 9.45 | C |
| ATOM | 701 | C | ASP | A | 92 | −7.983 | 28.523 | 5.981 | 1.00 | 8.51 | C |
| ATOM | 702 | O | ASP | A | 92 | −9.130 | 28.967 | 6.055 | 1.00 | 8.70 | O |
| ATOM | 703 | CB | ASP | A | 92 | −6.516 | 29.407 | 7.795 | 1.00 | 12.63 | C |
| ATOM | 704 | CG | ASP | A | 92 | −6.132 | 28.016 | 8.322 | 1.00 | 12.62 | C |
| ATOM | 705 | OD1 | ASP | A | 92 | −4.934 | 27.663 | 8.272 | 1.00 | 15.77 | O |
| ATOM | 706 | OD2 | ASP | A | 92 | −7.030 | 27.276 | 8.782 | 1.00 | 13.34 | O |
| ATOM | 707 | N | PHE | A | 93 | −7.714 | 27.266 | 5.644 | 1.00 | 7.96 | N |
| ATOM | 708 | CA | PHE | A | 93 | −8.783 | 26.351 | 5.260 | 1.00 | 9.18 | C |
| ATOM | 709 | C | PHE | A | 93 | −9.900 | 26.284 | 6.304 | 1.00 | 7.89 | C |
| ATOM | 710 | O | PHE | A | 93 | −11.059 | 26.057 | 5.975 | 1.00 | 8.19 | O |
| ATOM | 711 | CB | PHE | A | 93 | −8.233 | 24.949 | 4.997 | 1.00 | 8.72 | C |
| ATOM | 712 | CG | PHE | A | 93 | −9.171 | 24.080 | 4.204 | 1.00 | 8.08 | C |
| ATOM | 713 | CD1 | PHE | A | 93 | −9.243 | 24.196 | 2.822 | 1.00 | 9.70 | C |
| ATOM | 714 | CD2 | PHE | A | 93 | −9.994 | 23.163 | 4.834 | 1.00 | 9.05 | C |
| ATOM | 715 | CE1 | PHE | A | 93 | −10.117 | 23.401 | 2.082 | 1.00 | 8.73 | C |
| ATOM | 716 | CE2 | PHE | A | 93 | −10.870 | 22.363 | 4.105 | 1.00 | 9.40 | C |
| ATOM | 717 | CZ | PHE | A | 93 | −10.936 | 22.488 | 2.726 | 1.00 | 8.70 | C |
| ATOM | 718 | N | HIS | A | 94 | −9.546 | 26.468 | 7.572 | 1.00 | 7.76 | N |
| ATOM | 719 | CA | HIS | A | 94 | −10.545 | 26.363 | 8.621 | 1.00 | 9.12 | C |
| ATOM | 720 | C | HIS | A | 94 | −11.690 | 27.367 | 8.476 | 1.00 | 6.64 | C |
| ATOM | 721 | O | HIS | A | 94 | −12.782 | 27.138 | 8.982 | 1.00 | 8.47 | O |
| ATOM | 722 | CB | HIS | A | 94 | −9.922 | 26.487 | 10.014 | 1.00 | 10.83 | C |
| ATOM | 723 | CG | HIS | A | 94 | −10.891 | 26.175 | 11.107 | 1.00 | 12.48 | C |
| ATOM | 724 | ND1 | HIS | A | 94 | −11.497 | 27.153 | 11.868 | 1.00 | 18.24 | N |
| ATOM | 725 | CD2 | HIS | A | 94 | −11.407 | 24.996 | 11.526 | 1.00 | 14.58 | C |
| ATOM | 726 | CE1 | HIS | A | 94 | −12.323 | 26.586 | 12.729 | 1.00 | 18.04 | C |
| ATOM | 727 | NE2 | HIS | A | 94 | −12.289 | 25.278 | 12.541 | 1.00 | 20.93 | N |
| ATOM | 728 | N | VAL | A | 95 | −11.433 | 28.476 | 7.790 | 1.00 | 6.79 | N |
| ATOM | 729 | CA | VAL | A | 95 | −12.482 | 29.445 | 7.525 | 1.00 | 7.84 | C |
| ATOM | 730 | C | VAL | A | 95 | −13.713 | 28.751 | 6.923 | 1.00 | 5.99 | C |
| ATOM | 731 | O | VAL | A | 95 | −14.852 | 29.036 | 7.299 | 1.00 | 7.00 | O |
| ATOM | 732 | CB | VAL | A | 95 | −11.981 | 30.569 | 6.580 | 1.00 | 9.46 | C |
| ATOM | 733 | CG1 | VAL | A | 95 | −13.146 | 31.338 | 5.972 | 1.00 | 10.88 | C |
| ATOM | 734 | CG2 | VAL | A | 95 | −11.040 | 31.504 | 7.333 | 1.00 | 10.22 | C |
| ATOM | 735 | N | PHE | A | 96 | −13.482 | 27.834 | 5.976 | 1.00 | 5.97 | N |
| ATOM | 736 | CA | PHE | A | 96 | −14.606 | 27.148 | 5.328 | 1.00 | 6.34 | C |
| ATOM | 737 | C | PHE | A | 96 | −15.432 | 26.338 | 6.323 | 1.00 | 4.91 | C |
| ATOM | 738 | O | PHE | A | 96 | −16.661 | 26.310 | 6.262 | 1.00 | 6.56 | O |
| ATOM | 739 | CB | PHE | A | 96 | −14.124 | 26.191 | 4.231 | 1.00 | 7.50 | C |
| ATOM | 740 | CG | PHE | A | 96 | −13.463 | 26.855 | 3.057 | 1.00 | 6.47 | C |
| ATOM | 741 | CD1 | PHE | A | 96 | −13.997 | 27.991 | 2.453 | 1.00 | 7.28 | C |

TABLE 5-continued (Table 5 discloses SEQ ID NO: 10):

| ATOM | 742 | CD2 | PHE | A | 96 | −12.332 | 26.286 | 2.512 | 1.00 | 7.30 | C |
|---|---|---|---|---|---|---|---|---|---|---|---|
| ATOM | 743 | CE1 | PHE | A | 96 | −13.378 | 28.572 | 1.333 | 1.00 | 8.59 | C |
| ATOM | 744 | CE2 | PHE | A | 96 | −11.707 | 26.847 | 1.388 | 1.00 | 8.91 | C |
| ATOM | 745 | CZ | PHE | A | 96 | −12.237 | 27.993 | 0.794 | 1.00 | 7.27 | C |
| ATOM | 746 | N | VAL | A | 97 | −14.732 | 25.648 | 7.228 | 1.00 | 6.11 | N |
| ATOM | 747 | CA | VAL | A | 97 | −15.375 | 24.815 | 8.242 | 1.00 | 6.27 | C |
| ATOM | 748 | C | VAL | A | 97 | −16.135 | 25.682 | 9.259 | 1.00 | 5.36 | C |
| ATOM | 749 | O | VAL | A | 97 | −17.277 | 25.403 | 9.594 | 1.00 | 6.07 | O |
| ATOM | 750 | CB | VAL | A | 97 | −14.312 | 23.943 | 8.952 | 1.00 | 7.37 | C |
| ATOM | 751 | CG1 | VAL | A | 97 | −14.941 | 23.145 | 10.091 | 1.00 | 10.36 | C |
| ATOM | 752 | CG2 | VAL | A | 97 | −13.620 | 23.008 | 7.943 | 1.00 | 9.21 | C |
| ATOM | 753 | N | ARG | A | 98 | −15.480 | 26.734 | 9.740 | 1.00 | 6.54 | N |
| ATOM | 754 | CA | ARG | A | 98 | −16.117 | 27.695 | 10.638 | 1.00 | 7.12 | C |
| ATOM | 755 | C | ARG | A | 98 | −17.430 | 28.221 | 10.051 | 1.00 | 5.89 | C |
| ATOM | 756 | O | ARG | A | 98 | −18.456 | 28.299 | 10.723 | 1.00 | 6.29 | O |
| ATOM | 757 | CB | ARG | A | 98 | −15.142 | 28.850 | 10.852 | 1.00 | 8.63 | C |
| ATOM | 758 | CG | ARG | A | 98 | −15.637 | 29.977 | 11.756 | 1.00 | 10.60 | C |
| ATOM | 759 | CD | ARG | A | 98 | −14.744 | 31.189 | 11.573 | 1.00 | 10.59 | C |
| ATOM | 760 | NE | ARG | A | 98 | −15.017 | 31.792 | 10.268 | 1.00 | 10.15 | N |
| ATOM | 761 | CZ | ARG | A | 98 | −14.335 | 32.796 | 9.731 | 1.00 | 10.10 | C |
| ATOM | 762 | NH1 | ARG | A | 98 | −13.310 | 33.337 | 10.377 | 1.00 | 11.94 | N |
| ATOM | 763 | NH2 | ARG | A | 98 | −14.697 | 33.265 | 8.543 | 1.00 | 10.42 | N |
| ATOM | 764 | N | ASP | A | 99 | −17.395 | 28.585 | 8.770 | 1.00 | 6.39 | N |
| ATOM | 765 | CA | ASP | A | 99 | −18.579 | 29.151 | 8.127 | 1.00 | 7.52 | C |
| ATOM | 766 | C | ASP | A | 99 | −19.709 | 28.118 | 7.947 | 1.00 | 4.77 | C |
| ATOM | 767 | O | ASP | A | 99 | −20.882 | 28.438 | 8.121 | 1.00 | 5.81 | O |
| ATOM | 768 | CB | ASP | A | 99 | −18.211 | 29.818 | 6.795 | 1.00 | 7.19 | C |
| ATOM | 769 | CG | ASP | A | 99 | −17.358 | 31.083 | 6.974 | 1.00 | 9.39 | C |
| ATOM | 770 | OD1 | ASP | A | 99 | −17.061 | 31.490 | 8.129 | 1.00 | 9.24 | O |
| ATOM | 771 | OD2 | ASP | A | 99 | −16.950 | 31.677 | 5.948 | 1.00 | 8.90 | O |
| ATOM | 772 | N | VAL | A | 100 | −19.349 | 26.875 | 7.611 | 1.00 | 5.99 | N |
| ATOM | 773 | CA | VAL | A | 100 | −20.360 | 25.815 | 7.575 | 1.00 | 5.66 | C |
| ATOM | 774 | C | VAL | A | 100 | −21.017 | 25.659 | 8.958 | 1.00 | 4.09 | C |
| ATOM | 775 | O | VAL | A | 100 | −22.228 | 25.583 | 9.061 | 1.00 | 6.12 | O |
| ATOM | 776 | CB | VAL | A | 100 | −19.783 | 24.457 | 7.079 | 1.00 | 5.14 | C |
| ATOM | 777 | CG1 | VAL | A | 100 | −20.807 | 23.349 | 7.288 | 1.00 | 8.00 | C |
| ATOM | 778 | CG2 | VAL | A | 100 | −19.404 | 24.560 | 5.599 | 1.00 | 8.22 | C |
| ATOM | 779 | N | LEU | A | 101 | −20.184 | 25.628 | 10.001 | 1.00 | 5.14 | N |
| ATOM | 780 | CA | LEU | A | 101 | −20.722 | 25.484 | 11.361 | 1.00 | 6.56 | C |
| ATOM | 781 | C | LEU | A | 101 | −21.636 | 26.651 | 11.768 | 1.00 | 6.23 | C |
| ATOM | 782 | O | LEU | A | 101 | −22.652 | 26.444 | 12.419 | 1.00 | 6.91 | O |
| ATOM | 783 | CB | LEU | A | 101 | −19.591 | 25.278 | 12.369 | 1.00 | 7.60 | C |
| ATOM | 784 | CG | LEU | A | 101 | −18.909 | 23.905 | 12.286 | 1.00 | 9.07 | C |
| ATOM | 785 | CD1 | LEU | A | 101 | −17.675 | 23.904 | 13.156 | 1.00 | 13.36 | C |
| ATOM | 786 | CD2 | LEU | A | 101 | −19.878 | 22.797 | 12.691 | 1.00 | 12.74 | C |
| ATOM | 787 | N | GLN | A | 102 | −21.294 | 27.864 | 11.342 | 1.00 | 5.43 | N |
| ATOM | 788 | CA | GLN | A | 102 | −22.177 | 28.997 | 11.599 | 1.00 | 5.19 | C |
| ATOM | 789 | C | GLN | A | 102 | −23.543 | 28.772 | 10.970 | 1.00 | 6.32 | C |
| ATOM | 790 | O | GLN | A | 102 | −24.579 | 28.956 | 11.610 | 1.00 | 6.82 | O |
| ATOM | 791 | CB | GLN | A | 102 | −21.552 | 30.286 | 11.068 | 1.00 | 6.74 | C |
| ATOM | 792 | CG | GLN | A | 102 | −22.446 | 31.499 | 11.276 | 1.00 | 7.84 | C |
| ATOM | 793 | CD | GLN | A | 102 | −21.965 | 32.740 | 10.550 | 1.00 | 7.29 | C |
| ATOM | 794 | OE1 | GLN | A | 102 | −20.883 | 32.767 | 9.977 | 1.00 | 9.47 | O |
| ATOM | 795 | NE2 | GLN | A | 102 | −22.787 | 33.791 | 10.585 | 1.00 | 8.18 | N |
| ATOM | 796 | N | HIS | A | 103 | −23.552 | 28.370 | 9.699 | 1.00 | 5.94 | N |
| ATOM | 797 | CA | HIS | A | 103 | −24.801 | 28.171 | 9.002 | 1.00 | 6.08 | C |
| ATOM | 798 | C | HIS | A | 103 | −25.598 | 27.012 | 9.607 | 1.00 | 4.80 | C |
| ATOM | 799 | O | HIS | A | 103 | −26.801 | 27.111 | 9.797 | 1.00 | 6.26 | O |
| ATOM | 800 | CB | HIS | A | 103 | −24.531 | 27.925 | 7.515 | 1.00 | 6.90 | C |
| ATOM | 801 | CG | HIS | A | 103 | −25.677 | 28.278 | 6.631 | 1.00 | 7.96 | C |
| ATOM | 802 | ND1 | HIS | A | 103 | −25.565 | 28.282 | 5.256 | 1.00 | 8.59 | N |
| ATOM | 803 | CD2 | HIS | A | 103 | −26.945 | 28.655 | 6.910 | 1.00 | 6.64 | C |
| ATOM | 804 | CE1 | HIS | A | 103 | −26.719 | 28.655 | 4.728 | 1.00 | 8.29 | C |
| ATOM | 805 | NE2 | HIS | A | 103 | −27.581 | 28.872 | 5.708 | 1.00 | 9.02 | N |
| ATOM | 806 | N | VAL | A | 104 | −24.913 | 25.903 | 9.888 | 1.00 | 5.95 | N |
| ATOM | 807 | CA | VAL | A | 104 | −25.605 | 24.765 | 10.486 | 1.00 | 7.58 | C |
| ATOM | 808 | C | VAL | A | 104 | −26.224 | 25.153 | 11.843 | 1.00 | 5.80 | C |
| ATOM | 809 | O | VAL | A | 104 | −27.385 | 24.851 | 12.108 | 1.00 | 7.78 | O |
| ATOM | 810 | CB | VAL | A | 104 | −24.653 | 23.572 | 10.668 | 1.00 | 7.05 | C |
| ATOM | 811 | CG1 | VAL | A | 104 | −25.302 | 22.506 | 11.558 | 1.00 | 10.12 | C |
| ATOM | 812 | CG2 | VAL | A | 104 | −24.250 | 22.984 | 9.309 | 1.00 | 9.57 | C |
| ATOM | 813 | N | ASP | A | 105 | −25.434 | 25.831 | 12.676 | 1.00 | 6.23 | N |
| ATOM | 814 | CA | ASP | A | 105 | −25.933 | 26.244 | 13.994 | 1.00 | 6.14 | C |
| ATOM | 815 | C | ASP | A | 105 | −27.133 | 27.178 | 13.856 | 1.00 | 8.33 | C |
| ATOM | 816 | O | ASP | A | 105 | −28.112 | 27.052 | 14.592 | 1.00 | 8.56 | O |
| ATOM | 817 | CB | ASP | A | 105 | −24.839 | 26.905 | 14.843 | 1.00 | 7.42 | C |
| ATOM | 818 | CG | ASP | A | 105 | −23.776 | 25.920 | 15.336 | 1.00 | 13.92 | C |
| ATOM | 819 | OD1 | ASP | A | 105 | −24.061 | 24.704 | 15.406 | 1.00 | 16.13 | O |

TABLE 5-continued (Table 5 discloses SEQ ID NO: 10):

| ATOM | 820 | OD2 | ASP | A | 105 | −22.648 | 26.361 | 15.663 | 1.00 | 13.33 | O |
|---|---|---|---|---|---|---|---|---|---|---|---|
| ATOM | 821 | N | SER | A | 106 | −27.082 | 28.111 | 12.903 | 1.00 | 7.27 | N |
| ATOM | 822 | CA | ASER | A | 106 | −28.184 | 29.047 | 12.712 | 0.33 | 8.06 | C |
| ATOM | 823 | C | SER | A | 106 | −29.453 | 28.338 | 12.241 | 1.00 | 9.29 | C |
| ATOM | 824 | O | SER | A | 106 | −30.557 | 28.661 | 12.670 | 1.00 | 12.36 | O |
| ATOM | 825 | CB | ASER | A | 106 | −27.791 | 30.152 | 11.727 | 0.33 | 12.36 | C |
| ATOM | 826 | OG | ASER | A | 106 | −28.878 | 31.033 | 11.504 | 0.33 | 11.64 | O |
| ATOM | 827 | CA | BSER | A | 106 | −28.189 | 29.044 | 12.739 | 0.33 | 7.72 | C |
| ATOM | 828 | CB | BSER | A | 106 | −27.798 | 30.224 | 11.836 | 0.33 | 8.33 | C |
| ATOM | 829 | OG | BSER | A | 106 | −27.502 | 29.800 | 10.519 | 0.33 | 9.09 | O |
| ATOM | 830 | CA | CSER | A | 106 | −28.187 | 29.046 | 12.697 | 0.33 | 8.20 | C |
| ATOM | 831 | CB | CSER | A | 106 | −27.805 | 30.112 | 11.671 | 0.33 | 14.56 | C |
| ATOM | 832 | OG | CSER | A | 106 | −26.705 | 30.866 | 12.126 | 0.33 | 10.99 | O |
| ATOM | 833 | N | MET | A | 107 | −29.301 | 27.365 | 11.344 | 1.00 | 7.49 | N |
| ATOM | 834 | CA | AMET | A | 107 | −30.442 | 26.604 | 10.845 | 0.50 | 10.61 | C |
| ATOM | 835 | C | MET | A | 107 | −31.031 | 25.708 | 11.936 | 1.00 | 6.77 | C |
| ATOM | 836 | O | MET | A | 107 | −32.255 | 25.615 | 12.087 | 1.00 | 11.21 | O |
| ATOM | 837 | CB | AMET | A | 107 | −30.024 | 25.765 | 9.629 | 0.50 | 11.62 | C |
| ATOM | 838 | CG | AMET | A | 107 | −31.142 | 24.962 | 8.981 | 0.50 | 11.62 | C |
| ATOM | 839 | SD | AMET | A | 107 | −32.524 | 25.957 | 8.382 | 0.50 | 17.80 | S |
| ATOM | 840 | CE | AMET | A | 107 | −31.659 | 27.299 | 7.589 | 0.50 | 16.49 | C |
| ATOM | 841 | CA | BMET | A | 107 | −30.454 | 26.617 | 10.859 | 0.50 | 6.28 | C |
| ATOM | 842 | CB | BMET | A | 107 | −30.076 | 25.798 | 9.625 | 0.50 | 11.75 | C |
| ATOM | 843 | CG | BMET | A | 107 | −29.649 | 26.659 | 8.460 | 0.50 | 12.02 | C |
| ATOM | 844 | SD | BMET | A | 107 | −30.974 | 27.746 | 7.914 | 0.50 | 26.78 | S |
| ATOM | 845 | CE | BMET | A | 107 | −32.093 | 26.557 | 7.189 | 0.50 | 15.11 | C |
| ATOM | 846 | N | GLN | A | 108 | −30.154 | 25.044 | 12.688 | 1.00 | 9.49 | N |
| ATOM | 847 | CA | AGLN | A | 108 | −30.611 | 24.118 | 13.720 | 0.50 | 9.57 | C |
| ATOM | 848 | C | GLN | A | 108 | −31.458 | 24.812 | 14.782 | 1.00 | 11.46 | C |
| ATOM | 849 | O | GLN | A | 108 | −32.441 | 24.243 | 15.262 | 1.00 | 12.43 | O |
| ATOM | 850 | CB | AGLN | A | 108 | −29.439 | 23.367 | 14.357 | 0.50 | 12.58 | C |
| ATOM | 851 | CG | AGLN | A | 108 | −28.938 | 22.209 | 13.504 | 0.50 | 12.65 | C |
| ATOM | 852 | CD | AGLN | A | 108 | −28.137 | 21.196 | 14.294 | 0.50 | 68.54 | C |
| ATOM | 853 | OE1 | AGLN | A | 108 | −28.661 | 20.161 | 14.699 | 0.50 | 23.41 | O |
| ATOM | 854 | NE2 | AGLN | A | 108 | −26.864 | 21.489 | 14.521 | 0.50 | 7.83 | N |
| ATOM | 855 | CA | BGLN | A | 108 | −30.589 | 24.119 | 13.737 | 0.50 | 8.69 | C |
| ATOM | 856 | CB | BGLN | A | 108 | −29.391 | 23.463 | 14.430 | 0.50 | 9.25 | C |
| ATOM | 857 | CG | BGLN | A | 108 | −29.780 | 22.432 | 15.483 | 0.50 | 13.14 | C |
| ATOM | 858 | CD | BGLN | A | 108 | −30.122 | 21.075 | 14.882 | 0.50 | 70.97 | C |
| ATOM | 859 | OE1 | BGLN | A | 108 | −29.236 | 20.263 | 14.616 | 0.50 | 17.19 | O |
| ATOM | 860 | NE2 | BGLN | A | 108 | −31.413 | 20.820 | 14.679 | 0.50 | 9.82 | N |
| ATOM | 861 | N | LYS | A | 109 | −31.099 | 26.046 | 15.133 | 1.00 | 10.35 | N |
| ATOM | 862 | CA | LYS | A | 109 | −31.860 | 26.757 | 16.166 | 1.00 | 12.18 | C |
| ATOM | 863 | C | LYS | A | 109 | −33.260 | 27.117 | 15.670 | 1.00 | 15.37 | C |
| ATOM | 864 | O | LYS | A | 109 | −34.181 | 27.259 | 16.477 | 1.00 | 15.02 | O |
| ATOM | 865 | CB | LYS | A | 109 | −31.119 | 28.010 | 16.647 | 1.00 | 12.62 | C |
| ATOM | 866 | CG | LYS | A | 109 | −31.207 | 29.149 | 15.643 | 1.00 | 24.20 | C |
| ATOM | 867 | CD | LYS | A | 109 | −30.473 | 30.401 | 16.074 | 1.00 | 26.44 | C |
| ATOM | 868 | CE | LYS | A | 109 | −30.940 | 31.602 | 15.256 | 1.00 | 17.15 | C |
| ATOM | 869 | NZ | LYS | A | 109 | −31.147 | 31.297 | 13.808 | 1.00 | 22.59 | N |
| ATOM | 870 | N | ASP | A | 110 | −33.420 | 27.265 | 14.352 | 1.00 | 11.64 | N |
| ATOM | 871 | CA | ASP | A | 110 | −34.731 | 27.502 | 13.748 | 1.00 | 14.09 | C |
| ATOM | 872 | C | ASP | A | 110 | −35.540 | 26.202 | 13.650 | 1.00 | 17.43 | C |
| ATOM | 873 | O | ASP | A | 110 | −36.768 | 26.227 | 13.596 | 1.00 | 16.72 | O |
| ATOM | 874 | CB | ASP | A | 110 | −34.603 | 28.125 | 12.349 | 1.00 | 16.62 | C |
| ATOM | 875 | CG | ASP | A | 110 | −33.858 | 29.459 | 12.349 | 1.00 | 35.51 | C |
| ATOM | 876 | OD1 | ASP | A | 110 | −33.892 | 30.183 | 13.363 | 1.00 | 27.26 | O |
| ATOM | 877 | OD2 | ASP | A | 110 | −33.242 | 29.795 | 11.314 | 1.00 | 33.71 | O |
| ATOM | 878 | N | TYR | A | 111 | −34.838 | 25.070 | 13.614 | 1.00 | 12.88 | N |
| ATOM | 879 | CA | TYR | A | 111 | −35.463 | 23.749 | 13.495 | 1.00 | 11.95 | C |
| ATOM | 880 | C | TYR | A | 111 | −34.929 | 22.816 | 14.570 | 1.00 | 14.36 | C |
| ATOM | 881 | O | TYR | A | 111 | −34.283 | 21.805 | 14.270 | 1.00 | 15.37 | O |
| ATOM | 882 | CB | TYR | A | 111 | −35.195 | 23.153 | 12.104 | 1.00 | 14.49 | C |
| ATOM | 883 | CG | TYR | A | 111 | −35.903 | 23.906 | 11.010 | 1.00 | 11.25 | C |
| ATOM | 884 | CD1 | TYR | A | 111 | −35.303 | 24.996 | 10.389 | 1.00 | 11.70 | C |
| ATOM | 885 | CD2 | TYR | A | 111 | −37.177 | 23.536 | 10.605 | 1.00 | 13.97 | C |
| ATOM | 886 | CE1 | TYR | A | 111 | −35.964 | 25.702 | 9.397 | 1.00 | 12.73 | C |
| ATOM | 887 | CE2 | TYR | A | 111 | −37.842 | 24.229 | 9.609 | 1.00 | 13.65 | C |
| ATOM | 888 | CZ | TYR | A | 111 | −37.234 | 25.306 | 9.013 | 1.00 | 13.00 | C |
| ATOM | 889 | OH | TYR | A | 111 | −37.903 | 25.994 | 8.027 | 1.00 | 17.94 | O |
| ATOM | 890 | N | PRO | A | 112 | −35.184 | 23.159 | 15.842 | 1.00 | 16.22 | N |
| ATOM | 891 | CA | PRO | A | 112 | −34.592 | 22.419 | 16.956 | 1.00 | 17.66 | C |
| ATOM | 892 | C | PRO | A | 112 | −35.069 | 20.974 | 16.951 | 1.00 | 18.24 | C |
| ATOM | 893 | O | PRO | A | 112 | −36.225 | 20.702 | 16.616 | 1.00 | 23.82 | O |
| ATOM | 894 | CB | PRO | A | 112 | −35.132 | 23.166 | 18.190 | 1.00 | 24.32 | C |
| ATOM | 895 | CG | PRO | A | 112 | −36.365 | 23.857 | 17.695 | 1.00 | 22.23 | C |
| ATOM | 896 | CD | PRO | A | 112 | −35.988 | 24.298 | 16.318 | 1.00 | 19.06 | C |
| ATOM | 897 | N | GLY | A | 113 | −34.176 | 20.058 | 17.295 | 1.00 | 21.11 | N |

TABLE 5-continued (Table 5 discloses SEQ ID NO: 10):

| ATOM | 898 | CA | GLY | A | 113 | −34.537 | 18.657 | 17.369 | 1.00 | 27.87 | C |
|---|---|---|---|---|---|---|---|---|---|---|---|
| ATOM | 899 | C | GLY | A | 113 | −34.396 | 17.874 | 16.075 | 1.00 | 37.60 | C |
| ATOM | 900 | O | GLY | A | 113 | −34.388 | 16.645 | 16.105 | 1.00 | 26.73 | O |
| ATOM | 901 | N | LEU | A | 114 | −34.294 | 18.556 | 14.937 | 1.00 | 17.32 | N |
| ATOM | 902 | CA | LEU | A | 114 | −34.147 | 17.831 | 13.678 | 1.00 | 16.13 | C |
| ATOM | 903 | C | LEU | A | 114 | −32.712 | 17.349 | 13.481 | 1.00 | 14.38 | C |
| ATOM | 904 | O | LEU | A | 114 | −31.757 | 18.081 | 13.758 | 1.00 | 14.82 | O |
| ATOM | 905 | CB | LEU | A | 114 | −34.560 | 18.689 | 12.485 | 1.00 | 15.76 | C |
| ATOM | 906 | CG | LEU | A | 114 | −36.039 | 19.009 | 12.274 | 1.00 | 19.83 | C |
| ATOM | 907 | CD1 | LEU | A | 114 | −36.244 | 19.522 | 10.860 | 1.00 | 22.33 | C |
| ATOM | 908 | CD2 | LEU | A | 114 | −36.907 | 17.787 | 12.537 | 1.00 | 26.81 | C |
| ATOM | 909 | N | PRO | A | 115 | −32.559 | 16.110 | 12.993 | 1.00 | 14.51 | N |
| ATOM | 910 | CA | PRO | A | 115 | −31.241 | 15.578 | 12.631 | 1.00 | 14.94 | C |
| ATOM | 911 | C | PRO | A | 115 | −30.640 | 16.390 | 11.484 | 1.00 | 9.64 | C |
| ATOM | 912 | O | PRO | A | 115 | −31.386 | 16.881 | 10.636 | 1.00 | 12.08 | O |
| ATOM | 913 | CB | PRO | A | 115 | −31.554 | 14.159 | 12.140 | 1.00 | 16.54 | C |
| ATOM | 914 | CG | PRO | A | 115 | −32.911 | 13.846 | 12.664 | 1.00 | 25.57 | C |
| ATOM | 915 | CD | PRO | A | 115 | −33.640 | 15.148 | 12.735 | 1.00 | 14.61 | C |
| ATOM | 916 | N | VAL | A | 116 | −29.320 | 16.522 | 11.472 | 1.00 | 8.33 | N |
| ATOM | 917 | CA | AVAL | A | 116 | −28.656 | 17.245 | 10.396 | 0.50 | 6.55 | C |
| ATOM | 918 | C | VAL | A | 116 | −27.608 | 16.371 | 9.703 | 1.00 | 9.54 | C |
| ATOM | 919 | O | VAL | A | 116 | −26.774 | 15.730 | 10.337 | 1.00 | 9.56 | O |
| ATOM | 920 | CB | AVAL | A | 116 | −28.055 | 18.584 | 10.888 | 0.50 | 13.27 | C |
| ATOM | 921 | CG1 | AVAL | A | 116 | −27.021 | 18.342 | 11.977 | 0.50 | 10.54 | C |
| ATOM | 922 | CG2 | AVAL | A | 116 | −27.472 | 19.385 | 9.721 | 0.50 | 6.54 | C |
| ATOM | 923 | CA | BVAL | A | 116 | −28.606 | 17.265 | 10.430 | 0.50 | 11.46 | C |
| ATOM | 924 | CB | BVAL | A | 116 | −27.833 | 18.463 | 11.022 | 0.50 | 7.27 | C |
| ATOM | 925 | CG1 | BVAL | A | 116 | −26.972 | 19.144 | 9.954 | 0.50 | 10.48 | C |
| ATOM | 926 | CG2 | BVAL | A | 116 | −28.798 | 19.447 | 11.664 | 0.50 | 11.77 | C |
| ATOM | 927 | N | PHE | A | 117 | −27.694 | 16.350 | 8.377 | 1.00 | 8.25 | N |
| ATOM | 928 | CA | PHE | A | 117 | −26.766 | 15.613 | 7.523 | 1.00 | 6.73 | C |
| ATOM | 929 | C | PHE | A | 117 | −25.872 | 16.596 | 6.781 | 1.00 | 7.65 | C |
| ATOM | 930 | O | PHE | A | 117 | −26.221 | 17.782 | 6.646 | 1.00 | 7.95 | O |
| ATOM | 931 | CB | PHE | A | 117 | −27.544 | 14.791 | 6.495 | 1.00 | 7.19 | C |
| ATOM | 932 | CG | PHE | A | 117 | −28.342 | 13.659 | 7.089 | 1.00 | 9.66 | C |
| ATOM | 933 | CD1 | PHE | A | 117 | −29.578 | 13.888 | 7.675 | 1.00 | 9.86 | C |
| ATOM | 934 | CD2 | PHE | A | 117 | −27.858 | 12.366 | 7.035 | 1.00 | 11.39 | C |
| ATOM | 935 | CE1 | PHE | A | 117 | −30.315 | 12.846 | 8.221 | 1.00 | 11.17 | C |
| ATOM | 936 | CE2 | PHE | A | 117 | −28.592 | 11.316 | 7.576 | 1.00 | 12.02 | C |
| ATOM | 937 | CZ | PHE | A | 117 | −29.810 | 11.552 | 8.167 | 1.00 | 12.26 | C |
| ATOM | 938 | N | LEU | A | 118 | −24.751 | 16.093 | 6.272 | 1.00 | 6.39 | N |
| ATOM | 939 | CA | LEU | A | 118 | −23.844 | 16.851 | 5.409 | 1.00 | 6.79 | C |
| ATOM | 940 | C | LEU | A | 118 | −23.696 | 16.104 | 4.084 | 1.00 | 9.58 | C |
| ATOM | 941 | O | LEU | A | 118 | −23.659 | 14.869 | 4.053 | 1.00 | 10.15 | O |
| ATOM | 942 | CB | LEU | A | 118 | −22.467 | 16.990 | 6.054 | 1.00 | 8.39 | C |
| ATOM | 943 | CG | LEU | A | 118 | −22.423 | 17.678 | 7.421 | 1.00 | 7.65 | C |
| ATOM | 944 | CD1 | LEU | A | 118 | −21.069 | 17.514 | 8.065 | 1.00 | 12.05 | C |
| ATOM | 945 | CD2 | LEU | A | 118 | −22.805 | 19.163 | 7.274 | 1.00 | 14.26 | C |
| ATOM | 946 | N | LEU | A | 119 | −23.606 | 16.848 | 2.989 | 1.00 | 6.75 | N |
| ATOM | 947 | CA | LEU | A | 119 | −23.262 | 16.262 | 1.695 | 1.00 | 6.84 | C |
| ATOM | 948 | C | LEU | A | 119 | −22.159 | 17.111 | 1.091 | 1.00 | 6.93 | C |
| ATOM | 949 | O | LEU | A | 119 | −22.288 | 18.341 | 1.039 | 1.00 | 9.68 | O |
| ATOM | 950 | CB | LEU | A | 119 | −24.478 | 16.235 | 0.780 | 1.00 | 9.51 | C |
| ATOM | 951 | CG | LEU | A | 119 | −24.279 | 15.572 | −0.595 | 1.00 | 8.88 | C |
| ATOM | 952 | CD1 | LEU | A | 119 | −25.576 | 14.929 | −1.069 | 1.00 | 14.75 | C |
| ATOM | 953 | CD2 | LEU | A | 119 | −23.738 | 16.566 | −1.628 | 1.00 | 12.64 | C |
| ATOM | 954 | N | GLY | A | 120 | −21.076 | 16.486 | 0.640 | 1.00 | 5.97 | N |
| ATOM | 955 | CA | GLY | A | 120 | −19.986 | 17.265 | 0.088 | 1.00 | 6.20 | C |
| ATOM | 956 | C | GLY | A | 120 | −19.321 | 16.567 | −1.078 | 1.00 | 7.47 | C |
| ATOM | 957 | O | GLY | A | 120 | −19.260 | 15.334 | −1.112 | 1.00 | 8.48 | O |
| ATOM | 958 | N | HIS | A | 121 | −18.805 | 17.354 | −2.013 | 1.00 | 4.99 | N |
| ATOM | 959 | CA | HIS | A | 121 | −18.051 | 16.840 | −3.158 | 1.00 | 5.24 | C |
| ATOM | 960 | C | HIS | A | 121 | −16.656 | 17.442 | −3.172 | 1.00 | 4.93 | C |
| ATOM | 961 | O | HIS | A | 121 | −16.494 | 18.663 | −3.004 | 1.00 | 6.29 | O |
| ATOM | 962 | CB | HIS | A | 121 | −18.791 | 17.217 | −4.456 | 1.00 | 6.08 | C |
| ATOM | 963 | CG | HIS | A | 121 | −17.985 | 17.032 | −5.712 | 1.00 | 7.22 | C |
| ATOM | 964 | ND1 | HIS | A | 121 | −17.405 | 15.831 | −6.075 | 1.00 | 8.06 | N |
| ATOM | 965 | CD2 | HIS | A | 121 | −17.688 | 17.906 | −6.707 | 1.00 | 6.53 | C |
| ATOM | 966 | CE1 | HIS | A | 121 | −16.785 | 15.977 | −7.238 | 1.00 | 8.61 | C |
| ATOM | 967 | NE2 | HIS | A | 121 | −16.941 | 17.227 | −7.641 | 1.00 | 7.27 | N |
| ATOM | 968 | N | SER | A | 122 | −15.635 | 16.614 | −3.358 | 1.00 | 5.44 | N |
| ATOM | 969 | CA | SER | A | 122 | −14.288 | 17.105 | −3.623 | 1.00 | 6.10 | C |
| ATOM | 970 | C | SER | A | 122 | −13.779 | 17.939 | −2.431 | 1.00 | 7.18 | C |
| ATOM | 971 | O | SER | A | 122 | −13.808 | 17.447 | −1.292 | 1.00 | 6.60 | O |
| ATOM | 972 | CB | SER | A | 122 | −14.240 | 17.852 | −4.976 | 1.00 | 7.68 | C |
| ATOM | 973 | OG | SER | A | 122 | −12.925 | 17.935 | −5.480 | 1.00 | 8.60 | O |
| ATOM | 974 | N | MET | A | 123 | −13.298 | 19.163 | −2.648 | 1.00 | 7.05 | N |
| ATOM | 975 | CA | MET | A | 123 | −12.930 | 20.012 | −1.510 | 1.00 | 6.85 | C |

TABLE 5-continued (Table 5 discloses SEQ ID NO: 10):

| ATOM | 976 | C | MET | A | 123 | −14.067 | 20.114 | −0.498 | 1.00 | 5.95 | C |
|---|---|---|---|---|---|---|---|---|---|---|---|
| ATOM | 977 | O | MET | A | 123 | −13.825 | 20.180 | 0.715 | 1.00 | 6.61 | O |
| ATOM | 978 | CB | MET | A | 123 | −12.544 | 21.418 | −1.969 | 1.00 | 6.44 | C |
| ATOM | 979 | CG | MET | A | 123 | −12.132 | 22.321 | −0.808 | 1.00 | 6.74 | C |
| ATOM | 980 | SD | MET | A | 123 | −11.872 | 24.035 | −1.346 | 1.00 | 9.51 | S |
| ATOM | 981 | CE | MET | A | 123 | −13.527 | 24.679 | −1.392 | 1.00 | 11.77 | C |
| ATOM | 982 | N | GLY | A | 124 | −15.294 | 20.162 | −0.991 | 1.00 | 5.76 | N |
| ATOM | 983 | CA | GLY | A | 124 | −16.465 | 20.242 | −0.134 | 1.00 | 5.33 | C |
| ATOM | 984 | C | GLY | A | 124 | −16.644 | 19.005 | 0.733 | 1.00 | 6.28 | C |
| ATOM | 985 | O | GLY | A | 124 | −17.250 | 19.080 | 1.807 | 1.00 | 7.72 | O |
| ATOM | 986 | N | GLY | A | 125 | −16.131 | 17.871 | 0.258 | 1.00 | 6.88 | N |
| ATOM | 987 | CA | GLY | A | 125 | −16.123 | 16.647 | 1.048 | 1.00 | 6.32 | C |
| ATOM | 988 | C | GLY | A | 125 | −15.096 | 16.702 | 2.164 | 1.00 | 7.06 | C |
| ATOM | 989 | O | GLY | A | 125 | −15.362 | 16.219 | 3.275 | 1.00 | 8.26 | O |
| ATOM | 990 | N | ALA | A | 126 | −13.936 | 17.291 | 1.906 | 1.00 | 6.65 | N |
| ATOM | 991 | CA | ALA | A | 126 | −12.967 | 17.542 | 2.966 | 1.00 | 7.07 | C |
| ATOM | 992 | C | ALA | A | 126 | −13.560 | 18.468 | 4.027 | 1.00 | 8.51 | C |
| ATOM | 993 | O | ALA | A | 126 | −13.390 | 18.234 | 5.232 | 1.00 | 8.99 | O |
| ATOM | 994 | CB | ALA | A | 126 | −11.685 | 18.140 | 2.394 | 1.00 | 9.00 | C |
| ATOM | 995 | N | ILE | A | 127 | −14.256 | 19.510 | 3.587 | 1.00 | 5.80 | N |
| ATOM | 996 | CA | ILE | A | 127 | −14.899 | 20.425 | 4.512 | 1.00 | 5.81 | C |
| ATOM | 997 | C | ILE | A | 127 | −15.919 | 19.663 | 5.359 | 1.00 | 7.22 | C |
| ATOM | 998 | O | ILE | A | 127 | −15.978 | 19.846 | 6.586 | 1.00 | 8.40 | O |
| ATOM | 999 | CB | ILE | A | 127 | −15.560 | 21.585 | 3.757 | 1.00 | 5.20 | C |
| ATOM | 1000 | CG1 | ILE | A | 127 | −14.479 | 22.471 | 3.125 | 1.00 | 6.80 | C |
| ATOM | 1001 | CG2 | ILE | A | 127 | −16.455 | 22.395 | 4.692 | 1.00 | 7.18 | C |
| ATOM | 1002 | CD1 | ILE | A | 127 | −14.991 | 23.467 | 2.072 | 1.00 | 8.65 | C |
| ATOM | 1003 | N | ALA | A | 128 | −16.708 | 18.794 | 4.735 | 1.00 | 6.54 | N |
| ATOM | 1004 | CA | ALA | A | 128 | −17.685 | 17.983 | 5.472 | 1.00 | 6.61 | C |
| ATOM | 1005 | C | ALA | A | 128 | −17.014 | 17.098 | 6.525 | 1.00 | 6.98 | C |
| ATOM | 1006 | O | ALA | A | 128 | −17.470 | 17.038 | 7.676 | 1.00 | 8.44 | O |
| ATOM | 1007 | CB | ALA | A | 128 | −18.527 | 17.138 | 4.522 | 1.00 | 8.15 | C |
| ATOM | 1008 | N | ILE | A | 129 | −15.951 | 16.402 | 6.138 | 1.00 | 6.43 | N |
| ATOM | 1009 | CA | ILE | A | 129 | −15.234 | 15.541 | 7.073 | 1.00 | 8.20 | C |
| ATOM | 1010 | C | ILE | A | 129 | −14.742 | 16.355 | 8.274 | 1.00 | 7.24 | C |
| ATOM | 1011 | O | ILE | A | 129 | −14.921 | 15.943 | 9.432 | 1.00 | 9.40 | O |
| ATOM | 1012 | CB | ILE | A | 129 | −14.056 | 14.835 | 6.372 | 1.00 | 7.21 | C |
| ATOM | 1013 | CG1 | ILE | A | 129 | −14.577 | 13.788 | 5.374 | 1.00 | 8.59 | C |
| ATOM | 1014 | CG2 | ILE | A | 129 | −13.099 | 14.196 | 7.392 | 1.00 | 8.65 | C |
| ATOM | 1015 | CD1 | ILE | A | 129 | −13.518 | 13.302 | 4.381 | 1.00 | 8.43 | C |
| ATOM | 1016 | N | LEU | A | 130 | −14.109 | 17.494 | 8.016 | 1.00 | 7.88 | N |
| ATOM | 1017 | CA | LEU | A | 130 | −13.564 | 18.322 | 9.090 | 1.00 | 7.26 | C |
| ATOM | 1018 | C | LEU | A | 130 | −14.648 | 18.930 | 9.968 | 1.00 | 8.38 | C |
| ATOM | 1019 | O | LEU | A | 130 | −14.440 | 19.099 | 11.175 | 1.00 | 11.78 | O |
| ATOM | 1020 | CB | LEU | A | 130 | −12.629 | 19.396 | 8.522 | 1.00 | 7.43 | C |
| ATOM | 1021 | CG | LEU | A | 130 | −11.379 | 18.824 | 7.851 | 1.00 | 7.20 | C |
| ATOM | 1022 | CD1 | LEU | A | 130 | −10.588 | 19.932 | 7.164 | 1.00 | 11.26 | C |
| ATOM | 1023 | CD2 | LEU | A | 130 | −10.499 | 18.088 | 8.856 | 1.00 | 11.11 | C |
| ATOM | 1024 | N | THR | A | 131 | −15.792 | 19.247 | 9.381 | 1.00 | 6.76 | N |
| ATOM | 1025 | CA | THR | A | 131 | −16.937 | 19.765 | 10.120 | 1.00 | 7.15 | C |
| ATOM | 1026 | C | THR | A | 131 | −17.469 | 18.709 | 11.090 | 1.00 | 10.49 | C |
| ATOM | 1027 | O | THR | A | 131 | −17.694 | 18.990 | 12.278 | 1.00 | 10.09 | O |
| ATOM | 1028 | CB | THR | A | 131 | −18.044 | 20.221 | 9.142 | 1.00 | 6.73 | C |
| ATOM | 1029 | OG1 | THR | A | 131 | −17.544 | 21.303 | 8.342 | 1.00 | 9.73 | O |
| ATOM | 1030 | CG2 | THR | A | 131 | −19.293 | 20.695 | 9.876 | 1.00 | 9.04 | C |
| ATOM | 1031 | N | ALA | A | 132 | −17.667 | 17.493 | 10.591 | 1.00 | 8.54 | N |
| ATOM | 1032 | CA | ALA | A | 132 | −18.145 | 16.401 | 11.429 | 1.00 | 10.74 | C |
| ATOM | 1033 | C | ALA | A | 132 | −17.152 | 16.098 | 12.545 | 1.00 | 13.98 | C |
| ATOM | 1034 | O | ALA | A | 132 | −17.559 | 15.799 | 13.674 | 1.00 | 17.35 | O |
| ATOM | 1035 | CB | ALA | A | 132 | −18.395 | 15.153 | 10.588 | 1.00 | 12.21 | C |
| ATOM | 1036 | N | ALA | A | 133 | −15.862 | 16.190 | 12.247 | 1.00 | 11.80 | N |
| ATOM | 1037 | CA | ALA | A | 133 | −14.836 | 15.861 | 13.228 | 1.00 | 13.45 | C |
| ATOM | 1038 | C | ALA | A | 133 | −14.746 | 16.916 | 14.325 | 1.00 | 17.15 | C |
| ATOM | 1039 | O | ALA | A | 133 | −14.327 | 16.619 | 15.451 | 1.00 | 19.66 | O |
| ATOM | 1040 | CB | ALA | A | 133 | −13.475 | 15.669 | 12.546 | 1.00 | 15.60 | C |
| ATOM | 1041 | N | GLU | A | 134 | −15.139 | 18.143 | 14.001 | 1.00 | 16.89 | N |
| ATOM | 1042 | CA | GLU | A | 134 | −15.107 | 19.240 | 14.961 | 1.00 | 17.80 | C |
| ATOM | 1043 | C | GLU | A | 134 | −16.272 | 19.188 | 15.952 | 1.00 | 21.56 | C |
| ATOM | 1044 | O | GLU | A | 134 | −16.207 | 19.805 | 17.023 | 1.00 | 21.34 | O |
| ATOM | 1045 | CB | GLU | A | 134 | −15.086 | 20.585 | 14.232 | 1.00 | 19.70 | C |
| ATOM | 1046 | CG | GLU | A | 134 | −15.042 | 21.779 | 15.166 | 1.00 | 31.66 | C |
| ATOM | 1047 | CD | GLU | A | 134 | −14.422 | 22.997 | 14.524 | 1.00 | 77.78 | C |
| ATOM | 1048 | OE1 | GLU | A | 134 | −13.675 | 22.834 | 13.534 | 1.00 | 29.11 | O |
| ATOM | 1049 | OE2 | GLU | A | 134 | −14.678 | 24.116 | 15.017 | 1.00 | 32.70 | O |
| ATOM | 1050 | N | ARG | A | 135 | −17.328 | 18.457 | 15.597 | 1.00 | 15.43 | N |
| ATOM | 1051 | CA | ARG | A | 135 | −18.489 | 18.264 | 16.470 | 1.00 | 14.20 | C |
| ATOM | 1052 | C | ARG | A | 135 | −18.795 | 16.777 | 16.633 | 1.00 | 15.41 | C |
| ATOM | 1053 | O | ARG | A | 135 | −19.804 | 16.274 | 16.129 | 1.00 | 16.46 | O |

TABLE 5-continued (Table 5 discloses SEQ ID NO: 10):

| ATOM | 1054 | CB | ARG | A | 135 | −19.717 | 18.994 | 15.924 | 1.00 | 15.89 | C |
|---|---|---|---|---|---|---|---|---|---|---|---|
| ATOM | 1055 | CG | ARG | A | 135 | −19.520 | 20.485 | 15.716 | 1.00 | 19.46 | C |
| ATOM | 1056 | CD | ARG | A | 135 | −19.647 | 21.282 | 17.015 | 1.00 | 22.44 | C |
| ATOM | 1057 | NE | ARG | A | 135 | −19.498 | 22.713 | 16.762 | 1.00 | 17.05 | N |
| ATOM | 1058 | CZ | ARG | A | 135 | −20.503 | 23.518 | 16.428 | 1.00 | 13.79 | C |
| ATOM | 1059 | NH1 | ARG | A | 135 | −21.738 | 23.043 | 16.315 | 1.00 | 15.86 | N |
| ATOM | 1060 | NH2 | ARG | A | 135 | −20.264 | 24.802 | 16.195 | 1.00 | 15.95 | N |
| ATOM | 1061 | N | PRO | A | 136 | −17.921 | 16.062 | 17.353 | 1.00 | 20.51 | N |
| ATOM | 1062 | CA | PRO | A | 136 | −18.056 | 14.607 | 17.494 | 1.00 | 24.54 | C |
| ATOM | 1063 | C | PRO | A | 136 | −19.441 | 14.177 | 17.975 | 1.00 | 29.40 | C |
| ATOM | 1064 | O | PRO | A | 136 | −19.924 | 14.677 | 18.994 | 1.00 | 23.65 | O |
| ATOM | 1065 | CB | PRO | A | 136 | −17.007 | 14.262 | 18.554 | 1.00 | 27.33 | C |
| ATOM | 1066 | CG | PRO | A | 136 | −16.000 | 15.361 | 18.471 | 1.00 | 33.77 | C |
| ATOM | 1067 | CD | PRO | A | 136 | −16.774 | 16.596 | 18.109 | 1.00 | 22.45 | C |
| ATOM | 1068 | N | GLY | A | 137 | −20.063 | 13.257 | 17.244 | 1.00 | 19.62 | N |
| ATOM | 1069 | CA | GLY | A | 137 | −21.346 | 12.689 | 17.613 | 1.00 | 16.56 | C |
| ATOM | 1070 | C | GLY | A | 137 | −22.563 | 13.519 | 17.260 | 1.00 | 18.57 | C |
| ATOM | 1071 | O | GLY | A | 137 | −23.687 | 13.134 | 17.559 | 1.00 | 24.49 | O |
| ATOM | 1072 | N | HIS | A | 138 | −22.347 | 14.657 | 16.605 | 1.00 | 14.73 | N |
| ATOM | 1073 | CA | HIS | A | 138 | −23.423 | 15.610 | 16.384 | 1.00 | 14.81 | C |
| ATOM | 1074 | C | HIS | A | 138 | −24.243 | 15.369 | 15.103 | 1.00 | 13.75 | C |
| ATOM | 1075 | O | HIS | A | 138 | −25.472 | 15.419 | 15.122 | 1.00 | 17.01 | O |
| ATOM | 1076 | CB | HIS | A | 138 | −22.853 | 17.027 | 16.385 | 1.00 | 17.64 | C |
| ATOM | 1077 | CG | HIS | A | 138 | −23.888 | 18.087 | 16.192 | 1.00 | 19.02 | C |
| ATOM | 1078 | ND1 | HIS | A | 138 | −24.835 | 18.385 | 17.150 | 1.00 | 24.37 | N |
| ATOM | 1079 | CD2 | HIS | A | 138 | −24.131 | 18.918 | 15.151 | 1.00 | 21.19 | C |
| ATOM | 1080 | CE1 | HIS | A | 138 | −25.615 | 19.354 | 16.706 | 1.00 | 53.43 | C |
| ATOM | 1081 | NE2 | HIS | A | 138 | −25.210 | 19.695 | 15.496 | 1.00 | 28.81 | N |
| ATOM | 1082 | N | PHE | A | 139 | −23.557 | 15.105 | 13.993 | 1.00 | 12.98 | N |
| ATOM | 1083 | CA | PHE | A | 139 | −24.235 | 14.934 | 12.708 | 1.00 | 12.74 | C |
| ATOM | 1084 | C | PHE | A | 139 | −24.824 | 13.537 | 12.536 | 1.00 | 8.88 | C |
| ATOM | 1085 | O | PHE | A | 139 | −24.244 | 12.555 | 13.007 | 1.00 | 12.86 | O |
| ATOM | 1086 | CB | PHE | A | 139 | −23.280 | 15.293 | 11.558 | 1.00 | 11.40 | C |
| ATOM | 1087 | CG | PHE | A | 139 | −22.933 | 16.751 | 11.522 | 1.00 | 8.97 | C |
| ATOM | 1088 | CD1 | PHE | A | 139 | −23.765 | 17.647 | 10.875 | 1.00 | 10.65 | C |
| ATOM | 1089 | CD2 | PHE | A | 139 | −21.807 | 17.228 | 12.169 | 1.00 | 10.08 | C |
| ATOM | 1090 | CE1 | PHE | A | 139 | −23.456 | 19.002 | 10.856 | 1.00 | 11.55 | C |
| ATOM | 1091 | CE2 | PHE | A | 139 | −21.501 | 18.580 | 12.162 | 1.00 | 9.46 | C |
| ATOM | 1092 | CZ | PHE | A | 139 | −22.330 | 19.464 | 11.501 | 1.00 | 11.90 | C |
| ATOM | 1093 | N | ALA | A | 140 | −25.969 | 13.462 | 11.872 | 1.00 | 10.10 | N |
| ATOM | 1094 | CA | ALA | A | 140 | −26.681 | 12.201 | 11.680 | 1.00 | 11.80 | C |
| ATOM | 1095 | C | ALA | A | 140 | −26.034 | 11.356 | 10.589 | 1.00 | 12.36 | C |
| ATOM | 1096 | O | ALA | A | 140 | −26.193 | 10.135 | 10.557 | 1.00 | 13.34 | O |
| ATOM | 1097 | CB | ALA | A | 140 | −28.128 | 12.459 | 11.333 | 1.00 | 12.22 | C |
| ATOM | 1098 | N | GLY | A | 141 | −25.327 | 12.009 | 9.675 | 1.00 | 9.31 | N |
| ATOM | 1099 | CA | GLY | A | 141 | −24.774 | 11.289 | 8.546 | 1.00 | 9.56 | C |
| ATOM | 1100 | C | GLY | A | 141 | −24.130 | 12.212 | 7.548 | 1.00 | 11.98 | C |
| ATOM | 1101 | O | GLY | A | 141 | −24.391 | 13.420 | 7.525 | 1.00 | 10.18 | O |
| ATOM | 1102 | N | MET | A | 142 | −23.292 | 11.614 | 6.711 | 1.00 | 8.32 | N |
| ATOM | 1103 | CA | AMET | A | 142 | −22.502 | 12.331 | 5.725 | 0.70 | 8.58 | C |
| ATOM | 1104 | C | MET | A | 142 | −22.554 | 11.573 | 4.389 | 1.00 | 9.98 | C |
| ATOM | 1105 | O | MET | A | 142 | −22.320 | 10.356 | 4.367 | 1.00 | 10.51 | O |
| ATOM | 1106 | CB | AMET | A | 142 | −21.067 | 12.360 | 6.237 | 0.70 | 25.98 | C |
| ATOM | 1107 | CG | AMET | A | 142 | −20.126 | 13.326 | 5.579 | 0.70 | 16.80 | C |
| ATOM | 1108 | SD | AMET | A | 142 | −18.699 | 13.543 | 6.679 | 0.70 | 15.44 | S |
| ATOM | 1109 | CE | AMET | A | 142 | −18.032 | 11.891 | 6.773 | 0.70 | 13.72 | C |
| ATOM | 1110 | CA | BMET | A | 142 | −22.589 | 12.353 | 5.680 | 0.30 | 8.38 | C |
| ATOM | 1111 | CB | BMET | A | 142 | −21.163 | 12.652 | 6.104 | 0.30 | 4.61 | C |
| ATOM | 1112 | CG | BMET | A | 142 | −21.010 | 13.930 | 6.885 | 0.30 | 26.62 | C |
| ATOM | 1113 | SD | BMET | A | 142 | −19.322 | 14.124 | 7.459 | 0.30 | 21.03 | S |
| ATOM | 1114 | CE | BMET | A | 142 | −18.407 | 13.324 | 6.145 | 0.30 | 22.67 | C |
| ATOM | 1115 | N | VAL | A | 143 | −22.825 | 12.281 | 3.299 | 1.00 | 7.01 | N |
| ATOM | 1116 | CA | VAL | A | 143 | −22.730 | 11.708 | 1.964 | 1.00 | 7.21 | C |
| ATOM | 1117 | C | VAL | A | 143 | −21.561 | 12.389 | 1.268 | 1.00 | 7.22 | C |
| ATOM | 1118 | O | VAL | A | 143 | −21.534 | 13.624 | 1.135 | 1.00 | 7.86 | O |
| ATOM | 1119 | CB | VAL | A | 143 | −24.017 | 11.957 | 1.159 | 1.00 | 8.34 | C |
| ATOM | 1120 | CG1 | VAL | A | 143 | −23.839 | 11.460 | −0.286 | 1.00 | 10.34 | C |
| ATOM | 1121 | CG2 | VAL | A | 143 | −25.207 | 11.275 | 1.833 | 1.00 | 10.57 | C |
| ATOM | 1122 | N | LEU | A | 144 | −20.576 | 11.601 | 0.853 | 1.00 | 5.85 | N |
| ATOM | 1123 | CA | LEU | A | 144 | −19.357 | 12.139 | 0.276 | 1.00 | 6.51 | C |
| ATOM | 1124 | C | LEU | A | 144 | −19.222 | 11.661 | −1.160 | 1.00 | 8.86 | C |
| ATOM | 1125 | O | LEU | A | 144 | −19.195 | 10.456 | −1.439 | 1.00 | 7.94 | O |
| ATOM | 1126 | CB | LEU | A | 144 | −18.143 | 11.680 | 1.084 | 1.00 | 6.27 | C |
| ATOM | 1127 | CG | LEU | A | 144 | −18.117 | 12.083 | 2.559 | 1.00 | 9.97 | C |
| ATOM | 1128 | CD1 | LEU | A | 144 | −16.959 | 11.359 | 3.232 | 1.00 | 11.52 | C |
| ATOM | 1129 | CD2 | LEU | A | 144 | −17.983 | 13.615 | 2.693 | 1.00 | 11.05 | C |
| ATOM | 1130 | N | ILE | A | 145 | −19.179 | 12.618 | −2.079 | 1.00 | 5.85 | N |
| ATOM | 1131 | CA | ILE | A | 145 | −18.973 | 12.315 | −3.490 | 1.00 | 6.29 | C |

TABLE 5-continued (Table 5 discloses SEQ ID NO: 10):

| ATOM | 1132 | C | ILE | A | 145 | −17.545 | 12.689 | −3.844 | 1.00 | 6.81 | C |
|---|---|---|---|---|---|---|---|---|---|---|---|
| ATOM | 1133 | O | ILE | A | 145 | −17.194 | 13.876 | −3.904 | 1.00 | 6.91 | O |
| ATOM | 1134 | CB | ILE | A | 145 | −19.957 | 13.103 | −4.377 | 1.00 | 5.41 | C |
| ATOM | 1135 | CG1 | ILE | A | 145 | −21.400 | 12.836 | −3.954 | 1.00 | 9.22 | C |
| ATOM | 1136 | CG2 | ILE | A | 145 | −19.742 | 12.726 | −5.846 | 1.00 | 8.27 | C |
| ATOM | 1137 | CD1 | ILE | A | 145 | −22.431 | 13.717 | −4.651 | 1.00 | 9.95 | C |
| ATOM | 1138 | N | SER | A | 146 | −16.689 | 11.689 | −4.034 | 1.00 | 6.84 | N |
| ATOM | 1139 | CA | SER | A | 146 | −15.301 | 11.934 | −4.411 | 1.00 | 6.91 | C |
| ATOM | 1140 | C | SER | A | 146 | −14.655 | 12.966 | −3.493 | 1.00 | 7.51 | C |
| ATOM | 1141 | O | SER | A | 146 | −14.114 | 13.975 | −3.958 | 1.00 | 7.48 | O |
| ATOM | 1142 | CB | SER | A | 146 | −15.201 | 12.439 | −5.857 | 1.00 | 8.55 | C |
| ATOM | 1143 | OG | SER | A | 146 | −16.035 | 11.684 | −6.705 | 1.00 | 19.57 | O |
| ATOM | 1144 | N | PRO | A | 147 | −14.668 | 12.714 | −2.178 | 1.00 | 7.19 | N |
| ATOM | 1145 | CA | PRO | A | 147 | −14.114 | 13.708 | −1.250 | 1.00 | 6.02 | C |
| ATOM | 1146 | C | PRO | A | 147 | −12.612 | 13.828 | −1.423 | 1.00 | 8.82 | C |
| ATOM | 1147 | O | PRO | A | 147 | −11.933 | 12.854 | −1.765 | 1.00 | 8.83 | O |
| ATOM | 1148 | CB | PRO | A | 147 | −14.431 | 13.108 | 0.123 | 1.00 | 7.28 | C |
| ATOM | 1149 | CG | PRO | A | 147 | −14.419 | 11.598 | −0.149 | 1.00 | 7.97 | C |
| ATOM | 1150 | CD | PRO | A | 147 | −15.119 | 11.491 | −1.486 | 1.00 | 7.21 | C |
| ATOM | 1151 | N | LEU | A | 148 | −12.077 | 15.017 | −1.183 | 1.00 | 7.64 | N |
| ATOM | 1152 | CA | LEU | A | 148 | −10.643 | 15.212 | −1.171 | 1.00 | 7.57 | C |
| ATOM | 1153 | C | LEU | A | 148 | −10.037 | 14.612 | 0.100 | 1.00 | 10.69 | C |
| ATOM | 1154 | O | LEU | A | 148 | −10.082 | 15.230 | 1.180 | 1.00 | 13.01 | O |
| ATOM | 1155 | CB | LEU | A | 148 | −10.308 | 16.702 | −1.295 | 1.00 | 10.01 | C |
| ATOM | 1156 | CG | LEU | A | 148 | −8.831 | 17.084 | −1.238 | 1.00 | 13.54 | C |
| ATOM | 1157 | CD1 | LEU | A | 148 | −8.050 | 16.349 | −2.318 | 1.00 | 18.01 | C |
| ATOM | 1158 | CD2 | LEU | A | 148 | −8.660 | 18.592 | −1.378 | 1.00 | 19.64 | C |
| ATOM | 1159 | N | VAL | A | 149 | −9.491 | 13.403 | −0.029 | 1.00 | 10.28 | N |
| ATOM | 1160 | CA | VAL | A | 149 | −8.837 | 12.724 | 1.087 | 1.00 | 9.11 | C |
| ATOM | 1161 | C | VAL | A | 149 | −7.359 | 12.529 | 0.775 | 1.00 | 11.36 | C |
| ATOM | 1162 | O | VAL | A | 149 | −6.496 | 12.909 | 1.560 | 1.00 | 13.79 | O |
| ATOM | 1163 | CB | VAL | A | 149 | −9.514 | 11.374 | 1.410 | 1.00 | 7.75 | C |
| ATOM | 1164 | CG1 | VAL | A | 149 | −8.733 | 10.636 | 2.512 | 1.00 | 9.82 | C |
| ATOM | 1165 | CG2 | VAL | A | 149 | −10.957 | 11.592 | 1.816 | 1.00 | 8.89 | C |
| ATOM | 1166 | N | LEU | A | 150 | −7.069 | 11.934 | −0.380 | 1.00 | 10.74 | N |
| ATOM | 1167 | CA | LEU | A | 150 | −5.705 | 11.867 | −0.886 | 1.00 | 12.38 | C |
| ATOM | 1168 | C | LEU | A | 150 | −5.711 | 12.416 | −2.295 | 1.00 | 13.20 | C |
| ATOM | 1169 | O | LEU | A | 150 | −6.533 | 12.017 | −3.119 | 1.00 | 14.22 | O |
| ATOM | 1170 | CB | LEU | A | 150 | −5.185 | 10.428 | −0.916 | 1.00 | 13.51 | C |
| ATOM | 1171 | CG | LEU | A | 150 | −4.880 | 9.789 | 0.439 | 1.00 | 17.14 | C |
| ATOM | 1172 | CD1 | LEU | A | 150 | −3.807 | 10.577 | 1.181 | 1.00 | 19.78 | C |
| ATOM | 1173 | CD2 | LEU | A | 150 | −4.453 | 8.333 | 0.248 | 1.00 | 21.23 | C |
| ATOM | 1174 | N | ALA | A | 151 | −4.803 | 13.338 | −2.572 | 1.00 | 12.30 | N |
| ATOM | 1175 | CA | ALA | A | 151 | −4.701 | 13.879 | −3.917 | 1.00 | 16.69 | C |
| ATOM | 1176 | C | ALA | A | 151 | −3.972 | 12.890 | −4.819 | 1.00 | 15.92 | C |
| ATOM | 1177 | O | ALA | A | 151 | −3.240 | 12.021 | −4.344 | 1.00 | 15.20 | O |
| ATOM | 1178 | CB | ALA | A | 151 | −3.981 | 15.220 | −3.893 | 1.00 | 20.19 | C |
| ATOM | 1179 | N | ASN | A | 152 | −4.191 | 13.011 | −6.120 | 1.00 | 14.44 | N |
| ATOM | 1180 | CA | ASN | A | 152 | −3.363 | 12.292 | −7.071 | 1.00 | 13.52 | C |
| ATOM | 1181 | C | ASN | A | 152 | −1.896 | 12.543 | −6.728 | 1.00 | 14.72 | C |
| ATOM | 1182 | O | ASN | A | 152 | −1.469 | 13.694 | −6.634 | 1.00 | 15.93 | O |
| ATOM | 1183 | CB | ASN | A | 152 | −3.674 | 12.764 | −8.487 | 1.00 | 19.76 | C |
| ATOM | 1184 | CG | ASN | A | 152 | −2.809 | 12.089 | −9.524 | 1.00 | 18.69 | C |
| ATOM | 1185 | OD1 | ASN | A | 152 | −1.632 | 12.417 | −9.674 | 1.00 | 20.74 | O |
| ATOM | 1186 | ND2 | ASN | A | 152 | −3.389 | 11.138 | −10.251 | 1.00 | 23.13 | N |
| ATOM | 1187 | N | PRO | A | 153 | −1.122 | 11.467 | −6.513 | 1.00 | 16.79 | N |
| ATOM | 1188 | CA | PRO | A | 153 | 0.264 | 11.579 | −6.041 | 1.00 | 17.04 | C |
| ATOM | 1189 | C | PRO | A | 153 | 1.151 | 12.434 | −6.946 | 1.00 | 16.59 | C |
| ATOM | 1190 | O | PRO | A | 153 | 1.901 | 13.272 | −6.445 | 1.00 | 17.20 | O |
| ATOM | 1191 | CB | PRO | A | 153 | 0.749 | 10.125 | −6.034 | 1.00 | 23.14 | C |
| ATOM | 1192 | CG | PRO | A | 153 | −0.491 | 9.322 | −5.850 | 1.00 | 26.11 | C |
| ATOM | 1193 | CD | PRO | A | 153 | −1.570 | 10.065 | −6.589 | 1.00 | 18.51 | C |
| ATOM | 1194 | N | GLU | A | 154 | 1.072 | 12.222 | −8.254 | 1.00 | 17.01 | N |
| ATOM | 1195 | CA | GLU | A | 154 | 1.860 | 13.019 | −9.191 | 1.00 | 17.94 | C |
| ATOM | 1196 | C | GLU | A | 154 | 1.463 | 14.494 | −9.151 | 1.00 | 16.34 | C |
| ATOM | 1197 | O | GLU | A | 154 | 2.329 | 15.369 | −9.141 | 1.00 | 16.77 | O |
| ATOM | 1198 | CB | GLU | A | 154 | 1.754 | 12.464 | −10.616 | 1.00 | 19.72 | C |
| ATOM | 1199 | CG | GLU | A | 154 | 2.514 | 11.160 | −10.810 | 1.00 | 56.06 | C |
| ATOM | 1200 | CD | GLU | A | 154 | 2.713 | 10.806 | −12.270 | 1.00 | 91.32 | C |
| ATOM | 1201 | OE1 | GLU | A | 154 | 2.125 | 11.488 | −13.136 | 1.00 | 55.91 | O |
| ATOM | 1202 | OE2 | GLU | A | 154 | 3.462 | 9.845 | −12.549 | 1.00 | 63.05 | O |
| ATOM | 1203 | N | SER | A | 155 | 0.161 | 14.767 | −9.124 | 1.00 | 14.06 | N |
| ATOM | 1204 | CA | SER | A | 155 | −0.333 | 16.141 | −9.044 | 1.00 | 13.04 | C |
| ATOM | 1205 | C | SER | A | 155 | 0.097 | 16.835 | −7.752 | 1.00 | 13.20 | C |
| ATOM | 1206 | O | SER | A | 155 | 0.483 | 18.007 | −7.764 | 1.00 | 15.06 | O |
| ATOM | 1207 | CB | SER | A | 155 | −1.856 | 16.180 | −9.150 | 1.00 | 19.70 | C |
| ATOM | 1208 | OG | SER | A | 155 | −2.293 | 15.617 | −10.374 | 1.00 | 24.81 | O |
| ATOM | 1209 | N | ALA | A | 156 | 0.018 | 16.113 | −6.641 | 1.00 | 13.13 | N |

TABLE 5-continued (Table 5 discloses SEQ ID NO: 10):

| ATOM | 1210 | CA | ALA | A | 156 | 0.429 | 16.669 | −5.357 | 1.00 | 14.25 | C |
|---|---|---|---|---|---|---|---|---|---|---|---|
| ATOM | 1211 | C | ALA | A | 156 | 1.913 | 17.014 | −5.368 | 1.00 | 14.95 | C |
| ATOM | 1212 | O | ALA | A | 156 | 2.321 | 18.091 | −4.916 | 1.00 | 13.46 | O |
| ATOM | 1213 | CB | ALA | A | 156 | 0.118 | 15.696 | −4.224 | 1.00 | 16.70 | C |
| ATOM | 1214 | N | THR | A | 157 | 2.723 | 16.098 | −5.890 | 1.00 | 13.19 | N |
| ATOM | 1215 | CA | THR | A | 157 | 4.164 | 16.321 | −5.953 | 1.00 | 12.51 | C |
| ATOM | 1216 | C | THR | A | 157 | 4.494 | 17.494 | −6.868 | 1.00 | 11.38 | C |
| ATOM | 1217 | O | THR | A | 157 | 5.311 | 18.351 | −6.521 | 1.00 | 13.00 | O |
| ATOM | 1218 | CB | THR | A | 157 | 4.897 | 15.066 | −6.435 | 1.00 | 16.00 | C |
| ATOM | 1219 | OG1 | THR | A | 157 | 4.623 | 13.991 | −5.527 | 1.00 | 20.31 | O |
| ATOM | 1220 | CG2 | THR | A | 157 | 6.400 | 15.307 | −6.485 | 1.00 | 16.90 | C |
| ATOM | 1221 | N | THR | A | 158 | 3.858 | 17.525 | −8.036 | 1.00 | 11.66 | N |
| ATOM | 1222 | CA | THR | A | 158 | 4.036 | 18.639 | −8.965 | 1.00 | 12.58 | C |
| ATOM | 1223 | C | THR | A | 158 | 3.720 | 19.944 | −8.250 | 1.00 | 12.22 | C |
| ATOM | 1224 | O | THR | A | 158 | 4.459 | 20.927 | −8.360 | 1.00 | 11.34 | O |
| ATOM | 1225 | CB | THR | A | 158 | 3.119 | 18.502 | −10.194 | 1.00 | 13.07 | C |
| ATOM | 1226 | OG1 | THR | A | 158 | 3.539 | 17.373 | −10.972 | 1.00 | 16.60 | O |
| ATOM | 1227 | CG2 | THR | A | 158 | 3.174 | 19.755 | −11.065 | 1.00 | 12.95 | C |
| ATOM | 1228 | N | PHE | A | 159 | 2.620 | 19.962 | −7.506 | 1.00 | 10.44 | N |
| ATOM | 1229 | CA | PHE | A | 159 | 2.245 | 21.202 | −6.850 | 1.00 | 11.72 | C |
| ATOM | 1230 | C | PHE | A | 159 | 3.243 | 21.604 | −5.765 | 1.00 | 9.72 | C |
| ATOM | 1231 | O | PHE | A | 159 | 3.589 | 22.777 | −5.652 | 1.00 | 11.95 | O |
| ATOM | 1232 | CB | PHE | A | 159 | 0.842 | 21.161 | −6.256 | 1.00 | 10.51 | C |
| ATOM | 1233 | CG | PHE | A | 159 | 0.509 | 22.417 | −5.524 | 1.00 | 12.93 | C |
| ATOM | 1234 | CD1 | PHE | A | 159 | 0.146 | 23.552 | −6.224 | 1.00 | 12.61 | C |
| ATOM | 1235 | CD2 | PHE | A | 159 | 0.658 | 22.492 | −4.150 | 1.00 | 13.42 | C |
| ATOM | 1236 | CE1 | PHE | A | 159 | −0.113 | 24.742 | −5.566 | 1.00 | 15.13 | C |
| ATOM | 1237 | CE2 | PHE | A | 159 | 0.399 | 23.682 | −3.479 | 1.00 | 12.40 | C |
| ATOM | 1238 | CZ | PHE | A | 159 | 0.013 | 24.805 | −4.189 | 1.00 | 11.69 | C |
| ATOM | 1239 | N | LYS | A | 160 | 3.699 | 20.645 | −4.969 | 1.00 | 11.04 | N |
| ATOM | 1240 | CA | LYS | A | 160 | 4.644 | 20.969 | −3.906 | 1.00 | 13.94 | C |
| ATOM | 1241 | C | LYS | A | 160 | 5.937 | 21.531 | −4.483 | 1.00 | 14.48 | C |
| ATOM | 1242 | O | LYS | A | 160 | 6.520 | 22.463 | −3.936 | 1.00 | 14.62 | O |
| ATOM | 1243 | CB | LYS | A | 160 | 4.933 | 19.743 | −3.041 | 1.00 | 14.06 | C |
| ATOM | 1244 | CG | LYS | A | 160 | 3.750 | 19.302 | −2.200 | 1.00 | 16.18 | C |
| ATOM | 1245 | CD | LYS | A | 160 | 4.049 | 18.014 | −1.454 | 1.00 | 19.05 | C |
| ATOM | 1246 | CE | LYS | A | 160 | 2.930 | 17.694 | −0.473 | 1.00 | 30.54 | C |
| ATOM | 1247 | NZ | LYS | A | 160 | 3.310 | 16.609 | 0.472 | 1.00 | 58.66 | N |
| ATOM | 1248 | N | VAL | A | 161 | 6.391 | 20.961 | −5.591 | 1.00 | 13.06 | N |
| ATOM | 1249 | CA | VAL | A | 161 | 7.601 | 21.457 | −6.237 | 1.00 | 17.55 | C |
| ATOM | 1250 | C | VAL | A | 161 | 7.391 | 22.878 | −6.766 | 1.00 | 15.74 | C |
| ATOM | 1251 | O | VAL | A | 161 | 8.248 | 23.749 | −6.605 | 1.00 | 14.78 | O |
| ATOM | 1252 | CB | VAL | A | 161 | 8.044 | 20.524 | −7.372 | 1.00 | 14.83 | C |
| ATOM | 1253 | CG1 | VAL | A | 161 | 9.160 | 21.173 | −8.186 | 1.00 | 19.24 | C |
| ATOM | 1254 | CG2 | VAL | A | 161 | 8.494 | 19.183 | −6.797 | 1.00 | 18.97 | C |
| ATOM | 1255 | N | LEU | A | 162 | 6.239 | 23.110 | −7.380 | 1.00 | 11.62 | N |
| ATOM | 1256 | CA | LEU | A | 162 | 5.875 | 24.434 | −7.867 | 1.00 | 10.78 | C |
| ATOM | 1257 | C | LEU | A | 162 | 5.815 | 25.443 | −6.726 | 1.00 | 15.67 | C |
| ATOM | 1258 | O | LEU | A | 162 | 6.360 | 26.543 | −6.826 | 1.00 | 14.46 | O |
| ATOM | 1259 | CB | LEU | A | 162 | 4.520 | 24.381 | −8.572 | 1.00 | 14.81 | C |
| ATOM | 1260 | CG | LEU | A | 162 | 3.973 | 25.727 | −9.046 | 1.00 | 22.23 | C |
| ATOM | 1261 | CD1 | LEU | A | 162 | 4.800 | 26.249 | −10.206 | 1.00 | 23.30 | C |
| ATOM | 1262 | CD2 | LEU | A | 162 | 2.507 | 25.604 | −9.439 | 1.00 | 24.52 | C |
| ATOM | 1263 | N | ALA | A | 163 | 5.148 | 25.070 | −5.639 | 1.00 | 11.29 | N |
| ATOM | 1264 | CA | ALA | A | 163 | 4.999 | 25.983 | −4.509 | 1.00 | 14.76 | C |
| ATOM | 1265 | C | ALA | A | 163 | 6.362 | 26.338 | −3.922 | 1.00 | 14.91 | C |
| ATOM | 1266 | O | ALA | A | 163 | 6.602 | 27.491 | −3.560 | 1.00 | 16.78 | O |
| ATOM | 1267 | CB | ALA | A | 163 | 4.086 | 25.382 | −3.442 | 1.00 | 14.03 | C |
| ATOM | 1268 | N | ALA | A | 164 | 7.250 | 25.351 | −3.835 | 1.00 | 13.62 | N |
| ATOM | 1269 | CA | ALA | A | 164 | 8.598 | 25.582 | −3.322 | 1.00 | 18.16 | C |
| ATOM | 1270 | C | ALA | A | 164 | 9.400 | 26.525 | −4.226 | 1.00 | 23.79 | C |
| ATOM | 1271 | O | ALA | A | 164 | 10.109 | 27.402 | −3.732 | 1.00 | 18.76 | O |
| ATOM | 1272 | CB | ALA | A | 164 | 9.331 | 24.262 | −3.137 | 1.00 | 20.61 | C |
| ATOM | 1273 | N | LYS | A | 165 | 9.297 | 26.339 | −5.544 | 1.00 | 17.69 | N |
| ATOM | 1274 | CA | LYS | A | 165 | 9.950 | 27.243 | −6.494 | 1.00 | 23.27 | C |
| ATOM | 1275 | C | LYS | A | 165 | 9.456 | 28.657 | −6.279 | 1.00 | 23.11 | C |
| ATOM | 1276 | O | LYS | A | 165 | 10.238 | 29.600 | −6.157 | 1.00 | 33.57 | O |
| ATOM | 1277 | CB | LYS | A | 165 | 9.604 | 26.885 | −7.940 | 1.00 | 30.74 | C |
| ATOM | 1278 | CG | LYS | A | 165 | 10.148 | 25.590 | −8.486 | 1.00 | 58.56 | C |
| ATOM | 1279 | CD | LYS | A | 165 | 10.057 | 25.660 | −10.004 | 1.00 | 28.67 | C |
| ATOM | 1280 | CE | LYS | A | 165 | 9.648 | 24.348 | −10.632 | 1.00 | 63.54 | C |
| ATOM | 1281 | NZ | LYS | A | 165 | 9.245 | 24.586 | −12.048 | 1.00 | 25.56 | N |
| ATOM | 1282 | N | VAL | A | 166 | 8.137 | 28.800 | −6.273 | 1.00 | 19.68 | N |
| ATOM | 1283 | CA | VAL | A | 166 | 7.504 | 30.102 | −6.156 | 1.00 | 19.36 | C |
| ATOM | 1284 | C | VAL | A | 166 | 7.910 | 30.804 | −4.862 | 1.00 | 38.58 | C |
| ATOM | 1285 | O | VAL | A | 166 | 8.095 | 32.019 | −4.840 | 1.00 | 41.10 | O |
| ATOM | 1286 | CB | VAL | A | 166 | 5.966 | 29.992 | −6.274 | 1.00 | 23.38 | C |
| ATOM | 1287 | CG1 | VAL | A | 166 | 5.300 | 31.297 | −5.869 | 1.00 | 33.39 | C |

TABLE 5-continued (Table 5 discloses SEQ ID NO: 10):

| ATOM | 1288 | CG2 | VAL | A | 166 | 5.576 | 29.597 | −7.698 | 1.00 | 19.99 | C |
|---|---|---|---|---|---|---|---|---|---|---|---|
| ATOM | 1289 | N | LEU | A | 167 | 8.069 | 30.031 | −3.793 | 1.00 | 30.39 | N |
| ATOM | 1290 | CA | LEU | A | 167 | 8.493 | 30.578 | −2.504 | 1.00 | 29.35 | C |
| ATOM | 1291 | C | LEU | A | 167 | 10.005 | 30.798 | −2.400 | 1.00 | 37.42 | C |
| ATOM | 1292 | O | LEU | A | 167 | 10.451 | 31.869 | −1.989 | 1.00 | 45.82 | O |
| ATOM | 1293 | CB | LEU | A | 167 | 8.033 | 29.670 | −1.359 | 1.00 | 36.36 | C |
| ATOM | 1294 | CG | LEU | A | 167 | 8.823 | 29.820 | −0.053 | 1.00 | 72.40 | C |
| ATOM | 1295 | CD1 | LEU | A | 167 | 8.542 | 31.166 | 0.601 | 1.00 | 72.35 | C |
| ATOM | 1296 | CD2 | LEU | A | 167 | 8.525 | 28.677 | 0.910 | 1.00 | 57.03 | C |
| ATOM | 1297 | N | ASN | A | 168 | 10.787 | 29.784 | −2.765 | 1.00 | 27.55 | N |
| ATOM | 1298 | CA | ASN | A | 168 | 12.237 | 29.810 | −2.569 | 1.00 | 27.38 | C |
| ATOM | 1299 | C | ASN | A | 168 | 13.020 | 30.567 | −3.639 | 1.00 | 50.32 | C |
| ATOM | 1300 | O | ASN | A | 168 | 14.246 | 30.674 | −3.565 | 1.00 | 38.60 | O |
| ATOM | 1301 | CB | ASN | A | 168 | 12.791 | 28.387 | −2.456 | 1.00 | 31.18 | C |
| ATOM | 1302 | CG | ASN | A | 168 | 12.355 | 27.689 | −1.185 | 1.00 | 60.71 | C |
| ATOM | 1303 | OD1 | ASN | A | 168 | 12.552 | 26.483 | −1.028 | 1.00 | 56.08 | O |
| ATOM | 1304 | ND2 | ASN | A | 168 | 11.759 | 28.443 | −0.268 | 1.00 | 64.87 | N |
| ATOM | 1305 | N | SER | A | 169 | 12.313 | 31.077 | −4.639 | 1.00 | 23.88 | N |
| ATOM | 1306 | CA | SER | A | 169 | 12.939 | 31.844 | −5.708 | 1.00 | 29.73 | C |
| ATOM | 1307 | C | SER | A | 169 | 12.086 | 33.057 | −6.050 | 1.00 | 22.64 | C |
| ATOM | 1308 | CB | SER | A | 169 | 13.123 | 30.976 | −6.957 | 1.00 | 35.25 | C |
| ATOM | 1309 | OG | SER | A | 169 | 13.964 | 29.866 | −6.694 | 1.00 | 55.90 | O |
| ATOM | 1310 | O | SER | A | 169 | 12.359 | 33.753 | −7.029 | 1.00 | 27.12 | O |
| ATOM | 1311 | N | VAL | A | 170 | 11.059 | 33.298 | −5.237 | 1.00 | 20.95 | N |
| ATOM | 1312 | CA | VAL | A | 170 | 10.077 | 34.351 | −5.489 | 1.00 | 17.05 | C |
| ATOM | 1313 | C | VAL | A | 170 | 9.765 | 34.510 | −6.985 | 1.00 | 23.05 | C |
| ATOM | 1314 | O | VAL | A | 170 | 9.865 | 35.603 | −7.545 | 1.00 | 22.27 | O |
| ATOM | 1315 | CB | VAL | A | 170 | 10.503 | 35.708 | −4.858 | 1.00 | 23.73 | C |
| ATOM | 1316 | CG1 | VAL | A | 170 | 10.500 | 35.607 | −3.335 | 1.00 | 22.54 | C |
| ATOM | 1317 | CG2 | VAL | A | 170 | 11.874 | 36.134 | −5.362 | 1.00 | 28.79 | C |
| ATOM | 1318 | N | LEU | A | 171 | 9.395 | 33.406 | −7.632 | 1.00 | 19.61 | N |
| ATOM | 1319 | CA | LEU | A | 171 | 8.996 | 33.451 | −9.036 | 1.00 | 17.49 | C |
| ATOM | 1320 | C | LEU | A | 171 | 7.615 | 34.085 | −9.147 | 1.00 | 17.41 | C |
| ATOM | 1321 | O | LEU | A | 171 | 6.686 | 33.667 | −8.453 | 1.00 | 19.36 | O |
| ATOM | 1322 | CB | LEU | A | 171 | 8.963 | 32.047 | −9.636 | 1.00 | 18.63 | C |
| ATOM | 1323 | CG | LEU | A | 171 | 10.282 | 31.276 | −9.665 | 1.00 | 26.27 | C |
| ATOM | 1324 | CD1 | LEU | A | 171 | 10.099 | 29.942 | −10.378 | 1.00 | 25.23 | C |
| ATOM | 1325 | CD2 | LEU | A | 171 | 11.364 | 32.100 | −10.339 | 1.00 | 22.36 | C |
| ATOM | 1326 | N | PRO | A | 172 | 7.471 | 35.094 | −10.022 | 1.00 | 14.88 | N |
| ATOM | 1327 | CA | PRO | A | 172 | 6.223 | 35.853 | −10.159 | 1.00 | 14.86 | C |
| ATOM | 1328 | C | PRO | A | 172 | 5.302 | 35.268 | −11.227 | 1.00 | 19.81 | C |
| ATOM | 1329 | O | PRO | A | 172 | 5.760 | 34.501 | −12.068 | 1.00 | 19.14 | O |
| ATOM | 1330 | CB | PRO | A | 172 | 6.715 | 37.221 | −10.627 | 1.00 | 20.22 | C |
| ATOM | 1331 | CG | PRO | A | 172 | 7.938 | 36.910 | −11.435 | 1.00 | 18.21 | C |
| ATOM | 1332 | CD | PRO | A | 172 | 8.543 | 35.636 | −10.880 | 1.00 | 14.89 | C |
| ATOM | 1333 | N | ASN | A | 173 | 4.024 | 35.633 | −11.184 | 1.00 | 22.85 | N |
| ATOM | 1334 | CA | ASN | A | 173 | 3.073 | 35.266 | −12.235 | 1.00 | 29.29 | C |
| ATOM | 1335 | C | ASN | A | 173 | 3.027 | 33.769 | −12.528 | 1.00 | 31.64 | C |
| ATOM | 1336 | O | ASN | A | 173 | 2.795 | 33.356 | −13.665 | 1.00 | 39.41 | O |
| ATOM | 1337 | CB | ASN | A | 173 | 3.386 | 36.033 | −13.520 | 1.00 | 32.47 | C |
| ATOM | 1338 | CG | ASN | A | 173 | 3.475 | 37.531 | −13.296 | 1.00 | 85.40 | C |
| ATOM | 1339 | OD1 | ASN | A | 173 | 4.280 | 38.218 | −13.926 | 1.00 | 59.68 | O |
| ATOM | 1340 | ND2 | ASN | A | 173 | 2.652 | 38.044 | −12.388 | 1.00 | 49.78 | N |
| ATOM | 1341 | N | LEU | A | 174 | 3.262 | 32.962 | −11.499 | 1.00 | 20.60 | N |
| ATOM | 1342 | CA | LEU | A | 174 | 3.201 | 31.512 | −11.623 | 1.00 | 18.27 | C |
| ATOM | 1343 | C | LEU | A | 174 | 2.155 | 30.946 | −10.685 | 1.00 | 25.26 | C |
| ATOM | 1344 | O | LEU | A | 174 | 2.226 | 31.128 | −9.472 | 1.00 | 24.16 | O |
| ATOM | 1345 | CB | LEU | A | 174 | 4.550 | 30.872 | −11.296 | 1.00 | 24.24 | C |
| ATOM | 1346 | CG | LEU | A | 174 | 5.479 | 30.472 | −12.438 | 1.00 | 55.63 | C |
| ATOM | 1347 | CD1 | LEU | A | 174 | 6.625 | 29.655 | −11.870 | 1.00 | 27.72 | C |
| ATOM | 1348 | CD2 | LEU | A | 174 | 4.722 | 29.681 | −13.495 | 1.00 | 33.38 | C |
| ATOM | 1349 | N | SER | A | 175 | 1.178 | 30.253 | −11.247 | 1.00 | 19.56 | N |
| ATOM | 1350 | CA | SER | A | 175 | 0.212 | 29.552 | −10.427 | 1.00 | 21.54 | C |
| ATOM | 1351 | C | SER | A | 175 | 0.218 | 28.100 | −10.855 | 1.00 | 20.84 | C |
| ATOM | 1352 | O | SER | A | 175 | 0.958 | 27.711 | −11.761 | 1.00 | 18.86 | O |
| ATOM | 1353 | CB | SER | A | 175 | −1.182 | 30.157 | −10.597 | 1.00 | 21.73 | C |
| ATOM | 1354 | OG | SER | A | 175 | −1.679 | 29.929 | −11.903 | 1.00 | 27.11 | O |
| ATOM | 1355 | N | SER | A | 176 | −0.599 | 27.294 | −10.192 | 1.00 | 16.51 | N |
| ATOM | 1356 | CA | SER | A | 176 | −0.839 | 25.940 | −10.640 | 1.00 | 17.04 | C |
| ATOM | 1357 | C | SER | A | 176 | −1.830 | 26.028 | −11.798 | 1.00 | 16.54 | C |
| ATOM | 1358 | CB | SER | A | 176 | −1.400 | 25.104 | −9.485 | 1.00 | 17.23 | C |
| ATOM | 1359 | OG | SER | A | 176 | −1.399 | 23.728 | −9.797 | 1.00 | 20.69 | O |
| ATOM | 1360 | O | SER | A | 176 | −2.331 | 27.110 | −12.112 | 1.00 | 18.57 | O |
| ATOM | 1361 | N | GLY | A | 177 | −2.104 | 24.904 | −12.451 | 1.00 | 17.84 | N |
| ATOM | 1362 | CA | GLY | A | 177 | −3.036 | 24.906 | −13.564 | 1.00 | 18.83 | C |
| ATOM | 1363 | C | GLY | A | 177 | −4.467 | 25.206 | −13.144 | 1.00 | 14.12 | C |
| ATOM | 1364 | O | GLY | A | 177 | −4.815 | 25.120 | −11.960 | 1.00 | 14.14 | O |
| ATOM | 1365 | N | PRO | A | 178 | −5.312 | 25.585 | −14.105 | 1.00 | 13.09 | N |

TABLE 5-continued (Table 5 discloses SEQ ID NO: 10):

| | | | | | | | | | | |
|---|---|---|---|---|---|---|---|---|---|---|
| ATOM | 1366 | CA | PRO | A | 178 | −6.729 | 25.736 | −13.773 | 1.00 | 11.60 | C |
| ATOM | 1367 | C | PRO | A | 178 | −7.390 | 24.370 | −13.676 | 1.00 | 12.12 | C |
| ATOM | 1368 | CB | PRO | A | 178 | −7.290 | 26.513 | −14.962 | 1.00 | 13.40 | C |
| ATOM | 1369 | CG | PRO | A | 178 | −6.386 | 26.154 | −16.109 | 1.00 | 22.97 | C |
| ATOM | 1370 | CD | PRO | A | 178 | −5.029 | 25.841 | −15.532 | 1.00 | 16.39 | C |
| ATOM | 1371 | O | PRO | A | 178 | −6.763 | 23.345 | −13.972 | 1.00 | 14.28 | O |
| ATOM | 1372 | N | ILE | A | 179 | −8.640 | 24.359 | −13.244 | 1.00 | 11.60 | N |
| ATOM | 1373 | CA | ILE | A | 179 | −9.404 | 23.126 | −13.199 | 1.00 | 11.12 | C |
| ATOM | 1374 | C | ILE | A | 179 | −9.693 | 22.662 | −14.633 | 1.00 | 13.21 | C |
| ATOM | 1375 | O | ILE | A | 179 | −10.218 | 23.434 | −15.444 | 1.00 | 14.90 | O |
| ATOM | 1376 | CB | ILE | A | 179 | −10.707 | 23.357 | −12.430 | 1.00 | 10.34 | C |
| ATOM | 1377 | CG1 | ILE | A | 179 | −10.392 | 23.610 | −10.955 | 1.00 | 14.08 | C |
| ATOM | 1378 | CG2 | ILE | A | 179 | −11.661 | 22.179 | −12.590 | 1.00 | 14.20 | C |
| ATOM | 1379 | CD1 | ILE | A | 179 | −11.518 | 24.273 | −10.208 | 1.00 | 12.85 | C |
| ATOM | 1380 | N | ASP | A | 180 | −9.324 | 21.421 | −14.957 | 1.00 | 12.91 | N |
| ATOM | 1381 | CA | ASP | A | 180 | −9.567 | 20.876 | −16.302 | 1.00 | 10.51 | C |
| ATOM | 1382 | C | ASP | A | 180 | −10.792 | 19.985 | −16.253 | 1.00 | 10.15 | C |
| ATOM | 1383 | O | ASP | A | 180 | −10.707 | 18.794 | −15.928 | 1.00 | 12.02 | O |
| ATOM | 1384 | CB | ASP | A | 180 | −8.352 | 20.098 | −16.819 | 1.00 | 15.37 | C |
| ATOM | 1385 | CG | ASP | A | 180 | −8.568 | 19.517 | −18.225 | 1.00 | 13.01 | C |
| ATOM | 1386 | OD1 | ASP | A | 180 | −9.687 | 19.646 | −18.779 | 1.00 | 13.99 | O |
| ATOM | 1387 | OD2 | ASP | A | 180 | −7.603 | 18.924 | −18.759 | 1.00 | 17.65 | O |
| ATOM | 1388 | N | SER | A | 181 | −11.938 | 20.570 | −16.553 | 1.00 | 10.15 | N |
| ATOM | 1389 | CA | SER | A | 181 | −13.199 | 19.873 | −16.436 | 1.00 | 8.88 | C |
| ATOM | 1390 | C | SER | A | 181 | −13.310 | 18.686 | −17.396 | 1.00 | 8.77 | C |
| ATOM | 1391 | O | SER | A | 181 | −14.090 | 17.763 | −17.151 | 1.00 | 9.07 | O |
| ATOM | 1392 | CB | SER | A | 181 | −14.345 | 20.842 | −16.676 | 1.00 | 9.62 | C |
| ATOM | 1393 | OG | SER | A | 181 | −14.145 | 21.506 | −17.921 | 1.00 | 11.79 | O |
| ATOM | 1394 | N | SER | A | 182 | −12.554 | 18.727 | −18.494 | 1.00 | 8.53 | N |
| ATOM | 1395 | CA | SER | A | 182 | −12.675 | 17.689 | −19.518 | 1.00 | 8.81 | C |
| ATOM | 1396 | C | SER | A | 182 | −12.171 | 16.328 | −19.032 | 1.00 | 9.43 | C |
| ATOM | 1397 | O | SER | A | 182 | −12.534 | 15.295 | −19.607 | 1.00 | 11.89 | O |
| ATOM | 1398 | CB | SER | A | 182 | −11.943 | 18.093 | −20.807 | 1.00 | 10.60 | C |
| ATOM | 1399 | OG | SER | A | 182 | −10.552 | 17.939 | −20.670 | 1.00 | 14.76 | O |
| ATOM | 1400 | N | VAL | A | 183 | −11.337 | 16.319 | −17.996 | 1.00 | 8.40 | N |
| ATOM | 1401 | CA | VAL | A | 183 | −10.853 | 15.054 | −17.451 | 1.00 | 9.30 | C |
| ATOM | 1402 | C | VAL | A | 183 | −11.542 | 14.715 | −16.136 | 1.00 | 7.84 | C |
| ATOM | 1403 | O | VAL | A | 183 | −11.115 | 13.791 | −15.443 | 1.00 | 9.46 | O |
| ATOM | 1404 | CB | VAL | A | 183 | −9.327 | 15.039 | −17.257 | 1.00 | 9.77 | C |
| ATOM | 1405 | CG1 | VAL | A | 183 | −8.625 | 15.275 | −18.591 | 1.00 | 13.98 | C |
| ATOM | 1406 | CG2 | VAL | A | 183 | −8.889 | 16.064 | −16.216 | 1.00 | 12.72 | C |
| ATOM | 1407 | N | LEU | A | 184 | −12.597 | 15.457 | −15.809 | 1.00 | 6.49 | N |
| ATOM | 1408 | CA | LEU | A | 184 | −13.291 | 15.282 | −14.531 | 1.00 | 7.18 | C |
| ATOM | 1409 | C | LEU | A | 184 | −14.721 | 14.767 | −14.699 | 1.00 | 8.94 | C |
| ATOM | 1410 | O | LEU | A | 184 | −15.369 | 14.390 | −13.728 | 1.00 | 7.03 | O |
| ATOM | 1411 | CB | LEU | A | 184 | −13.225 | 16.574 | −13.686 | 1.00 | 7.27 | C |
| ATOM | 1412 | CG | LEU | A | 184 | −11.797 | 17.033 | −13.382 | 1.00 | 5.81 | C |
| ATOM | 1413 | CD1 | LEU | A | 184 | −11.784 | 18.379 | −12.656 | 1.00 | 8.64 | C |
| ATOM | 1414 | CD2 | LEU | A | 184 | −11.033 | 15.993 | −12.570 | 1.00 | 8.78 | C |
| ATOM | 1415 | N | SER | A | 185 | −15.217 | 14.731 | −15.934 | 1.00 | 6.60 | N |
| ATOM | 1416 | CA | SER | A | 185 | −16.447 | 14.011 | −16.253 | 1.00 | 8.04 | C |
| ATOM | 1417 | C | SER | A | 185 | −16.374 | 13.507 | −17.684 | 1.00 | 9.06 | C |
| ATOM | 1418 | O | SER | A | 185 | −15.879 | 14.221 | −18.562 | 1.00 | 9.74 | O |
| ATOM | 1419 | CB | SER | A | 185 | −17.690 | 14.892 | −16.123 | 1.00 | 7.37 | C |
| ATOM | 1420 | OG | SER | A | 185 | −18.831 | 14.192 | −16.585 | 1.00 | 7.90 | O |
| ATOM | 1421 | N | ARG | A | 186 | −16.913 | 12.318 | −17.932 | 1.00 | 7.99 | N |
| ATOM | 1422 | CA | ARG | A | 186 | −16.986 | 11.784 | −19.296 | 1.00 | 8.17 | C |
| ATOM | 1423 | C | ARG | A | 186 | −18.178 | 12.352 | −20.056 | 1.00 | 11.97 | C |
| ATOM | 1424 | O | ARG | A | 186 | −18.309 | 12.136 | −21.264 | 1.00 | 11.61 | O |
| ATOM | 1425 | CB | ARG | A | 186 | −17.057 | 10.250 | −19.272 | 1.00 | 10.81 | C |
| ATOM | 1426 | CG | ARG | A | 186 | −15.777 | 9.591 | −18.788 | 1.00 | 10.26 | C |
| ATOM | 1427 | CD | ARG | A | 186 | −15.960 | 8.081 | −18.583 | 1.00 | 10.74 | C |
| ATOM | 1428 | NE | ARG | A | 186 | −17.037 | 7.816 | −17.635 | 1.00 | 10.08 | N |
| ATOM | 1429 | CZ | ARG | A | 186 | −17.587 | 6.622 | −17.426 | 1.00 | 13.38 | C |
| ATOM | 1430 | NH1 | ARG | A | 186 | −17.149 | 5.566 | −18.108 | 1.00 | 14.05 | N |
| ATOM | 1431 | NH2 | ARG | A | 186 | −18.572 | 6.479 | −16.551 | 1.00 | 12.05 | N |
| ATOM | 1432 | N | ASN | A | 187 | −19.062 | 13.055 | −19.358 | 1.00 | 8.13 | N |
| ATOM | 1433 | CA | ASN | A | 187 | −20.254 | 13.610 | −19.978 | 1.00 | 8.18 | C |
| ATOM | 1434 | C | ASN | A | 187 | −19.929 | 14.967 | −20.601 | 1.00 | 10.33 | C |
| ATOM | 1435 | O | ASN | A | 187 | −19.820 | 15.977 | −19.899 | 1.00 | 9.28 | O |
| ATOM | 1436 | CB | ASN | A | 187 | −21.383 | 13.720 | −18.943 | 1.00 | 7.71 | C |
| ATOM | 1437 | CG | ASN | A | 187 | −22.700 | 14.159 | −19.548 | 1.00 | 8.65 | C |
| ATOM | 1438 | OD1 | ASN | A | 187 | −22.731 | 14.989 | −20.462 | 1.00 | 10.78 | O |
| ATOM | 1439 | ND2 | ASN | A | 187 | −23.797 | 13.613 | −19.046 | 1.00 | 11.01 | N |
| ATOM | 1440 | N | LYS | A | 188 | −19.750 | 14.982 | −21.918 | 1.00 | 10.09 | N |
| ATOM | 1441 | CA | LYS | A | 188 | −19.290 | 16.182 | −22.611 | 1.00 | 10.45 | C |
| ATOM | 1442 | C | LYS | A | 188 | −20.274 | 17.335 | −22.497 | 1.00 | 8.22 | C |
| ATOM | 1443 | O | LYS | A | 188 | −19.854 | 18.498 | −22.440 | 1.00 | 10.20 | O |

TABLE 5-continued (Table 5 discloses SEQ ID NO: 10):

| ATOM | 1444 | CB  | LYS  | A | 188 | −18.984 | 15.865 | −24.079 | 1.00 | 12.84 | C |
|------|------|-----|------|---|-----|---------|--------|---------|------|-------|---|
| ATOM | 1445 | CG  | LYS  | A | 188 | −17.682 | 15.087 | −24.242 | 1.00 | 16.21 | C |
| ATOM | 1446 | CD  | LYS  | A | 188 | −17.316 | 14.886 | −25.702 | 1.00 | 30.25 | C |
| ATOM | 1447 | CE  | LYS  | A | 188 | −17.788 | 13.538 | −26.215 | 1.00 | 59.11 | C |
| ATOM | 1448 | NZ  | LYS  | A | 188 | −16.968 | 12.425 | −25.656 | 1.00 | 62.44 | N |
| ATOM | 1449 | N   | THR  | A | 189 | −21.558 | 17.018 | −22.461 | 1.00 | 8.16  | N |
| ATOM | 1450 | CA  | THR  | A | 189 | −22.590 | 18.029 | −22.287 | 1.00 | 9.52  | C |
| ATOM | 1451 | C   | THR  | A | 189 | −22.440 | 18.716 | −20.921 | 1.00 | 11.14 | C |
| ATOM | 1452 | O   | THR  | A | 189 | −22.499 | 19.947 | −20.822 | 1.00 | 10.76 | O |
| ATOM | 1453 | CB  | THR  | A | 189 | −24.002 | 17.422 | −22.419 | 1.00 | 11.47 | C |
| ATOM | 1454 | OG1 | THR  | A | 189 | −24.083 | 16.672 | −23.641 | 1.00 | 21.86 | O |
| ATOM | 1455 | CG2 | THR  | A | 189 | −25.069 | 18.514 | −22.442 | 1.00 | 15.48 | C |
| ATOM | 1456 | N   | GLU  | A | 190 | −22.243 | 17.917 | −19.866 | 1.00 | 7.70  | N |
| ATOM | 1457 | CA  | GLU  | A | 190 | −22.042 | 18.473 | −18.525 | 1.00 | 6.48  | C |
| ATOM | 1458 | C   | GLU  | A | 190 | −20.762 | 19.295 | −18.456 | 1.00 | 6.09  | C |
| ATOM | 1459 | O   | GLU  | A | 190 | −20.723 | 20.327 | −17.779 | 1.00 | 7.57  | O |
| ATOM | 1460 | CB  | GLU  | A | 190 | −22.047 | 17.360 | −17.468 | 1.00 | 7.78  | C |
| ATOM | 1461 | CG  | GLU  | A | 190 | −23.387 | 16.671 | −17.321 | 1.00 | 10.63 | C |
| ATOM | 1462 | CD  | GLU  | A | 190 | −24.469 | 17.574 | −16.735 | 1.00 | 19.84 | C |
| ATOM | 1463 | OE1 | GLU  | A | 190 | −24.149 | 18.687 | −16.262 | 1.00 | 14.70 | O |
| ATOM | 1464 | OE2 | GLU  | A | 190 | −25.650 | 17.164 | −16.743 | 1.00 | 48.07 | O |
| ATOM | 1465 | N   | VAL  | A | 191 | −19.709 | 18.864 | −19.139 | 1.00 | 6.34  | N |
| ATOM | 1466 | CA  | VAL  | A | 191 | −18.481 | 19.653 | −19.206 | 1.00 | 7.23  | C |
| ATOM | 1467 | C   | VAL  | A | 191 | −18.752 | 21.037 | −19.820 | 1.00 | 9.26  | C |
| ATOM | 1468 | O   | VAL  | A | 191 | −18.303 | 22.054 | −19.289 | 1.00 | 8.62  | O |
| ATOM | 1469 | CB  | VAL  | A | 191 | −17.369 | 18.914 | −19.990 | 1.00 | 7.21  | C |
| ATOM | 1470 | CG1 | VAL  | A | 191 | −16.176 | 19.816 | −20.252 | 1.00 | 10.02 | C |
| ATOM | 1471 | CG2 | VAL  | A | 191 | −16.945 | 17.649 | −19.229 | 1.00 | 9.40  | C |
| ATOM | 1472 | N   | ASP  | A | 192 | −19.496 | 21.067 | −20.924 | 1.00 | 8.63  | N |
| ATOM | 1473 | CA  | ASP  | A | 192 | −19.794 | 22.326 | −21.601 | 1.00 | 9.12  | C |
| ATOM | 1474 | C   | ASP  | A | 192 | −20.662 | 23.232 | −20.723 | 1.00 | 7.92  | C |
| ATOM | 1475 | O   | ASP  | A | 192 | −20.481 | 24.456 | −20.705 | 1.00 | 8.58  | O |
| ATOM | 1476 | CB  | ASP  | A | 192 | −20.505 | 22.061 | −22.930 | 1.00 | 8.58  | C |
| ATOM | 1477 | CG  | ASP  | A | 192 | −19.550 | 21.589 | −24.026 | 1.00 | 12.97 | C |
| ATOM | 1478 | OD1 | ASP  | A | 192 | −18.343 | 21.894 | −23.950 | 1.00 | 19.09 | O |
| ATOM | 1479 | OD2 | ASP  | A | 192 | −20.020 | 20.912 | −24.968 | 1.00 | 13.65 | O |
| ATOM | 1480 | N   | ILE  | A | 193 | −21.614 | 22.636 | −20.014 | 1.00 | 6.50  | N |
| ATOM | 1481 | CA  | ILE  | A | 193 | −22.479 | 23.391 | −19.111 | 1.00 | 6.64  | C |
| ATOM | 1482 | C   | ILE  | A | 193 | −21.658 | 24.019 | −17.992 | 1.00 | 8.30  | C |
| ATOM | 1483 | O   | ILE  | A | 193 | −21.797 | 25.211 | −17.684 | 1.00 | 9.16  | O |
| ATOM | 1484 | CB  | ILE  | A | 193 | −23.594 | 22.499 | −18.555 | 1.00 | 6.90  | C |
| ATOM | 1485 | CG1 | ILE  | A | 193 | −24.608 | 22.219 | −19.667 | 1.00 | 9.28  | C |
| ATOM | 1486 | CG2 | ILE  | A | 193 | −24.291 | 23.153 | −17.355 | 1.00 | 9.32  | C |
| ATOM | 1487 | CD1 | ILE  | A | 193 | −25.635 | 21.164 | −19.323 | 1.00 | 11.81 | C |
| ATOM | 1488 | N   | TYR  | A | 194 | −20.766 | 23.230 | −17.403 | 1.00 | 6.21  | N |
| ATOM | 1489 | CA  | TYR  | A | 194 | −19.902 | 23.749 | −16.359 | 1.00 | 6.09  | C |
| ATOM | 1490 | C   | TYR  | A | 194 | −19.037 | 24.896 | −16.880 | 1.00 | 6.70  | C |
| ATOM | 1491 | O   | TYR  | A | 194 | −18.930 | 25.955 | −16.238 | 1.00 | 7.31  | O |
| ATOM | 1492 | CB  | TYR  | A | 194 | −19.023 | 22.623 | −15.814 | 1.00 | 6.50  | C |
| ATOM | 1493 | CG  | TYR  | A | 194 | −17.954 | 23.098 | −14.861 | 1.00 | 6.88  | C |
| ATOM | 1494 | CD1 | TYR  | A | 194 | −18.239 | 23.297 | −13.501 | 1.00 | 7.46  | C |
| ATOM | 1495 | CD2 | TYR  | A | 194 | −16.670 | 23.355 | −15.305 | 1.00 | 6.99  | C |
| ATOM | 1496 | CE1 | TYR  | A | 194 | −17.254 | 23.734 | −12.635 | 1.00 | 6.75  | C |
| ATOM | 1497 | CE2 | TYR  | A | 194 | −15.681 | 23.774 | −14.445 | 1.00 | 8.92  | C |
| ATOM | 1498 | CZ  | TYR  | A | 194 | −15.981 | 23.965 | −13.105 | 1.00 | 7.57  | C |
| ATOM | 1499 | OH  | TYR  | A | 194 | −14.961 | 24.384 | −12.276 | 1.00 | 11.18 | O |
| ATOM | 1500 | N   | ASN  | A | 195 | −18.401 | 24.688 | −18.028 | 1.00 | 6.89  | N |
| ATOM | 1501 | CA  | ASN  | A | 195 | −17.462 | 25.666 | −18.552 | 1.00 | 8.53  | C |
| ATOM | 1502 | C   | ASN  | A | 195 | −18.103 | 27.032 | −18.812 | 1.00 | 8.54  | C |
| ATOM | 1503 | O   | ASN  | A | 195 | −17.411 | 28.044 | −18.744 | 1.00 | 10.97 | O |
| ATOM | 1504 | CB  | ASN  | A | 195 | −16.820 | 25.175 | −19.856 | 1.00 | 8.26  | C |
| ATOM | 1505 | CG  | ASN  | A | 195 | −15.794 | 24.074 | −19.648 | 1.00 | 13.25 | C |
| ATOM | 1506 | OD1 | ASN  | A | 195 | −15.364 | 23.433 | −20.610 | 1.00 | 14.63 | O |
| ATOM | 1507 | ND2 | ASN  | A | 195 | −15.385 | 23.861 | −18.416 | 1.00 | 9.36  | N |
| ATOM | 1508 | N   | SER  | A | 196 | −19.388 | 27.069 | −19.120 | 1.00 | 6.92  | N |
| ATOM | 1509 | CA  | ASER | A | 196 | −20.047 | 28.337 | −19.432 | 0.35 | 8.60  | C |
| ATOM | 1510 | C   | SER  | A | 196 | −20.869 | 28.885 | −18.264 | 1.00 | 8.11  | C |
| ATOM | 1511 | O   | SER  | A | 196 | −21.634 | 29.832 | −18.424 | 1.00 | 8.53  | O |
| ATOM | 1512 | CB  | ASER | A | 196 | −20.917 | 28.198 | −20.679 | 0.35 | 15.69 | C |
| ATOM | 1513 | OG  | ASER | A | 196 | −21.879 | 27.180 | −20.503 | 0.35 | 10.54 | O |
| ATOM | 1514 | CA  | BSER | A | 196 | −20.047 | 28.337 | −19.432 | 0.35 | 8.84  | C |
| ATOM | 1515 | CB  | BSER | A | 196 | −20.917 | 28.198 | −20.679 | 0.35 | 15.69 | C |
| ATOM | 1516 | OG  | BSER | A | 196 | −21.878 | 27.179 | −20.504 | 0.35 | 10.54 | O |
| ATOM | 1517 | CA  | CSER | A | 196 | −20.030 | 28.350 | −19.424 | 0.30 | 7.88  | C |
| ATOM | 1518 | CB  | CSER | A | 196 | −20.829 | 28.311 | −20.741 | 0.30 | 17.42 | C |
| ATOM | 1519 | OG  | CSER | A | 196 | −21.208 | 26.999 | −21.123 | 0.30 | 5.94  | O |
| ATOM | 1520 | N   | ASP  | A | 197 | −20.712 | 28.283 | −17.088 | 1.00 | 7.36  | N |
| ATOM | 1521 | CA  | ASP  | A | 197 | −21.378 | 28.788 | −15.890 | 1.00 | 7.39  | C |

TABLE 5-continued (Table 5 discloses SEQ ID NO: 10):

| ATOM | 1522 | C | ASP | A | 197 | −20.675 | 30.091 | −15.452 | 1.00 | 5.11 | C |
|---|---|---|---|---|---|---|---|---|---|---|---|
| ATOM | 1523 | O | ASP | A | 197 | −19.472 | 30.105 | −15.231 | 1.00 | 7.19 | O |
| ATOM | 1524 | CB | ASP | A | 197 | −21.307 | 27.710 | −14.799 | 1.00 | 7.00 | C |
| ATOM | 1525 | CG | ASP | A | 197 | −22.001 | 28.111 | −13.506 | 1.00 | 12.88 | C |
| ATOM | 1526 | OD1 | ASP | A | 197 | −22.176 | 29.315 | −13.216 | 1.00 | 9.53 | O |
| ATOM | 1527 | OD2 | ASP | A | 197 | −22.354 | 27.193 | −12.734 | 1.00 | 9.68 | O |
| ATOM | 1528 | N | PRO | A | 198 | −21.441 | 31.197 | −15.362 | 1.00 | 7.84 | N |
| ATOM | 1529 | CA | PRO | A | 198 | −20.779 | 32.480 | −15.077 | 1.00 | 8.09 | C |
| ATOM | 1530 | C | PRO | A | 198 | −20.238 | 32.580 | −13.644 | 1.00 | 9.46 | C |
| ATOM | 1531 | O | PRO | A | 198 | −19.519 | 33.532 | −13.335 | 1.00 | 12.16 | O |
| ATOM | 1532 | CB | PRO | A | 198 | −21.895 | 33.517 | −15.282 | 1.00 | 8.81 | C |
| ATOM | 1533 | CG | PRO | A | 198 | −23.166 | 32.783 | −15.271 | 1.00 | 12.52 | C |
| ATOM | 1534 | CD | PRO | A | 198 | −22.891 | 31.321 | −15.544 | 1.00 | 8.16 | C |
| ATOM | 1535 | N | LEU | A | 199 | −20.561 | 31.604 | −12.796 | 1.00 | 7.46 | N |
| ATOM | 1536 | CA | LEU | A | 199 | −20.220 | 31.683 | −11.372 | 1.00 | 10.37 | C |
| ATOM | 1537 | C | LEU | A | 199 | −19.048 | 30.798 | −10.951 | 1.00 | 12.05 | C |
| ATOM | 1538 | O | LEU | A | 199 | −18.687 | 30.775 | −9.763 | 1.00 | 11.02 | O |
| ATOM | 1539 | CB | LEU | A | 199 | −21.451 | 31.367 | −10.526 | 1.00 | 7.80 | C |
| ATOM | 1540 | CG | LEU | A | 199 | −22.611 | 32.350 | −10.675 | 1.00 | 10.76 | C |
| ATOM | 1541 | CD1 | LEU | A | 199 | −23.818 | 31.905 | −9.861 | 1.00 | 11.32 | C |
| ATOM | 1542 | CD2 | LEU | A | 199 | −22.164 | 33.760 | −10.266 | 1.00 | 14.15 | C |
| ATOM | 1543 | N | ILE | A | 200 | −18.459 | 30.065 | −11.895 | 1.00 | 8.07 | N |
| ATOM | 1544 | CA | ILE | A | 200 | −17.275 | 29.255 | −11.599 | 1.00 | 6.42 | C |
| ATOM | 1545 | C | ILE | A | 200 | −16.006 | 30.084 | −11.705 | 1.00 | 7.71 | C |
| ATOM | 1546 | O | ILE | A | 200 | −16.051 | 31.229 | −12.184 | 1.00 | 12.31 | O |
| ATOM | 1547 | CB | ILE | A | 200 | −17.172 | 28.017 | −12.531 | 1.00 | 7.22 | C |
| ATOM | 1548 | CG1 | ILE | A | 200 | −16.906 | 28.441 | −13.992 | 1.00 | 10.03 | C |
| ATOM | 1549 | CG2 | ILE | A | 200 | −18.421 | 27.151 | −12.401 | 1.00 | 8.89 | C |
| ATOM | 1550 | CD1 | ILE | A | 200 | −16.361 | 27.315 | −14.869 | 1.00 | 10.39 | C |
| ATOM | 1551 | N | CYS | A | 201 | −14.875 | 29.524 | −11.293 | 1.00 | 7.95 | N |
| ATOM | 1552 | CA | CYS | A | 201 | −13.587 | 30.182 | −11.468 | 1.00 | 9.49 | C |
| ATOM | 1553 | C | CYS | A | 201 | −12.723 | 29.352 | −12.404 | 1.00 | 13.48 | C |
| ATOM | 1554 | O | CYS | A | 201 | −12.434 | 28.187 | −12.106 | 1.00 | 13.84 | O |
| ATOM | 1555 | CB | CYS | A | 201 | −12.870 | 30.343 | −10.125 | 1.00 | 12.53 | C |
| ATOM | 1556 | SG | CYS | A | 201 | −11.270 | 31.173 | −10.289 | 1.00 | 17.94 | S |
| ATOM | 1557 | N | ARG | A | 202 | −12.303 | 29.959 | −13.515 | 1.00 | 11.34 | N |
| ATOM | 1558 | CA | ARG | A | 202 | −11.533 | 29.264 | −14.554 | 1.00 | 11.13 | C |
| ATOM | 1559 | C | ARG | A | 202 | −10.064 | 29.653 | −14.550 | 1.00 | 12.74 | C |
| ATOM | 1560 | O | ARG | A | 202 | −9.317 | 29.269 | −15.449 | 1.00 | 14.37 | O |
| ATOM | 1561 | CB | ARG | A | 202 | −12.123 | 29.558 | −15.936 | 1.00 | 12.12 | C |
| ATOM | 1562 | CG | ARG | A | 202 | −13.617 | 29.317 | −16.013 | 1.00 | 15.07 | C |
| ATOM | 1563 | CD | ARG | A | 202 | −14.121 | 29.443 | −17.439 | 1.00 | 19.32 | C |
| ATOM | 1564 | NE | ARG | A | 202 | −13.749 | 28.272 | −18.222 | 1.00 | 18.70 | N |
| ATOM | 1565 | CZ | ARG | A | 202 | −13.869 | 28.184 | −19.543 | 1.00 | 26.00 | C |
| ATOM | 1566 | NH1 | ARG | A | 202 | −14.349 | 29.207 | −20.236 | 1.00 | 22.12 | N |
| ATOM | 1567 | NH2 | ARG | A | 202 | −13.509 | 27.071 | −20.166 | 1.00 | 19.47 | N |
| ATOM | 1568 | N | ALA | A | 203 | −9.646 | 30.408 | −13.538 | 1.00 | 12.06 | N |
| ATOM | 1569 | CA | ALA | A | 203 | −8.263 | 30.859 | −13.438 | 1.00 | 13.49 | C |
| ATOM | 1570 | C | ALA | A | 203 | −7.346 | 29.766 | −12.897 | 1.00 | 12.80 | C |
| ATOM | 1571 | O | ALA | A | 203 | −7.812 | 28.796 | −12.294 | 1.00 | 12.79 | O |
| ATOM | 1572 | CB | ALA | A | 203 | −8.180 | 32.109 | −12.557 | 1.00 | 16.80 | C |
| ATOM | 1573 | N | GLY | A | 204 | −6.043 | 29.919 | −13.104 | 1.00 | 12.71 | N |
| ATOM | 1574 | CA | GLY | A | 204 | −5.083 | 29.005 | −12.518 | 1.00 | 13.49 | C |
| ATOM | 1575 | C | GLY | A | 204 | −5.213 | 29.001 | −11.006 | 1.00 | 14.76 | C |
| ATOM | 1576 | O | GLY | A | 204 | −5.478 | 30.037 | −10.395 | 1.00 | 14.87 | O |
| ATOM | 1577 | N | LEU | A | 205 | −5.053 | 27.838 | −10.394 | 1.00 | 12.15 | N |
| ATOM | 1578 | CA | ALEU | A | 205 | −5.099 | 27.763 | −8.938 | 0.50 | 12.52 | C |
| ATOM | 1579 | C | LEU | A | 205 | −3.877 | 28.430 | −8.323 | 1.00 | 12.12 | C |
| ATOM | 1580 | O | LEU | A | 205 | −2.738 | 28.073 | −8.617 | 1.00 | 14.37 | O |
| ATOM | 1581 | CB | ALEU | A | 205 | −5.233 | 26.317 | −8.455 | 0.50 | 21.10 | C |
| ATOM | 1582 | CG | ALEU | A | 205 | −6.675 | 25.832 | −8.280 | 0.50 | 22.60 | C |
| ATOM | 1583 | CD1 | ALEU | A | 205 | −7.347 | 25.614 | −9.629 | 0.50 | 46.72 | C |
| ATOM | 1584 | CD2 | ALEU | A | 205 | −6.729 | 24.565 | −7.437 | 0.50 | 21.86 | C |
| ATOM | 1585 | CA | BLEU | A | 205 | −5.093 | 27.740 | −8.941 | 0.50 | 14.43 | C |
| ATOM | 1586 | CB | BLEU | A | 205 | −5.152 | 26.271 | −8.524 | 0.50 | 15.12 | C |
| ATOM | 1587 | CG | BLEU | A | 205 | −5.569 | 25.980 | −7.083 | 0.50 | 25.82 | C |
| ATOM | 1588 | CD1 | BLEU | A | 205 | −6.333 | 24.666 | −6.994 | 0.50 | 50.50 | C |
| ATOM | 1589 | CD2 | BLEU | A | 205 | −4.358 | 25.965 | −6.180 | 0.50 | 39.57 | C |
| ATOM | 1590 | N | LYS | A | 206 | −4.119 | 29.419 | −7.467 | 1.00 | 10.85 | N |
| ATOM | 1591 | CA | LYS | A | 206 | −3.027 | 30.161 | −6.853 | 1.00 | 11.66 | C |
| ATOM | 1592 | C | LYS | A | 206 | −2.265 | 29.295 | −5.866 | 1.00 | 12.14 | C |
| ATOM | 1593 | O | LYS | A | 206 | −2.852 | 28.446 | −5.188 | 1.00 | 11.48 | O |
| ATOM | 1594 | CB | LYS | A | 206 | −3.563 | 31.409 | −6.157 | 1.00 | 15.47 | C |
| ATOM | 1595 | CG | LYS | A | 206 | −4.079 | 32.451 | −7.138 | 1.00 | 20.12 | C |
| ATOM | 1596 | CD | LYS | A | 206 | −4.787 | 33.588 | −6.426 | 1.00 | 37.03 | C |
| ATOM | 1597 | CE | LYS | A | 206 | −5.080 | 34.727 | −7.388 | 1.00 | 51.15 | C |
| ATOM | 1598 | NZ | LYS | A | 206 | −3.843 | 35.225 | −8.052 | 1.00 | 92.27 | N |
| ATOM | 1599 | N | VAL | A | 207 | −0.959 | 29.503 | −5.774 | 1.00 | 10.91 | N |

TABLE 5-continued (Table 5 discloses SEQ ID NO: 10):

| ATOM | 1600 | CA  | VAL | A | 207 | −0.145 | 28.709 | −4.867 | 1.00 | 11.61 | C |
|------|------|-----|-----|---|-----|--------|--------|--------|------|-------|---|
| ATOM | 1601 | C   | VAL | A | 207 | −0.645 | 28.809 | −3.421 | 1.00 | 12.70 | C |
| ATOM | 1602 | O   | VAL | A | 207 | −0.680 | 27.816 | −2.702 | 1.00 | 12.20 | O |
| ATOM | 1603 | CB  | VAL | A | 207 | 1.347  | 29.092 | −4.957 | 1.00 | 13.57 | C |
| ATOM | 1604 | CG1 | VAL | A | 207 | 2.124  | 28.508 | −3.785 | 1.00 | 16.27 | C |
| ATOM | 1605 | CG2 | VAL | A | 207 | 1.918  | 28.614 | −6.280 | 1.00 | 15.13 | C |
| ATOM | 1606 | N   | CYS | A | 208 | −1.043 | 30.001 | −2.988 | 1.00 | 10.56 | N |
| ATOM | 1607 | CA  | CYS | A | 208 | −1.537 | 30.138 | −1.619 | 1.00 | 12.51 | C |
| ATOM | 1608 | C   | CYS | A | 208 | −2.766 | 29.252 | −1.368 | 1.00 | 12.06 | C |
| ATOM | 1609 | O   | CYS | A | 208 | −2.927 | 28.698 | −0.284 | 1.00 | 12.63 | O |
| ATOM | 1610 | CB  | CYS | A | 208 | −1.844 | 31.602 | −1.287 | 1.00 | 13.86 | C |
| ATOM | 1611 | SG  | CYS | A | 208 | −3.147 | 32.334 | −2.291 | 1.00 | 19.08 | S |
| ATOM | 1612 | N   | PHE | A | 209 | −3.620 | 29.107 | −2.378 | 1.00 | 10.09 | N |
| ATOM | 1613 | CA  | PHE | A | 209 | −4.827 | 28.297 | −2.226 | 1.00 | 10.18 | C |
| ATOM | 1614 | C   | PHE | A | 209 | −4.474 | 26.817 | −2.261 | 1.00 | 9.52  | C |
| ATOM | 1615 | O   | PHE | A | 209 | −4.999 | 26.045 | −1.466 | 1.00 | 9.70  | O |
| ATOM | 1616 | CB  | PHE | A | 209 | −5.862 | 28.632 | −3.298 | 1.00 | 8.96  | C |
| ATOM | 1617 | CG  | PHE | A | 209 | −7.213 | 28.020 | −3.047 | 1.00 | 10.85 | C |
| ATOM | 1618 | CD1 | PHE | A | 209 | −7.979 | 28.421 | −1.965 | 1.00 | 15.24 | C |
| ATOM | 1619 | CD2 | PHE | A | 209 | −7.721 | 27.055 | −3.904 | 1.00 | 11.35 | C |
| ATOM | 1620 | CE1 | PHE | A | 209 | −9.230 | 27.863 | −1.737 | 1.00 | 19.47 | C |
| ATOM | 1621 | CE2 | PHE | A | 209 | −8.967 | 26.493 | −3.680 | 1.00 | 13.97 | C |
| ATOM | 1622 | CZ  | PHE | A | 209 | −9.722 | 26.901 | −2.603 | 1.00 | 16.68 | C |
| ATOM | 1623 | N   | GLY | A | 210 | −3.596 | 26.423 | −3.179 | 1.00 | 10.17 | N |
| ATOM | 1624 | CA  | GLY | A | 210 | −3.119 | 25.054 | −3.215 | 1.00 | 10.27 | C |
| ATOM | 1625 | C   | GLY | A | 210 | −2.529 | 24.619 | −1.887 | 1.00 | 9.64  | C |
| ATOM | 1626 | O   | GLY | A | 210 | −2.727 | 23.483 | −1.453 | 1.00 | 10.94 | O |
| ATOM | 1627 | N   | ILE | A | 211 | −1.798 | 25.525 | −1.246 | 1.00 | 9.76  | N |
| ATOM | 1628 | CA  | ILE | A | 211 | −1.219 | 25.237 | 0.060  | 1.00 | 10.73 | C |
| ATOM | 1629 | C   | ILE | A | 211 | −2.334 | 24.946 | 1.064  | 1.00 | 9.63  | C |
| ATOM | 1630 | O   | ILE | A | 211 | −2.225 | 24.023 | 1.872  | 1.00 | 11.27 | O |
| ATOM | 1631 | CB  | ILE | A | 211 | −0.326 | 26.394 | 0.547  | 1.00 | 10.51 | C |
| ATOM | 1632 | CG1 | ILE | A | 211 | 0.968  | 26.424 | −0.264 | 1.00 | 14.10 | C |
| ATOM | 1633 | CG2 | ILE | A | 211 | −0.019 | 26.260 | 2.051  | 1.00 | 15.16 | C |
| ATOM | 1634 | CD1 | ILE | A | 211 | 1.777  | 27.688 | −0.060 | 1.00 | 19.74 | C |
| ATOM | 1635 | N   | GLN | A | 212 | −3.415 | 25.716 | 0.999  | 1.00 | 8.87  | N |
| ATOM | 1636 | CA  | GLN | A | 212 | −4.550 | 25.457 | 1.887  | 1.00 | 9.46  | C |
| ATOM | 1637 | C   | GLN | A | 212 | −5.228 | 24.114 | 1.579  | 1.00 | 10.55 | C |
| ATOM | 1638 | O   | GLN | A | 212 | −5.725 | 23.448 | 2.492  | 1.00 | 10.09 | O |
| ATOM | 1639 | CB  | GLN | A | 212 | −5.549 | 26.618 | 1.865  | 1.00 | 8.41  | C |
| ATOM | 1640 | CG  | GLN | A | 212 | −4.979 | 27.899 | 2.496  | 1.00 | 9.42  | C |
| ATOM | 1641 | CD  | GLN | A | 212 | −4.434 | 27.662 | 3.902  | 1.00 | 10.45 | C |
| ATOM | 1642 | OE1 | GLN | A | 212 | −5.011 | 26.906 | 4.686  | 1.00 | 11.66 | O |
| ATOM | 1643 | NE2 | GLN | A | 212 | −3.323 | 28.311 | 4.222  | 1.00 | 14.57 | N |
| ATOM | 1644 | N   | LEU | A | 213 | −5.241 | 23.704 | 0.306  | 1.00 | 9.40  | N |
| ATOM | 1645 | CA  | LEU | A | 213 | −5.764 | 22.378 | −0.036 | 1.00 | 10.49 | C |
| ATOM | 1646 | C   | LEU | A | 213 | −4.854 | 21.266 | 0.505  | 1.00 | 9.28  | C |
| ATOM | 1647 | O   | LEU | A | 213 | −5.343 | 20.236 | 0.962  | 1.00 | 10.04 | O |
| ATOM | 1648 | CB  | LEU | A | 213 | −5.973 | 22.236 | −1.546 | 1.00 | 9.58  | C |
| ATOM | 1649 | CG  | LEU | A | 213 | −7.050 | 23.140 | −2.143 | 1.00 | 10.05 | C |
| ATOM | 1650 | CD1 | LEU | A | 213 | −7.097 | 22.976 | −3.663 | 1.00 | 14.31 | C |
| ATOM | 1651 | CD2 | LEU | A | 213 | −8.407 | 22.838 | −1.528 | 1.00 | 14.79 | C |
| ATOM | 1652 | N   | LEU | A | 214 | −3.541 | 21.477 | 0.478  | 1.00 | 9.43  | N |
| ATOM | 1653 | CA  | LEU | A | 214 | −2.616 | 20.540 | 1.123  | 1.00 | 11.38 | C |
| ATOM | 1654 | C   | LEU | A | 214 | −2.855 | 20.488 | 2.634  | 1.00 | 11.40 | C |
| ATOM | 1655 | O   | LEU | A | 214 | −2.800 | 19.411 | 3.249  | 1.00 | 11.93 | O |
| ATOM | 1656 | CB  | LEU | A | 214 | −1.157 | 20.914 | 0.856  | 1.00 | 12.30 | C |
| ATOM | 1657 | CG  | LEU | A | 214 | −0.639 | 20.817 | −0.582 | 1.00 | 17.43 | C |
| ATOM | 1658 | CD1 | LEU | A | 214 | 0.811  | 21.288 | −0.643 | 1.00 | 17.60 | C |
| ATOM | 1659 | CD2 | LEU | A | 214 | −0.764 | 19.397 | −1.091 | 1.00 | 18.65 | C |
| ATOM | 1660 | N   | ASN | A | 215 | −3.105 | 21.650 | 3.234  | 1.00 | 10.49 | N |
| ATOM | 1661 | CA  | ASN | A | 215 | −3.460 | 21.701 | 4.651  | 1.00 | 11.90 | C |
| ATOM | 1662 | C   | ASN | A | 215 | −4.717 | 20.879 | 4.909  | 1.00 | 10.86 | C |
| ATOM | 1663 | O   | ASN | A | 215 | −4.788 | 20.130 | 5.884  | 1.00 | 12.49 | O |
| ATOM | 1664 | CB  | ASN | A | 215 | −3.696 | 23.143 | 5.109  | 1.00 | 9.81  | C |
| ATOM | 1665 | CG  | ASN | A | 215 | −2.413 | 23.943 | 5.231  | 1.00 | 13.81 | C |
| ATOM | 1666 | OD1 | ASN | A | 215 | −1.309 | 23.393 | 5.195  | 1.00 | 15.52 | O |
| ATOM | 1667 | ND2 | ASN | A | 215 | −2.556 | 25.257 | 5.381  | 1.00 | 15.57 | N |
| ATOM | 1668 | N   | ALA | A | 216 | −5.709 | 21.009 | 4.031  | 1.00 | 9.70  | N |
| ATOM | 1669 | CA  | ALA | A | 216 | −6.940 | 20.245 | 4.172  | 1.00 | 10.39 | C |
| ATOM | 1670 | C   | ALA | A | 216 | −6.662 | 18.742 | 4.172  | 1.00 | 11.63 | C |
| ATOM | 1671 | O   | ALA | A | 216 | −7.177 | 18.013 | 5.021  | 1.00 | 11.59 | O |
| ATOM | 1672 | CB  | ALA | A | 216 | −7.942 | 20.617 | 3.078  | 1.00 | 11.90 | C |
| ATOM | 1673 | N   | VAL | A | 217 | −5.856 | 18.282 | 3.217  | 1.00 | 11.05 | N |
| ATOM | 1674 | CA  | VAL | A | 217 | −5.522 | 16.864 | 3.131  | 1.00 | 12.23 | C |
| ATOM | 1675 | C   | VAL | A | 217 | −4.844 | 16.383 | 4.417  | 1.00 | 11.43 | C |
| ATOM | 1676 | O   | VAL | A | 217 | −5.205 | 15.340 | 4.961  | 1.00 | 11.37 | O |
| ATOM | 1677 | CB  | VAL | A | 217 | −4.642 | 16.575 | 1.898  | 1.00 | 12.66 | C |

TABLE 5-continued (Table 5 discloses SEQ ID NO: 10):

| ATOM | 1678 | CG1 | VAL | A | 217 | −4.053 | 15.157 | 1.955 | 1.00 | 15.90 | C |
|---|---|---|---|---|---|---|---|---|---|---|---|
| ATOM | 1679 | CG2 | VAL | A | 217 | −5.449 | 16.780 | 0.618 | 1.00 | 13.74 | C |
| ATOM | 1680 | N | SER | A | 218 | −3.884 | 17.155 | 4.910 | 1.00 | 10.49 | N |
| ATOM | 1681 | CA | ASER | A | 218 | −3.194 | 16.822 | 6.152 | 0.50 | 11.81 | C |
| ATOM | 1682 | C | SER | A | 218 | −4.174 | 16.752 | 7.322 | 1.00 | 12.18 | C |
| ATOM | 1683 | O | SER | A | 218 | −4.142 | 15.814 | 8.127 | 1.00 | 13.97 | O |
| ATOM | 1684 | CB | ASER | A | 218 | −2.103 | 17.853 | 6.442 | 0.50 | 15.09 | C |
| ATOM | 1685 | OG | ASER | A | 218 | −1.031 | 17.731 | 5.527 | 0.50 | 17.82 | O |
| ATOM | 1686 | CA | BSER | A | 218 | −3.194 | 16.811 | 6.151 | 0.50 | 10.96 | C |
| ATOM | 1687 | CB | BSER | A | 218 | −2.072 | 17.812 | 6.439 | 0.50 | 14.67 | C |
| ATOM | 1688 | OG | BSER | A | 218 | −1.434 | 17.523 | 7.675 | 0.50 | 19.05 | O |
| ATOM | 1689 | N | ARG | A | 219 | −5.054 | 17.740 | 7.415 | 1.00 | 9.30 | N |
| ATOM | 1690 | CA | ARG | A | 219 | −6.019 | 17.783 | 8.511 | 1.00 | 11.05 | C |
| ATOM | 1691 | C | ARG | A | 219 | −7.045 | 16.657 | 8.422 | 1.00 | 10.10 | C |
| ATOM | 1692 | O | ARG | A | 219 | −7.451 | 16.091 | 9.439 | 1.00 | 10.71 | O |
| ATOM | 1693 | CB | ARG | A | 219 | −6.700 | 19.152 | 8.579 | 1.00 | 10.50 | C |
| ATOM | 1694 | CG | ARG | A | 219 | −5.708 | 20.260 | 8.925 | 1.00 | 10.95 | C |
| ATOM | 1695 | CD | ARG | A | 219 | −6.290 | 21.639 | 8.732 | 1.00 | 13.38 | C |
| ATOM | 1696 | NE | ARG | A | 219 | −5.238 | 22.651 | 8.755 | 1.00 | 13.54 | N |
| ATOM | 1697 | CZ | ARG | A | 219 | −5.455 | 23.955 | 8.635 | 1.00 | 12.88 | C |
| ATOM | 1698 | NH1 | ARG | A | 219 | −6.690 | 24.413 | 8.499 | 1.00 | 12.45 | N |
| ATOM | 1699 | NH2 | ARG | A | 219 | −4.427 | 24.797 | 8.662 | 1.00 | 14.24 | N |
| ATOM | 1700 | N | VAL | A | 220 | −7.466 | 16.320 | 7.206 | 1.00 | 9.48 | N |
| ATOM | 1701 | CA | VAL | A | 220 | −8.391 | 15.216 | 7.021 | 1.00 | 10.61 | C |
| ATOM | 1702 | C | VAL | A | 220 | −7.758 | 13.921 | 7.526 | 1.00 | 10.79 | C |
| ATOM | 1703 | O | VAL | A | 220 | −8.403 | 13.143 | 8.223 | 1.00 | 11.64 | O |
| ATOM | 1704 | CB | VAL | A | 220 | −8.834 | 15.084 | 5.547 | 1.00 | 9.99 | C |
| ATOM | 1705 | CG1 | VAL | A | 220 | −9.476 | 13.727 | 5.296 | 1.00 | 10.95 | C |
| ATOM | 1706 | CG2 | VAL | A | 220 | −9.802 | 16.210 | 5.190 | 1.00 | 11.57 | C |
| ATOM | 1707 | N | GLU | A | 221 | −6.489 | 13.706 | 7.198 | 1.00 | 13.35 | N |
| ATOM | 1708 | CA | GLU | A | 221 | −5.800 | 12.492 | 7.633 | 1.00 | 14.85 | C |
| ATOM | 1709 | C | GLU | A | 221 | −5.815 | 12.368 | 9.157 | 1.00 | 18.26 | C |
| ATOM | 1710 | O | GLU | A | 221 | −6.082 | 11.295 | 9.701 | 1.00 | 18.73 | O |
| ATOM | 1711 | CB | GLU | A | 221 | −4.362 | 12.481 | 7.115 | 1.00 | 18.69 | C |
| ATOM | 1712 | CG | GLU | A | 221 | −3.543 | 11.285 | 7.574 | 1.00 | 51.12 | C |
| ATOM | 1713 | CD | GLU | A | 221 | −2.103 | 11.354 | 7.102 | 1.00 | 92.75 | C |
| ATOM | 1714 | OE1 | GLU | A | 221 | −1.704 | 12.403 | 6.551 | 1.00 | 79.10 | O |
| ATOM | 1715 | OE2 | GLU | A | 221 | −1.369 | 10.358 | 7.283 | 1.00 | 103.53 | O |
| ATOM | 1716 | N | ARG | A | 222 | −5.545 | 13.473 | 9.844 | 1.00 | 14.30 | N |
| ATOM | 1717 | CA | ARG | A | 222 | −5.568 | 13.479 | 11.305 | 1.00 | 15.32 | C |
| ATOM | 1718 | C | ARG | A | 222 | −6.967 | 13.282 | 11.865 | 1.00 | 13.43 | C |
| ATOM | 1719 | O | ARG | A | 222 | −7.139 | 12.698 | 12.936 | 1.00 | 19.93 | O |
| ATOM | 1720 | CB | ARG | A | 222 | −4.954 | 14.774 | 11.853 | 1.00 | 20.09 | C |
| ATOM | 1721 | CG | ARG | A | 222 | −3.440 | 14.809 | 11.778 | 1.00 | 30.84 | C |
| ATOM | 1722 | CD | ARG | A | 222 | −2.868 | 16.013 | 12.513 | 1.00 | 36.59 | C |
| ATOM | 1723 | NE | ARG | A | 222 | −3.115 | 17.262 | 11.798 | 1.00 | 51.40 | N |
| ATOM | 1724 | CZ | ARG | A | 222 | −2.332 | 17.740 | 10.837 | 1.00 | 65.64 | C |
| ATOM | 1725 | NH1 | ARG | A | 222 | −1.245 | 17.073 | 10.471 | 1.00 | 72.52 | N |
| ATOM | 1726 | NH2 | ARG | A | 222 | −2.635 | 18.885 | 10.240 | 1.00 | 34.72 | N |
| ATOM | 1727 | N | ALA | A | 223 | −7.971 | 13.770 | 11.149 | 1.00 | 12.61 | N |
| ATOM | 1728 | CA | ALA | A | 223 | −9.345 | 13.670 | 11.607 | 1.00 | 14.25 | C |
| ATOM | 1729 | C | ALA | A | 223 | −9.941 | 12.264 | 11.444 | 1.00 | 14.35 | C |
| ATOM | 1730 | O | ALA | A | 223 | −10.856 | 11.894 | 12.178 | 1.00 | 17.85 | O |
| ATOM | 1731 | CB | ALA | A | 223 | −10.211 | 14.692 | 10.886 | 1.00 | 15.85 | C |
| ATOM | 1732 | N | LEU | A | 224 | −9.429 | 11.502 | 10.476 | 1.00 | 14.85 | N |
| ATOM | 1733 | CA | LEU | A | 224 | −10.055 | 10.231 | 10.085 | 1.00 | 19.59 | C |
| ATOM | 1734 | C | LEU | A | 224 | −10.274 | 9.268 | 11.252 | 1.00 | 18.08 | C |
| ATOM | 1735 | O | LEU | A | 224 | −11.392 | 8.799 | 11.455 | 1.00 | 21.08 | O |
| ATOM | 1736 | CB | LEU | A | 224 | −9.277 | 9.537 | 8.958 | 1.00 | 18.13 | C |
| ATOM | 1737 | CG | LEU | A | 224 | −9.303 | 10.188 | 7.572 | 1.00 | 21.40 | C |
| ATOM | 1738 | CD1 | LEU | A | 224 | −8.687 | 9.260 | 6.531 | 1.00 | 28.66 | C |
| ATOM | 1739 | CD2 | LEU | A | 224 | −10.712 | 10.584 | 7.173 | 1.00 | 23.13 | C |
| ATOM | 1740 | N | PRO | A | 225 | −9.213 | 8.985 | 12.031 | 1.00 | 23.78 | N |
| ATOM | 1741 | CA | PRO | A | 225 | −9.334 | 8.027 | 13.138 | 1.00 | 24.17 | C |
| ATOM | 1742 | C | PRO | A | 225 | −10.310 | 8.479 | 14.215 | 1.00 | 26.85 | C |
| ATOM | 1743 | O | PRO | A | 225 | −10.636 | 7.694 | 15.106 | 1.00 | 34.94 | O |
| ATOM | 1744 | CB | PRO | A | 225 | −7.915 | 7.974 | 13.713 | 1.00 | 28.13 | C |
| ATOM | 1745 | CG | PRO | A | 225 | −7.034 | 8.443 | 12.608 | 1.00 | 36.69 | C |
| ATOM | 1746 | CD | PRO | A | 225 | −7.833 | 9.477 | 11.884 | 1.00 | 20.63 | C |
| ATOM | 1747 | N | LYS | A | 226 | −10.771 | 9.723 | 14.130 | 1.00 | 25.36 | N |
| ATOM | 1748 | CA | LYS | A | 226 | −11.684 | 10.280 | 15.120 | 1.00 | 25.72 | C |
| ATOM | 1749 | C | LYS | A | 226 | −13.132 | 10.300 | 14.630 | 1.00 | 33.01 | C |
| ATOM | 1750 | O | LYS | A | 226 | −14.058 | 10.524 | 15.408 | 1.00 | 28.49 | O |
| ATOM | 1751 | CB | LYS | A | 226 | −11.248 | 11.700 | 15.486 | 1.00 | 44.44 | C |
| ATOM | 1752 | CG | LYS | A | 226 | −9.761 | 11.834 | 15.776 | 1.00 | 42.51 | C |
| ATOM | 1753 | CD | LYS | A | 226 | −9.371 | 13.289 | 15.988 | 1.00 | 69.34 | C |
| ATOM | 1754 | CE | LYS | A | 226 | −7.876 | 13.432 | 16.224 | 1.00 | 70.90 | C |
| ATOM | 1755 | NZ | LYS | A | 226 | −7.485 | 14.853 | 16.441 | 1.00 | 84.95 | N |

TABLE 5-continued (Table 5 discloses SEQ ID NO: 10):

| ATOM | 1756 | N | LEU | A | 227 | −13.318 | 10.062 | 13.336 | 1.00 | 20.18 | N |
|---|---|---|---|---|---|---|---|---|---|---|---|
| ATOM | 1757 | CA | ALEU | A | 227 | −14.637 | 10.116 | 12.716 | 0.50 | 15.98 | C |
| ATOM | 1758 | C | LEU | A | 227 | −15.525 | 8.981 | 13.183 | 1.00 | 13.40 | C |
| ATOM | 1759 | O | LEU | A | 227 | −15.109 | 7.818 | 13.166 | 1.00 | 17.01 | O |
| ATOM | 1760 | CB | ALEU | A | 227 | −14.512 | 10.017 | 11.196 | 0.50 | 17.93 | C |
| ATOM | 1761 | CG | ALEU | A | 227 | −14.149 | 11.259 | 10.394 | 0.50 | 13.32 | C |
| ATOM | 1762 | CD1 | ALEU | A | 227 | −14.050 | 10.874 | 8.923 | 0.50 | 13.43 | C |
| ATOM | 1763 | CD2 | ALEU | A | 227 | −15.179 | 12.355 | 10.601 | 0.50 | 15.66 | C |
| ATOM | 1764 | CA | BLEU | A | 227 | −14.632 | 10.132 | 12.717 | 0.50 | 15.66 | C |
| ATOM | 1765 | CB | BLEU | A | 227 | −14.470 | 10.100 | 11.192 | 0.50 | 18.07 | C |
| ATOM | 1766 | CG | BLEU | A | 227 | −15.573 | 10.629 | 10.274 | 0.50 | 15.22 | C |
| ATOM | 1767 | CD1 | BLEU | A | 227 | −15.891 | 12.088 | 10.568 | 0.50 | 24.87 | C |
| ATOM | 1768 | CD2 | BLEU | A | 227 | −15.155 | 10.453 | 8.822 | 0.50 | 11.89 | C |
| ATOM | 1769 | N | THR | A | 228 | −16.746 | 9.311 | 13.596 | 1.00 | 10.05 | N |
| ATOM | 1770 | CA | THR | A | 228 | −17.727 | 8.299 | 13.997 | 1.00 | 12.36 | C |
| ATOM | 1771 | C | THR | A | 228 | −19.067 | 8.438 | 13.272 | 1.00 | 10.02 | C |
| ATOM | 1772 | O | THR | A | 228 | −19.946 | 7.580 | 13.400 | 1.00 | 10.20 | O |
| ATOM | 1773 | CB | THR | A | 228 | −17.994 | 8.324 | 15.523 | 1.00 | 15.46 | C |
| ATOM | 1774 | OG1 | THR | A | 228 | −18.544 | 9.596 | 15.893 | 1.00 | 17.33 | O |
| ATOM | 1775 | CG2 | THR | A | 228 | −16.710 | 8.077 | 16.300 | 1.00 | 16.53 | C |
| ATOM | 1776 | N | VAL | A | 229 | −19.231 | 9.526 | 12.518 | 1.00 | 10.47 | N |
| ATOM | 1777 | CA | VAL | A | 229 | −20.485 | 9.808 | 11.826 | 1.00 | 9.15 | C |
| ATOM | 1778 | C | VAL | A | 229 | −20.779 | 8.746 | 10.744 | 1.00 | 7.39 | C |
| ATOM | 1779 | O | VAL | A | 229 | −19.859 | 8.294 | 10.059 | 1.00 | 8.94 | O |
| ATOM | 1780 | CB | VAL | A | 229 | −20.438 | 11.233 | 11.185 | 1.00 | 11.08 | C |
| ATOM | 1781 | CG1 | VAL | A | 229 | −19.367 | 11.300 | 10.106 | 1.00 | 13.13 | C |
| ATOM | 1782 | CG2 | VAL | A | 229 | −21.788 | 11.640 | 10.626 | 1.00 | 12.72 | C |
| ATOM | 1783 | N | PRO | A | 230 | −22.041 | 8.320 | 10.620 | 1.00 | 7.45 | N |
| ATOM | 1784 | CA | PRO | A | 230 | −22.387 | 7.423 | 9.507 | 1.00 | 6.36 | C |
| ATOM | 1785 | C | PRO | A | 230 | −22.051 | 8.070 | 8.168 | 1.00 | 9.18 | C |
| ATOM | 1786 | O | PRO | A | 230 | −22.254 | 9.273 | 8.002 | 1.00 | 10.77 | O |
| ATOM | 1787 | CB | PRO | A | 230 | −23.898 | 7.272 | 9.630 | 1.00 | 9.15 | C |
| ATOM | 1788 | CG | PRO | A | 230 | −24.173 | 7.499 | 11.112 | 1.00 | 9.93 | C |
| ATOM | 1789 | CD | PRO | A | 230 | −23.181 | 8.547 | 11.527 | 1.00 | 10.30 | C |
| ATOM | 1790 | N | PHE | A | 231 | −21.543 | 7.296 | 7.211 | 1.00 | 6.79 | N |
| ATOM | 1791 | CA | PHE | A | 231 | −21.343 | 7.874 | 5.886 | 1.00 | 7.46 | C |
| ATOM | 1792 | C | PHE | A | 231 | −21.514 | 6.920 | 4.722 | 1.00 | 7.73 | C |
| ATOM | 1793 | O | PHE | A | 231 | −21.356 | 5.690 | 4.853 | 1.00 | 7.65 | O |
| ATOM | 1794 | CB | PHE | A | 231 | −20.019 | 8.643 | 5.779 | 1.00 | 7.69 | C |
| ATOM | 1795 | CG | PHE | A | 231 | −18.787 | 7.796 | 5.905 | 1.00 | 7.77 | C |
| ATOM | 1796 | CD1 | PHE | A | 231 | −18.230 | 7.177 | 4.784 | 1.00 | 9.21 | C |
| ATOM | 1797 | CD2 | PHE | A | 231 | −18.145 | 7.656 | 7.125 | 1.00 | 8.70 | C |
| ATOM | 1798 | CE1 | PHE | A | 231 | −17.076 | 6.414 | 4.892 | 1.00 | 10.86 | C |
| ATOM | 1799 | CE2 | PHE | A | 231 | −16.986 | 6.901 | 7.243 | 1.00 | 9.68 | C |
| ATOM | 1800 | CZ | PHE | A | 231 | −16.446 | 6.274 | 6.122 | 1.00 | 10.56 | C |
| ATOM | 1801 | N | LEU | A | 232 | −21.861 | 7.532 | 3.590 | 1.00 | 7.02 | N |
| ATOM | 1802 | CA | LEU | A | 232 | −21.907 | 6.871 | 2.291 | 1.00 | 5.67 | C |
| ATOM | 1803 | C | LEU | A | 232 | −20.836 | 7.551 | 1.462 | 1.00 | 7.56 | C |
| ATOM | 1804 | O | LEU | A | 232 | −20.824 | 8.788 | 1.349 | 1.00 | 8.41 | O |
| ATOM | 1805 | CB | LEU | A | 232 | −23.257 | 7.105 | 1.638 | 1.00 | 7.44 | C |
| ATOM | 1806 | CG | LEU | A | 232 | −23.360 | 6.631 | 0.181 | 1.00 | 8.89 | C |
| ATOM | 1807 | CD1 | LEU | A | 232 | −23.158 | 5.113 | 0.097 | 1.00 | 9.59 | C |
| ATOM | 1808 | CD2 | LEU | A | 232 | −24.689 | 7.035 | −0.430 | 1.00 | 9.38 | C |
| ATOM | 1809 | N | LEU | A | 233 | −19.937 | 6.755 | 0.893 | 1.00 | 5.98 | N |
| ATOM | 1810 | CA | LEU | A | 233 | −18.816 | 7.251 | 0.123 | 1.00 | 5.46 | C |
| ATOM | 1811 | C | LEU | A | 233 | −18.961 | 6.736 | −1.311 | 1.00 | 6.46 | C |
| ATOM | 1812 | O | LEU | A | 233 | −19.020 | 5.524 | −1.546 | 1.00 | 8.99 | O |
| ATOM | 1813 | CB | LEU | A | 233 | −17.536 | 6.719 | 0.749 | 1.00 | 6.96 | C |
| ATOM | 1814 | CG | LEU | A | 233 | −16.204 | 6.995 | 0.085 | 1.00 | 11.73 | C |
| ATOM | 1815 | CD1 | LEU | A | 233 | −15.985 | 8.484 | −0.098 | 1.00 | 11.86 | C |
| ATOM | 1816 | CD2 | LEU | A | 233 | −15.087 | 6.376 | 0.926 | 1.00 | 11.71 | C |
| ATOM | 1817 | N | LEU | A | 234 | −19.047 | 7.664 | −2.266 | 1.00 | 6.30 | N |
| ATOM | 1818 | CA | LEU | A | 234 | −19.146 | 7.328 | −3.690 | 1.00 | 5.53 | C |
| ATOM | 1819 | C | LEU | A | 234 | −17.887 | 7.806 | −4.387 | 1.00 | 6.67 | C |
| ATOM | 1820 | O | LEU | A | 234 | −17.482 | 8.964 | −4.214 | 1.00 | 7.50 | O |
| ATOM | 1821 | CB | LEU | A | 234 | −20.366 | 8.015 | −4.299 | 1.00 | 7.09 | C |
| ATOM | 1822 | CG | LEU | A | 234 | −21.692 | 7.778 | −3.587 | 1.00 | 7.45 | C |
| ATOM | 1823 | CD1 | LEU | A | 234 | −22.809 | 8.556 | −4.278 | 1.00 | 12.21 | C |
| ATOM | 1824 | CD2 | LEU | A | 234 | −22.056 | 6.295 | −3.498 | 1.00 | 10.51 | C |
| ATOM | 1825 | N | GLN | A | 235 | −17.263 | 6.930 | −5.172 | 1.00 | 6.02 | N |
| ATOM | 1826 | CA | GLN | A | 235 | −15.962 | 7.230 | −5.746 | 1.00 | 6.69 | C |
| ATOM | 1827 | C | GLN | A | 235 | −15.826 | 6.601 | −7.122 | 1.00 | 7.26 | C |
| ATOM | 1828 | O | GLN | A | 235 | −16.188 | 5.433 | −7.310 | 1.00 | 9.83 | O |
| ATOM | 1829 | CB | GLN | A | 235 | −14.878 | 6.664 | −4.823 | 1.00 | 8.10 | C |
| ATOM | 1830 | CG | GLN | A | 235 | −13.460 | 6.805 | −5.331 | 1.00 | 8.78 | C |
| ATOM | 1831 | CD | GLN | A | 235 | −12.945 | 8.235 | −5.263 | 1.00 | 14.60 | C |
| ATOM | 1832 | OE1 | GLN | A | 235 | −13.229 | 8.969 | −4.310 | 1.00 | 11.92 | O |
| ATOM | 1833 | NE2 | GLN | A | 235 | −12.176 | 8.639 | −6.273 | 1.00 | 14.30 | N |

TABLE 5-continued (Table 5 discloses SEQ ID NO: 10):

| ATOM | 1834 | N | GLY | A | 236 | −15.324 | 7.367 | −8.092 | 1.00 | 7.16 | N |
|---|---|---|---|---|---|---|---|---|---|---|---|
| ATOM | 1835 | CA | GLY | A | 236 | −15.027 | 6.814 | −9.410 | 1.00 | 7.05 | C |
| ATOM | 1836 | C | GLY | A | 236 | −13.626 | 6.241 | −9.448 | 1.00 | 7.13 | C |
| ATOM | 1837 | O | GLY | A | 236 | −12.698 | 6.781 | −8.847 | 1.00 | 9.31 | O |
| ATOM | 1838 | N | SER | A | 237 | −13.451 | 5.143 | −10.182 | 1.00 | 7.90 | N |
| ATOM | 1839 | CA | SER | A | 237 | −12.139 | 4.515 | −10.244 | 1.00 | 10.56 | C |
| ATOM | 1840 | C | SER | A | 237 | −11.158 | 5.288 | −11.122 | 1.00 | 8.69 | C |
| ATOM | 1841 | O | SER | A | 237 | −9.947 | 5.107 | −11.016 | 1.00 | 12.81 | O |
| ATOM | 1842 | CB | SER | A | 237 | −12.244 | 3.065 | −10.734 | 1.00 | 14.27 | C |
| ATOM | 1843 | OG | SER | A | 237 | −12.468 | 3.007 | −12.137 | 1.00 | 14.14 | O |
| ATOM | 1844 | N | ALA | A | 238 | −11.676 | 6.132 | −12.009 | 1.00 | 8.64 | N |
| ATOM | 1845 | CA | ALA | A | 238 | −10.806 | 6.884 | −12.918 | 1.00 | 12.93 | C |
| ATOM | 1846 | C | ALA | A | 238 | −10.783 | 8.358 | −12.539 | 1.00 | 12.31 | C |
| ATOM | 1847 | O | ALA | A | 238 | −10.740 | 9.239 | −13.402 | 1.00 | 11.93 | O |
| ATOM | 1848 | CB | ALA | A | 238 | −11.257 | 6.704 | −14.359 | 1.00 | 11.58 | C |
| ATOM | 1849 | N | ASP | A | 239 | −10.803 | 8.616 | −11.238 | 1.00 | 9.91 | N |
| ATOM | 1850 | CA | ASP | A | 239 | −10.753 | 9.975 | −10.703 | 1.00 | 11.61 | C |
| ATOM | 1851 | C | ASP | A | 239 | −9.331 | 10.528 | −10.745 | 1.00 | 11.01 | C |
| ATOM | 1852 | O | ASP | A | 239 | −8.434 | 10.018 | −10.070 | 1.00 | 12.82 | O |
| ATOM | 1853 | CB | ASP | A | 239 | −11.255 | 9.950 | −9.260 | 1.00 | 9.49 | C |
| ATOM | 1854 | CG | ASP | A | 239 | −11.495 | 11.338 | −8.701 | 1.00 | 10.07 | C |
| ATOM | 1855 | OD1 | ASP | A | 239 | −10.756 | 12.276 | −9.080 | 1.00 | 9.43 | O |
| ATOM | 1856 | OD2 | ASP | A | 239 | −12.430 | 11.490 | −7.888 | 1.00 | 10.75 | O |
| ATOM | 1857 | N | ARG | A | 240 | −9.131 | 11.573 | −11.549 | 1.00 | 10.38 | N |
| ATOM | 1858 | CA | ARG | A | 240 | −7.807 | 12.154 | −11.748 | 1.00 | 11.86 | C |
| ATOM | 1859 | C | ARG | A | 240 | −7.387 | 13.173 | −10.695 | 1.00 | 13.94 | C |
| ATOM | 1860 | O | ARG | A | 240 | −6.243 | 13.631 | −10.692 | 1.00 | 15.63 | O |
| ATOM | 1861 | CB | ARG | A | 240 | −7.736 | 12.819 | −13.124 | 1.00 | 15.76 | C |
| ATOM | 1862 | CG | ARG | A | 240 | −7.703 | 11.848 | −14.277 | 1.00 | 26.43 | C |
| ATOM | 1863 | CD | ARG | A | 240 | −6.677 | 12.317 | −15.281 | 1.00 | 32.76 | C |
| ATOM | 1864 | NE | ARG | A | 240 | −6.988 | 11.882 | −16.633 | 1.00 | 71.10 | N |
| ATOM | 1865 | CZ | ARG | A | 240 | −6.466 | 12.441 | −17.716 | 1.00 | 19.70 | C |
| ATOM | 1866 | NH1 | ARG | A | 240 | −5.618 | 13.457 | −17.587 | 1.00 | 26.60 | N |
| ATOM | 1867 | NH2 | ARG | A | 240 | −6.798 | 11.989 | −18.914 | 1.00 | 79.96 | N |
| ATOM | 1868 | N | LEU | A | 241 | −8.305 | 13.521 | −9.803 | 1.00 | 10.36 | N |
| ATOM | 1869 | CA | LEU | A | 241 | −8.077 | 14.586 | −8.841 | 1.00 | 12.06 | C |
| ATOM | 1870 | C | LEU | A | 241 | −8.030 | 14.068 | −7.404 | 1.00 | 14.79 | C |
| ATOM | 1871 | O | LEU | A | 241 | −7.048 | 14.283 | −6.685 | 1.00 | 17.27 | O |
| ATOM | 1872 | CB | LEU | A | 241 | −9.189 | 15.621 | −8.995 | 1.00 | 12.48 | C |
| ATOM | 1873 | CG | LEU | A | 241 | −8.962 | 16.968 | −8.329 | 1.00 | 17.56 | C |
| ATOM | 1874 | CD1 | LEU | A | 241 | −7.606 | 17.547 | −8.721 | 1.00 | 17.75 | C |
| ATOM | 1875 | CD2 | LEU | A | 241 | −10.086 | 17.899 | −8.744 | 1.00 | 14.80 | C |
| ATOM | 1876 | N | CYS | A | 242 | −9.103 | 13.402 | −6.990 | 1.00 | 13.17 | N |
| ATOM | 1877 | CA | CYS | A | 242 | −9.172 | 12.777 | −5.674 | 1.00 | 14.00 | C |
| ATOM | 1878 | C | CYS | A | 242 | −8.910 | 11.295 | −5.861 | 1.00 | 12.30 | C |
| ATOM | 1879 | O | CYS | A | 242 | −9.775 | 10.554 | −6.343 | 1.00 | 16.19 | O |
| ATOM | 1880 | CB | CYS | A | 242 | −10.531 | 13.035 | −5.026 | 1.00 | 14.14 | C |
| ATOM | 1881 | SG | CYS | A | 242 | −10.791 | 14.786 | −4.632 | 1.00 | 17.18 | S |
| ATOM | 1882 | N | ASP | A | 243 | −7.701 | 10.872 | −5.514 | 1.00 | 14.74 | N |
| ATOM | 1883 | CA | ASP | A | 243 | −7.270 | 9.511 | −5.787 | 1.00 | 15.90 | C |
| ATOM | 1884 | C | ASP | A | 243 | −8.125 | 8.489 | −5.046 | 1.00 | 18.69 | C |
| ATOM | 1885 | O | ASP | A | 243 | −8.421 | 8.649 | −3.860 | 1.00 | 14.40 | O |
| ATOM | 1886 | CB | ASP | A | 243 | −5.804 | 9.327 | −5.418 | 1.00 | 17.66 | C |
| ATOM | 1887 | CG | ASP | A | 243 | −5.180 | 8.144 | −6.122 | 1.00 | 49.96 | C |
| ATOM | 1888 | OD1 | ASP | A | 243 | −4.757 | 8.299 | −7.289 | 1.00 | 39.78 | O |
| ATOM | 1889 | OD2 | ASP | A | 243 | −5.123 | 7.057 | −5.512 | 1.00 | 25.88 | O |
| ATOM | 1890 | N | SER | A | 244 | −8.527 | 7.436 | −5.748 | 1.00 | 15.66 | N |
| ATOM | 1891 | CA | SER | A | 244 | −9.378 | 6.416 | −5.142 | 1.00 | 17.72 | C |
| ATOM | 1892 | C | SER | A | 244 | −8.736 | 5.808 | −3.894 | 1.00 | 15.64 | C |
| ATOM | 1893 | O | SER | A | 244 | −9.435 | 5.302 | −3.025 | 1.00 | 15.29 | O |
| ATOM | 1894 | CB | SER | A | 244 | −9.721 | 5.322 | −6.155 | 1.00 | 17.74 | C |
| ATOM | 1895 | OG | SER | A | 244 | −8.542 | 4.671 | −6.580 | 1.00 | 20.33 | O |
| ATOM | 1896 | N | LYS | A | 245 | −7.412 | 5.860 | −3.800 | 1.00 | 14.32 | N |
| ATOM | 1897 | CA | LYS | A | 245 | −6.711 | 5.394 | −2.606 | 1.00 | 12.72 | C |
| ATOM | 1898 | C | LYS | A | 245 | −7.198 | 6.097 | −1.339 | 1.00 | 16.08 | C |
| ATOM | 1899 | O | LYS | A | 245 | −7.211 | 5.508 | −0.255 | 1.00 | 15.31 | O |
| ATOM | 1900 | CB | LYS | A | 245 | −5.203 | 5.593 | −2.754 | 1.00 | 18.83 | C |
| ATOM | 1901 | CG | LYS | A | 245 | −4.394 | 5.124 | −1.557 | 1.00 | 44.09 | C |
| ATOM | 1902 | CD | LYS | A | 245 | −2.929 | 5.507 | −1.692 | 1.00 | 75.26 | C |
| ATOM | 1903 | CE | LYS | A | 245 | −2.150 | 5.169 | −0.430 | 1.00 | 60.92 | C |
| ATOM | 1904 | NZ | LYS | A | 245 | −0.732 | 5.618 | −0.513 | 1.00 | 81.77 | N |
| ATOM | 1905 | N | GLY | A | 246 | −7.597 | 7.357 | −1.475 | 1.00 | 12.05 | N |
| ATOM | 1906 | CA | GLY | A | 246 | −8.129 | 8.112 | −0.354 | 1.00 | 11.97 | C |
| ATOM | 1907 | C | GLY | A | 246 | −9.462 | 7.569 | 0.115 | 1.00 | 12.09 | C |
| ATOM | 1908 | O | GLY | A | 246 | −9.752 | 7.562 | 1.312 | 1.00 | 11.82 | O |
| ATOM | 1909 | N | ALA | A | 247 | −10.288 | 7.118 | −0.820 | 1.00 | 11.78 | N |
| ATOM | 1910 | CA | ALA | A | 247 | −11.562 | 6.515 | −0.461 | 1.00 | 12.42 | C |
| ATOM | 1911 | C | ALA | A | 247 | −11.315 | 5.279 | 0.404 | 1.00 | 11.27 | C |

TABLE 5-continued (Table 5 discloses SEQ ID NO: 10):

| ATOM | 1912 | O | ALA | A | 247 | −11.993 | 5.079 | 1.417 | 1.00 | 11.32 | O |
|---|---|---|---|---|---|---|---|---|---|---|---|
| ATOM | 1913 | CB | ALA | A | 247 | −12.369 | 6.151 | −1.713 | 1.00 | 11.97 | C |
| ATOM | 1914 | N | TYR | A | 248 | −10.349 | 4.451 | 0.001 | 1.00 | 11.26 | N |
| ATOM | 1915 | CA | TYR | A | 248 | −10.022 | 3.256 | 0.776 | 1.00 | 12.36 | C |
| ATOM | 1916 | C | TYR | A | 248 | −9.458 | 3.631 | 2.155 | 1.00 | 12.09 | C |
| ATOM | 1917 | O | TYR | A | 248 | −9.752 | 2.971 | 3.152 | 1.00 | 11.59 | O |
| ATOM | 1918 | CB | TYR | A | 248 | −9.074 | 2.322 | 0.001 | 1.00 | 11.60 | C |
| ATOM | 1919 | CG | TYR | A | 248 | −9.652 | 1.861 | −1.322 | 1.00 | 14.61 | C |
| ATOM | 1920 | CD1 | TYR | A | 248 | −10.872 | 1.201 | −1.371 | 1.00 | 13.55 | C |
| ATOM | 1921 | CD2 | TYR | A | 248 | −8.985 | 2.092 | −2.520 | 1.00 | 19.12 | C |
| ATOM | 1922 | CE1 | TYR | A | 248 | −11.419 | 0.784 | −2.571 | 1.00 | 18.03 | C |
| ATOM | 1923 | CE2 | TYR | A | 248 | −9.528 | 1.677 | −3.728 | 1.00 | 19.37 | C |
| ATOM | 1924 | CZ | TYR | A | 248 | −10.743 | 1.025 | −3.742 | 1.00 | 16.03 | C |
| ATOM | 1925 | OH | TYR | A | 248 | −11.302 | 0.600 | −4.929 | 1.00 | 19.87 | O |
| ATOM | 1926 | N | LEU | A | 249 | −8.673 | 4.703 | 2.215 | 1.00 | 11.41 | N |
| ATOM | 1927 | CA | LEU | A | 249 | −8.116 | 5.181 | 3.484 | 1.00 | 10.25 | C |
| ATOM | 1928 | C | LEU | A | 249 | −9.220 | 5.627 | 4.447 | 1.00 | 10.35 | C |
| ATOM | 1929 | O | LEU | A | 249 | −9.189 | 5.328 | 5.647 | 1.00 | 10.53 | O |
| ATOM | 1930 | CB | LEU | A | 249 | −7.150 | 6.339 | 3.226 | 1.00 | 13.46 | C |
| ATOM | 1931 | CG | LEU | A | 249 | −6.365 | 6.824 | 4.444 | 1.00 | 18.08 | C |
| ATOM | 1932 | CD1 | LEU | A | 249 | −5.351 | 5.760 | 4.858 | 1.00 | 19.06 | C |
| ATOM | 1933 | CD2 | LEU | A | 249 | −5.667 | 8.146 | 4.150 | 1.00 | 18.48 | C |
| ATOM | 1934 | N | LEU | A | 250 | −10.209 | 6.336 | 3.923 | 1.00 | 9.37 | N |
| ATOM | 1935 | CA | LEU | A | 250 | −11.329 | 6.757 | 4.724 | 1.00 | 9.21 | C |
| ATOM | 1936 | C | LEU | A | 250 | −12.080 | 5.543 | 5.271 | 1.00 | 12.66 | C |
| ATOM | 1937 | O | LEU | A | 250 | −12.435 | 5.510 | 6.450 | 1.00 | 11.83 | O |
| ATOM | 1938 | CB | LEU | A | 250 | −12.235 | 7.661 | 3.897 | 1.00 | 13.06 | C |
| ATOM | 1939 | CG | LEU | A | 250 | −13.559 | 8.092 | 4.496 | 1.00 | 13.37 | C |
| ATOM | 1940 | CD1 | LEU | A | 250 | −13.375 | 8.747 | 5.858 | 1.00 | 14.48 | C |
| ATOM | 1941 | CD2 | LEU | A | 250 | −14.209 | 9.066 | 3.529 | 1.00 | 16.04 | C |
| ATOM | 1942 | N | MET | A | 251 | −12.304 | 4.531 | 4.431 | 1.00 | 9.91 | N |
| ATOM | 1943 | CA | MET | A | 251 | −12.998 | 3.327 | 4.888 | 1.00 | 10.56 | C |
| ATOM | 1944 | C | MET | A | 251 | −12.189 | 2.596 | 5.950 | 1.00 | 10.04 | C |
| ATOM | 1945 | O | MET | A | 251 | −12.759 | 1.991 | 6.860 | 1.00 | 13.87 | O |
| ATOM | 1946 | CB | MET | A | 251 | −13.284 | 2.381 | 3.719 | 1.00 | 9.50 | C |
| ATOM | 1947 | CG | MET | A | 251 | −14.342 | 2.899 | 2.762 | 1.00 | 13.01 | C |
| ATOM | 1948 | SD | MET | A | 251 | −15.992 | 3.057 | 3.473 | 1.00 | 11.08 | S |
| ATOM | 1949 | CE | MET | A | 251 | −16.458 | 1.331 | 3.656 | 1.00 | 12.29 | C |
| ATOM | 1950 | N | GLU | A | 252 | −10.872 | 2.640 | 5.835 | 1.00 | 8.28 | N |
| ATOM | 1951 | CA | GLU | A | 252 | −10.013 | 1.916 | 6.763 | 1.00 | 10.79 | C |
| ATOM | 1952 | C | GLU | A | 252 | −9.890 | 2.619 | 8.110 | 1.00 | 14.17 | C |
| ATOM | 1953 | O | GLU | A | 252 | −9.960 | 1.979 | 9.162 | 1.00 | 16.34 | O |
| ATOM | 1954 | CB | GLU | A | 252 | −8.620 | 1.717 | 6.171 | 1.00 | 14.04 | C |
| ATOM | 1955 | CG | GLU | A | 252 | −7.682 | 0.962 | 7.109 | 1.00 | 18.86 | C |
| ATOM | 1956 | CD | GLU | A | 252 | −6.248 | 0.940 | 6.620 | 1.00 | 88.82 | C |
| ATOM | 1957 | OE1 | GLU | A | 252 | −5.970 | 1.541 | 5.561 | 1.00 | 68.03 | O |
| ATOM | 1958 | OE2 | GLU | A | 252 | −5.398 | 0.324 | 7.297 | 1.00 | 99.02 | O |
| ATOM | 1959 | N | LEU | A | 253 | −9.701 | 3.933 | 8.082 | 1.00 | 11.41 | N |
| ATOM | 1960 | CA | LEU | A | 253 | −9.336 | 4.662 | 9.294 | 1.00 | 11.04 | C |
| ATOM | 1961 | C | LEU | A | 253 | −10.506 | 5.218 | 10.100 | 1.00 | 11.58 | C |
| ATOM | 1962 | O | LEU | A | 253 | −10.383 | 5.395 | 11.309 | 1.00 | 14.92 | O |
| ATOM | 1963 | CB | LEU | A | 253 | −8.355 | 5.785 | 8.958 | 1.00 | 14.04 | C |
| ATOM | 1964 | CG | LEU | A | 253 | −6.961 | 5.350 | 8.512 | 1.00 | 15.41 | C |
| ATOM | 1965 | CD1 | LEU | A | 253 | −6.066 | 6.565 | 8.335 | 1.00 | 19.75 | C |
| ATOM | 1966 | CD2 | LEU | A | 253 | −6.354 | 4.367 | 9.504 | 1.00 | 26.28 | C |
| ATOM | 1967 | N | ALA | A | 254 | −11.625 | 5.526 | 9.451 | 1.00 | 9.74 | N |
| ATOM | 1968 | CA | ALA | A | 254 | −12.783 | 6.055 | 10.171 | 1.00 | 10.79 | C |
| ATOM | 1969 | C | ALA | A | 254 | −13.301 | 5.031 | 11.184 | 1.00 | 12.72 | C |
| ATOM | 1970 | O | ALA | A | 254 | −13.301 | 3.828 | 10.913 | 1.00 | 13.12 | O |
| ATOM | 1971 | CB | ALA | A | 254 | −13.887 | 6.452 | 9.198 | 1.00 | 13.02 | C |
| ATOM | 1972 | N | LYS | A | 255 | −13.738 | 5.502 | 12.347 | 1.00 | 11.30 | N |
| ATOM | 1973 | CA | LYS | A | 255 | −14.265 | 4.593 | 13.360 | 1.00 | 13.33 | C |
| ATOM | 1974 | C | LYS | A | 255 | −15.774 | 4.394 | 13.233 | 1.00 | 14.71 | C |
| ATOM | 1975 | O | LYS | A | 255 | −16.377 | 3.634 | 13.992 | 1.00 | 16.28 | O |
| ATOM | 1976 | CB | LYS | A | 255 | −13.899 | 5.072 | 14.772 | 1.00 | 17.14 | C |
| ATOM | 1977 | CG | LYS | A | 255 | −12.399 | 5.098 | 15.036 | 1.00 | 23.75 | C |
| ATOM | 1978 | CD | LYS | A | 255 | −11.776 | 3.721 | 14.861 | 1.00 | 30.83 | C |
| ATOM | 1979 | CE | LYS | A | 255 | −10.267 | 3.744 | 15.092 | 1.00 | 45.25 | C |
| ATOM | 1980 | NZ | LYS | A | 255 | −9.509 | 4.223 | 13.898 | 1.00 | 43.77 | N |
| ATOM | 1981 | N | SER | A | 256 | −16.387 | 5.067 | 12.265 | 1.00 | 10.29 | N |
| ATOM | 1982 | CA | SER | A | 256 | −17.821 | 4.987 | 12.074 | 1.00 | 9.83 | C |
| ATOM | 1983 | C | SER | A | 256 | −18.307 | 3.548 | 12.017 | 1.00 | 9.52 | C |
| ATOM | 1984 | O | SER | A | 256 | −17.734 | 2.720 | 11.306 | 1.00 | 12.49 | O |
| ATOM | 1985 | CB | SER | A | 256 | −18.221 | 5.704 | 10.779 | 1.00 | 11.18 | C |
| ATOM | 1986 | OG | SER | A | 256 | −17.631 | 6.993 | 10.743 | 1.00 | 11.20 | O |
| ATOM | 1987 | N | GLN | A | 257 | −19.374 | 3.264 | 12.747 | 1.00 | 9.12 | N |
| ATOM | 1988 | CA | GLN | A | 257 | −20.003 | 1.942 | 12.704 | 1.00 | 12.22 | C |
| ATOM | 1989 | C | GLN | A | 257 | −20.865 | 1.739 | 11.464 | 1.00 | 13.06 | C |

TABLE 5-continued (Table 5 discloses SEQ ID NO: 10):

| ATOM | 1990 | O | GLN | A | 257 | −21.242 | 0.613 | 11.143 | 1.00 | 14.98 | O |
|---|---|---|---|---|---|---|---|---|---|---|---|
| ATOM | 1991 | CB | GLN | A | 257 | −20.847 | 1.714 | 13.959 | 1.00 | 13.19 | C |
| ATOM | 1992 | CG | GLN | A | 257 | −20.018 | 1.658 | 15.238 | 1.00 | 16.99 | C |
| ATOM | 1993 | CD | GLN | A | 257 | −20.834 | 1.258 | 16.450 | 1.00 | 67.11 | C |
| ATOM | 1994 | OE1 | GLN | A | 257 | −22.052 | 1.432 | 16.479 | 1.00 | 74.68 | O |
| ATOM | 1995 | NE2 | GLN | A | 257 | −20.163 | 0.719 | 17.462 | 1.00 | 83.33 | N |
| ATOM | 1996 | N | ASP | A | 258 | −21.186 | 2.829 | 10.772 | 1.00 | 8.32 | N |
| ATOM | 1997 | CA | ASP | A | 258 | −22.065 | 2.767 | 9.614 | 1.00 | 9.96 | C |
| ATOM | 1998 | C | ASP | A | 258 | −21.342 | 3.413 | 8.433 | 1.00 | 9.10 | C |
| ATOM | 1999 | O | ASP | A | 258 | −21.434 | 4.625 | 8.226 | 1.00 | 10.80 | O |
| ATOM | 2000 | CB | ASP | A | 258 | −23.365 | 3.512 | 9.942 | 1.00 | 8.32 | C |
| ATOM | 2001 | CG | ASP | A | 258 | −24.395 | 3.468 | 8.825 | 1.00 | 11.84 | C |
| ATOM | 2002 | OD1 | ASP | A | 258 | −24.184 | 2.773 | 7.806 | 1.00 | 11.26 | O |
| ATOM | 2003 | OD2 | ASP | A | 258 | −25.450 | 4.120 | 8.973 | 1.00 | 13.37 | O |
| ATOM | 2004 | N | LYS | A | 259 | −20.599 | 2.614 | 7.677 | 1.00 | 6.95 | N |
| ATOM | 2005 | CA | LYS | A | 259 | −19.839 | 3.150 | 6.547 | 1.00 | 7.68 | C |
| ATOM | 2006 | C | LYS | A | 259 | −19.924 | 2.230 | 5.339 | 1.00 | 9.90 | C |
| ATOM | 2007 | O | LYS | A | 259 | −19.757 | 1.001 | 5.443 | 1.00 | 10.58 | O |
| ATOM | 2008 | CB | LYS | A | 259 | −18.389 | 3.463 | 6.914 | 1.00 | 12.50 | C |
| ATOM | 2009 | CG | LYS | A | 259 | −17.667 | 2.376 | 7.675 | 1.00 | 10.44 | C |
| ATOM | 2010 | CD | LYS | A | 259 | −16.259 | 2.799 | 8.055 | 1.00 | 10.64 | C |
| ATOM | 2011 | CE | LYS | A | 259 | −15.610 | 1.749 | 8.959 | 1.00 | 11.27 | C |
| ATOM | 2012 | NZ | LYS | A | 259 | −14.164 | 1.975 | 9.132 | 1.00 | 11.78 | N |
| ATOM | 2013 | N | THR | A | 260 | −20.192 | 2.846 | 4.192 | 1.00 | 6.48 | N |
| ATOM | 2014 | CA | ATHR | A | 260 | −20.426 | 2.128 | 2.937 | 0.70 | 5.21 | C |
| ATOM | 2015 | C | THR | A | 260 | −19.679 | 2.820 | 1.804 | 1.00 | 7.56 | C |
| ATOM | 2016 | O | THR | A | 260 | −19.699 | 4.058 | 1.710 | 1.00 | 8.70 | O |
| ATOM | 2017 | CB | ATHR | A | 260 | −21.925 | 2.119 | 2.590 | 0.70 | 7.13 | C |
| ATOM | 2018 | OG1 | ATHR | A | 260 | −22.686 | 1.596 | 3.693 | 0.70 | 8.97 | O |
| ATOM | 2019 | CG2 | ATHR | A | 260 | −22.190 | 1.270 | 1.340 | 0.70 | 8.35 | C |
| ATOM | 2020 | CA | BTHR | A | 260 | −20.360 | 2.105 | 2.955 | 0.30 | 8.55 | C |
| ATOM | 2021 | CB | BTHR | A | 260 | −21.842 | 1.896 | 2.629 | 0.30 | 10.28 | C |
| ATOM | 2022 | OG1 | BTHR | A | 260 | −22.498 | 3.164 | 2.524 | 0.30 | 15.39 | O |
| ATOM | 2023 | CG2 | BTHR | A | 260 | −22.511 | 1.083 | 3.722 | 0.30 | 17.62 | C |
| ATOM | 2024 | N | LEU | A | 261 | −19.051 | 2.029 | 0.942 | 1.00 | 5.66 | N |
| ATOM | 2025 | CA | LEU | A | 261 | −18.343 | 2.540 | −0.225 | 1.00 | 7.03 | C |
| ATOM | 2026 | C | LEU | A | 261 | −18.930 | 1.930 | −1.486 | 1.00 | 8.11 | C |
| ATOM | 2027 | O | LEU | A | 261 | −19.079 | 0.710 | −1.580 | 1.00 | 8.85 | O |
| ATOM | 2028 | CB | LEU | A | 261 | −16.878 | 2.162 | −0.147 | 1.00 | 8.55 | C |
| ATOM | 2029 | CG | LEU | A | 261 | −16.055 | 2.355 | −1.429 | 1.00 | 7.61 | C |
| ATOM | 2030 | CD1 | LEU | A | 261 | −15.940 | 3.844 | −1.802 | 1.00 | 10.12 | C |
| ATOM | 2031 | CD2 | LEU | A | 261 | −14.679 | 1.753 | −1.241 | 1.00 | 9.79 | C |
| ATOM | 2032 | N | LYS | A | 262 | −19.273 | 2.775 | −2.459 | 1.00 | 5.57 | N |
| ATOM | 2033 | CA | LYS | A | 262 | −19.587 | 2.288 | −3.810 | 1.00 | 7.37 | C |
| ATOM | 2034 | C | LYS | A | 262 | −18.569 | 2.856 | −4.785 | 1.00 | 9.49 | C |
| ATOM | 2035 | O | LYS | A | 262 | −18.314 | 4.066 | −4.798 | 1.00 | 9.23 | O |
| ATOM | 2036 | CB | LYS | A | 262 | −20.996 | 2.686 | −4.224 | 1.00 | 9.44 | C |
| ATOM | 2037 | CG | LYS | A | 262 | −21.487 | 2.018 | −5.527 | 1.00 | 14.01 | C |
| ATOM | 2038 | CD | LYS | A | 262 | −22.988 | 2.224 | −5.735 | 1.00 | 17.20 | C |
| ATOM | 2039 | CE | LYS | A | 262 | −23.449 | 1.716 | −7.104 | 1.00 | 18.72 | C |
| ATOM | 2040 | NZ | LYS | A | 262 | −23.405 | 0.223 | −7.191 | 1.00 | 18.42 | N |
| ATOM | 2041 | N | ILE | A | 263 | −17.949 | 1.975 | −5.567 | 1.00 | 7.42 | N |
| ATOM | 2042 | CA | AILE | A | 263 | −16.971 | 2.372 | −6.583 | 0.90 | 9.22 | C |
| ATOM | 2043 | C | ILE | A | 263 | −17.617 | 2.289 | −7.953 | 1.00 | 7.84 | C |
| ATOM | 2044 | O | ILE | A | 263 | −18.215 | 1.266 | −8.303 | 1.00 | 9.35 | O |
| ATOM | 2045 | CB | AILE | A | 263 | −15.715 | 1.470 | −6.574 | 0.90 | 9.09 | C |
| ATOM | 2046 | CG1 | AILE | A | 263 | −14.885 | 1.681 | −5.301 | 0.90 | 11.72 | C |
| ATOM | 2047 | CG2 | AILE | A | 263 | −14.865 | 1.719 | −7.834 | 0.90 | 11.99 | C |
| ATOM | 2048 | CD1 | AILE | A | 263 | −14.085 | 2.991 | −5.280 | 0.90 | 11.94 | C |
| ATOM | 2049 | CA | BILE | A | 263 | −16.994 | 2.399 | −6.575 | 0.10 | 10.98 | C |
| ATOM | 2050 | CB | BILE | A | 263 | −15.721 | 1.559 | −6.521 | 0.10 | 6.66 | C |
| ATOM | 2051 | CG1 | BILE | A | 263 | −15.124 | 1.623 | −5.119 | 0.10 | 7.98 | C |
| ATOM | 2052 | CG2 | BILE | A | 263 | −14.718 | 2.040 | −7.561 | 0.10 | 17.27 | C |
| ATOM | 2053 | CD1 | BILE | A | 263 | −13.981 | 0.698 | −4.927 | 0.10 | 3.99 | C |
| ATOM | 2054 | N | TYR | A | 264 | −17.498 | 3.363 | −8.726 | 1.00 | 7.78 | N |
| ATOM | 2055 | CA | TYR | A | 264 | −18.012 | 3.401 | −10.095 | 1.00 | 9.35 | C |
| ATOM | 2056 | C | TYR | A | 264 | −16.856 | 3.194 | −11.063 | 1.00 | 8.73 | C |
| ATOM | 2057 | O | TYR | A | 264 | −16.002 | 4.063 | −11.239 | 1.00 | 7.97 | O |
| ATOM | 2058 | CB | TYR | A | 264 | −18.727 | 4.723 | −10.348 | 1.00 | 9.49 | C |
| ATOM | 2059 | CG | TYR | A | 264 | −20.043 | 4.815 | −9.615 | 1.00 | 5.92 | C |
| ATOM | 2060 | CD1 | TYR | A | 264 | −21.221 | 4.371 | −10.195 | 1.00 | 9.53 | C |
| ATOM | 2061 | CD2 | TYR | A | 264 | −20.108 | 5.343 | −8.330 | 1.00 | 10.30 | C |
| ATOM | 2062 | CE1 | TYR | A | 264 | −22.440 | 4.448 | −9.525 | 1.00 | 10.75 | C |
| ATOM | 2063 | CE2 | TYR | A | 264 | −21.316 | 5.425 | −7.650 | 1.00 | 8.15 | C |
| ATOM | 2064 | CZ | TYR | A | 264 | −22.476 | 4.978 | −8.241 | 1.00 | 8.75 | C |
| ATOM | 2065 | OH | TYR | A | 264 | −23.684 | 5.059 | −7.585 | 1.00 | 10.60 | O |
| ATOM | 2066 | N | GLU | A | 265 | −16.811 | 2.008 | −11.667 | 1.00 | 9.58 | N |
| ATOM | 2067 | CA | GLU | A | 265 | −15.690 | 1.611 | −12.504 | 1.00 | 12.10 | C |

TABLE 5-continued (Table 5 discloses SEQ ID NO: 10):

| ATOM | 2068 | C   | GLU | A | 265 | −15.638 | 2.432  | −13.796 | 1.00 | 8.46  | C |
|------|------|-----|-----|---|-----|---------|--------|---------|------|-------|---|
| ATOM | 2069 | O   | GLU | A | 265 | −16.606 | 2.477  | −14.549 | 1.00 | 11.89 | O |
| ATOM | 2070 | CB  | GLU | A | 265 | −15.789 | 0.114  | −12.824 | 1.00 | 16.13 | C |
| ATOM | 2071 | CG  | GLU | A | 265 | −14.547 | −0.464 | −13.462 | 1.00 | 17.85 | C |
| ATOM | 2072 | CD  | GLU | A | 265 | −13.347 | −0.469 | −12.534 | 1.00 | 21.43 | C |
| ATOM | 2073 | OE1 | GLU | A | 265 | −13.508 | −0.218 | −11.312 | 1.00 | 20.61 | O |
| ATOM | 2074 | OE2 | GLU | A | 265 | −12.227 | −0.726 | −13.020 | 1.00 | 32.40 | O |
| ATOM | 2075 | N   | GLY | A | 266 | −14.507 | 3.096  | −14.005 | 1.00 | 9.44  | N |
| ATOM | 2076 | CA  | GLY | A | 266 | −14.289 | 3.887  | −15.205 | 1.00 | 11.21 | C |
| ATOM | 2077 | C   | GLY | A | 266 | −14.797 | 5.313  | −15.075 | 1.00 | 11.31 | C |
| ATOM | 2078 | O   | GLY | A | 266 | −14.514 | 6.145  | −15.936 | 1.00 | 10.95 | O |
| ATOM | 2079 | N   | ALA | A | 267 | −15.548 | 5.598  | −14.015 | 1.00 | 9.68  | N |
| ATOM | 2080 | CA  | ALA | A | 267 | −16.150 | 6.920  | −13.851 | 1.00 | 10.27 | C |
| ATOM | 2081 | C   | ALA | A | 267 | −15.114 | 7.942  | −13.397 | 1.00 | 6.06  | C |
| ATOM | 2082 | O   | ALA | A | 267 | −14.166 | 7.627  | −12.691 | 1.00 | 7.71  | O |
| ATOM | 2083 | CB  | ALA | A | 267 | −17.324 | 6.859  | −12.875 | 1.00 | 9.22  | C |
| ATOM | 2084 | N   | TYR | A | 268 | −15.291 | 9.176  | −13.865 | 1.00 | 7.32  | N |
| ATOM | 2085 | CA  | TYR | A | 268 | −14.391 | 10.267 | −13.504 | 1.00 | 7.50  | C |
| ATOM | 2086 | C   | TYR | A | 268 | −14.858 | 10.929 | −12.194 | 1.00 | 9.01  | C |
| ATOM | 2087 | O   | TYR | A | 268 | −15.804 | 10.481 | −11.556 | 1.00 | 11.16 | O |
| ATOM | 2088 | CB  | TYR | A | 268 | −14.357 | 11.317 | −14.632 | 1.00 | 8.84  | C |
| ATOM | 2089 | CG  | TYR | A | 268 | −13.629 | 10.892 | −15.905 | 1.00 | 9.04  | C |
| ATOM | 2090 | CD1 | TYR | A | 268 | −13.218 | 9.575  | −16.106 | 1.00 | 12.36 | C |
| ATOM | 2091 | CD2 | TYR | A | 268 | −13.385 | 11.812 | −16.915 | 1.00 | 10.68 | C |
| ATOM | 2092 | CE1 | TYR | A | 268 | −12.557 | 9.193  | −17.278 | 1.00 | 13.18 | C |
| ATOM | 2093 | CE2 | TYR | A | 268 | −12.736 | 11.442 | −18.087 | 1.00 | 15.29 | C |
| ATOM | 2094 | CZ  | TYR | A | 268 | −12.324 | 10.140 | −18.259 | 1.00 | 14.67 | C |
| ATOM | 2095 | OH  | TYR | A | 268 | −11.687 | 9.783  | −19.436 | 1.00 | 17.75 | O |
| ATOM | 2096 | N   | HIS | A | 269 | −14.191 | 12.013 | −11.834 | 1.00 | 7.57  | N |
| ATOM | 2097 | CA  | HIS | A | 269 | −14.368 | 12.696 | −10.548 | 1.00 | 6.36  | C |
| ATOM | 2098 | C   | HIS | A | 269 | −15.795 | 13.154 | −10.224 | 1.00 | 7.22  | C |
| ATOM | 2099 | O   | HIS | A | 269 | −16.295 | 12.928 | −9.115  | 1.00 | 7.15  | O |
| ATOM | 2100 | CB  | HIS | A | 269 | −13.421 | 13.898 | −10.549 | 1.00 | 7.11  | C |
| ATOM | 2101 | CG  | HIS | A | 269 | −13.401 | 14.689 | −9.274  | 1.00 | 7.54  | C |
| ATOM | 2102 | ND1 | HIS | A | 269 | −13.058 | 14.144 | −8.053  | 1.00 | 9.09  | N |
| ATOM | 2103 | CD2 | HIS | A | 269 | −13.599 | 16.012 | −9.051  | 1.00 | 9.50  | C |
| ATOM | 2104 | CE1 | HIS | A | 269 | −13.070 | 15.096 | −7.130  | 1.00 | 8.18  | C |
| ATOM | 2105 | NE2 | HIS | A | 269 | −13.393 | 16.237 | −7.711  | 1.00 | 10.12 | N |
| ATOM | 2106 | N   | VAL | A | 270 | −16.464 | 13.813 | −11.161 | 1.00 | 6.45  | N |
| ATOM | 2107 | CA  | VAL | A | 270 | −17.721 | 14.471 | −10.832 | 1.00 | 6.65  | C |
| ATOM | 2108 | C   | VAL | A | 270 | −18.897 | 13.531 | −11.071 | 1.00 | 7.38  | C |
| ATOM | 2109 | O   | VAL | A | 270 | −19.610 | 13.613 | −12.081 | 1.00 | 6.78  | O |
| ATOM | 2110 | CB  | VAL | A | 270 | −17.896 | 15.798 | −11.602 | 1.00 | 5.79  | C |
| ATOM | 2111 | CG1 | VAL | A | 270 | −19.038 | 16.584 | −10.997 | 1.00 | 7.82  | C |
| ATOM | 2112 | CG2 | VAL | A | 270 | −16.630 | 16.622 | −11.516 | 1.00 | 7.71  | C |
| ATOM | 2113 | N   | LEU | A | 271 | −19.103 | 12.637 | −10.108 | 1.00 | 6.65  | N |
| ATOM | 2114 | CA  | LEU | A | 271 | −20.053 | 11.534 | −10.285 | 1.00 | 6.15  | C |
| ATOM | 2115 | C   | LEU | A | 271 | −21.499 | 11.970 | −10.477 | 1.00 | 5.91  | C |
| ATOM | 2116 | O   | LEU | A | 271 | −22.285 | 11.283 | −11.133 | 1.00 | 7.39  | O |
| ATOM | 2117 | CB  | LEU | A | 271 | −19.957 | 10.556 | −9.105  | 1.00 | 6.48  | C |
| ATOM | 2118 | CG  | LEU | A | 271 | −18.615 | 9.871  | −8.906  | 1.00 | 5.62  | C |
| ATOM | 2119 | CD1 | LEU | A | 271 | −18.659 | 9.055  | −7.613  | 1.00 | 9.62  | C |
| ATOM | 2120 | CD2 | LEU | A | 271 | −18.321 | 8.957  | −10.089 | 1.00 | 8.14  | C |
| ATOM | 2121 | N   | HIS | A | 272 | −21.873 | 13.103 | −9.886  | 1.00 | 5.74  | N |
| ATOM | 2122 | CA  | HIS | A | 272 | −23.233 | 13.610 | −10.006 | 1.00 | 5.90  | C |
| ATOM | 2123 | C   | HIS | A | 272 | −23.448 | 14.420 | −11.291 | 1.00 | 5.61  | C |
| ATOM | 2124 | O   | HTS | A | 272 | −24.538 | 14.940 | −11.511 | 1.00 | 8.27  | O |
| ATOM | 2125 | CB  | HIS | A | 272 | −23.602 | 14.449 | −8.773  | 1.00 | 6.29  | C |
| ATOM | 2126 | CG  | HIS | A | 272 | −22.612 | 15.529 | −8.463  | 1.00 | 8.33  | C |
| ATOM | 2127 | ND1 | HIS | A | 272 | −21.309 | 15.262 | −8.108  | 1.00 | 8.50  | N |
| ATOM | 2128 | CD2 | HIS | A | 272 | −22.731 | 16.879 | −8.481  | 1.00 | 11.04 | C |
| ATOM | 2129 | CE1 | HIS | A | 272 | −20.669 | 16.402 | −7.905  | 1.00 | 12.80 | C |
| ATOM | 2130 | NE2 | HIS | A | 272 | −21.510 | 17.396 | −8.128  | 1.00 | 11.63 | N |
| ATOM | 2131 | N   | LYS | A | 273 | −22.403 | 14.505 | −12.121 | 1.00 | 6.91  | N |
| ATOM | 2132 | CA  | LYS | A | 273 | −22.487 | 15.162 | −13.432 | 1.00 | 7.10  | C |
| ATOM | 2133 | C   | LYS | A | 273 | −21.801 | 14.293 | −14.470 | 1.00 | 7.81  | C |
| ATOM | 2134 | O   | LYS | A | 273 | −21.114 | 14.800 | −15.363 | 1.00 | 8.13  | O |
| ATOM | 2135 | CB  | LYS | A | 273 | −21.778 | 16.519 | −13.399 | 1.00 | 8.99  | C |
| ATOM | 2136 | CG  | LYS | A | 273 | −22.307 | 17.505 | −12.362 | 1.00 | 9.49  | C |
| ATOM | 2137 | CD  | LYS | A | 273 | −23.666 | 18.011 | −12.739 | 1.00 | 9.39  | C |
| ATOM | 2138 | CE  | LYS | A | 273 | −24.085 | 19.150 | −11.798 | 1.00 | 11.48 | C |
| ATOM | 2139 | NZ  | LYS | A | 273 | −25.494 | 19.505 | −12.017 | 1.00 | 16.06 | N |
| ATOM | 2140 | N   | GLU | A | 274 | −21.948 | 12.978 | −14.319 | 1.00 | 7.75  | N |
| ATOM | 2141 | CA  | GLU | A | 274 | −21.254 | 12.023 | −15.169 | 1.00 | 7.79  | C |
| ATOM | 2142 | C   | GLU | A | 274 | −22.186 | 11.460 | −16.249 | 1.00 | 7.03  | C |
| ATOM | 2143 | O   | GLU | A | 274 | −23.236 | 12.024 | −16.542 | 1.00 | 9.33  | O |
| ATOM | 2144 | CB  | GLU | A | 274 | −20.654 | 10.908 | −14.297 | 1.00 | 10.21 | C |
| ATOM | 2145 | CG  | GLU | A | 274 | −19.145 | 10.870 | −14.300 | 1.00 | 9.08  | C |

TABLE 5-continued (Table 5 discloses SEQ ID NO: 10):

| ATOM | 2146 | CD | GLU | A | 274 | −18.598 | 10.004 | −15.429 | 1.00 | 8.56 | C |
|---|---|---|---|---|---|---|---|---|---|---|---|
| ATOM | 2147 | OE1 | GLU | A | 274 | −17.403 | 10.118 | −15.749 | 1.00 | 10.56 | O |
| ATOM | 2148 | OE2 | GLU | A | 274 | −19.388 | 9.210 | −15.979 | 1.00 | 11.18 | O |
| ATOM | 2149 | N | LEU | A | 275 | −21.787 | 10.352 | −16.869 | 1.00 | 8.50 | N |
| ATOM | 2150 | CA | LEU | A | 275 | −22.669 | 9.703 | −17.836 | 1.00 | 9.61 | C |
| ATOM | 2151 | C | LEU | A | 275 | −23.985 | 9.365 | −17.146 | 1.00 | 11.58 | C |
| ATOM | 2152 | O | LEU | A | 275 | −23.991 | 9.062 | −15.954 | 1.00 | 10.17 | O |
| ATOM | 2153 | CB | LEU | A | 275 | −22.016 | 8.439 | −18.394 | 1.00 | 9.97 | C |
| ATOM | 2154 | CG | LEU | A | 275 | −20.737 | 8.703 | −19.181 | 1.00 | 12.18 | C |
| ATOM | 2155 | CD1 | LEU | A | 275 | −20.108 | 7.415 | −19.713 | 1.00 | 14.42 | C |
| ATOM | 2156 | CD2 | LEU | A | 275 | −21.026 | 9.667 | −20.329 | 1.00 | 15.54 | C |
| ATOM | 2157 | N | PRO | A | 276 | −25.107 | 9.413 | −17.881 | 1.00 | 11.73 | N |
| ATOM | 2158 | CA | PRO | A | 276 | −26.427 | 9.164 | −17.288 | 1.00 | 14.10 | C |
| ATOM | 2159 | C | PRO | A | 276 | −26.511 | 7.906 | −16.417 | 1.00 | 16.89 | C |
| ATOM | 2160 | O | PRO | A | 276 | −27.109 | 7.964 | −15.336 | 1.00 | 17.36 | O |
| ATOM | 2161 | CB | PRO | A | 276 | −27.334 | 9.016 | −18.512 | 1.00 | 16.90 | C |
| ATOM | 2162 | CG | PRO | A | 276 | −26.692 | 9.878 | −19.538 | 1.00 | 21.28 | C |
| ATOM | 2163 | CD | PRO | A | 276 | −25.205 | 9.809 | −19.300 | 1.00 | 13.96 | C |
| ATOM | 2164 | N | GLU | A | 277 | −25.939 | 6.792 | −16.870 | 1.00 | 14.89 | N |
| ATOM | 2165 | CA | GLU | A | 277 | −25.994 | 5.547 | −16.100 | 1.00 | 16.63 | C |
| ATOM | 2166 | C | GLU | A | 277 | −25.385 | 5.732 | −14.712 | 1.00 | 16.38 | C |
| ATOM | 2167 | O | GLU | A | 277 | −25.934 | 5.261 | −13.712 | 1.00 | 19.95 | O |
| ATOM | 2168 | CB | GLU | A | 277 | −25.286 | 4.408 | −16.841 | 1.00 | 21.94 | C |
| ATOM | 2169 | CG | GLU | A | 277 | −26.111 | 3.796 | −17.961 | 1.00 | 85.26 | C |
| ATOM | 2170 | CD | GLU | A | 277 | −25.461 | 2.565 | −18.564 | 1.00 | 121.84 | C |
| ATOM | 2171 | OE1 | GLU | A | 277 | −24.359 | 2.187 | −18.112 | 1.00 | 109.89 | O |
| ATOM | 2172 | OE2 | GLU | A | 277 | −26.055 | 1.973 | −19.490 | 1.00 | 104.17 | O |
| ATOM | 2173 | N | VAL | A | 278 | −24.252 | 6.421 | −14.655 | 1.00 | 10.73 | N |
| ATOM | 2174 | CA | VAL | A | 278 | −23.595 | 6.693 | −13.384 | 1.00 | 9.85 | C |
| ATOM | 2175 | C | VAL | A | 278 | −24.407 | 7.674 | −12.541 | 1.00 | 11.95 | C |
| ATOM | 2176 | O | VAL | A | 278 | −24.734 | 7.391 | −11.387 | 1.00 | 11.20 | O |
| ATOM | 2177 | CB | VAL | A | 278 | −22.169 | 7.242 | −13.601 | 1.00 | 9.03 | C |
| ATOM | 2178 | CG1 | VAL | A | 278 | −21.597 | 7.780 | −12.299 | 1.00 | 12.15 | C |
| ATOM | 2179 | CG2 | VAL | A | 278 | −21.269 | 6.158 | −14.196 | 1.00 | 13.85 | C |
| ATOM | 2180 | N | THR | A | 279 | −24.757 | 8.814 | −13.119 | 1.00 | 9.26 | N |
| ATOM | 2181 | CA | THR | A | 279 | −25.478 | 9.838 | −12.372 | 1.00 | 10.05 | C |
| ATOM | 2182 | C | THR | A | 279 | −26.818 | 9.334 | −11.848 | 1.00 | 9.97 | C |
| ATOM | 2183 | O | THR | A | 279 | −27.201 | 9.644 | −10.721 | 1.00 | 10.35 | O |
| ATOM | 2184 | CB | THR | A | 279 | −25.640 | 11.119 | −13.200 | 1.00 | 10.89 | C |
| ATOM | 2185 | OG1 | THR | A | 279 | −24.336 | 11.655 | −13.456 | 1.00 | 15.41 | O |
| ATOM | 2186 | CG2 | THR | A | 279 | −26.464 | 12.144 | −12.443 | 1.00 | 11.76 | C |
| ATOM | 2187 | N | ASN | A | 280 | −27.534 | 8.562 | −12.660 | 1.00 | 10.65 | N |
| ATOM | 2188 | CA | ASN | A | 280 | −28.815 | 8.023 | −12.224 | 1.00 | 11.97 | C |
| ATOM | 2189 | C | ASN | A | 280 | −28.632 | 7.108 | −11.016 | 1.00 | 9.96 | C |
| ATOM | 2190 | O | ASN | A | 280 | −29.428 | 7.140 | −10.067 | 1.00 | 10.76 | O |
| ATOM | 2191 | CB | ASN | A | 280 | −29.510 | 7.269 | −13.360 | 1.00 | 11.47 | C |
| ATOM | 2192 | CG | ASN | A | 280 | −30.038 | 8.195 | −14.441 | 1.00 | 21.55 | C |
| ATOM | 2193 | OD1 | ASN | A | 280 | −30.206 | 9.391 | −14.221 | 1.00 | 21.86 | O |
| ATOM | 2194 | ND2 | ASN | A | 280 | −30.305 | 7.639 | −15.617 | 1.00 | 25.48 | N |
| ATOM | 2195 | N | SER | A | 281 | −27.577 | 6.303 | −11.056 | 1.00 | 9.62 | N |
| ATOM | 2196 | CA | SER | A | 281 | −27.240 | 5.423 | −9.943 | 1.00 | 9.05 | C |
| ATOM | 2197 | C | SER | A | 281 | −26.862 | 6.227 | −8.703 | 1.00 | 10.69 | C |
| ATOM | 2198 | O | SER | A | 281 | −27.311 | 5.922 | −7.607 | 1.00 | 10.10 | O |
| ATOM | 2199 | CB | SER | A | 281 | −26.089 | 4.494 | −10.331 | 1.00 | 9.22 | C |
| ATOM | 2200 | OG | SER | A | 281 | −25.601 | 3.798 | −9.193 | 1.00 | 11.41 | O |
| ATOM | 2201 | N | VAL | A | 282 | −26.029 | 7.250 | −8.878 | 1.00 | 8.01 | N |
| ATOM | 2202 | CA | VAL | A | 282 | −25.625 | 8.113 | −7.769 | 1.00 | 9.36 | C |
| ATOM | 2203 | C | VAL | A | 282 | −26.851 | 8.703 | −7.059 | 1.00 | 8.59 | C |
| ATOM | 2204 | O | VAL | A | 282 | −26.955 | 8.650 | −5.827 | 1.00 | 8.36 | O |
| ATOM | 2205 | CB | VAL | A | 282 | −24.668 | 9.223 | −8.262 | 1.00 | 8.18 | C |
| ATOM | 2206 | CG1 | VAL | A | 282 | −24.550 | 10.343 | −7.228 | 1.00 | 8.83 | C |
| ATOM | 2207 | CG2 | VAL | A | 282 | −23.313 | 8.620 | −8.597 | 1.00 | 9.21 | C |
| ATOM | 2208 | N | PHE | A | 283 | −27.787 | 9.254 | −7.828 | 1.00 | 7.90 | N |
| ATOM | 2209 | CA | PHE | A | 283 | −29.005 | 9.804 | −7.247 | 1.00 | 7.68 | C |
| ATOM | 2210 | C | PHE | A | 283 | −29.799 | 8.730 | −6.507 | 1.00 | 10.02 | C |
| ATOM | 2211 | O | PHE | A | 283 | −30.290 | 8.961 | −5.403 | 1.00 | 10.89 | O |
| ATOM | 2212 | CB | PHE | A | 283 | −29.881 | 10.463 | −8.316 | 1.00 | 8.60 | C |
| ATOM | 2213 | CG | PHE | A | 283 | −29.534 | 11.907 | −8.593 | 1.00 | 8.21 | C |
| ATOM | 2214 | CD1 | PHE | A | 283 | −28.295 | 12.257 | −9.084 | 1.00 | 9.31 | C |
| ATOM | 2215 | CD2 | PHE | A | 283 | −30.478 | 12.907 | −8.395 | 1.00 | 9.23 | C |
| ATOM | 2216 | CE1 | PHE | A | 283 | −27.977 | 13.595 | −9.350 | 1.00 | 10.77 | C |
| ATOM | 2217 | CE2 | PHE | A | 283 | −30.172 | 14.238 | −8.666 | 1.00 | 10.37 | C |
| ATOM | 2218 | CZ | PHE | A | 283 | −28.929 | 14.575 | −9.137 | 1.00 | 10.84 | C |
| ATOM | 2219 | N | HIS | A | 284 | −29.932 | 7.556 | −7.121 | 1.00 | 9.09 | N |
| ATOM | 2220 | CA | HIS | A | 284 | −30.675 | 6.463 | −6.508 | 1.00 | 9.12 | C |
| ATOM | 2221 | C | HIS | A | 284 | −30.033 | 6.025 | −5.189 | 1.00 | 9.99 | C |
| ATOM | 2222 | O | HIS | A | 284 | −30.737 | 5.828 | −4.188 | 1.00 | 9.74 | O |
| ATOM | 2223 | CB | HIS | A | 284 | −30.765 | 5.290 | −7.492 | 1.00 | 11.67 | C |

TABLE 5-continued (Table 5 discloses SEQ ID NO: 10):

| ATOM | 2224 | CG | HIS | A | 284 | −31.431 | 4.069 | −6.935 | 1.00 | 14.61 | C |
|---|---|---|---|---|---|---|---|---|---|---|---|
| ATOM | 2225 | ND1 | HIS | A | 284 | −32.760 | 4.046 | −6.573 | 1.00 | 20.82 | N |
| ATOM | 2226 | CD2 | HIS | A | 284 | −30.958 | 2.820 | −6.717 | 1.00 | 21.94 | C |
| ATOM | 2227 | CE1 | HIS | A | 284 | −33.074 | 2.837 | −6.138 | 1.00 | 19.80 | C |
| ATOM | 2228 | NE2 | HIS | A | 284 | −31.998 | 2.075 | −6.216 | 1.00 | 23.11 | N |
| ATOM | 2229 | N | GLU | A | 285 | −28.713 | 5.876 | −5.181 | 1.00 | 8.55 | N |
| ATOM | 2230 | CA | GLU | A | 285 | −28.016 | 5.410 | −3.977 | 1.00 | 8.60 | C |
| ATOM | 2231 | C | GLU | A | 285 | −28.134 | 6.419 | −2.836 | 1.00 | 9.27 | C |
| ATOM | 2232 | O | GLU | A | 285 | −28.337 | 6.043 | −1.678 | 1.00 | 10.15 | O |
| ATOM | 2233 | CB | GLU | A | 285 | −26.548 | 5.102 | −4.266 | 1.00 | 10.27 | C |
| ATOM | 2234 | CG | GLU | A | 285 | −26.341 | 3.975 | −5.284 | 1.00 | 12.66 | C |
| ATOM | 2235 | CD | GLU | A | 285 | −26.784 | 2.615 | −4.761 | 1.00 | 48.46 | C |
| ATOM | 2236 | OE1 | GLU | A | 285 | −26.861 | 2.438 | −3.526 | 1.00 | 24.33 | O |
| ATOM | 2237 | OE2 | GLU | A | 285 | −27.051 | 1.714 | −5.586 | 1.00 | 26.17 | O |
| ATOM | 2238 | N | ILE | A | 286 | −27.999 | 7.703 | −3.158 | 1.00 | 8.06 | N |
| ATOM | 2239 | CA | ILE | A | 286 | −28.130 | 8.738 | −2.137 | 1.00 | 7.60 | C |
| ATOM | 2240 | C | ILE | A | 286 | −29.561 | 8.758 | −1.615 | 1.00 | 8.03 | C |
| ATOM | 2241 | O | ILE | A | 286 | −29.797 | 8.844 | −0.404 | 1.00 | 9.29 | O |
| ATOM | 2242 | CB | ILE | A | 286 | −27.726 | 10.117 | −2.697 | 1.00 | 7.44 | C |
| ATOM | 2243 | CG1 | ILE | A | 286 | −26.225 | 10.131 | −2.982 | 1.00 | 8.11 | C |
| ATOM | 2244 | CG2 | ILE | A | 286 | −28.104 | 11.222 | −1.702 | 1.00 | 9.25 | C |
| ATOM | 2245 | CD1 | ILE | A | 286 | −25.730 | 11.355 | −3.736 | 1.00 | 8.46 | C |
| ATOM | 2246 | N | ASN | A | 287 | −30.525 | 8.668 | −2.524 | 1.00 | 7.56 | N |
| ATOM | 2247 | CA | ASN | A | 287 | −31.927 | 8.632 | −2.145 | 1.00 | 9.10 | C |
| ATOM | 2248 | C | ASN | A | 287 | −32.196 | 7.506 | −1.135 | 1.00 | 9.78 | C |
| ATOM | 2249 | O | ASN | A | 287 | −32.777 | 7.731 | −0.068 | 1.00 | 10.92 | O |
| ATOM | 2250 | CB | ASN | A | 287 | −32.792 | 8.481 | −3.408 | 1.00 | 9.77 | C |
| ATOM | 2251 | CG | ASN | A | 287 | −34.280 | 8.468 | −3.121 | 1.00 | 16.23 | C |
| ATOM | 2252 | OD1 | ASN | A | 287 | −34.738 | 7.846 | −2.167 | 1.00 | 16.90 | O |
| ATOM | 2253 | ND2 | ASN | A | 287 | −35.046 | 9.144 | −3.968 | 1.00 | 17.83 | N |
| ATOM | 2254 | N | MET | A | 288 | −31.756 | 6.295 | −1.457 | 1.00 | 9.68 | N |
| ATOM | 2255 | CA | AMET | A | 288 | −32.008 | 5.164 | −0.571 | 0.75 | 10.52 | C |
| ATOM | 2256 | C | MET | A | 288 | −31.283 | 5.304 | 0.765 | 1.00 | 10.26 | C |
| ATOM | 2257 | O | MET | A | 288 | −31.858 | 5.002 | 1.817 | 1.00 | 11.11 | O |
| ATOM | 2258 | CB | AMET | A | 288 | −31.618 | 3.853 | −1.246 | 0.75 | 13.43 | C |
| ATOM | 2259 | CG | AMET | A | 288 | −32.543 | 3.452 | −2.384 | 0.75 | 11.44 | C |
| ATOM | 2260 | SD | AMET | A | 288 | −32.159 | 1.788 | −2.967 | 0.75 | 19.23 | S |
| ATOM | 2261 | CE | AMET | A | 288 | −30.435 | 1.981 | −3.415 | 0.75 | 25.05 | C |
| ATOM | 2262 | CA | BMET | A | 288 | −31.970 | 5.141 | −0.586 | 0.25 | 13.65 | C |
| ATOM | 2263 | CB | BMET | A | 288 | −31.454 | 3.872 | −1.264 | 0.25 | 10.56 | C |
| ATOM | 2264 | CG | BMET | A | 288 | −32.177 | 3.528 | −2.550 | 0.25 | 11.01 | C |
| ATOM | 2265 | SD | BMET | A | 288 | −33.911 | 3.126 | −2.263 | 0.25 | 15.84 | S |
| ATOM | 2266 | CE | BMET | A | 288 | −33.757 | 1.686 | −1.209 | 0.25 | 35.78 | C |
| ATOM | 2267 | N | TRP | A | 289 | −30.041 | 5.768 | 0.732 | 1.00 | 8.12 | N |
| ATOM | 2268 | CA | TRP | A | 289 | −29.239 | 5.874 | 1.947 | 1.00 | 8.46 | C |
| ATOM | 2269 | C | TRP | A | 289 | −29.847 | 6.893 | 2.916 | 1.00 | 10.60 | C |
| ATOM | 2270 | O | TRP | A | 289 | −30.013 | 6.619 | 4.106 | 1.00 | 10.10 | O |
| ATOM | 2271 | CB | TRP | A | 289 | −27.809 | 6.262 | 1.588 | 1.00 | 8.04 | C |
| ATOM | 2272 | CG | TRP | A | 289 | −26.829 | 6.080 | 2.699 | 1.00 | 8.76 | C |
| ATOM | 2273 | CD1 | TRP | A | 289 | −26.110 | 4.953 | 2.987 | 1.00 | 8.96 | C |
| ATOM | 2274 | CD2 | TRP | A | 289 | −26.452 | 7.057 | 3.681 | 1.00 | 7.64 | C |
| ATOM | 2275 | NE1 | TRP | A | 289 | −25.307 | 5.171 | 4.076 | 1.00 | 8.96 | N |
| ATOM | 2276 | CE2 | TRP | A | 289 | −25.501 | 6.452 | 4.525 | 1.00 | 7.40 | C |
| ATOM | 2277 | CE3 | TRP | A | 289 | −26.815 | 8.386 | 3.916 | 1.00 | 8.72 | C |
| ATOM | 2278 | CZ2 | TRP | A | 289 | −24.912 | 7.130 | 5.594 | 1.00 | 8.56 | C |
| ATOM | 2279 | CZ3 | TRP | A | 289 | −26.232 | 9.055 | 4.981 | 1.00 | 9.78 | C |
| ATOM | 2280 | CH2 | TRP | A | 289 | −25.292 | 8.429 | 5.801 | 1.00 | 7.77 | C |
| ATOM | 2281 | N | VAL | A | 290 | −30.202 | 8.061 | 2.392 | 1.00 | 7.61 | N |
| ATOM | 2282 | CA | VAL | A | 290 | −30.822 | 9.098 | 3.210 | 1.00 | 8.87 | C |
| ATOM | 2283 | C | VAL | A | 290 | −32.228 | 8.697 | 3.658 | 1.00 | 11.01 | C |
| ATOM | 2284 | O | VAL | A | 290 | −32.591 | 8.898 | 4.821 | 1.00 | 12.42 | O |
| ATOM | 2285 | CB | VAL | A | 290 | −30.834 | 10.451 | 2.465 | 1.00 | 10.20 | C |
| ATOM | 2286 | CG1 | VAL | A | 290 | −31.622 | 11.483 | 3.254 | 1.00 | 13.69 | C |
| ATOM | 2287 | CG2 | VAL | A | 290 | −29.410 | 10.923 | 2.232 | 1.00 | 10.54 | C |
| ATOM | 2288 | N | SER | A | 291 | −33.018 | 8.122 | 2.757 | 1.00 | 11.05 | N |
| ATOM | 2289 | CA | SER | A | 291 | −34.362 | 7.653 | 3.105 | 1.00 | 12.68 | C |
| ATOM | 2290 | C | SER | A | 291 | −34.337 | 6.683 | 4.286 | 1.00 | 15.97 | C |
| ATOM | 2291 | O | SER | A | 291 | −35.128 | 6.805 | 5.226 | 1.00 | 16.56 | O |
| ATOM | 2292 | CB | SER | A | 291 | −35.013 | 6.968 | 1.903 | 1.00 | 14.10 | C |
| ATOM | 2293 | OG | SER | A | 291 | −35.461 | 7.922 | 0.957 | 1.00 | 20.61 | O |
| ATOM | 2294 | N | GLN | A | 292 | −33.428 | 5.717 | 4.236 | 1.00 | 13.80 | N |
| ATOM | 2295 | CA | GLN | A | 292 | −33.346 | 4.702 | 5.281 | 1.00 | 13.65 | C |
| ATOM | 2296 | C | GLN | A | 292 | −32.926 | 5.283 | 6.628 | 1.00 | 15.92 | C |
| ATOM | 2297 | O | GLN | A | 292 | −33.192 | 4.697 | 7.676 | 1.00 | 19.93 | O |
| ATOM | 2298 | CB | GLN | A | 292 | −32.414 | 3.577 | 4.841 | 1.00 | 15.28 | C |
| ATOM | 2299 | CG | GLN | A | 292 | −33.016 | 2.750 | 3.714 | 1.00 | 31.36 | C |
| ATOM | 2300 | CD | GLN | A | 292 | −32.018 | 1.827 | 3.059 | 1.00 | 59.35 | C |
| ATOM | 2301 | OE1 | GLN | A | 292 | −31.042 | 1.409 | 3.679 | 1.00 | 46.54 | O |

TABLE 5-continued (Table 5 discloses SEQ ID NO: 10):

| | | | | | | | | | | |
|---|---|---|---|---|---|---|---|---|---|---|
| ATOM | 2302 | NE2 | GLN | A | 292 | −32.259 | 1.500 | 1.795 | 1.00 | 52.18 | N |
| ATOM | 2303 | N | ARG | A | 293 | −32.290 | 6.449 | 6.604 | 1.00 | 11.83 | N |
| ATOM | 2304 | CA | ARG | A | 293 | −31.758 | 7.049 | 7.818 | 1.00 | 11.03 | C |
| ATOM | 2305 | C | ARG | A | 293 | −32.577 | 8.254 | 8.293 | 1.00 | 10.89 | C |
| ATOM | 2306 | O | ARG | A | 293 | −32.172 | 8.968 | 9.215 | 1.00 | 14.96 | O |
| ATOM | 2307 | CB | ARG | A | 293 | −30.273 | 7.380 | 7.632 | 1.00 | 9.52 | C |
| ATOM | 2308 | CG | ARG | A | 293 | −29.406 | 6.126 | 7.665 | 1.00 | 10.01 | C |
| ATOM | 2309 | CD | ARG | A | 293 | −28.042 | 6.325 | 7.036 | 1.00 | 10.98 | C |
| ATOM | 2310 | NE | ARG | A | 293 | −27.297 | 5.065 | 7.004 | 1.00 | 9.60 | N |
| ATOM | 2311 | CZ | ARG | A | 293 | −27.508 | 4.099 | 6.111 | 1.00 | 9.62 | C |
| ATOM | 2312 | NH1 | ARG | A | 293 | −28.431 | 4.249 | 5.166 | 1.00 | 9.87 | N |
| ATOM | 2313 | NH2 | ARG | A | 293 | −26.789 | 2.987 | 6.171 | 1.00 | 11.78 | N |
| ATOM | 2314 | N | THR | A | 294 | −33.731 | 8.453 | 7.667 | 1.00 | 14.09 | N |
| ATOM | 2315 | CA | THR | A | 294 | −34.681 | 9.485 | 8.068 | 1.00 | 15.85 | C |
| ATOM | 2316 | C | THR | A | 294 | −36.072 | 8.869 | 8.199 | 1.00 | 22.42 | C |
| ATOM | 2317 | O | THR | A | 294 | −37.067 | 9.584 | 8.311 | 1.00 | 36.87 | O |
| ATOM | 2318 | CB | THR | A | 294 | −34.731 | 10.651 | 7.053 | 1.00 | 16.73 | C |
| ATOM | 2319 | OG1 | THR | A | 294 | −35.000 | 10.137 | 5.743 | 1.00 | 18.85 | O |
| ATOM | 2320 | CG2 | THR | A | 294 | −33.417 | 11.393 | 7.022 | 1.00 | 15.10 | C |
| ATOM | 2321 | O01 | INH | I | 1 | −12.895 | 20.823 | −4.999 | 1.00 | 7.09 | O |
| ATOM | 2322 | C02 | INH | I | 1 | −12.391 | 20.703 | −6.129 | 1.00 | 8.09 | C |
| ATOM | 2323 | C03 | INH | I | 1 | −10.917 | 20.735 | −6.329 | 1.00 | 7.66 | C |
| ATOM | 2324 | C04 | INH | I | 1 | −10.371 | 21.511 | −7.372 | 1.00 | 8.80 | C |
| ATOM | 2325 | C05 | INH | I | 1 | −9.002 | 21.548 | −7.621 | 1.00 | 11.29 | C |
| ATOM | 2326 | C06 | INH | I | 1 | −8.161 | 20.785 | −6.808 | 1.00 | 9.74 | C |
| ATOM | 2327 | N07 | INH | I | 1 | −6.763 | 20.578 | −6.783 | 1.00 | 12.42 | N |
| ATOM | 2328 | C08 | INH | I | 1 | −6.533 | 19.727 | −5.790 | 1.00 | 14.65 | C |
| ATOM | 2329 | O09 | INH | I | 1 | −7.712 | 19.334 | −5.112 | 1.00 | 13.07 | O |
| ATOM | 2330 | C10 | INH | I | 1 | −8.755 | 19.997 | −5.760 | 1.00 | 9.91 | C |
| ATOM | 2331 | C11 | INH | I | 1 | −10.110 | 19.953 | −5.499 | 1.00 | 7.61 | C |
| ATOM | 2332 | C12 | INH | I | 1 | −5.241 | 19.125 | −5.317 | 1.00 | 16.69 | C |
| ATOM | 2333 | C13 | INH | I | 1 | −4.117 | 19.335 | −6.328 | 1.00 | 15.09 | C |
| ATOM | 2334 | C14 | INH | I | 1 | −2.767 | 18.863 | −5.823 | 1.00 | 19.81 | C |
| ATOM | 2335 | C15 | INH | I | 1 | −2.421 | 19.447 | −4.476 | 1.00 | 19.20 | C |
| ATOM | 2336 | C16 | INH | I | 1 | −3.512 | 19.142 | −3.467 | 1.00 | 19.60 | C |
| ATOM | 2337 | C17 | INH | I | 1 | −4.893 | 19.592 | −3.914 | 1.00 | 17.98 | C |
| ATOM | 2338 | N18 | INH | I | 1 | −13.235 | 20.690 | −7.197 | 1.00 | 6.87 | N |
| ATOM | 2339 | C19 | INH | I | 1 | −14.672 | 20.540 | −7.283 | 1.00 | 6.93 | C |
| ATOM | 2340 | C20 | INH | I | 1 | −14.471 | 19.893 | −8.684 | 1.00 | 6.67 | C |
| ATOM | 2341 | C21 | INH | I | 1 | −12.952 | 20.266 | −8.587 | 1.00 | 8.77 | C |
| ATOM | 2342 | N22 | INH | I | 1 | −15.178 | 20.424 | −9.813 | 1.00 | 6.45 | N |
| ATOM | 2343 | C23 | INH | I | 1 | −16.588 | 20.190 | −9.789 | 1.00 | 5.98 | C |
| ATOM | 2344 | C24 | INH | I | 1 | −17.328 | 20.733 | −11.042 | 1.00 | 6.80 | C |
| ATOM | 2345 | N25 | INH | I | 1 | −16.634 | 20.331 | −12.248 | 1.00 | 7.33 | N |
| ATOM | 2346 | C26 | INH | I | 1 | −15.203 | 20.541 | −12.284 | 1.00 | 10.22 | C |
| ATOM | 2347 | C27 | INH | I | 1 | −14.523 | 19.973 | −11.038 | 1.00 | 7.33 | C |
| ATOM | 2348 | C28 | INH | I | 1 | −17.296 | 19.725 | −13.318 | 1.00 | 6.80 | C |
| ATOM | 2349 | N29 | INH | I | 1 | −16.488 | 19.205 | −14.329 | 1.00 | 7.30 | N |
| ATOM | 2350 | C30 | INH | I | 1 | −17.138 | 18.618 | −15.336 | 1.00 | 7.90 | C |
| ATOM | 2351 | C31 | INH | I | 1 | −18.527 | 18.508 | −15.408 | 1.00 | 7.42 | C |
| ATOM | 2352 | C32 | INH | I | 1 | −19.257 | 19.048 | −14.354 | 1.00 | 7.83 | C |
| ATOM | 2353 | N33 | INH | I | 1 | −18.670 | 19.648 | −13.307 | 1.00 | 6.45 | N |
| HETATM | 2354 | O | HOH | W | 1 | −17.954 | 27.691 | 4.082 | 1.00 | 7.52 | O |
| HETATM | 2355 | O | HOH | W | 2 | −16.687 | 30.118 | 3.647 | 1.00 | 7.58 | O |
| HETATM | 2356 | O | HOH | W | 3 | −16.903 | 29.964 | −7.861 | 1.00 | 8.56 | O |
| HETATM | 2357 | O | HOH | W | 4 | −24.521 | 30.541 | −6.460 | 1.00 | 8.76 | O |
| HETATM | 2358 | O | HOH | W | 5 | −18.264 | 32.412 | 10.389 | 1.00 | 8.02 | O |
| HETATM | 2359 | O | HOH | W | 6 | −23.247 | 3.675 | 5.398 | 1.00 | 9.13 | O |
| HETATM | 2360 | O | HOH | W | 7 | −15.105 | 23.282 | −9.818 | 1.00 | 10.08 | O |
| HETATM | 2361 | O | HOH | W | 8 | −20.744 | 0.215 | −8.443 | 1.00 | 9.73 | O |
| HETATM | 2362 | O | HOH | W | 9 | −11.897 | 30.578 | −1.691 | 1.00 | 10.64 | O |
| HETATM | 2363 | O | HOH | W | 10 | −22.252 | 20.341 | −15.373 | 1.00 | 11.45 | O |
| HETATM | 2364 | O | HOH | W | 11 | −27.187 | 18.469 | −8.872 | 1.00 | 12.11 | O |
| HETATM | 2365 | O | HOH | W | 12 | −11.733 | 34.673 | −0.588 | 1.00 | 12.31 | O |
| HETATM | 2366 | O | HOH | W | 13 | −11.423 | 12.123 | −13.304 | 1.00 | 11.25 | O |
| HETATM | 2367 | O | HOH | W | 14 | −18.816 | 28.913 | 13.424 | 1.00 | 11.56 | O |
| HETATM | 2368 | O | HOH | W | 15 | −9.196 | 10.830 | −2.094 | 1.00 | 12.11 | O |
| HETATM | 2369 | O | HOH | W | 16 | −9.803 | 26.896 | −12.434 | 1.00 | 12.21 | O |
| HETATM | 2370 | O | HOH | W | 17 | −21.490 | 5.488 | 12.067 | 1.00 | 12.81 | O |
| HETATM | 2371 | O | HOH | W | 18 | −32.761 | 29.987 | −2.012 | 1.00 | 14.02 | O |
| HETATM | 2372 | O | HOH | W | 19 | −18.414 | 31.657 | 13.060 | 1.00 | 12.16 | O |
| HETATM | 2373 | O | HOH | W | 20 | −5.462 | 30.956 | −0.225 | 1.00 | 13.69 | O |
| HETATM | 2374 | O | HOH | W | 21 | −11.248 | 35.923 | 1.786 | 1.00 | 14.53 | O |
| HETATM | 2375 | O | HOH | W | 22 | −30.857 | 31.479 | −3.105 | 1.00 | 12.95 | O |
| HETATM | 2376 | O | HOH | W | 23 | −17.537 | 30.497 | −17.209 | 1.00 | 13.52 | O |
| HETATM | 2377 | O | HOH | W | 24 | −27.943 | 15.491 | 13.891 | 1.00 | 15.19 | O |
| HETATM | 2378 | O | HOH | W | 25 | −6.754 | 29.942 | −6.600 | 1.00 | 14.74 | O |
| HETATM | 2379 | O | HOH | W | 26 | −21.995 | 24.699 | −0.661 | 1.00 | 15.81 | O |

TABLE 5-continued (Table 5 discloses SEQ ID NO: 10):

| HETATM | 2380 | O | HOH | W | 27 | −24.620 | 37.557 | −8.143 | 1.00 | 14.70 | O |
|---|---|---|---|---|---|---|---|---|---|---|---|
| HETATM | 2381 | O | HOH | W | 28 | −11.836 | 10.105 | −2.131 | 1.00 | 13.84 | O |
| HETATM | 2382 | O | HOH | W | 29 | −6.977 | 17.152 | −20.873 | 1.00 | 14.48 | O |
| HETATM | 2383 | O | HOH | W | 30 | −27.778 | 25.779 | 17.062 | 1.00 | 14.55 | O |
| HETATM | 2384 | O | HOH | W | 31 | −28.099 | 20.389 | −10.972 | 1.00 | 15.25 | O |
| HETATM | 2385 | O | HOH | W | 32 | −26.572 | 16.678 | −10.935 | 1.00 | 15.41 | O |
| HETATM | 2386 | O | HOH | W | 33 | −21.236 | 20.183 | −9.116 | 1.00 | 14.32 | O |
| HETATM | 2387 | O | HOH | W | 34 | −21.239 | 28.606 | 14.850 | 1.00 | 15.96 | O |
| HETATM | 2388 | O | HOH | W | 35 | −24.773 | 29.548 | −12.422 | 1.00 | 15.43 | O |
| HETATM | 2389 | O | HOH | W | 36 | −20.822 | 20.806 | −11.819 | 1.00 | 14.61 | O |
| HETATM | 2390 | O | HOH | W | 37 | −9.275 | 15.936 | −22.055 | 1.00 | 14.71 | O |
| HETATM | 2391 | O | HOH | W | 38 | −20.594 | 14.589 | 13.855 | 1.00 | 17.78 | O |
| HETATM | 2392 | O | HOH | W | 39 | 5.208 | 15.094 | −10.204 | 1.00 | 16.41 | O |
| HETATM | 2393 | O | HOH | W | 40 | −20.072 | 5.193 | 14.956 | 1.00 | 15.13 | O |
| HETATM | 2394 | O | HOH | W | 41 | −13.159 | 26.020 | −13.404 | 1.00 | 16.62 | O |
| HETATM | 2395 | O | HOH | W | 42 | −26.282 | 23.518 | 16.511 | 1.00 | 20.84 | O |
| HETATM | 2396 | O | HOH | W | 43 | −10.302 | 34.220 | 3.868 | 1.00 | 18.17 | O |
| HETATM | 2397 | O | HOH | W | 44 | −1.928 | 29.772 | 2.061 | 1.00 | 15.99 | O |
| HETATM | 2398 | O | HOH | W | 45 | −2.744 | 28.535 | 7.126 | 1.00 | 19.79 | O |
| HETATM | 2399 | O | HOH | W | 46 | −5.515 | 17.879 | −17.351 | 1.00 | 19.09 | O |
| HETATM | 2400 | O | HOH | W | 47 | −12.817 | 5.509 | −17.997 | 1.00 | 18.20 | O |
| HETATM | 2401 | O | HOH | W | 48 | −14.357 | 31.242 | −7.410 | 1.00 | 17.27 | O |
| HETATM | 2402 | O | HOH | W | 49 | −14.923 | 14.930 | −21.033 | 1.00 | 17.02 | O |
| HETATM | 2403 | O | HOH | W | 50 | −9.458 | 23.156 | 9.139 | 1.00 | 21.87 | O |
| HETATM | 2404 | O | HOH | W | 51 | 0.257 | 31.525 | −7.428 | 1.00 | 18.65 | O |
| HETATM | 2405 | O | HOH | W | 52 | −25.578 | 20.460 | −14.720 | 1.00 | 18.62 | O |
| HETATM | 2406 | O | HOH | W | 53 | −20.547 | 12.617 | −23.501 | 1.00 | 20.46 | O |
| HETATM | 2407 | O | HOH | W | 54 | −23.950 | 26.787 | −18.563 | 1.00 | 17.02 | O |
| HETATM | 2408 | O | HOH | W | 55 | −14.696 | 9.975 | −8.189 | 1.00 | 19.62 | O |
| HETATM | 2409 | O | HOH | W | 56 | −25.051 | 13.877 | −15.630 | 1.00 | 17.92 | O |
| HETATM | 2410 | O | HOH | W | 57 | −8.564 | 7.506 | −8.708 | 1.00 | 18.44 | O |
| HETATM | 2411 | O | HOH | W | 58 | −26.198 | 31.102 | −16.423 | 1.00 | 16.37 | O |
| HETATM | 2412 | O | HOH | W | 59 | −37.176 | 12.986 | −4.281 | 1.00 | 21.18 | O |
| HETATM | 2413 | O | HOH | W | 60 | −0.408 | 19.850 | −9.658 | 1.00 | 20.96 | O |
| HETATM | 2414 | O | HOH | W | 61 | −27.390 | 2.115 | −8.137 | 1.00 | 20.41 | O |
| HETATM | 2415 | O | HOH | W | 62 | −18.345 | 0.114 | 10.794 | 1.00 | 19.73 | O |
| HETATM | 2416 | O | HOH | W | 63 | −7.560 | 17.472 | 11.844 | 1.00 | 20.82 | O |
| HETATM | 2417 | O | HOH | W | 64 | −10.060 | 27.021 | −17.033 | 1.00 | 19.15 | O |
| HETATM | 2418 | O | HOH | W | 65 | −11.889 | 25.550 | −15.567 | 1.00 | 17.58 | O |
| HETATM | 2419 | O | HOH | W | 66 | −0.270 | 32.535 | −4.292 | 1.00 | 23.13 | O |
| HETATM | 2420 | O | HOH | W | 67 | −2.409 | 13.621 | −0.840 | 1.00 | 20.38 | O |
| HETATM | 2421 | O | HOH | W | 68 | −26.262 | 31.478 | −13.675 | 1.00 | 20.59 | O |
| HETATM | 2422 | O | HOH | W | 69 | −28.229 | 3.738 | −13.695 | 1.00 | 21.62 | O |
| HETATM | 2423 | O | HOH | W | 70 | −31.712 | 27.290 | −6.129 | 1.00 | 18.31 | O |
| HETATM | 2424 | O | HOH | W | 71 | −6.300 | 21.250 | −19.853 | 1.00 | 16.05 | O |
| HETATM | 2425 | O | HOH | W | 72 | −28.617 | 2.134 | 3.116 | 1.00 | 24.09 | O |
| HETATM | 2426 | O | HOH | W | 73 | −6.265 | 12.778 | −21.032 | 1.00 | 20.88 | O |
| HETATM | 2427 | O | HOH | W | 74 | −5.345 | 21.003 | −9.170 | 1.00 | 20.95 | O |
| HETATM | 2428 | O | HOH | W | 75 | −13.672 | 40.032 | 1.481 | 1.00 | 20.82 | O |
| HETATM | 2429 | O | HOH | W | 76 | 3.970 | 33.284 | −8.733 | 1.00 | 21.52 | O |
| HETATM | 2430 | O | HOH | W | 77 | −27.601 | 3.453 | −1.085 | 1.00 | 19.94 | O |
| HETATM | 2431 | O | HOH | W | 78 | −16.463 | 32.339 | 14.904 | 1.00 | 20.41 | O |
| HETATM | 2432 | O | HOH | W | 79 | −30.731 | 36.819 | 4.054 | 1.00 | 22.74 | O |
| HETATM | 2433 | O | HOH | W | 80 | −10.846 | 1.831 | −7.270 | 1.00 | 21.37 | O |
| HETATM | 2434 | O | HOH | W | 81 | −27.313 | 22.838 | −11.310 | 1.00 | 24.03 | O |
| HETATM | 2435 | O | HOH | W | 82 | −15.217 | 31.789 | −19.315 | 1.00 | 23.88 | O |
| HETATM | 2436 | O | HOH | W | 83 | −33.912 | 16.169 | −9.052 | 1.00 | 22.87 | O |
| HETATM | 2437 | O | HOH | W | 84 | −20.209 | −1.679 | 12.463 | 1.00 | 21.35 | O |
| HETATM | 2438 | O | HOH | W | 85 | −5.913 | 10.247 | −9.105 | 1.00 | 22.32 | O |
| HETATM | 2439 | O | HOH | W | 86 | −0.959 | 17.408 | 2.354 | 1.00 | 20.98 | O |
| HETATM | 2440 | O | HOH | W | 87 | −10.503 | 38.192 | 0.316 | 1.00 | 24.62 | O |
| HETATM | 2441 | O | HOH | W | 88 | −32.112 | 7.871 | −10.243 | 1.00 | 21.94 | O |
| HETATM | 2442 | O | HOH | W | 89 | −13.180 | 25.290 | −17.756 | 1.00 | 19.54 | O |
| HETATM | 2443 | O | HOH | W | 90 | −7.804 | 19.778 | −13.041 | 1.00 | 24.06 | O |
| HETATM | 2444 | O | HOH | W | 91 | −33.427 | 27.311 | −4.139 | 1.00 | 23.94 | O |
| HETATM | 2445 | O | HOH | W | 92 | −12.229 | 34.941 | 5.552 | 1.00 | 22.55 | O |
| HETATM | 2446 | O | HOH | W | 93 | −40.268 | 22.945 | 5.322 | 1.00 | 24.66 | O |
| HETATM | 2447 | O | HOH | W | 94 | −11.361 | −0.276 | 9.385 | 1.00 | 24.33 | O |
| HETATM | 2448 | O | HOH | W | 95 | −5.594 | 12.673 | 4.154 | 1.00 | 21.98 | O |
| HETATM | 2449 | O | HOH | W | 96 | −30.277 | 8.393 | 11.189 | 1.00 | 23.95 | O |
| HETATM | 2450 | O | HOH | W | 97 | −3.885 | 31.646 | 2.132 | 1.00 | 23.08 | O |
| HETATM | 2451 | O | HOH | W | 98 | −15.349 | 37.712 | −10.155 | 1.00 | 22.78 | O |
| HETATM | 2452 | O | HOH | W | 99 | −27.793 | 8.032 | 10.121 | 1.00 | 21.52 | O |
| HETATM | 2453 | O | HOH | W | 100 | 1.726 | 25.595 | −13.323 | 1.00 | 24.61 | O |
| HETATM | 2454 | O | HOH | W | 101 | −4.022 | 23.204 | −10.234 | 1.00 | 23.85 | O |
| HETATM | 2455 | O | HOH | W | 102 | −0.283 | 27.133 | 5.706 | 1.00 | 27.07 | O |
| HETATM | 2456 | O | HOH | W | 103 | −17.612 | 12.195 | 13.686 | 1.00 | 22.47 | O |
| HETATM | 2457 | O | HOH | W | 104 | −20.617 | 38.511 | 11.379 | 1.00 | 22.85 | O |

TABLE 5-continued (Table 5 discloses SEQ ID NO: 10):

| HETATM | 2458 | O | HOH | W | 105 | −12.949 | 21.628 | −20.519 | 1.00 | 22.65 | O |
|---|---|---|---|---|---|---|---|---|---|---|---|
| HETATM | 2459 | O | HOH | W | 106 | −8.950 | 13.120 | −21.827 | 1.00 | 24.72 | O |
| HETATM | 2460 | O | HOH | W | 107 | −24.860 | 6.230 | −19.460 | 1.00 | 22.27 | O |
| HETATM | 2461 | O | HOH | W | 108 | −19.286 | 25.663 | −23.124 | 1.00 | 24.09 | O |
| HETATM | 2462 | O | HOH | W | 109 | −4.483 | 32.563 | −11.039 | 1.00 | 27.41 | O |
| HETATM | 2463 | O | HOH | W | 110 | −29.993 | 33.249 | 4.804 | 1.00 | 24.16 | O |
| HETATM | 2464 | O | HOH | W | 111 | 12.207 | 32.873 | 0.335 | 1.00 | 25.14 | O |
| HETATM | 2465 | O | HOH | W | 112 | −34.084 | 27.205 | 19.146 | 1.00 | 21.94 | O |
| HETATM | 2466 | O | HOH | W | 113 | −26.787 | 5.452 | 10.766 | 1.00 | 22.13 | O |
| HETATM | 2467 | O | HOH | W | 114 | 1.550 | 16.445 | −12.673 | 1.00 | 29.27 | O |
| HETATM | 2468 | O | HOH | W | 115 | 0.773 | 22.236 | −9.903 | 1.00 | 21.44 | O |
| HETATM | 2469 | O | HOH | W | 116 | −15.044 | 17.209 | −22.620 | 1.00 | 21.87 | O |
| HETATM | 2470 | O | HOH | W | 117 | −25.901 | 32.220 | 9.915 | 1.00 | 21.85 | O |
| HETATM | 2471 | O | HOH | W | 118 | −15.258 | 40.579 | −2.244 | 1.00 | 27.72 | O |
| HETATM | 2472 | O | HOH | W | 119 | −7.794 | 30.680 | −9.041 | 1.00 | 23.66 | O |
| HETATM | 2473 | O | HOH | W | 120 | −18.635 | 35.461 | −11.584 | 1.00 | 24.31 | O |
| HETATM | 2474 | O | HOH | W | 121 | −26.081 | 16.654 | −25.505 | 1.00 | 22.43 | O |
| HETATM | 2475 | O | HOH | W | 122 | −9.221 | 9.291 | −15.768 | 1.00 | 27.18 | O |
| HETATM | 2476 | O | HOH | W | 123 | −28.859 | 32.651 | −7.827 | 1.00 | 31.44 | O |
| HETATM | 2477 | O | HOH | W | 124 | −1.147 | 11.892 | −2.485 | 1.00 | 25.34 | O |
| HETATM | 2478 | O | HOH | W | 125 | −16.717 | 23.990 | −23.206 | 1.00 | 22.72 | O |
| HETATM | 2479 | O | HOH | W | 126 | −16.904 | 27.933 | 15.146 | 1.00 | 28.48 | O |
| HETATM | 2480 | O | HOH | W | 127 | −24.881 | −0.157 | −9.675 | 1.00 | 30.44 | O |
| HETATM | 2481 | O | HOH | W | 128 | −12.528 | 32.808 | −13.738 | 1.00 | 23.97 | O |
| HETATM | 2482 | O | HOH | W | 129 | −31.526 | 33.432 | −4.910 | 1.00 | 29.01 | O |
| HETATM | 2483 | O | HOH | W | 130 | −10.048 | 37.820 | −7.038 | 1.00 | 29.37 | O |
| HETATM | 2484 | O | HOH | W | 131 | −11.867 | 19.403 | 12.228 | 1.00 | 29.42 | O |
| HETATM | 2485 | O | HOH | W | 132 | −37.133 | 10.668 | 3.881 | 1.00 | 30.27 | O |
| HETATM | 2486 | O | HOH | W | 133 | −19.747 | 3.815 | −16.456 | 1.00 | 27.29 | O |
| HETATM | 2487 | O | HOH | W | 134 | −7.880 | 35.404 | −6.844 | 1.00 | 24.86 | O |
| HETATM | 2488 | O | HOH | W | 135 | −8.998 | 3.716 | −9.036 | 1.00 | 28.14 | O |
| HETATM | 2489 | O | HOH | W | 136 | −2.967 | 12.137 | 4.048 | 1.00 | 26.40 | O |
| HETATM | 2490 | O | HOH | W | 137 | −17.049 | 39.326 | −11.678 | 1.00 | 25.80 | O |
| HETATM | 2491 | O | HOH | W | 138 | −10.257 | −2.109 | −12.040 | 1.00 | 29.56 | O |
| HETATM | 2492 | O | HOH | W | 139 | −26.119 | 34.050 | −13.125 | 1.00 | 25.74 | O |
| HETATM | 2493 | O | HOH | W | 140 | −16.994 | 38.359 | 14.121 | 1.00 | 32.67 | O |
| HETATM | 2494 | O | HOH | W | 141 | −10.346 | 37.403 | −10.034 | 1.00 | 28.07 | O |
| HETATM | 2495 | O | HOH | W | 142 | 6.226 | 22.804 | −1.176 | 1.00 | 26.21 | O |
| HETATM | 2496 | O | HOH | W | 143 | −7.855 | 32.548 | 9.121 | 1.00 | 31.08 | O |
| HETATM | 2497 | O | HOH | W | 144 | −38.520 | 18.008 | −5.332 | 1.00 | 28.74 | O |
| HETATM | 2498 | O | HOH | W | 145 | 0.863 | 30.021 | −14.155 | 1.00 | 25.22 | O |
| HETATM | 2499 | O | HOH | W | 146 | −14.539 | 12.832 | −22.506 | 1.00 | 34.74 | O |
| HETATM | 2500 | O | HOH | W | 147 | −9.685 | 35.266 | 7.783 | 1.00 | 39.75 | O |
| HETATM | 2501 | O | HOH | W | 148 | −4.940 | 15.663 | −7.095 | 1.00 | 28.86 | O |
| HETATM | 2502 | O | HOH | W | 149 | −19.875 | 12.007 | 14.866 | 1.00 | 29.93 | O |
| HETATM | 2503 | O | HOH | W | 150 | −25.128 | −0.534 | −5.095 | 1.00 | 28.37 | O |
| HETATM | 2504 | O | HOH | W | 151 | −1.385 | 12.790 | 1.731 | 1.00 | 27.27 | O |
| HETATM | 2505 | O | HOH | W | 152 | −28.589 | 35.688 | −8.140 | 1.00 | 29.37 | O |
| HETATM | 2506 | O | HOH | W | 153 | −39.946 | 16.242 | 11.666 | 1.00 | 27.63 | O |
| HETATM | 2507 | O | HOH | W | 154 | −12.005 | 32.563 | 12.899 | 1.00 | 28.89 | O |
| HETATM | 2508 | O | HOH | W | 155 | −32.382 | 11.270 | 10.718 | 1.00 | 27.03 | O |
| HETATM | 2509 | O | HOH | W | 156 | −6.547 | 26.498 | 11.420 | 1.00 | 26.38 | O |
| HETATM | 2510 | O | HOH | W | 157 | −15.098 | 4.994 | −20.108 | 1.00 | 30.09 | O |
| HETATM | 2511 | O | HOH | W | 158 | −40.304 | 25.037 | 6.932 | 1.00 | 29.28 | O |
| HETATM | 2512 | O | HOH | W | 159 | −19.654 | 42.452 | −11.933 | 1.00 | 28.67 | O |
| HETATM | 2513 | O | HOH | W | 160 | 7.165 | 33.655 | −14.239 | 1.00 | 29.40 | O |
| HETATM | 2514 | O | HOH | W | 161 | −29.918 | 4.810 | −15.685 | 1.00 | 30.16 | O |
| HETATM | 2515 | O | HOH | W | 162 | 10.935 | 23.184 | −6.110 | 1.00 | 32.43 | O |
| HETATM | 2516 | O | HOH | W | 163 | −26.145 | 2.186 | 1.054 | 1.00 | 36.44 | O |
| HETATM | 2517 | O | HOH | W | 164 | −34.339 | 6.200 | −6.038 | 1.00 | 31.60 | O |
| HETATM | 2518 | O | HOH | W | 165 | −7.577 | 23.852 | 11.873 | 1.00 | 37.15 | O |
| HETATM | 2519 | O | HOH | W | 166 | −28.374 | 17.766 | 15.757 | 1.00 | 33.08 | O |
| HETATM | 2520 | O | HOH | W | 167 | −8.878 | 30.353 | 10.450 | 1.00 | 33.65 | O |
| HETATM | 2521 | O | HOH | W | 168 | −39.240 | 24.455 | 13.603 | 1.00 | 32.18 | O |
| HETATM | 2522 | O | HOH | W | 169 | −5.259 | 32.467 | −14.521 | 1.00 | 30.28 | O |
| HETATM | 2523 | O | HOH | W | 170 | −19.002 | 44.014 | −6.429 | 1.00 | 36.88 | O |
| HETATM | 2524 | O | HOH | W | 171 | −41.472 | 23.045 | −1.746 | 1.00 | 34.68 | O |
| HETATM | 2525 | O | HOH | W | 172 | −41.240 | 17.380 | −0.287 | 1.00 | 30.69 | O |
| HETATM | 2526 | O | HOH | W | 173 | −18.871 | 43.325 | −2.077 | 1.00 | 32.89 | O |
| HETATM | 2527 | O | HOH | W | 174 | −15.823 | 41.421 | 2.253 | 1.00 | 29.64 | O |
| HETATM | 2528 | O | HOH | W | 175 | −7.050 | 21.485 | −11.124 | 1.00 | 32.96 | O |
| HETATM | 2529 | O | HOH | W | 176 | −37.741 | 26.386 | −1.056 | 1.00 | 29.25 | O |
| HETATM | 2530 | O | HOH | W | 177 | −37.633 | 14.168 | 12.267 | 1.00 | 41.58 | O |
| HETATM | 2531 | O | HOH | W | 178 | −36.152 | 30.566 | 14.397 | 1.00 | 32.08 | O |
| HETATM | 2532 | O | HOH | W | 179 | −16.547 | 10.926 | −22.860 | 1.00 | 29.03 | O |
| HETATM | 2533 | O | HOH | W | 180 | −41.727 | 23.706 | 9.092 | 1.00 | 33.88 | O |
| HETATM | 2534 | O | HOH | W | 181 | 6.999 | 23.263 | −12.013 | 1.00 | 36.81 | O |
| HETATM | 2535 | O | HOH | W | 182 | −17.044 | 8.041 | −22.415 | 1.00 | 38.12 | O |

TABLE 5-continued (Table 5 discloses SEQ ID NO: 10):

| HETATM | 2536 | O | HOH | W | 183 | −35.338 | 12.042 | 10.329 | 1.00 | 31.94 | O |
|---|---|---|---|---|---|---|---|---|---|---|---|
| HETATM | 2537 | O | HOH | W | 184 | 2.050 | 23.137 | −12.328 | 1.00 | 30.75 | O |
| HETATM | 2538 | O | HOH | W | 185 | −19.726 | 45.933 | −2.467 | 1.00 | 38.74 | O |
| HETATM | 2539 | O | HOH | W | 186 | −0.301 | 9.788 | −9.818 | 1.00 | 33.75 | O |
| HETATM | 2540 | O | HOH | W | 187 | −5.231 | 11.780 | 14.591 | 1.00 | 34.83 | O |
| HETATM | 2541 | O | HOH | W | 188 | −14.916 | 41.932 | 5.514 | 1.00 | 41.07 | O |
| HETATM | 2542 | O | HOH | W | 189 | −42.696 | 19.572 | −0.424 | 1.00 | 32.59 | O |
| HETATM | 2543 | O | HOH | W | 190 | −0.895 | 14.955 | 4.198 | 1.00 | 36.30 | O |
| HETATM | 2544 | O | HOH | W | 191 | −18.995 | 3.659 | −13.597 | 1.00 | 34.12 | O |
| HETATM | 2545 | O | HOH | W | 192 | −37.998 | 28.389 | 15.014 | 1.00 | 31.37 | O |
| HETATM | 2546 | O | HOH | W | 193 | −30.890 | 10.641 | 13.026 | 1.00 | 32.22 | O |
| HETATM | 2547 | O | HOH | W | 194 | −11.626 | 11.766 | −21.687 | 1.00 | 36.98 | O |
| HETATM | 2548 | O | HOH | W | 195 | −14.658 | 39.550 | −8.121 | 1.00 | 38.81 | O |
| HETATM | 2549 | O | HOH | W | 196 | −29.019 | 13.051 | 14.830 | 1.00 | 36.98 | O |
| HETATM | 2550 | O | HOH | W | 197 | −4.504 | 18.598 | −10.348 | 1.00 | 38.67 | O |
| HETATM | 2551 | O | HOH | W | 198 | −0.549 | 14.853 | −12.387 | 1.00 | 44.66 | O |
| HETATM | 2552 | O | HOH | W | 199 | −4.956 | 22.211 | −15.525 | 1.00 | 36.99 | O |
| HETATM | 2553 | O | HOH | W | 200 | −4.889 | 15.947 | −10.022 | 1.00 | 35.93 | O |
| HETATM | 2554 | O | HOH | W | 201 | −23.924 | 21.128 | −22.907 | 1.00 | 33.50 | O |
| HETATM | 2555 | O | HOH | W | 202 | −15.047 | 33.244 | −10.368 | 1.00 | 35.92 | O |
| HETATM | 2556 | O | HOH | W | 203 | −38.527 | 11.133 | 10.261 | 1.00 | 37.83 | O |
| HETATM | 2557 | O | HOH | W | 204 | −9.009 | 31.981 | −16.860 | 1.00 | 31.39 | O |
| HETATM | 2558 | O | HOH | W | 205 | −38.191 | 21.671 | 15.013 | 1.00 | 36.15 | O |
| HETATM | 2559 | O | HOH | W | 206 | −18.868 | 10.333 | −23.932 | 1.00 | 46.13 | O |
| HETATM | 2560 | O | HOH | W | 207 | −35.132 | 25.919 | −6.614 | 1.00 | 52.07 | O |
| HETATM | 2561 | O | HOH | W | 208 | −27.841 | 21.763 | −15.855 | 1.00 | 41.85 | O |
| HETATM | 2562 | O | HOH | W | 209 | −34.644 | 43.404 | −1.444 | 1.00 | 38.81 | O |
| HETATM | 2563 | O | HOH | W | 210 | −30.201 | 3.894 | −11.360 | 1.00 | 37.63 | O |
| HETATM | 2564 | O | HOH | W | 211 | −22.748 | 49.399 | −4.251 | 1.00 | 36.11 | O |
| HETATM | 2565 | O | HOH | W | 212 | −1.483 | 14.264 | 8.431 | 1.00 | 41.49 | O |
| HETATM | 2566 | O | HOH | W | 213 | −23.051 | 11.708 | −21.920 | 1.00 | 36.32 | O |
| HETATM | 2567 | O | HOH | W | 214 | 1.620 | 18.299 | 2.516 | 1.00 | 40.18 | O |
| HETATM | 2568 | O | HOH | W | 215 | −24.103 | 43.355 | −12.751 | 1.00 | 37.49 | O |
| HETATM | 2569 | O | HOH | W | 216 | −26.738 | 0.134 | −2.192 | 1.00 | 40.25 | O |
| HETATM | 2570 | O | HOH | W | 217 | 11.242 | 21.332 | −4.106 | 1.00 | 38.90 | O |
| HETATM | 2571 | O | HOH | W | 218 | −14.341 | 33.661 | 14.752 | 1.00 | 43.39 | O |
| HETATM | 2572 | O | HOH | W | 219 | −42.307 | 15.549 | 8.867 | 1.00 | 48.18 | O |
| HETATM | 2573 | O | HOH | W | 220 | −36.432 | 28.737 | −0.897 | 1.00 | 39.64 | O |
| HETATM | 2574 | O | HOH | W | 221 | −25.417 | 28.494 | −16.695 | 1.00 | 29.40 | O |
| HETATM | 2575 | O | HOH | W | 222 | −19.511 | 43.409 | 6.951 | 1.00 | 28.17 | O |
| HETATM | 2576 | O | HOH | W | 223 | −10.123 | 16.512 | −24.639 | 1.00 | 31.70 | O |
| HETATM | 2577 | O | HOH | W | 224 | −25.245 | 45.166 | −11.086 | 1.00 | 29.38 | O |
| HETATM | 2578 | O | HOH | W | 225 | −23.616 | 45.957 | 4.604 | 1.00 | 46.22 | O |
| HETATM | 2579 | O | HOH | W | 226 | −4.587 | 19.737 | −15.634 | 1.00 | 37.60 | O |
| HETATM | 2580 | O | HOH | W | 227 | −24.137 | 7.274 | −21.752 | 1.00 | 39.86 | O |
| HETATM | 2581 | O | HOH | W | 228 | −12.824 | 13.338 | 18.692 | 1.00 | 35.98 | O |
| HETATM | 2582 | O | HOH | W | 229 | −0.643 | 15.774 | −0.049 | 1.00 | 38.98 | O |
| HETATM | 2583 | O | HOH | W | 230 | −19.204 | 39.608 | 13.339 | 1.00 | 44.88 | O |
| HETATM | 2584 | O | HOH | W | 231 | −40.196 | 18.266 | 13.870 | 1.00 | 39.93 | O |
| HETATM | 2585 | O | HOH | W | 232 | −18.669 | 36.100 | 15.012 | 1.00 | 40.93 | O |
| HETATM | 2586 | O | HOH | W | 233 | −29.410 | 26.628 | −9.566 | 1.00 | 40.47 | O |
| HETATM | 2587 | O | HOH | W | 234 | −30.809 | 34.598 | −7.203 | 1.00 | 42.41 | O |
| HETATM | 2588 | O | HOH | W | 235 | −22.479 | 15.485 | 19.837 | 1.00 | 46.47 | O |
| HETATM | 2589 | O | HOH | W | 236 | −22.471 | 4.871 | 16.342 | 1.00 | 44.82 | O |
| HETATM | 2590 | O | HOH | W | 237 | −34.347 | 29.636 | −4.151 | 1.00 | 41.68 | O |
| HETATM | 2591 | O | HOH | W | 238 | −36.466 | 16.190 | −8.418 | 1.00 | 38.78 | O |
| HETATM | 2592 | O | HOH | W | 239 | −17.832 | 41.337 | −3.943 | 1.00 | 40.59 | O |
| HETATM | 2593 | O | HOH | W | 240 | −5.599 | 3.373 | 1.035 | 1.00 | 37.39 | O |
| HETATM | 2594 | O | HOH | W | 241 | −31.315 | 43.021 | 6.641 | 1.00 | 44.12 | O |
| HETATM | 2595 | O | HOH | W | 242 | −0.730 | 9.262 | −1.771 | 1.00 | 40.88 | O |
| HETATM | 2596 | O | HOH | W | 243 | 4.759 | 11.224 | −6.950 | 1.00 | 47.42 | O |
| HETATM | 2597 | O | HOH | W | 244 | −10.999 | 3.648 | −16.952 | 1.00 | 46.46 | O |
| HETATM | 2598 | O | HOH | W | 245 | −5.652 | 21.836 | 12.464 | 1.00 | 42.81 | O |
| HETATM | 2599 | O | HOH | W | 246 | −14.550 | 10.917 | 18.018 | 1.00 | 41.09 | O |
| HETATM | 2600 | O | HOH | W | 247 | −4.947 | 4.565 | −7.195 | 1.00 | 46.09 | O |
| HETATM | 2601 | O | HOH | W | 248 | −24.134 | 51.667 | −5.997 | 1.00 | 46.36 | O |
| HETATM | 2602 | O | HOH | W | 249 | −37.327 | 13.552 | −6.997 | 1.00 | 53.05 | O |
| HETATM | 2603 | O | HOH | W | 250 | 0.506 | 22.694 | 3.267 | 1.00 | 47.90 | O |
| HETATM | 2604 | O | HOH | W | 251 | −13.591 | 16.310 | −24.807 | 1.00 | 50.85 | O |
| HETATM | 2605 | O | HOH | W | 252 | −9.018 | 7.158 | −17.757 | 1.00 | 46.53 | O |
| HETATM | 2606 | O | HOH | W | 253 | −26.754 | 28.420 | −10.600 | 1.00 | 29.06 | O |
| HETATM | 2607 | O | HOH | W | 254 | −18.410 | 44.305 | 9.205 | 1.00 | 29.63 | O |
| HETATM | 2608 | O | HOH | W | 255 | −32.584 | 10.434 | −11.160 | 1.00 | 41.22 | O |
| HETATM | 2609 | O | HOH | W | 256 | −16.091 | 1.690 | 16.162 | 1.00 | 36.96 | O |
| HETATM | 2610 | O | HOH | W | 257 | −4.505 | 9.349 | 11.016 | 1.00 | 39.86 | O |
| HETATM | 2611 | O | HOH | W | 258 | −40.947 | 18.159 | −3.757 | 1.00 | 43.42 | O |
| HETATM | 2612 | O | HOH | W | 259 | 0.000 | 24.141 | −15.150 | 1.00 | 38.32 | O |
| HETATM | 2613 | O | HOH | W | 260 | −44.582 | 24.137 | 6.565 | 1.00 | 51.92 | O |

TABLE 5-continued (Table 5 discloses SEQ ID NO: 10):

| HETATM | 2614 | O | HOH | W | 261 | −35.232 | 13.693 | −8.515 | 1.00 | 55.39 | O |
|---|---|---|---|---|---|---|---|---|---|---|---|
| HETATM | 2615 | O | HOH | W | 262 | −29.872 | 45.235 | 6.694 | 1.00 | 17.67 | O |
| HETATM | 2616 | O | HOH | W | 263 | −27.113 | 45.109 | −0.458 | 1.00 | 22.65 | O |
| HETATM | 2617 | O | HOH | W | 264 | −25.323 | 47.035 | 2.382 | 1.00 | 28.79 | O |
| HETATM | 2618 | O | HOH | W | 265 | 0.000 | 26.981 | −15.150 | 1.00 | 32.82 | O |
| HETATM | 2619 | O | HOH | W | 266 | −18.156 | 20.703 | −27.017 | 1.00 | 35.61 | O |
| HETATM | 2620 | O | HOH | W | 267 | −37.722 | 10.433 | −4.365 | 1.00 | 45.06 | O |
| HETATM | 2621 | O | HOH | W | 268 | −16.805 | 35.390 | −9.635 | 1.00 | 40.40 | O |
| HETATM | 2622 | O | HOH | W | 269 | −16.918 | 18.529 | −26.281 | 1.00 | 39.96 | O |
| HETATM | 2623 | O | HOH | W | 270 | −13.491 | 38.406 | −6.271 | 1.00 | 39.29 | O |
| HETATM | 2624 | O | HOH | W | 271 | −8.148 | 20.081 | 11.966 | 1.00 | 44.03 | O |
| HETATM | 2625 | O | HOH | W | 272 | −6.821 | 1.644 | 3.126 | 1.00 | 40.41 | O |
| HETATM | 2626 | O | HOH | W | 273 | −18.313 | 5.740 | −22.619 | 1.00 | 47.63 | O |
| HETATM | 2627 | O | HOH | W | 274 | −13.103 | 2.644 | −18.422 | 1.00 | 45.18 | O |
| HETATM | 2628 | O | HOH | W | 275 | −0.862 | 26.991 | 8.197 | 1.00 | 49.93 | O |
| HETATM | 2629 | O | HOH | W | 276 | −12.480 | 35.715 | 13.919 | 1.00 | 48.53 | O |
| HETATM | 2630 | O | HOH | W | 277 | −6.665 | 2.991 | −5.698 | 1.00 | 47.86 | O |
| HETATM | 2631 | O | HOH | W | 278 | −6.235 | 34.850 | −10.896 | 1.00 | 49.10 | O |
| HETATM | 2632 | O | HOH | W | 279 | −15.224 | 26.534 | 14.107 | 1.00 | 34.50 | O |
| HETATM | 2633 | O | HOH | W | 280 | −26.785 | 17.717 | −14.048 | 1.00 | 32.29 | O |
| HETATM | 2634 | O | HOH | W | 281 | −10.359 | 3.127 | −14.054 | 1.00 | 35.76 | O |
| HETATM | 2635 | O | HOH | W | 282 | −9.964 | 34.823 | −10.668 | 1.00 | 36.66 | O |
| HETATM | 2636 | O | HOH | W | 283 | −10.871 | 37.987 | 5.889 | 1.00 | 39.81 | O |
| HETATM | 2637 | O | HOH | W | 284 | −26.828 | 12.543 | −16.696 | 1.00 | 39.23 | O |
| HETATM | 2638 | O | HOH | W | 285 | −28.134 | 16.073 | −12.715 | 1.00 | 39.10 | O |
| HETATM | 2639 | O | HOH | W | 286 | −8.308 | 33.139 | −8.609 | 1.00 | 41.47 | O |
| HETATM | 2640 | O | HOH | W | 287 | 4.685 | 22.519 | −12.295 | 1.00 | 43.15 | O |
| HETATM | 2641 | O | HOH | W | 288 | −6.455 | 17.658 | −13.209 | 1.00 | 43.22 | O |
| HETATM | 2642 | O | HOH | W | 289 | −29.264 | 4.527 | 11.185 | 1.00 | 38.52 | O |
| HETATM | 2643 | O | HOH | W | 290 | 1.948 | 31.540 | −15.946 | 1.00 | 42.96 | O |
| HETATM | 2644 | O | HOH | W | 291 | −28.001 | 47.360 | −9.030 | 1.00 | 42.25 | O |
| HETATM | 2645 | O | HOH | W | 292 | −21.578 | 9.488 | 15.696 | 1.00 | 48.22 | O |
| HETATM | 2646 | O | HOH | W | 293 | −36.209 | 19.343 | −11.413 | 1.00 | 43.75 | O |
| HETATM | 2647 | O | HOH | W | 294 | 0.319 | 29.212 | 4.405 | 1.00 | 42.45 | O |
| HETATM | 2648 | O | HOH | W | 295 | −43.593 | 18.340 | 3.119 | 1.00 | 44.30 | O |
| HETATM | 2649 | O | HOH | W | 296 | −8.690 | 9.796 | −18.360 | 1.00 | 48.63 | O |
| HETATM | 2650 | O | HOH | W | 297 | −13.183 | 20.728 | −23.025 | 1.00 | 42.14 | O |
| HETATM | 2651 | O | HOH | W | 298 | −28.554 | 16.113 | −23.692 | 1.00 | 44.64 | O |
| HETATM | 2652 | O | HOH | W | 299 | −11.671 | 39.418 | 10.822 | 1.00 | 44.26 | O |
| HETATM | 2653 | O | HOH | W | 300 | −7.956 | 4.305 | −13.456 | 1.00 | 46.03 | O |
| HETATM | 2654 | O | HOH | W | 301 | −39.821 | 23.326 | 16.353 | 1.00 | 43.78 | O |
| HETATM | 2655 | O | HOH | W | 302 | −13.526 | 31.064 | 14.928 | 1.00 | 53.12 | O |
| HETATM | 2656 | O | HOH | W | 303 | −17.878 | 33.786 | 16.873 | 1.00 | 50.15 | O |
| HETATM | 2657 | O | HOH | W | 304 | −33.678 | 7.362 | −8.182 | 1.00 | 49.39 | O |
| HETATM | 2658 | O | HOH | W | 305 | −11.597 | 39.294 | −8.859 | 1.00 | 53.94 | O |
| HETATM | 2659 | O | HOH | W | 306 | 2.882 | 29.239 | 3.191 | 1.00 | 45.89 | O |
| HETATM | 2660 | O | HOH | W | 307 | −38.649 | 20.156 | −7.082 | 1.00 | 49.36 | O |
| HETATM | 2661 | O | HOH | W | 308 | −40.591 | 26.658 | 0.275 | 1.00 | 43.29 | O |
| HETATM | 2662 | O | HOH | W | 309 | −6.537 | 4.311 | 13.825 | 1.00 | 47.40 | O |
| HETATM | 2663 | O | HOH | W | 310 | −5.558 | 35.013 | −13.517 | 1.00 | 48.80 | O |
| HETATM | 2664 | O | HOH | W | 311 | −28.826 | 11.425 | −15.322 | 1.00 | 49.38 | O |
| HETATM | 2665 | O | HOH | W | 312 | −38.320 | 28.225 | 17.606 | 1.00 | 55.51 | O |
| HETATM | 2666 | O | HOH | W | 313 | −23.593 | 4.828 | 13.752 | 1.00 | 27.36 | O |
| HETATM | 2667 | O | HOH | W | 314 | −23.921 | 26.545 | −16.243 | 1.00 | 34.27 | O |
| HETATM | 2668 | O | HOH | W | 315 | −22.322 | 11.653 | 14.462 | 1.00 | 34.83 | O |
| HETATM | 2669 | O | HOH | W | 316 | −12.651 | 34.045 | −11.232 | 1.00 | 31.40 | O |
| HETATM | 2670 | O | HOH | W | 317 | −11.298 | 29.991 | 11.215 | 1.00 | 37.94 | O |
| HETATM | 2671 | O | HOH | W | 318 | −22.524 | 14.427 | −23.824 | 1.00 | 34.38 | O |
| HETATM | 2672 | O | HOH | W | 319 | −17.894 | 26.130 | 16.911 | 1.00 | 40.42 | O |
| HETATM | 2673 | O | HOH | W | 320 | −30.095 | 30.303 | 9.084 | 1.00 | 43.47 | O |
| HETATM | 2674 | O | HOH | W | 321 | −13.730 | 28.546 | 14.642 | 1.00 | 45.76 | O |
| HETATM | 2675 | O | HOH | W | 322 | 0.192 | 20.485 | 4.996 | 1.00 | 42.15 | O |
| HETATM | 2676 | O | HOH | W | 323 | 8.773 | 19.721 | −2.795 | 1.00 | 41.00 | O |
| HETATM | 2677 | O | HOH | W | 324 | −24.325 | 35.749 | −12.402 | 1.00 | 41.84 | O |
| HETATM | 2678 | O | HOH | W | 325 | −24.805 | 13.589 | −22.690 | 1.00 | 42.74 | O |
| HETATM | 2679 | O | HOH | W | 326 | −16.673 | 23.836 | 17.169 | 1.00 | 42.32 | O |
| HETATM | 2680 | O | HOH | W | 327 | −26.618 | 15.414 | −14.762 | 1.00 | 52.87 | O |
| HETATM | 2681 | O | HOH | W | 328 | −17.876 | 41.703 | 11.298 | 1.00 | 40.21 | O |
| HETATM | 2682 | O | HOH | W | 329 | 2.710 | 12.479 | −3.493 | 1.00 | 41.71 | O |
| HETATM | 2683 | O | HOH | W | 330 | −40.522 | 22.831 | 11.667 | 1.00 | 40.68 | O |
| HETATM | 2684 | O | HOH | W | 331 | −5.318 | 8.894 | −11.975 | 1.00 | 45.24 | O |
| HETATM | 2685 | O | HOH | W | 332 | 6.465 | 34.844 | −5.820 | 1.00 | 41.37 | O |
| HETATM | 2686 | O | HOH | W | 333 | −7.294 | 7.847 | −13.196 | 1.00 | 46.21 | O |
| HETATM | 2687 | O | HOH | W | 334 | −27.575 | −1.555 | −9.482 | 1.00 | 43.31 | O |
| HETATM | 2688 | O | HOH | W | 335 | −16.302 | 44.157 | 6.300 | 1.00 | 50.65 | O |
| HETATM | 2689 | O | HOH | W | 336 | 7.324 | 25.112 | −0.042 | 1.00 | 46.30 | O |
| HETATM | 2690 | O | HOH | W | 337 | −25.386 | 14.745 | −27.433 | 1.00 | 48.90 | O |
| HETATM | 2691 | O | HOH | W | 338 | −11.898 | 7.106 | −19.877 | 1.00 | 48.25 | O |

TABLE 5-continued (Table 5 discloses SEQ ID NO: 10):

| | | | | | | | | | | |
|---|---|---|---|---|---|---|---|---|---|---|
| HETATM | 2692 | O | HOH | W | 339 | −6.543 | 5.813 | −9.614 | 1.00 | 50.85 | O |
| HETATM | 2693 | O | HOH | W | 340 | −24.469 | 1.696 | −2.733 | 1.00 | 49.67 | O |
| HETATM | 2694 | O | HOH | W | 341 | −25.761 | 37.027 | −10.672 | 1.00 | 43.85 | O |
| HETATM | 2695 | O | HOH | W | 342 | −37.486 | 7.329 | −1.731 | 1.00 | 48.83 | O |
| HETATM | 2696 | O | HOH | W | 343 | −17.291 | 4.085 | 16.803 | 1.00 | 48.72 | O |
| HETATM | 2697 | O | HOH | W | 344 | −14.036 | 26.435 | −22.926 | 1.00 | 43.49 | O |
| HETATM | 2698 | O | HOH | W | 345 | 0.692 | 30.664 | 2.086 | 1.00 | 53.06 | O |
| HETATM | 2699 | O | HOH | W | 346 | −41.805 | 14.047 | −3.004 | 1.00 | 45.34 | O |
| HETATM | 2700 | O | HOH | W | 347 | −5.313 | 18.738 | 12.526 | 1.00 | 56.10 | O |
| HETATM | 2701 | O | HOH | W | 348 | −15.979 | 2.222 | −18.286 | 1.00 | 52.97 | O |
| HETATM | 2702 | O | HOH | W | 349 | 12.845 | 27.550 | 2.215 | 1.00 | 51.89 | O |
| HETATM | 2703 | O | HOH | W | 350 | −24.703 | 2.114 | 13.280 | 1.00 | 52.54 | O |
| HETATM | 2704 | O | HOH | W | 351 | −13.629 | 8.385 | 17.755 | 1.00 | 53.31 | O |
| HETATM | 2705 | O | HOH | W | 352 | 0.600 | 10.756 | 1.065 | 1.00 | 52.20 | O |
| HETATM | 2706 | O | HOH | W | 353 | −6.584 | 3.294 | −8.664 | 1.00 | 58.25 | O |
| HETATM | 2707 | O | HOH | W | 354 | −19.526 | 1.509 | −15.069 | 1.00 | 58.64 | O |
| HETATM | 2708 | O | HOH | W | 355 | −37.744 | 8.976 | −6.842 | 1.00 | 49.38 | O |
| HETATM | 2709 | O | HOH | W | 356 | 11.571 | 31.022 | 2.199 | 1.00 | 49.80 | O |
| HETATM | 2710 | O | HOH | W | 357 | −5.947 | 36.986 | −4.732 | 1.00 | 50.31 | O |
| HETATM | 2711 | O | HOH | W | 358 | −15.405 | 41.052 | 11.474 | 1.00 | 51.49 | O |
| HETATM | 2712 | O | HOH | W | 359 | −12.833 | 40.449 | −4.727 | 1.00 | 51.48 | O |
| HETATM | 2713 | O | HOH | W | 360 | −5.438 | 1.935 | −3.550 | 1.00 | 50.92 | O |
| HETATM | 2714 | O | HOH | W | 361 | −10.249 | 0.894 | −12.528 | 1.00 | 59.44 | O |
| HETATM | 2715 | O | HOH | W | 362 | −31.963 | 40.849 | 5.308 | 1.00 | 56.17 | O |
| HETATM | 2716 | O | HOH | W | 363 | −20.396 | 19.502 | −28.110 | 1.00 | 57.97 | O |
| HETATM | 2717 | O | HOH | W | 364 | −38.545 | 15.892 | −6.873 | 1.00 | 53.86 | O |
| HETATM | 2718 | O | HOH | W | 365 | −8.651 | 36.740 | 4.818 | 1.00 | 56.42 | O |
| HETATM | 2719 | O | HOH | W | 366 | −16.900 | 45.179 | −0.086 | 1.00 | 57.28 | O |
| HETATM | 2720 | O | HOH | W | 367 | −15.600 | 42.705 | −0.411 | 1.00 | 53.55 | O |
| HETATM | 2721 | O | HOH | W | 368 | −1.122 | 22.193 | −13.088 | 1.00 | 50.00 | O |
| HETATM | 2722 | O | HOH | W | 369 | −3.015 | 2.725 | 5.944 | 1.00 | 49.17 | O |
| HETATM | 2723 | O | HOH | W | 370 | −32.840 | 41.664 | 3.046 | 1.00 | 55.05 | O |
| HETATM | 2724 | O | HOH | W | 371 | −31.332 | 6.082 | 11.720 | 1.00 | 55.05 | O |
| HETATM | 2725 | O | HOH | W | 372 | −5.263 | 32.737 | 9.359 | 1.00 | 53.35 | O |
| HETATM | 2726 | O | HOH | W | 373 | −17.185 | 11.511 | 17.118 | 1.00 | 55.25 | O |
| HETATM | 2727 | O | HOH | W | 374 | −9.075 | 41.015 | −9.468 | 1.00 | 55.28 | O |
| HETATM | 2728 | O | HOH | W | 375 | −2.683 | 7.946 | 9.076 | 1.00 | 55.07 | O |
| HETATM | 2729 | O | HOH | W | 376 | 7.720 | 16.995 | −3.341 | 1.00 | 52.87 | O |
| HETATM | 2730 | O | HOH | W | 377 | −4.253 | 13.777 | −12.953 | 1.00 | 51.97 | O |
| END | | | | | | | | | | | |

REFERENCES

Patents

U.S. Pat. No. 4,906,122A. Coupling for molecular models
U.S. Pat. No. 5,030,103A. Dynamic molecular model
U.S. Pat. No. 5,200,911A. Method for modelling the electron density of a crystal
U.S. Pat. No. 5,365,456A. Method for modelling the electron density of a crystal
U.S. Pat. No. 5,583,973A. Molecular modeling method and system
U.S. Pat. No. 5,612,894A. System and method for molecular modeling utilizing a sensitivity factor
U.S. Pat. No. 5,733,720A. Genetically engineered cell lines for detecting infectious herpesvirus and methods therefor
U.S. Pat. No. 5,763,263A. Method and apparatus for producing position addressable combinatorial libraries
U.S. Pat. No. 5,942,428A. Crystals of the tyrosine kinase domain of non-insulin receptor tyrosine kinases
U.S. Pat. No. 5,994,503A. Nucleotide and protein sequences of lats genes and methods based thereon
U.S. Pat. No. 5,998,593A. Fluorescent enzyme substrates
U.S. Pat. No. 6,037,117A. Methods using the *Staphylococcus aureus* glycyl tRNA synthetase crystalline structure
U.S. Pat. No. 6,071,700A. Heterologous polypeptide production in the absence of nonsense-mediated mRNA decay functions
U.S. Pat. No. 6,075,014A. Inhibitors of &bgr; -lactamases and uses therefor
U.S. Pat. No. 6,075,123A. Cyclin-C variants, and diagnostic and therapeutic uses thereof
U.S. Pat. No. 6,080,576A. Vectors for gene trapping and gene activation
U.S. Pat. No. 6,093,573A. Three-dimensional structure of bactericidal/permeability-increasing protein (BPI)
U.S. Pat. No. 6,172,262B1. Amphiphilic agents for membrane protein solubilization

Other References

Adams, P. D., K. Gopal, et al. (2004). "Recent developments in the PHENIX software for automated crystallographic structure determination." *J Synchrotron Radiat* 11 (Pt 1): 53-5.
Adams, P. D., R. W. Grosse-Kunstleve, et al. (2002). "PHENIX: building new software for automated crystallographic structure determination." *Acta Crystallogr D Biol Crystallogr* 58(Pt 11): 1948-54.
Altschul, S. F. (1993). "A protein alignment scoring system sensitive at all evolutionary distances." *J. Mol. Evol.* 36: 290-300.
Altschul, S. F., M. S. Boguski, et al. (1994). "Issues in searching molecular sequence databases." *Nature Genetics* 6: 119-129.
Altschul, S. F., W. Gish, et al. (1990). "Basic local alignment search tool." *J Mol Biol* 215(3): 403-10.

Bacon, D. J. and J. Moult (1992). "Docking by Least-squares Fitting of Molecular Surface Patterns." *J. Mol. Biol.* 225: 849-858.

Bartlett, P. A., G. T. Shea, et al. (1989). "CAVEAT: A Program to Facilitate the Structure-Derived Design of Biologically Active Molecules." *In Molecular Recognition in Chemical and Biological Problems, Special Pub., Royal Chem. Soc.* 78: 82-196.

Bohm, H.-J. (1992). "The Computer Program LUDI: A New Method for the De Novo Design of Enzyme Inhibitors." *J. Computer-Aided Molecular Design* 6: 61-78.

Boutselakis, H., D. Dimitropoulos, et al. (2003). "E-MSD: the European Bioinformatics Institute Macromolecular Structure Database." *Nucleic Acids Res* 31(1): 458-62.

Bradford, M. M. (1976). "A rapid and sensitive method for the quantitation of microgram quantities of protein utilizing the principle of protein-dye binding." *Anal Biochem* 72: 248-54.

Brady, L., A. M. Brzozowski, et al. (1990). "A serine protease triad forms the catalytic centre of a triacylglycerol lipase." *Nature* 343(6260): 767-70.

Brunger, A. T. (1993). *X-Flor Version 3.1: A system for X-ray crystallography and NMR*. New Haven, Conn., Yale Univ. Pr.

Brzozowski, A. M., U. Derewenda, et al. (1991). "A model for interfacial activation in lipases from the structure of a fungal lipase-inhibitor complex." *Nature* 351(6326): 491-4.

Campbell (1984). *Biological Spectroscopy*. Menlo Park, Calif., The Benjamin/Cummings Publishing Co., Inc.

Cantor, C. R. and P. R. Schimmel (1980). *Biophysical Chemistry, Part II, "Techniques for the Study of Biological Structure and Function"*, W.H. Freeman & Co.

Carriere, F., K. Thirstrup, et al. (1997). "Pancreatic lipase structure-function relationships by domain exchange." *Biochemistry* 36(1): 239-48.

Chahinian, H., L. Nini, et al. (2002). "Distinction between esterases and lipases: a kinetic study with vinyl esters and TAG." *Lipids* 37(7): 653-62.

Cohen (Editor), N.C. (1996). *Guidebook on Molecular Modeling in Drug Design*, Academic Press.

Cohen, N., J. Blaney, et al. (1990). "Molecular Modeling Software and Methods for Medicinal Chemistry." *J. Med. Chem.* 33: 883-894.

Crowther, J. R. (1995). *ELISA: Theory and Practice (Methods in Molecular Biology)*, Humana Press.

Delano, W. L. (2002). The PyMOL Molecular Graphics System. Palo Alto, Calif., USA.

Devlin (Editor), J. P. (1998). *In High Throughput Screening: The Discovery of Bioactive Substances*. New York, Marcel Dekker Inc.

Dinh, T. P., T. F. Freund, et al. (2002). "A role for monoglyceride lipase in 2-arachidonoylglycerol inactivation." *Chem Phys Lipids* 121(1-2): 149-58.

Dinh, T. P., S. Kathuria, et al. (2004). "RNA interference suggests a primary role for monoacylglycerol lipase in the degradation of the endocannabinoid 2-arachidonoylglycerol." *Mol Pharmacol* 66(5): 1260-4.

Drenth, J. (1999). *Principles of Protein X-ray Crystallography (Springer Advanced Texts in Chemistry)*. Berlin, Springer Verlag.

Dugi, K. A., H. L. Dichek, et al. (1995). "Human hepatic and lipoprotein lipase: the loop covering the catalytic site mediates lipase substrate specificity." *J Biol Chem* 270(43): 25396-401.

Dugi, K. A., H. L. Dichek, et al. (1992). "Human lipoprotein lipase: the loop covering the catalytic site is essential for interaction with lipid substrates." *J Biol Chem* 267(35): 25086-91.

Emsley, P. and K. Cowtan (2004). "Coot: model-building tools for molecular graphics." *Acta Crystallogr D Biol Crystallogr* 60(Pt 12 Pt 1): 2126-32.

Farquhar-Smith, W. P., M. Egertova, et al. (2000). "Cannabinoid CB(1) receptor expression in rat spinal cord." *Mol Cell Neurosci* 15(6): 510-21.

Faustinella, F., L. C. Smith, et al. (1992). "Functional topology of a surface loop shielding the catalytic center in lipoprotein lipase." *Biochemistry* 31(32): 7219-23.

Frisch, M. J., G. W. Trucks, et al. (1992). "Gaussian 92, Revision C." *Gaussian, Inc.*

Galiegue, S., S. Mary, et al. (1995). "Expression of central and peripheral cannabinoid receptors in human immune tissues and leukocyte subpopulations." *Eur J Biochem* 232 (1): 54-61.

Gans, W., A. Amann, et al. (1996). *Fundamental Principals of Molecular Modeling*, Plenum Pub. Corp.

Gonsiorek, W., C. Lunn, et al. (2000). "Endocannabinoid 2-arachidonyl glycerol is a full agonist through human type 2 cannabinoid receptor: antagonism by anandamide." *Mol Pharmacol* 57(5): 1045-50.

Goodford, P. J. (1985). "A Computational Procedure for Determining Energetically Favorable Binding Sites on Biologically Important Macromolecules." *J. Med. Chem.* 28: 849-857.

Goodsell, D. S, and A. J. Olsen (1990). "Automated Docking of Substrates to Proteins by Simulated Annealing." *Proteins: Structure. Function, and Genetics* 8: 195-202.

Guindon, J., J. Desroches, et al. (2007). "The antinociceptive effects of intraplantar injections of 2-arachidonoyl glycerol are mediated by cannabinoid CB2 receptors." *Br J Pharmacol* 150(6): 693-701.

Hanus, L., A. Breuer, et al. (1999). "HU-308: a specific agonist for CB(2), a peripheral cannabinoid receptor." *Proc Natl Acad Sci USA* 96(25): 14228-33.

Heikinheimo, P., A. Goldman, et al. (1999). "Of barn owls and bankers: a lush variety of alpha/beta hydrolases." *Structure* 7(6): R141-6.

Henikoff, J. G. (1992). "Amino acid substitution matrices from protein blocks." *Proc. Natl. Acad. Sci. USA* (89): 10915-10919.

Higgins, D. G., J. D. Thompson, et al. (1996). "Using CLUSTAL for multiple sequence alignments." *Methods Enzymol* 266: 383-402.

Hohmann, A. G. (2002). "Spinal and peripheral mechanisms of cannabinoid antinociception: behavioral, neurophysiological and neuroanatomical perspectives." *Chem Phys Lipids* 121(1-2): 173-90.

Hohmann, A. G., J. N. Farthing, et al. (2004). "Selective activation of cannabinoid CB2 receptors suppresses hyperalgesia evoked by intradermal capsaicin." *J Pharmacol Exp Ther* 308(2): 446-53.

Hohmann, A. G. and M. Herkenham (1999). "Cannabinoid receptors undergo axonal flow in sensory nerves." *Neuroscience* 92(4): 1171-5.

Hohmann, A. G., R. L. Suplita, et al. (2005). "An endocannabinoid mechanism for stress-induced analgesia." *Nature* 435(7045): 1108-12.

Holmquist, M. (2000). "Alpha/Beta-hydrolase fold enzymes: structures, functions and mechanisms." *Curr Protein Pept Sci* 1(2): 209-35.

Ibrahim, M. M., M. L. Rude, et al. (2006). "CB2 cannabinoid receptor mediation of antinociception." *Pain* 122(1-2): 36-42.

Ishikawa, E. (1999). *Ultrasensitive and rapid enzyme immunoassay, In: Laboratory Techniques in Biochemistry and Molecular Biology*. Amsterdam, Elsevier.

Kaneko, T., N. Tanaka, et al. (2005). "Crystal structures of RsbQ, a stress-response regulator in *Bacillus subtilis*." *Protein Sci* 14(2): 558-65.

Karlin, S, and S. F. Altschul (1990). "Methods for assessing the statistical significance of molecular sequence features by using general scoring schemes." *Proc. Natl. Acad. Sci. USA* 87: 2264-2268.

Karlsson, M., J. A. Contreras, et al. (1997). "cDNA cloning, tissue distribution, and identification of the catalytic triad of monoglyceride lipase. Evolutionary relationship to esterases, lysophospholipases, and haloperoxidases." *J Biol Chem* 272(43): 27218-23.

Karlsson, M., K. Reue, et al. (2001). "Exon-intron organization and chromosomal localization of the mouse monoglyceride lipase gene." *Gene* 272(1-2): 11-8.

Karlsson, M., H. Tornqvist, et al. (2000). "Expression, purification, and characterization of histidine-tagged mouse monoglyceride lipase from baculovirus-infected insect cells." *Protein Expr Purif* 18(3): 286-92.

Kemeny (Editor), D. M. and S. J. Challacombe (Editor) (1988). *Elisa and Other Solid Phase Immunoassays Theoretical and Practical Aspects*, New York, John Wiley and Sons.

Kemeny, D. M. (1991). *A Practical Guide to ELISA*, Pergamon Press.

Kuntz, I. D., J. M. Blaney, et al. (1982). "A geometric approach to macromolecule-ligand interactions." *J Mol Biol* 161(2): 269-88.

Lee, C. and K. Irizarry (2001). "The GeneMine system for genome/proteome annotation and collaborative data-mining." *IBM Systems Journal* 40(2).

Levitt, M. (1992). "Accurate modeling of protein conformation by automatic segment matching." *J Mol Biol* 226(2): 507-33.

Lipinski, C., F. Lombardo, et al. (1997). "Experimental and computational approaches to estimate solubility and permeability in drug discovery and development settings" *Advanced Drug Delivery Reviews* 23(1-3): 3-25.

Longenecker, K. L., S. M. Garrard, et al. (2001). "Protein crystallization by rational mutagenesis of surface residues: Lys to Ala mutations promote crystallization of RhoGDI." *Acta Crystallogr D Biol Crystallogr* 57(Pt 5): 679-88.

Makara, J. K., M. Mor, et al. (2005). "Selective inhibition of 2-AG hydrolysis enhances endocannabinoid signaling in hippocampus." *Nat Neurosci* 8(9): 1139-41.

Malan, T. P., Jr., M. M. Ibrahim, et al. (2001). "CB2 cannabinoid receptor-mediated peripheral antinociception." *Pain* 93(3): 239-45.

Malan, T. P., Jr., M. M. Ibrahim, et al. (2002). "Inhibition of pain responses by activation of CB(2) cannabinoid receptors." *Chem Phys Lipids* 121(1-2): 191-200.

Maresz, K., E. J. Carrier, et al. (2005). "Modulation of the cannabinoid CB2 receptor in microglial cells in response to inflammatory stimuli." *J Neurochem* 95(2): 437-45.

Martin, Y. C. (1992). "3D Database Searching in Drug Design." *J. Med. Chem.* 35: 2145-2154.

Mary Ann Liebert (Publishers), I. (1995). *The BIOTECHNOLOGY SOFTWARE DIRECTORY, A Buyer's Guide*. Larchmont, N.Y. Mary Ann Liebert, Inc., Publishers.

Mateja, A., Y. Devedjiev, et al. (2002). "The impact of Glu→Ala and Glu→Asp mutations on the crystallization properties of RhoGDI: the structure of RhoGDI at 1.3 A resolution." *Acta Crystallogr D Biol Crystallogr* 58(Pt 12): 1983-91.

Matsuda, L. A., S. J. Lolait, et al. (1990). "Structure of a cannabinoid receptor and functional expression of the cloned cDNA." *Nature* 346(6284): 561-4.

Matteucci and J. Caruthers (1981). *J. Am. Chem. Soc.* 103(3): 185-3191.

Mccoy, A. J., R. W. Grosse-Kunstleve, et al. (2007). "Phaser crystallographic software." *Journal of Applied Crystallography* 40(4): 658-674.

Meng, E. C., B. K. Shoichet, et al. (1992). "Automated docking with grid-based energy evaluation." *J. Comp. Chem.* 13: 505-524.

Miranker, A. and M. Karplus (1991). "Functionality Maps of Binding Sites: A Multiple Copy Simultaneous Search Method." *Proteins: Structure, Function and Genetics* 11: 29-34.

Munro, S., K. L. Thomas, et al. (1993). "Molecular characterization of a peripheral receptor for cannabinoids." *Nature* 365(6441): 61-5.

Navia, M. A. and M. A. Murcko (1992). "The Use of Structural Information in Drug Design." *Current Opinions in Structural Biology* 2: 202-210

Nini, L., L. Sarda, et al. (2001). "Lipase-catalysed hydrolysis of short-chain substrates in solution and in emulsion: a kinetic study." *Biochim Biophys Acta* 1534(1): 34-44.

Nishibata, Y. and A. Itai (1991). "Automatic creation of drug candidate structures based on receptor structure. Starting point for artificial lead generation." *Tetrahedron* 47: 8985-8990.

Norton, P. A. and J. M. Coffin (1985). "Bacterial beta-galactosidase as a marker of Rous sarcoma virus gene expression and replication." *Mol Cell Biol* 5(2): 281-90.

Ollis, D. L., E. Cheah, et al. (1992). "The alpha/beta hydrolase fold." *Protein Eng* 5(3): 197-211.

Otwinowski, Z. and W. Minor (1997). Processing of X-ray Diffraction Data Collected in Oscillation Mode. *Methods in Enzymology*. C. W. Carter and R. M. Sweet. New York, Academic Press. 276: 307-326.

Pantoliano, M. W., E. C. Petrella, et al. (2001). "High-density miniaturized thermal shift assays as a general strategy for drug discovery." *J Biomol Screen* 6(6): 429-40.

Quartilho, A., H. P. Mata, et al. (2003). "Inhibition of inflammatory hyperalgesia by activation of peripheral CB2 cannabinoid receptors." *Anesthesiology* 99(4): 955-60.

Rice, A. S., W. P. Farquhar-Smith, et al. (2002). "Endocannabinoids and pain: spinal and peripheral analgesia in inflammation and neuropathy." *Prostaglandins Leukot Essent Fatty Acids* 66(2-3): 243-56.

Richardson, J. D. (2000). "Cannabinoids modulate pain by multiple mechanisms of actions." *The Journal of Pain* 1(1): 2-14.

Richardson, J. D., S. Kilo, et al. (1998). "Cannabinoids reduce hyperalgesia and inflammation via interaction with peripheral CB1 receptors." *Pain* 75(1): 111-9.

Rossmann, M. G. (1972). *The molecular replacement method; a collection of papers on the use of non-crystallographic symmetry.*, Gordon & Breach, New York.

Rotstein, S. H. and M. A. Murcko (1993). "GroupBuild: a fragment-based method for de novo drug design." *J Med Chem* 36(12): 1700-10.

Roussel, A., S. Canaan, et al. (1999). "Crystal structure of human gastric lipase and model of lysosomal acid lipase, two lipolytic enzymes of medical interest." *J Biol Chem* 274(24): 16995-7002.

Roussel, A., N. Miled, et al. (2002). "Crystal structure of the open form of dog gastric lipase in complex with a phosphonate inhibitor." *J Biol Chem* 277(3): 2266-74.

Saario, S. M., A. Poso, et al. (2006). "Fatty acid amide hydrolase inhibitors from virtual screening of the endocannabinoid system." *J Med Chem* 49(15): 4650-6.

Saario, S. M., O. M. Salo, et al. (2005). "Characterization of the sulfhydryl-sensitive site in the enzyme responsible for hydrolysis of 2-arachidonoyl-glycerol in rat cerebellar membranes." *Chem Biol* 12(6): 649-56.

Saario, S. M., J. R. Savinainen, et al. (2004). "Monoglyceride lipase-like enzymatic activity is responsible for hydrolysis of 2-arachidonoylglycerol in rat cerebellar membranes." *Biochem Pharmacol* 67(7): 1381-7.

Sambrook, J., E. F. Fritsch, et al. (1989). *Molecular cloning*. 2nd ed. New York: Cold Spring Harbor Laboratory Press.

Schlecht, M. (1998). *Molecular Modeling on the PC*, John Wiley & Sons.

Schrag, J. D., Y. G. Li, et al. (1991). "Ser-His-Glu triad forms the catalytic site of the lipase from *Geotrichum candidum*." *Nature* 351(6329): 761-4.

Segel, I. H. (1975). *Enzyme Kinetics: Behavior and Analysis of Rapid Equilibrium and Steady-State Enzyme Systems*, J. Willey & Sons.

Smith, W. B. (1996). *Introduction to Theoretical Organic. Chemistry and Molecular Modeling*. New York, VCH Publishers.

Somma-Delpero, C., A. Valette, et al. (1995). "Purification and properties of a monoacylglycerol lipase in human erythrocytes." *Biochem J* 312 (Pt 2): 519-25.

Sugiura, T., S. Kondo, et al. (2000). "Evidence that 2-arachidonoylglycerol but not N-palmitoylethanolamine or anandamide is the physiological ligand for the cannabinoid CB2 receptor. Comparison of the agonistic activities of various cannabinoid receptor ligands in HL-60 cells." *J Biol Chem* 275(1): 605-12.

Sussman, J. L., D. Lin, et al. (1998). "Protein Data Bank (PDB): database of three-dimensional structural information of biological macromolecules." *Acta Crystallogr D Biol Crystallogr* 54(Pt 6 Pt 1): 1078-84.

Tatusova, T. A. and T. L. Madden (1999). "BLAST 2 Sequences, a new tool for comparing protein and nucleotide sequences." *FEMS Microbiol Lett* 174(2): 247-50.

Terwilliger, T. C., R. W. Grosse-Kunstleve, et al. (2008). "Iterative model building, structure refinement and density modification with the PHENIX AutoBuild wizard." *Acta Crystallogr D Biol Crystallogr* 64(Pt 1): 61-9.

Thompson, J. D., D. G. Higgins, et al. (1994). "CLUSTAL W: improving the sensitivity of progressive multiple sequence alignment through sequence weighting, position-specific gap penalties and weight matrix choice." *Nucleic Acids Res* 22(22): 4673-80.

Tornqvist, H. and P. Belfrage (1976). "Purification and some properties of a monoacylglycerol-hydrolyzing enzyme of rat adipose tissue." *J Biol Chem* 251(3): 813-9.

Travis, J. (1993). "Proteins and Organic Solvents Make an Eye-Opening Mix." *Science* 262:1374

Tsirelson, V. G. and R. P. Ozerov (1996). *Electron Density and Bonding in Crystals: Principles, Theory and X-ray Diffraction Experiments in Solid State Physics and Chemistry*, Inst. of Physics Pub.

Van Den Berg, B., M. Tessari, et al. (1995). "NMR structures of phospholipase A2 reveal conformational changes during interfacial activation." *Nat Struct Biol* 2(5): 402-6.

Van Den Berg, B., M. Tessari, et al. (1995). "Solution structure of porcine pancreatic phospholipase A2 complexed with micelles and a competitive inhibitor." *J Biomol NMR* 5(2): 110-21.

Van Tilbeurgh, H., L. Sarda, et al. (1992). "Structure of the pancreatic lipase-procolipase complex." *Nature* 359(6391): 159-62.

Vandevoorde, S, and D. M. Lambert (2005). "Focus on the three key enzymes hydrolysing endocannabinoids as new drug targets." *Curr Pharm Des* 11(20): 2647-68.

Walczak, J. S., V. Pichette, et al. (2005). "Behavioral, pharmacological and molecular characterization of the saphenous nerve partial ligation: a new model of neuropathic pain." *Neuroscience* 132(4): 1093-102.

Wall, E. M., J. Cao, et al. (1997). "A novel poxvirus gene and its human homolog are similar to an *E. coli* lysophospholipase." *Virus Res* 52(2): 157-67.

Wang, X., C. S. Wang, et al. (1997). "The crystal structure of bovine bile salt activated lipase: insights into the bile salt activation mechanism." *Structure* 5(9): 1209-18.

Winkler, F. K., A. D'arcy, et al. (1990). "Structure of human pancreatic lipase." *Nature* 343(6260): 771-4.

Woolfson, M. M. (1997). *An Introduction to X-ray Crystallography*. Cambridge, UK, Cambridge Univ. Pr.

What is claimed is:

1. The A crystal comprising monoacylglycerol lipase (MGLL) peptide consisting of SEQ ID NO: 7 and a ligand, wherein said ligand is selected from the group consisting of the following structures:

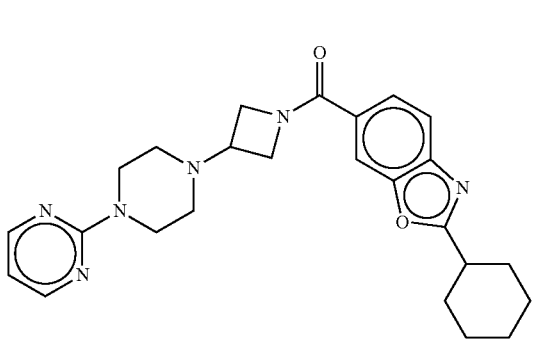

and

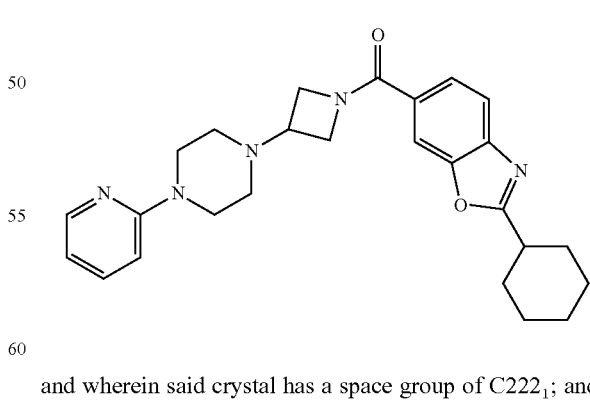

and wherein said crystal has a space group of $C222_1$; and a unit cell having dimensions of a=93.95 Å, b=128.45 Å, c=60.6 Å.

2. A method for the production of a crystal complex comprising a monoacylglycerol lipase (MGLL) peptide consisting of SEQ ID NO: 7 with a ligand of the following structure:

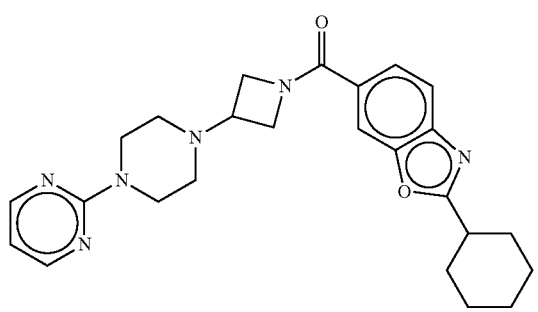
comprising:
a. contacting the MGLL polypeptide with said ligand in a suitable solution comprising 8% PEG MME 5K, 100 mM Na Citrate pH5.5 and 2% n-Octyl-Beta-D-Glucopyranoside, and,
b. crystallizing said resulting complex of MGLL polypeptide-ligand from said solution.
* * * * *

SEQUENCE LISTING

```
<160> NUMBER OF SEQ ID NOS: 11

<210> SEQ ID NO 1
<211> LENGTH: 304
<212> TYPE: PRT
<213> ORGANISM: Homo sapiens

<400> SEQUENCE: 1

Met Pro Glu Glu Ser Ser Pro Arg Arg Thr Pro Gln Ser Ile Pro Tyr
1               5                   10                  15

Gln Asp Leu Pro His Leu Val Asn Ala Asp Gly Gln Tyr Leu Phe Cys
            20                  25                  30

Arg Tyr Trp Lys Pro Thr Gly Thr Pro Lys Ala Leu Ile Phe Val Ser
        35                  40                  45

His Gly Ala Gly Glu His Ser Gly Arg Tyr Glu Glu Leu Ala Arg Met
    50                  55                  60
```

Leu Met Gly Leu Leu Asp Leu Val Phe Ala His Asp His Val Gly
65                  70                  75                  80

His Gly Gln Ser Glu Gly Glu Arg Met Val Val Ser Asp Phe His Val
            85                  90                  95

Phe Val Arg Asp Val Leu Gln His Val Asp Ser Met Gln Lys Asp Tyr
                100                 105                 110

Pro Gly Leu Pro Val Phe Leu Leu Gly His Ser Met Gly Gly Ala Ile
            115                 120                 125

Ala Ile Leu Thr Ala Ala Glu Arg Pro Gly His Phe Ala Gly Met Val
            130                 135                 140

Leu Ile Ser Pro Leu Val Leu Ala Asn Pro Glu Ser Ala Thr Thr Phe
145                 150                 155                 160

Lys Val Leu Ala Ala Lys Val Leu Asn Leu Val Leu Pro Asn Leu Ser
                165                 170                 175

Leu Gly Pro Ile Asp Ser Ser Val Leu Ser Arg Asn Lys Thr Glu Val
            180                 185                 190

Asp Ile Tyr Asn Ser Asp Pro Leu Ile Cys Arg Ala Gly Leu Lys Val
                195                 200                 205

Cys Phe Gly Ile Gln Leu Leu Asn Ala Val Ser Arg Val Glu Arg Ala
210                 215                 220

Leu Pro Lys Leu Thr Val Pro Phe Leu Leu Leu Gln Gly Ser Ala Asp
225                 230                 235                 240

Arg Leu Cys Asp Ser Lys Gly Ala Tyr Leu Leu Met Glu Leu Ala Lys
                245                 250                 255

Ser Gln Asp Lys Thr Leu Lys Ile Tyr Glu Gly Ala Tyr His Val Leu
            260                 265                 270

His Lys Glu Leu Pro Glu Val Thr Asn Ser Val Phe His Glu Ile Asn
            275                 280                 285

Met Trp Val Ser Gln Arg Thr Ala Thr Ala Gly Thr Ala Ser Pro Pro
290                 295                 300

<210> SEQ ID NO 2
<211> LENGTH: 314
<212> TYPE: PRT
<213> ORGANISM: Homo sapiens

<400> SEQUENCE: 2

Met Glu Thr Gly Pro Glu Asp Pro Ser Ser Met Pro Glu Glu Ser Ser
1               5                   10                  15

Pro Arg Arg Thr Pro Gln Ser Ile Pro Tyr Gln Asp Leu Pro His Leu
            20                  25                  30

Val Asn Ala Asp Gly Gln Tyr Leu Phe Cys Arg Tyr Trp Lys Pro Thr
        35                  40                  45

Gly Thr Pro Lys Ala Leu Ile Phe Val Ser His Gly Ala Gly Glu His
50                  55                  60

Ser Gly Arg Tyr Glu Glu Leu Ala Arg Met Leu Met Gly Leu Leu Asp
65                  70                  75                  80

Leu Leu Val Phe Ala His Asp His Val Gly His Gly Gln Ser Glu Gly
                85                  90                  95

Glu Arg Met Val Val Ser Asp Phe His Val Phe Val Arg Asp Val Leu
            100                 105                 110

Gln His Val Asp Ser Met Gln Lys Asp Tyr Pro Gly Leu Pro Val Phe
        115                 120                 125

Leu Leu Gly His Ser Met Gly Gly Ala Ile Ala Ile Leu Thr Ala Ala
130                 135                 140

-continued

```
Glu Arg Pro Gly His Phe Ala Gly Met Val Leu Ile Ser Pro Leu Val
145                 150                 155                 160

Leu Ala Asn Pro Glu Ser Ala Thr Thr Phe Lys Val Leu Ala Ala Lys
            165                 170                 175

Val Leu Asn Leu Val Leu Pro Asn Leu Ser Leu Gly Pro Ile Asp Ser
        180                 185                 190

Ser Val Leu Ser Arg Asn Lys Thr Glu Val Asp Ile Tyr Asn Ser Asp
    195                 200                 205

Pro Leu Ile Cys Arg Ala Gly Leu Lys Val Cys Phe Gly Ile Gln Leu
210                 215                 220

Leu Asn Ala Val Ser Arg Val Glu Arg Ala Leu Pro Lys Leu Thr Val
225                 230                 235                 240

Pro Phe Leu Leu Gln Gly Ser Ala Asp Arg Leu Cys Asp Ser Lys
            245                 250                 255

Gly Ala Tyr Leu Leu Met Glu Leu Ala Lys Ser Gln Asp Lys Thr Leu
        260                 265                 270

Lys Ile Tyr Glu Gly Ala Tyr His Val Leu His Lys Glu Leu Pro Glu
        275                 280                 285

Val Thr Asn Ser Val Phe His Glu Ile Asn Met Trp Val Ser Gln Arg
        290                 295                 300

Thr Ala Thr Ala Gly Thr Ala Ser Pro Pro
305                 310
```

<210> SEQ ID NO 3
<211> LENGTH: 319
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 3

```
Met Val Asp His His His His His His Glu Asn Leu Tyr Phe Gln Gly
1               5                   10                  15

Met Pro Glu Glu Ser Ser Pro Arg Arg Thr Pro Gln Ser Ile Pro Tyr
            20                  25                  30

Gln Asp Leu Pro His Leu Val Asn Ala Asp Gly Gln Tyr Leu Phe Cys
        35                  40                  45

Arg Tyr Trp Lys Pro Thr Gly Thr Pro Lys Ala Leu Ile Phe Val Ser
    50                  55                  60

His Gly Ala Gly Glu His Ser Gly Arg Tyr Glu Glu Leu Ala Arg Met
65                  70                  75                  80

Leu Met Gly Leu Asp Leu Leu Val Phe Ala His Asp His Val Gly His
            85                  90                  95

Gly Gln Ser Glu Gly Glu Arg Met Val Val Ser Asp Phe His Val Phe
        100                 105                 110

Val Arg Asp Val Leu Gln His Val Asp Ser Met Gln Lys Asp Tyr Pro
    115                 120                 125

Gly Leu Pro Val Phe Leu Leu Gly His Ser Met Gly Gly Ala Ile Ala
130                 135                 140

Ile Leu Thr Ala Ala Glu Arg Pro Gly His Phe Ala Gly Met Val Leu
145                 150                 155                 160

Ile Ser Pro Leu Val Leu Ala Asn Pro Glu Ser Ala Thr Thr Phe Lys
            165                 170                 175

Val Leu Ala Ala Lys Val Leu Asn Leu Val Leu Pro Asn Leu Ser Leu
        180                 185                 190
```

```
Gly Pro Ile Asp Ser Ser Val Leu Ser Arg Asn Lys Thr Glu Val Asp
        195                 200                 205

Ile Tyr Asn Ser Asp Pro Leu Ile Cys Arg Ala Gly Leu Lys Val Cys
    210                 215                 220

Phe Gly Ile Gln Leu Leu Asn Ala Val Ser Arg Val Glu Arg Ala Leu
225                 230                 235                 240

Pro Lys Leu Thr Val Pro Phe Leu Leu Gln Gly Ser Ala Asp Arg
                245                 250                 255

Leu Cys Asp Ser Lys Gly Ala Tyr Leu Leu Met Glu Leu Ala Lys Ser
                260                 265                 270

Gln Asp Lys Thr Leu Lys Ile Tyr Glu Gly Ala Tyr His Val Leu His
                275                 280                 285

Lys Glu Leu Pro Glu Val Thr Asn Ser Val Phe His Glu Ile Asn Met
        290                 295                 300

Trp Val Ser Gln Arg Thr Ala Thr Ala Gly Thr Ala Ser Pro Pro
305                 310                 315
```

<210> SEQ ID NO 4
<211> LENGTH: 319
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 4

```
Met Val Asp His His His His His His Glu Asn Leu Tyr Phe Gln Gly
1               5                   10                  15

Met Pro Glu Glu Ser Ser Pro Arg Arg Thr Pro Gln Ser Ile Pro Tyr
            20                  25                  30

Gln Asp Leu Pro His Leu Val Asn Ala Asp Gly Gln Tyr Leu Phe Cys
        35                  40                  45

Arg Tyr Trp Lys Pro Thr Gly Thr Pro Lys Ala Leu Ile Phe Val Ser
    50                  55                  60

His Gly Ala Gly Glu His Ser Gly Arg Tyr Glu Glu Leu Ala Arg Met
65                  70                  75                  80

Leu Met Gly Leu Asp Leu Leu Val Phe Ala His Asp His Val Gly His
                85                  90                  95

Gly Gln Ser Glu Gly Glu Arg Met Val Val Ser Asp Phe His Val Phe
            100                 105                 110

Val Arg Asp Val Leu Gln His Val Asp Ser Met Gln Lys Asp Tyr Pro
        115                 120                 125

Gly Leu Pro Val Phe Leu Leu Gly His Ser Met Gly Gly Ala Ile Ala
        130                 135                 140

Ile Leu Thr Ala Ala Glu Arg Pro Gly His Phe Ala Gly Met Val Leu
145                 150                 155                 160

Ile Ser Pro Leu Val Leu Ala Asn Pro Glu Ser Ala Thr Thr Phe Lys
                165                 170                 175

Val Leu Ala Ala Lys Val Leu Asn Ser Val Leu Pro Asn Leu Ser Ser
            180                 185                 190

Gly Pro Ile Asp Ser Ser Val Leu Ser Arg Asn Lys Thr Glu Val Asp
        195                 200                 205

Ile Tyr Asn Ser Asp Pro Leu Ile Cys Arg Ala Gly Leu Lys Val Cys
    210                 215                 220

Phe Gly Ile Gln Leu Leu Asn Ala Val Ser Arg Val Glu Arg Ala Leu
225                 230                 235                 240
```

```
Pro Lys Leu Thr Val Pro Phe Leu Leu Leu Gln Gly Ser Ala Asp Arg
            245                 250                 255

Leu Cys Asp Ser Lys Gly Ala Tyr Leu Leu Met Glu Leu Ala Lys Ser
        260                 265                 270

Gln Asp Lys Thr Leu Lys Ile Tyr Glu Gly Ala Tyr His Val Leu His
            275                 280                 285

Lys Glu Leu Pro Glu Val Thr Asn Ser Val Phe His Glu Ile Asn Met
        290                 295                 300

Trp Val Ser Gln Arg Thr Ala Thr Ala Gly Thr Ala Ser Pro Pro
305                 310                 315

<210> SEQ ID NO 5
<211> LENGTH: 304
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Gly Met Pro Glu Glu Ser Ser Pro Arg Arg Thr Pro Gln Ser Ile Pro
1               5                   10                  15

Tyr Gln Asp Leu Pro His Leu Val Asn Ala Asp Gly Gln Tyr Leu Phe
            20                  25                  30

Cys Arg Tyr Trp Lys Pro Thr Gly Thr Pro Lys Ala Leu Ile Phe Val
        35                  40                  45

Ser His Gly Ala Gly Glu His Ser Gly Arg Tyr Glu Glu Leu Ala Arg
    50                  55                  60

Met Leu Met Gly Leu Asp Leu Leu Val Phe Ala His Asp His Val Gly
65                  70                  75                  80

His Gly Gln Ser Glu Gly Glu Arg Met Val Val Ser Asp Phe His Val
                85                  90                  95

Phe Val Arg Asp Val Leu Gln His Val Asp Ser Met Gln Lys Asp Tyr
            100                 105                 110

Pro Gly Leu Pro Val Phe Leu Leu Gly His Ser Met Gly Gly Ala Ile
        115                 120                 125

Ala Ile Leu Thr Ala Ala Glu Arg Pro Gly His Phe Ala Gly Met Val
    130                 135                 140

Leu Ile Ser Pro Leu Val Leu Ala Asn Pro Glu Ser Ala Thr Thr Phe
145                 150                 155                 160

Lys Val Leu Ala Ala Lys Val Leu Asn Ser Val Leu Pro Asn Leu Ser
                165                 170                 175

Ser Gly Pro Ile Asp Ser Ser Val Leu Ser Arg Asn Lys Thr Glu Val
            180                 185                 190

Asp Ile Tyr Asn Ser Asp Pro Leu Ile Cys Arg Ala Gly Leu Lys Val
        195                 200                 205

Cys Phe Gly Ile Gln Leu Leu Asn Ala Val Ser Arg Val Glu Arg Ala
    210                 215                 220

Leu Pro Lys Leu Thr Val Pro Phe Leu Leu Leu Gln Gly Ser Ala Asp
225                 230                 235                 240

Arg Leu Cys Asp Ser Lys Gly Ala Tyr Leu Leu Met Glu Leu Ala Lys
                245                 250                 255

Ser Gln Asp Lys Thr Leu Lys Ile Tyr Glu Gly Ala Tyr His Val Leu
            260                 265                 270

His Lys Glu Leu Pro Glu Val Thr Asn Ser Val Phe His Glu Ile Asn
        275                 280                 285
```

```
Met Trp Val Ser Gln Arg Thr Ala Thr Ala Gly Thr Ala Ser Pro Pro
        290                 295                 300
```

<210> SEQ ID NO 6
<211> LENGTH: 319
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

```
Met Val Asp His His His His His His Glu Asn Leu Tyr Phe Gln Gly
  1               5                  10                  15

Met Pro Glu Glu Ser Ser Pro Arg Arg Thr Pro Gln Ser Ile Pro Tyr
             20                  25                  30

Gln Asp Leu Pro His Leu Val Asn Ala Asp Gly Gln Tyr Leu Phe Cys
         35                  40                  45

Arg Tyr Trp Ala Pro Thr Gly Thr Pro Lys Ala Leu Ile Phe Val Ser
     50                  55                  60

His Gly Ala Gly Glu His Ser Gly Arg Tyr Glu Glu Leu Ala Arg Met
 65                  70                  75                  80

Leu Met Gly Leu Asp Leu Leu Val Phe Ala His Asp His Val Gly His
                 85                  90                  95

Gly Gln Ser Glu Gly Glu Arg Met Val Val Ser Asp Phe His Val Phe
            100                 105                 110

Val Arg Asp Val Leu Gln His Val Asp Ser Met Gln Lys Asp Tyr Pro
        115                 120                 125

Gly Leu Pro Val Phe Leu Leu Gly His Ser Met Gly Gly Ala Ile Ala
    130                 135                 140

Ile Leu Thr Ala Ala Glu Arg Pro Gly His Phe Ala Gly Met Val Leu
145                 150                 155                 160

Ile Ser Pro Leu Val Leu Ala Asn Pro Glu Ser Ala Thr Thr Phe Lys
                165                 170                 175

Val Leu Ala Ala Lys Val Leu Asn Ser Val Leu Pro Asn Leu Ser Ser
            180                 185                 190

Gly Pro Ile Asp Ser Ser Val Leu Ser Arg Asn Lys Thr Glu Val Asp
        195                 200                 205

Ile Tyr Asn Ser Asp Pro Leu Ile Cys Arg Ala Gly Leu Lys Val Cys
    210                 215                 220

Phe Gly Ile Gln Leu Leu Asn Ala Val Ser Arg Val Glu Arg Ala Leu
225                 230                 235                 240

Pro Lys Leu Thr Val Pro Phe Leu Leu Leu Gln Gly Ser Ala Asp Arg
                245                 250                 255

Leu Cys Asp Ser Lys Gly Ala Tyr Leu Leu Met Glu Leu Ala Lys Ser
            260                 265                 270

Gln Asp Lys Thr Leu Lys Ile Tyr Glu Gly Ala Tyr His Val Leu His
        275                 280                 285

Lys Glu Leu Pro Glu Val Thr Asn Ser Val Phe His Glu Ile Asn Met
    290                 295                 300

Trp Val Ser Gln Arg Thr Ala Thr Ala Gly Thr Ala Ser Pro Pro
305                 310                 315
```

<210> SEQ ID NO 7
<211> LENGTH: 304
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 7

Gly Met Pro Glu Glu Ser Ser Pro Arg Arg Thr Pro Gln Ser Ile Pro
1               5                   10                  15

Tyr Gln Asp Leu Pro His Leu Val Asn Ala Asp Gly Gln Tyr Leu Phe
                20                  25                  30

Cys Arg Tyr Trp Ala Pro Thr Gly Thr Pro Lys Ala Leu Ile Phe Val
            35                  40                  45

Ser His Gly Ala Gly Glu His Ser Gly Arg Tyr Glu Glu Leu Ala Arg
        50                  55                  60

Met Leu Met Gly Leu Asp Leu Val Phe Ala His Asp His Val Gly
65                  70                  75                  80

His Gly Gln Ser Glu Gly Glu Arg Met Val Val Ser Asp Phe His Val
                85                  90                  95

Phe Val Arg Asp Val Leu Gln His Val Asp Ser Met Gln Lys Asp Tyr
                100                 105                 110

Pro Gly Leu Pro Val Phe Leu Leu Gly His Ser Met Gly Gly Ala Ile
            115                 120                 125

Ala Ile Leu Thr Ala Ala Glu Arg Pro Gly His Phe Ala Gly Met Val
130                 135                 140

Leu Ile Ser Pro Leu Val Leu Ala Asn Pro Glu Ser Ala Thr Thr Phe
145                 150                 155                 160

Lys Val Leu Ala Ala Lys Val Leu Asn Ser Val Leu Pro Asn Leu Ser
                165                 170                 175

Ser Gly Pro Ile Asp Ser Ser Val Leu Ser Arg Asn Lys Thr Glu Val
                180                 185                 190

Asp Ile Tyr Asn Ser Asp Pro Leu Ile Cys Arg Ala Gly Leu Lys Val
            195                 200                 205

Cys Phe Gly Ile Gln Leu Leu Asn Ala Val Ser Arg Val Glu Arg Ala
210                 215                 220

Leu Pro Lys Leu Thr Val Pro Phe Leu Leu Leu Gln Gly Ser Ala Asp
225                 230                 235                 240

Arg Leu Cys Asp Ser Lys Gly Ala Tyr Leu Leu Met Glu Leu Ala Lys
                245                 250                 255

Ser Gln Asp Lys Thr Leu Lys Ile Tyr Glu Gly Ala Tyr His Val Leu
                260                 265                 270

His Lys Glu Leu Pro Glu Val Thr Asn Ser Val Phe His Glu Ile Asn
            275                 280                 285

Met Trp Val Ser Gln Arg Thr Ala Thr Ala Gly Thr Ala Ser Pro Pro
290                 295                 300

<210> SEQ ID NO 8
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gagaatttgg tattttcaag gtatgccaga ggaaagttcc cc                          42

<210> SEQ ID NO 9
<211> LENGTH: 39
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 9
tggatgtgta tgtttctatc agggtgggga cgaagttcc                           39

<210> SEQ ID NO 10
<211> LENGTH: 288
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10
```

| | | | | | | | | | | | | | | | |
|---|---|---|---|---|---|---|---|---|---|---|---|---|---|---|---|
| Pro | Arg | Arg | Thr | Pro | Gln | Ser | Ile | Pro | Tyr | Gln | Asp | Leu | Pro | His | Leu |
| 1 | | | | 5 | | | | | 10 | | | | | 15 | |
| Val | Asn | Ala | Asp | Gly | Gln | Tyr | Leu | Phe | Cys | Arg | Tyr | Trp | Ala | Pro | Thr |
| | | | 20 | | | | | 25 | | | | | 30 | | |
| Gly | Thr | Pro | Lys | Ala | Leu | Ile | Phe | Val | Ser | His | Gly | Ala | Gly | Glu | His |
| | | 35 | | | | | 40 | | | | | 45 | | | |
| Ser | Gly | Arg | Tyr | Glu | Glu | Leu | Ala | Arg | Met | Leu | Met | Gly | Leu | Asp | Leu |
| 50 | | | | | 55 | | | | | 60 | | | | | |
| Leu | Val | Phe | Ala | His | Asp | His | Val | Gly | His | Gly | Gln | Ser | Glu | Gly | Glu |
| 65 | | | | 70 | | | | | 75 | | | | | 80 | |
| Arg | Met | Val | Val | Ser | Asp | Phe | His | Val | Phe | Val | Arg | Asp | Val | Leu | Gln |
| | | | | 85 | | | | | 90 | | | | | 95 | |
| His | Val | Asp | Ser | Met | Gln | Lys | Asp | Tyr | Pro | Gly | Leu | Pro | Val | Phe | Leu |
| | | | 100 | | | | | 105 | | | | | 110 | | |
| Leu | Gly | His | Ser | Met | Gly | Gly | Ala | Ile | Ala | Ile | Leu | Thr | Ala | Ala | Glu |
| | | 115 | | | | | 120 | | | | | 125 | | | |
| Arg | Pro | Gly | His | Phe | Ala | Gly | Met | Val | Leu | Ile | Ser | Pro | Leu | Val | Leu |
| 130 | | | | | 135 | | | | | 140 | | | | | |
| Ala | Asn | Pro | Glu | Ser | Ala | Thr | Thr | Phe | Lys | Val | Leu | Ala | Ala | Lys | Val |
| 145 | | | | 150 | | | | | 155 | | | | | 160 | |
| Leu | Asn | Ser | Val | Leu | Pro | Asn | Leu | Ser | Ser | Gly | Pro | Ile | Asp | Ser | Ser |
| | | | | 165 | | | | | 170 | | | | | 175 | |
| Val | Leu | Ser | Arg | Asn | Lys | Thr | Glu | Val | Asp | Ile | Tyr | Asn | Ser | Asp | Pro |
| | | | 180 | | | | | 185 | | | | | 190 | | |
| Leu | Ile | Cys | Arg | Ala | Gly | Leu | Lys | Val | Cys | Phe | Gly | Ile | Gln | Leu | Leu |
| | | 195 | | | | | 200 | | | | | 205 | | | |
| Asn | Ala | Val | Ser | Arg | Val | Glu | Arg | Ala | Leu | Pro | Lys | Leu | Thr | Val | Pro |
| 210 | | | | | 215 | | | | | 220 | | | | | |
| Phe | Leu | Leu | Leu | Gln | Gly | Ser | Ala | Asp | Arg | Leu | Cys | Asp | Ser | Lys | Gly |
| 225 | | | | | 230 | | | | | 235 | | | | | 240 |
| Ala | Tyr | Leu | Leu | Met | Glu | Leu | Ala | Lys | Ser | Gln | Asp | Lys | Thr | Leu | Lys |
| | | | | 245 | | | | | 250 | | | | | 255 | |
| Ile | Tyr | Glu | Gly | Ala | Tyr | His | Val | Leu | His | Lys | Glu | Leu | Pro | Glu | Val |
| | | | | 260 | | | | | 265 | | | | | 270 | |
| Thr | Asn | Ser | Val | Phe | His | Glu | Ile | Asn | Met | Trp | Val | Ser | Gln | Arg | Thr |
| | | | | 275 | | | | | 280 | | | | | 285 | |

```
<210> SEQ ID NO 11
<211> LENGTH: 271
<212> TYPE: PRT
<213> ORGANISM: Bacillus subtilis

<400> SEQUENCE: 11
```

```
Ala Gly His Met Thr Ser Ile Leu Ser Arg Asn His Val Lys Val Lys
1               5                   10                  15

Gly Ser Gly Lys Ala Ser Ile Met Phe Ala Pro Gly Phe Gly Cys Asp
                20                  25              30

Gln Ser Val Trp Asn Ala Val Ala Pro Ala Phe Glu Asp His Arg
            35              40              45

Val Ile Leu Phe Asp Tyr Val Gly Ser Gly His Ser Asp Leu Arg Ala
    50                  55              60

Tyr Asp Leu Asn Arg Tyr Gln Thr Leu Asp Gly Tyr Ala Gln Asp Val
65                  70              75                      80

Leu Asp Val Cys Glu Ala Leu Asp Leu Lys Glu Thr Val Phe Val Gly
                85              90                      95

His Ser Val Gly Ala Leu Ile Gly Met Leu Ala Ser Ile Arg Arg Pro
                100             105             110

Glu Leu Phe Ser His Leu Val Met Val Gly Pro Ser Pro Cys Tyr Leu
            115             120             125

Asn Asp Pro Pro Glu Tyr Tyr Gly Gly Phe Glu Glu Glu Gln Leu Leu
            130             135             140

Gly Leu Leu Glu Met Met Glu Lys Asn Tyr Ile Gly Trp Ala Thr Val
145             150             155                     160

Phe Ala Ala Thr Val Leu Asn Gln Pro Asp Arg Pro Glu Ile Lys Glu
                165             170             175

Glu Leu Glu Ser Arg Phe Cys Ser Thr Asp Pro Val Ile Ala Arg Gln
            180             185             190

Phe Ala Lys Ala Ala Phe Phe Ser Asp His Arg Glu Asp Leu Ser Lys
            195             200             205

Val Thr Val Pro Ser Leu Ile Leu Gln Cys Ala Asp Asp Ile Ile Ala
    210             215             220

Pro Ala Thr Val Gly Lys Tyr Met His Gln His Leu Pro Tyr Ser Ser
225             230             235                     240

Leu Lys Gln Met Glu Ala Arg Gly His Cys Pro His Met Ser His Pro
                245             250             255

Asp Glu Thr Ile Gln Leu Ile Gly Asp Tyr Leu Lys Ala His Val
            260             265             270
```